US011840725B2

(12) United States Patent
Doudna et al.

(10) Patent No.: US 11,840,725 B2
(45) Date of Patent: *Dec. 12, 2023

(54) METHODS AND COMPOSITIONS FOR DETECTING A TARGET RNA

(71) Applicant: The Regents of the University of California, Oakland, CA (US)

(72) Inventors: Jennifer A. Doudna, Berkeley, CA (US); Mitchell Ray O'Connell, Oakland, CA (US); Alexandra East-Seletsky, San Francisco, CA (US); Spencer Charles Knight, Berkeley, CA (US); James Harrison Doudna Cate, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/281,939

(22) Filed: Feb. 21, 2019

(65) Prior Publication Data

US 2019/0177775 A1 Jun. 13, 2019

Related U.S. Application Data

(60) Continuation of application No. 15/920,222, filed on Mar. 13, 2018, now Pat. No. 10,494,664, which is a division of application No. 15/467,922, filed on Mar. 23, 2017, now Pat. No. 10,337,051.

(60) Provisional application No. 62/378,156, filed on Aug. 22, 2016, provisional application No. 62/351,172, filed on Jun. 16, 2016.

(51) Int. Cl.
C12Q 1/6823 (2018.01)

(52) U.S. Cl.
CPC ............ *C12Q 1/6823* (2013.01); *Y02A 50/30* (2018.01)

(58) Field of Classification Search
None
See application file for complete search history.

(56) References Cited

U.S. PATENT DOCUMENTS

| 6,773,885 | B1 | 8/2004 | Walder et al. |
| 8,597,886 | B2* | 12/2013 | Smith ..................... C12Q 1/683 435/6.11 |
| 8,815,782 | B2 | 8/2014 | Zeiner et al. |
| 9,730,967 | B2 | 6/2017 | Kovarik et al. |
| 9,790,490 | B2 | 10/2017 | Zhang et al. |
| 10,253,365 | B1 | 4/2019 | Doudna et al. |
| 10,266,886 | B2 | 4/2019 | Abudayyeh et al. |
| 10,316,324 | B2 | 6/2019 | Begemann et al. |
| 10,337,051 | B2 | 7/2019 | Doudna et al. |
| 10,494,664 | B2 | 12/2019 | Doudna et al. |
| 10,570,415 | B2 | 2/2020 | Doudna et al. |
| 11,180,743 | B2 | 11/2021 | Doudna et al. |
| 11,453,866 | B2 | 9/2022 | Doudna et al. |
| 2013/0261196 | A1 | 10/2013 | Diamond et al. |
| 2015/0211058 | A1* | 7/2015 | Carstens ............... C12Q 1/6844 435/5 |
| 2016/0017366 | A1 | 1/2016 | Chen et al. |
| 2016/0289659 | A1 | 10/2016 | Doudna et al. |
| 2017/0051276 | A1 | 2/2017 | May et al. |
| 2017/0175104 | A1 | 6/2017 | Doudna et al. |
| 2017/0198277 | A1 | 7/2017 | Kmiec et al. |
| 2017/0211142 | A1 | 7/2017 | Smargon et al. |
| 2017/0233756 | A1 | 8/2017 | Begemann et al. |
| 2017/0306335 | A1 | 10/2017 | Zhang et al. |
| 2017/0321198 | A1* | 11/2017 | Severinov ................ C12N 9/22 |
| 2017/0321214 | A1 | 11/2017 | Zhang et al. |
| 2017/0369870 | A1 | 12/2017 | Gill et al. |
| 2018/0340218 | A1 | 11/2018 | Abudayyeh et al. |
| 2019/0276842 | A1 | 9/2019 | Doudna et al. |
| 2019/0300908 | A1 | 10/2019 | Doudna et al. |
| 2020/0017879 | A1 | 1/2020 | Doudna et al. |
| 2020/0087640 | A1 | 3/2020 | Doudna et al. |
| 2020/0255858 | A1 | 8/2020 | Doudna et al. |
| 2020/0339967 | A1 | 10/2020 | Doudna et al. |
| 2021/0166783 | A1 | 6/2021 | Shmakov et al. |

FOREIGN PATENT DOCUMENTS

| CN | 1886512 A | 12/2006 |
| CN | 101283089 A | 10/2008 |
| CN | 106701830 A | 5/2017 |
| EP | 1580273 A1 | 9/2005 |
| EP | 3009511 A2 | 4/2016 |
| JP | 2004521606 A | 7/2004 |
| WO | WO 2015/071474 | 5/2015 |
| WO | WO 2015/139139 | 9/2015 |
| WO | WO 2015/191693 | 12/2015 |

(Continued)

OTHER PUBLICATIONS

Shmakov et al. (2015) Discovery and Functional Characterization of Diverse Class 2 CRISPR-Cas Systems. Molecular Cell, 60:385-397 (Year: 2015).*
Koonin et al. (2017) Diversity, classification and evolution of CRISPR-Cas systems. Current Opinion in Microbiology, 37:67-78 (Year: 2017).*
Smargon et al. (2017) Cas 13b Is a Type VI-B CRISPR-Associated RNA Guided RNase Differentially Regulated by Accessory Proteins Csx27 and Csx28. Molecular Cell, 65:618-630 (Year: 2017).*
Yan et al. (2018) Cas13d Is a Compact RNA-Targeting Type VI CRISPR Effector Positively Modulated by a WYL-Domain-Containing Accessory Protein. Molecular Cell, 70(2):327-339 (Year: 2018).*

(Continued)

*Primary Examiner* — Gary Benzion
*Assistant Examiner* — Kelly Nichet Hassell
(74) *Attorney, Agent, or Firm* — BOZICEVIC, FIELD & FRANCIS LLP; Shweta Chandra

(57) ABSTRACT

The present disclosure provides methods for detecting a single-stranded target RNA. The present disclosure provides methods of cleaving a precursor C2c2 guide RNA array into two or more C2c2 guide RNAs. The present disclosure provides a kit for detecting a target RNA in a sample.

26 Claims, 79 Drawing Sheets

Specification includes a Sequence Listing.

(56) References Cited

FOREIGN PATENT DOCUMENTS

| WO | WO 2016/094872 | 12/2015 |
|---|---|---|
| WO | WO 2016/106236 | 12/2015 |
| WO | WO 2016/028843 | 2/2016 |
| WO | WO 2016/094867 A1 | 6/2016 |
| WO | WO 2016/205711 | 6/2016 |
| WO | WO 2016/123243 | 8/2016 |
| WO | WO 2016/205613 | 12/2016 |
| WO | WO 2016/205749 | 12/2016 |
| WO | WO 2016/205764 | 12/2016 |
| WO | WO 2017/070605 | 4/2017 |
| WO | WO 2017/205668 | 5/2017 |
| WO | WO 2017/120410 | 7/2017 |
| WO | WO 2017/147345 | 8/2017 |
| WO | WO 2017/176529 | 10/2017 |
| WO | WO 2017/218573 | 12/2017 |
| WO | WO 2017/219027 | 12/2017 |
| WO | WO 2017/223538 | 12/2017 |
| WO | WO 2018/064352 | 4/2018 |
| WO | WO 2018/064371 | 4/2018 |
| WO | WO 2018/107129 | 6/2018 |
| WO | WO 2018/172556 | 9/2018 |
| WO | WO 2018/195545 | 10/2018 |
| WO | WO 2019/089796 | 5/2019 |
| WO | WO 2019/089804 | 5/2019 |
| WO | WO 2019/089808 | 5/2019 |
| WO | WO 2019/089820 | 5/2019 |
| WO | WO 2019/126577 | 6/2019 |

OTHER PUBLICATIONS

Yang et al. "Using Molecular Beacons for Sensitive Fluorescence Assays of the Enzymatic Cleavage of Nucleic Acids", from: Methods in Molecular Biology, vol. 335: Edited by V. V. Didenko (Totowa, NJ, Humana Press Inc., 2006), pp. 71-81 (Year: 2006).*
Kim et al. (2007) Specific and sensitive detection of nucleic acids and RNases using gold nanoparticle-RNA-fluorescent dye conjugates. Chemical Communications, 42:4342-4344 (Year: 2007).*
RNaseAlert Lab Test Kit (Applied Biosystems, Fluorometric RNase Detection Assay, 2008, 12 pages) (Year: 2008).*
Koonin, et al.; "CRISPR-Cas: an adaptive immunity system in prokaryotes"; F1000 Biology Reports; vol. 1, No. 95, 6 pages (Dec. 9, 2009).
Makarova, et al.; "SnapShot: Class 2 CRISPR-Cas Systems"; Cell; vol. 168, 2 pages (Jan. 12, 2017).
Mohanraju, et al.; "Diverse evolutionary roots and mechanistic variations of the CRISPR-Cas systems"; Science; vol. 353, No. 6299, 14 pages (Aug. 5, 2016).
Chen, et al.; "CRISPR-Cas 12a target binding unleashes indiscriminate single-stranded DNase activity"; Science; vol. 360, pp. 436-439 (2018).
Liu, et al.; "Delivery strategies of the CRISPR-Cas9 gene-editing system for therapeutic applications"; Journal of Controlled Release; vol. 266, pp. 17-26 (2017).
Makarova, et al.; "An updated evolutionary classification of CRISPR-Cas systems"; Nat. Rev. Microbiol.; vol. 13, No. 11, pp. 722-736 (Nov. 2015).
Price, et al.; "Cas9-mediated targeting of viral RNA in eukaryotic cells"; PNAS; vol. 112, No. 19, pp. 6164-6169 (May 12, 2015).
Sampson, et al.; "A CRISPR/Cas system mediates bacterial innate immune evasion and virulence"; Nature; vol. 497, No. 7448; pp. 254-257 (May 9, 2013).
Wright, et al.; "Biology and Applications of CRISPR Systems: Harnessing Nature's Toolbox for Genome Engineering"; Cell; vol. 164, pp. 29-44 (2016).
Yamano, et al.; "Crystal Structure of Cpf1 in Complex with Guide RNA and Target DNA"; Cell; vol. 165, pp. 949-962 (2016).
Zetsche, et al.; "Cpf1 Is a Single RNA-Guided Endonuclease of a Class 2 CRISPR-Cas System"; Cell; vol. 163, pp. 759-771 (Oct. 22, 2015).
Koonin, et al.; "Origins and evolution of CRISPR-Cas systems"; Phil. Trans. R. Soc. B.; vol. 374, No. 1772, 6 pages (Mar. 25, 2019).
NCBI Accession No. KZX85786, May 2, 2016, 2 pages.
Hyun, et al., (2015) "Site-directed mutagenesis in *Arabidopsis thaliana* using dividing tissue-targeted RGEN of the CRISPR/Cas system to generate heritable null alleles" Planta; vol. 241, pp. 271-284.
Xie et al. (2013) " RNA-Guided Genome Editing in Plants Using a CRISPR-Cas System." Molecular Plant, vol. 6, No. 6 , pp. 1975-1983.
Anantharaman, et al.; "Thousands of microbial genomes shed light on interconnected biogeochemical processes in an aquifer system"; Nature Communications; vol. 7, No. 13210, 11 pages (Oct. 24, 2016).
Baker, et al.; "Enigmatic, ultrasmall, uncultivated Archaea"; PNAS; vol. 107, No. 19, pp. 8806-8811 (May 11, 2010).
Bautista, et al.; "Virus-Induced Dormancy in the Archaeon Sulfolobus islandicus"; mBio; vol. 6, No. 2, 8 pages (2015).
Burstein, et al.; "New CRISPR-Cas systems from uncultivated microbes"; Nature; vol. 542, No. 7640, pp. 237-241 (Feb. 9, 2017).
Choudhury, et al.; "CRISPR-dCas9 mediated TET1 targeting for selective DNA demethylation at BRCA1 promoter"; Oncotarget; vol. 7, No. 29, pp. 46545-46556 (2016).
Deltcheva, et al.; "CRISPR RNA maturation by trans-encoded small RNA and host factor RNase III"; Nature; vol. 471, pp. 1-19 (Mar. 31, 2011).
Fonfara, et al.; "Phylogeny of Cas9 determines functional exchangeability of dual-RNA and Cas9 among orthologous type II CRISPR-Cas systems"; Nucleic Acids Research; vol. 42, No. 4, pp. 2577-2590 (2014).
GenBank OHA03494.1 (hypothetical protein A3J58_03210 [Candidatus Sung bacteria bacterium RIFCSPH IGHO2_02_FULL_52_23], NCBI Reference Sequence, priority to Oct. 21, 2016, 2 pages) (Year: 2016).
Hooton et al. "The Bacteriophage Carrier State of Campylobacter jejuni Features Changes in Host Non-coding RNAs and the Acquisition of New Host-derived CRISPR Spacer Sequences," Frontiers in Microbiology; vol. 7, Article 355, pp. 1-8 (Mar. 23, 2016).
Karvelis, et al.; "PAM recognition by miniature CRISPR-Cas12f nucleases triggers programmable double-stranded DNA target cleavage"; Nucleic Acids Research; pp. 1-8 (2020).
Le Cong, et al.; "Multiplex Genome Engineering Using CRISPR/Cas Systems"; Science; vol. 339, pp. 819-823 (Feb. 15, 2013).
Liu, et al.; "CasX enzymes comprise a distinct family of RNA-guided genome editors"; Nature; vol. 566, pp. 23 pages (Feb. 14, 2019).
Ngo, et al.; "Computational Complexity, Protein Structure Prediction, and the Levinthal Paradox"; The Protein Folding Problem and Tertiary Structure Prediction; pp. 433 and 492-495 (1994).
OHA03494.1 (hypothetical protein A3J58_03210 [Candidatus Sung bacteria bacterium RIFCSPH IGHO2_02_FU LL_52_23], NCBI Reference Sequence, priority to Oct. 21, 2016, 2 pages) (Year: 2016).
Shmakov, et al.; "Diversity and evolution of class 2 CRISPR-Cas systems"; Nature Reviews Microbiology; vol. 15, pp. 169-182 (2017).
Yang, et al.; "New CRISPR-Cas systems discovered"; Cell Res.; vol. 27, pp. 313-314 (Feb. 21, 2017).
Harrington, et al.; "Programmed DNA destruction by miniature CRISPR-Cas14 enzymes"; Science; vol. 362, pp. 839-842 (Nov. 16, 2018).
Strauβ, et al.; "Zinc Fingers, TAL Effectors, or Cas9-Based DNA Binding Proteins: What's Best for Targeting Desired Genome Loci?"; Molecular Plant; vol. 6, No. 5, pp. 1384-1387 (Sep. 2013).
GenBank CRL33181.1; Hypothetical protein T1815_05231 [[Eubacterium] rectale], priority to Apr. 6, 2016, 2 pages (Year: 2016).
NCBI Reference Sequence: WP_021746003.1 (Sep. 24, 2013).
NCBI Reference Sequence: WP_021746774.1 (Sep. 24, 2013).
NCBI Reference Sequence: WP_021747205.1 (Sep. 24, 2013).
Gootenberg, et al.; "Multiplexed and portable nucleic acid detection platform with Cas13, Cas12a, and Csm6"; Science; vol. 360, pp. 439-444 (2018).

(56) References Cited

OTHER PUBLICATIONS

Makarova, et al.; "Evolutionary classification of CRISPR-Cas systems: a burst of class 2 and derived variants"; Nature Reviews Microbiology; vol. 18, pp. 67-83 (Feb. 2020).
O'Connell; "Molecular Mechanisms of RNA Targeting by Cas13-containing Type VI CRISPR-Cas Systems"; J Mol Biol; vol. 431, pp. 66-87 (2019).
Abudayyeh, et al.; "C2c2 is a single-component programmable RNA-guided RNA-targeting CRISPR effector"; Science; vol. 353, No. 6299, 23 pages (Aug. 5, 2016).
Abudayyeh, et al.; "C2c2 is a single-component programmable RNA-guided RNA-targeting CRISPR effector; Supplementary Information"; Science; vol. 353, vol. 6299, 31 pages (Aug. 5, 2016).
Abudayyeh, et al.; "RNA targeting with CRISPR-Cas13"; Nature; vol. 550, 18 pages (Oct. 12, 2017).
Ambion; "RnaseAlert Lab Test Kit v2, User Guide"; 12 pages (Mar. 1, 2013).
Applied Biosystems/Ambion; "RNaseAlert Lab Test Kit"; 12 pages (2008).
Armitage, et al.; "Hairpin-Forming Peptide Nucleic Acid Oligomers"; Biochemistry; vol. 37, pp. 9417-9425 (1998).
Barrangou, et al.; "Expanding the CRISPR Toolbox: Targeting RNA with Cas13b"; Molecular Cell; vol. 65, No. 4, pp. 582-584 (Feb. 16, 2017).
Chylinski, et al.; "Classification and evolution of type II CRISPR-Cas systems"; Nucleic Acids Research; vol. 42, No. 10, pp. 6091-6105 (2014).
Cong, et al.; "Multiplex Genome Engineering Using CRISPR/Cas Systems"; Science; vol. 339, No. 6121, pp. 819-823 (Feb. 15, 2013).
Cox, et al.; "RNA editing with CRISPR-Cas13"; Science; vol. 358, No. 6366, 15 pages (Nov. 24, 2017).
CRZ3554.1 (hypothetical protein HHT344_2368 [Herbinix hemicellulosilytica], Gen Bank Accession sequence, priority to Jul. 24, 2015, 1 page) (Year: 2015).
East-Seletsky, et al.; "RNA Targeting by Functionally Orthogonal Type VI-A CRISPR-Cas Enzymes"; Molecular Cell; vol. 66, pp. 373-383 (May 4, 2017).
East-Seletsky, et al.; "Two distinct Rnase activities of CRISPR-C2c2 enable guide-RNA processing and RNA detection"; Nature; vol. 538, Issue 7624, pp. 270-273 (Oct. 13, 2016).
GenBank CRZ35554 1; "Hypothetical protein HHT355_2368 [Herbinix hemicellulosilytica]"; 1 page (Oct. 11, 2018).
Gootenberg, et al.; "Nucleic acid detection with CRISPR-Cas13a/C2c2"; Science; 9 pages (Apr. 13, 2017).
Hale, et al.; "RNA-Guided RNA Cleavage by a CRISPR RNA-Cas Protein Complex"; Cell; vol. 139, No. 5, pp. 945-956 (Nov. 25, 2009).
Hale, et al.; "Target RNA capture and cleavage by the Cmr type III-B CRISPR-Cas effector complex"; Genes & Development; vol. 28, No. 21, pp. 2432-2443 (Nov. 1, 2014).
Kelemen, et al.; "Hypersensitive substrate for ribonucleases"; Nucleic Acids Research; vol. 27, No. 18, pp. 3696-3701 (1999).
Kim, et al.; "Specific and sensitive detection of nucleic acids and RNases using gold nanoparticle-RNA-fluorescent dye conjugates"; Chemical Communications; vol. 14, No. 42, pp. 4342-4344 (Sep. 19, 2007).
Knott, et al.; "Guide-bound structures of an RNA-targeting A-cleaving CRISPR-Cas13a enzyme"; Nature Structural & Molecular Biology; vol. 24, No. 10, 13 pages (Oct. 2017).
Kodak (Gel Logic 100 System User's Guide, 2005, 98 pages) (Year: 2005).
Li, et al.; "Using molecular beacons as a sensitive fluorescence assay for enzymatic cleavage of single-stranded DNA"; Nucleic Acids Research; vol. 28, No. 11, 6 pages (2000).
Liu, et al.; "The Molecular Architecture for RNA-Guided RNA Cleavage by Cas13a"; Cell; vol. 170, pp. 714-126 (Aug. 10, 2017).
Liu, et al.; "Two Distant Catalytic Sites Are Responsible for C2c2 RNase Activities"; Cell; vol. 168, pp. 121-134 (Jan. 12, 2017).
Sato, et al.; "Highly Sensitive Nuclease Assays Based on Chemically Modified DNA or RNA"; Sensors; vol. 14, No. 7, pp. 12437-12450 (2014).
Shmakov, et al.; "Discovery and functional characterization of diverse Class 2 CRISPR-Cas systems"; Mol. Cell.; vol. 60, No. 3, pp. 385-397 (Nov. 5, 2015).
Smargon, et al.; "Cas 13b is a Type VI-B CRISPR-associated RNA-Guided RNAse differentially regulated by accessory proteins Csx27 and Csx28"; Molecular Cell; vol. 65, No. 4, pp. 618-630 (Feb. 16, 2017).
Stephen Floor; "CV"; 6 pages (Jun. 11, 2018).
Stephen Floor; "Tweets cited in third party observation filed on Oct. 15, 2018"; 1 page (date of tweets are May 21, 2016).
Third Party Observations filed on Oct. 15, 2018 in UK patent application No. GB 1804822.3 (18 pages).
Yang, et al.; "Using Molecular Beacons for Sensitive Fluorescence Assays of the Enzymatic Cleavage of Nucleic Acids"; Methods in Molecular Biology; vol. 335, pp. 71-81 (2006).
Zhang, et al.; "Design of a Molecular Beacon DNA Probe with Two Fluorophores"; Angew. Chem.; vol. 113, No. 2, pp. 416-419 (2001).
CLUSTL; "Omega Multiple Sequence Alignment. https://www.ebi.ac.uk/Tools/msa/clustalo/" [Retrieved from internet Feb. 2, 2022]. Alignment and Percent identity matrix. (Year: 2022).
NCBI Reference Sequence: WP_012985477.1 (May 18, 2013).
NCBI Reference Sequence: WP_015770004.1 (May 20, 2013).
NCBI Reference Sequence: WP_023911507.1 (Oct. 23, 2013).
NCBI Reference Sequence: WP_034560163.1 (Oct. 22, 2015).
Stella, et al.; "Class 2 CRISPR-Cas RNA-guided endonucleases: Swiss Army knives of genome editing"; Nature Structural & Molecular Biology; vol. 24, No. 11, pp. 882-892 (Nov. 2017).

\* cited by examiner

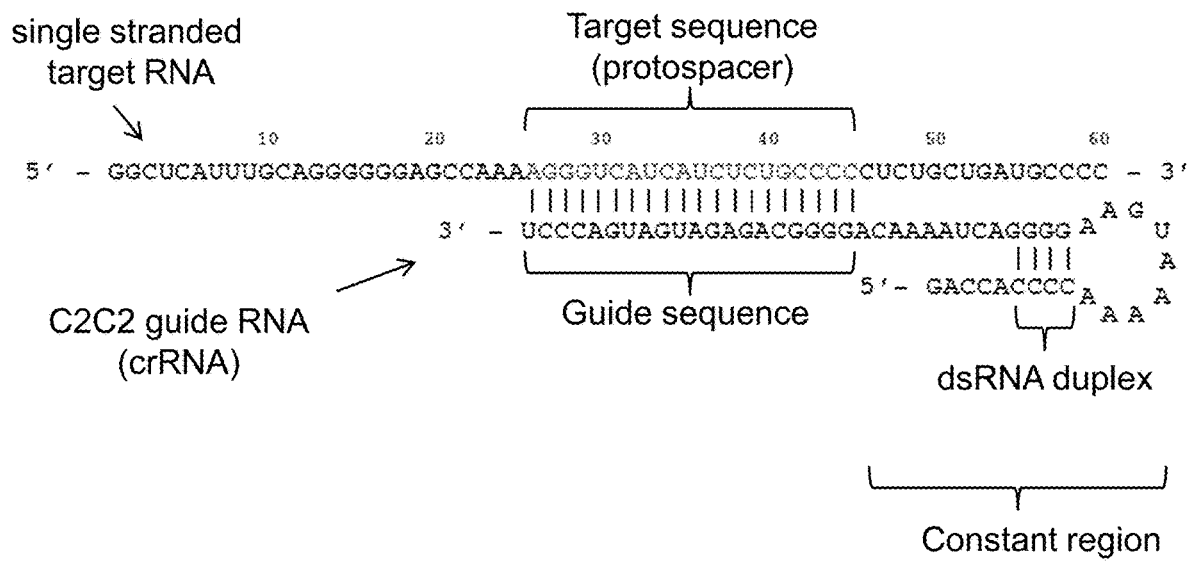

FIG. 8A

>Listeria seeligeri (WP_012985477.1)

MWISIKTLIHHLGVLFFCDYMYNRREKKIIEVKTMRITKVEVDRKKVLISRDKNGGKLVY
ENEMQDNTEQIMHHKKSSFYKSVVNKTICRPEQKQMKKLVHGLLQENSQEKIKVSDVTKL
NISNFLNHRFKKSLYYFPENSPDKSEEYRIEINLSQLLEDSLKKQQGTFICWESFSKDME
LYINWAENYISSKTKLIKKSIRNNRIQSTESRSGQLMDRYMKDILNKNKPFDIQSVSEKY
QLEKLTSALKATFKEAKKNDKEINYKLKSTLQNHERQIEELKENSELNQFNIEIRKHLE
TYFPIKKTNRKVGDIRNLEIGEIQKIVNHRLKNKIVQRILQEGKLASYEIESTVNSNSLQ
KIKIEEAFALKFINACLFASNNLRNMVYPVCKKDILMIGEFKNSFKEIKHKKFIRQWSQF
FSQEITVDDIELASWGLRGAIAPIRNEIIHLKKHSWKKFFNNPTFKVKKSKIINGKTKDV
TSEFLYKETLFKDYFYSELDSVPELIINKMESSKILDYSSDQLNQVFTIPNFELSLLTS
AVPFAPSFKRVYLKGFDYQNQDEAQPDYNLKLNIYNEKAFNSEAFQAQYSLFKMVYQVF
LPQFTTNNDLFKSSVDFILTLNKERKGYAKAFQDIRKMNKDEKPSEYMSYIQSQLMLYQK
KQEEKEKINHFEKFINQVFIKGFNSFIEKNRLTYICHPTKNTVPENDNIEIPFHTDMDDS
NIAFWLMCKLLDAKQLSELRNEMIKFSCSLQSTEEISTFTKAREVIGLALLNGEKGCNDW
KELFDDKEAWKKNMSLYVSEELLQSLPYTQEDGQTPVINRSIDLVKKYGTETILEKLFSS
SDDYKVSAKDIAKLHEYDVTEKIAQQESLHKQWIEKPGLARDSAWTKKYQNVINDISNYQ
WAKTKVELTQVRHLHQLTIDLLSRLAGYMSIADRDFQFSSNYILERENSEYRVTSWILLS
ENKNKNKNYNDYELYNLKNASIKVSSKNDPQLKVDLKQLRLTLEYLELFDNRLKEKRNNIS
HFNYLNGQLGNSIIELFDDARDVLSYDRKLKNAVSKSLKEILSSHGMEVTFKPLYQTNHH
LKIDKLQPKKIHHLGEKSTVSSNQVSNEYCQLVRTLLTMK    (SEQ ID NO: 1)

FIG. 8B

>Leptotrichia buccalis (WP_015770004.1)
MKVTKVGGISHKKYTSEGRLVKSESEENRTDERLSALLNMRLDMYIKNPSSTETKENQKR
IGKLKFFSNKMVYLKDNTLSLKNGKKENIDREYSETDILESDVRDKKNFAVLKKIYLNE
NVNSEELEVFRNDIKKKLNINSLKYSFEKNKANYQKINENNIEKVEGKSKRNIIYDYYR
ESAKRDAYVSNVKEAFDKLYKEEDIAKLVLEIENLTKLEKYKIREFYHEIIGRKNDKENF
AKIIYEEIQNVNNMKELIEKVPDMSELKKSQVFYKYLDKEELNDKNIKYAFCHFVEIEM
SQLLKNYVYKRLSNISNDKIKRIFEYQNLKKLIENKLLNKLDTYVRNCGKYNYYLQDGEI
ATSDFIARNRQNEAFLRNIIGVSSVAYFSLRNILETENENDITGRMRGKTVKNNKGEEKY
VSGEVDKIYNENKKNEVKENLKMFYSYDFNMDNKNEIEDFFANIDEAISSIRHGIVHFNL
ELEGKDIFAFKNIAPSEISKKMFQNEINEKKLKLKIFRQLNSANVFRYLEKYKILNYLKR
TREEFVNKNIPFVPSFTKLYSRIDDLKNSLGIYWKTPKTNDDNKTKEIIDAQIYLLKNIY
YGEFLNYFMSNNGNFFEISKEIIELNKNDKRNLKTGFYKLQKFEDIQEKIPKEYLANIQS
LYMINAGNQDEEEKDTYIDFIQKIFLKGFMTYLANNGRLSLIYIGSDEETNTSLAEKKQE
FDKFLKKYEQNNNIKIPYEINEFLREIKLGNIIKYTERLNMFYLILKLLNHKELTNLKGS
LEKYQSANKEEAFSDQLELINLINLDNNRVTEDFELEADEIGKFLDFNGNKVKDNKELKK
FDTNKIYFDGENIIKHRAFYNIKKYGMINLLEKIADKAGYKISIEELKKYSNKKNEIEKN
HKMQENLHRKYARPRKDEKFTDEDYESYKQAIENIEEYTHLKNKVEFNELNLLQGLLLRI
LHRLVGYTSIWERDLRFRLKGEFPENQYIEEIFNFENKKNVKYKGGQIVEKYIKFYKELH
QNDEVKINKYSSANIKVLKQEKKDLYIAHFNYIPHAEISLLEVLENLRKLLSYDRK
LKNAVMKSVVDILKEYGFVATFKIGADKKIGIQTLESEKIVHLKNLKKKLMTDRNSEEL
CKLVKIMFEYKMEEKKSEN (SEQ ID NO: 2)

FIG. 8C

> Leptotrichia shahii (WP_018451595.1)
MGNLFGHKRWYEVRDKKDFKIKRKVKVKRNYDGNKYILNINENNNKEKIDNNKFIRKYIN
YKKNDNILKEFTRKFHAGNILFKLKGKEGIRIENNDFLETEEVVLYIEAYGKSEKLKA
LGITKKKIIDEAIRQGITKDDKKIEIKRQENEEEIEIDIRDEYTNKTLNDCSIILRIIEN
DELETKKSIYEIFKNINMSLYKIIEKIIENETEKVFENRYYEEHLREKLLKDDKIDVLT
NFMEIREKIKSNLEILGFVKFYLNVGGDKKKSKNKKMLVEKILNINVDLTVEDIADFVIK
ELEFWNITKRIEKVKKVNNEFLEKRRNRTYIKSYVLLDKHEKFKIERENKKDKIVKFFVE
NIKNNSIKEKIEKILAEFKIDELIKKLEKELKKGNCDTEIFGIFKKHYKVNFDSKKFSKK
SDEEKELYKIIYRYLKGRIEKILVNEQKVRLKKMEKIEIEKILNESILSEKILKRVKQYT
LEHIMYLGKLRHNDIDMTTVNTDDFSRLHAKEELDLELITFFASTNMELNKIFSRENINN
DENIDFFGGDREKNYVLDKKILNSKIKIIRDLDFIDNKNNITNNFIRKFTKIGTNERNRI
LHAISKERDLQGTQDDYNKVINIIQNLKISDEEVSKALNLDVVFKDKKNITTKINDIKIS
EENNNDIKYLPSFSKVLPEILNLYRNNPKNEPFDTIETEKIVLNALIYVNKELYKKLILE
DDLEENESKNIFLQELKKTLGNIDEIDENIIENYYKNAQISASKGNNKAIKKYQKKVIEC
YIGYLRKNYEELFDFSDFKMNIQEIKKQIKDINDNKTYERITVKTSDKTIVINDDFEYII
SIFALLNSNAVINKIRNRFFATSVWLNTSEYQNIIDILDEIMQLNTLRNECITENWNLNL
EEFIQKMKEIEKDFDDFKIQTKKEIFNNYYEDIKNNILTEFKDDINGCDVLEKKLEKIVI
FDDETKFEIDKKSNILQDEQRKLSNINKKDLKKKVDQYIKDKDQEIKSKILCRIIFNSDF
LKKYKKEIDNLIEDMESENENKFQEIYPKERKNELYIYKKNLFLNIGNPNFDKIYGLIS
NDIKMADAKFLFNIDGKNIRKNKISEIDAILKNLNDKLNGYSKEYKEKYIKKLKENDDFF
AKNIQNKNYKSFEKDYNRVSEYKKIRDLVEFNYLNKIESYLIDINWKLAIQMARFERDMH
YIVNGLRELGIIKLSGYNTGISRAYPKRNGSDGFYTTAYKFFDEESYKKFEKICYGFG
IDLSENSEINKPENESIRNYISHFYIVRNPFADYSIAEQIDRVSNLLSYSTRYNNSTYAS
VFEVFKKDVNLDYDELKKKFKLIGNNDILERLMKPKKVSVLELESYNSDYIKNLIIELLT
KIENTNDTL (SEQ ID NO: 3)

FIG. 8D

\> Rhodobacter capsulatus (R121) (ETD76934.1) (U717_11515)
MQIGKVQGRTISEFGDPAGGLKRKISTDGKNRKELPAHLSSDPKALIGQWISGIDKIYRK
PDSRKSDGKAIHSPTPSKMQFDARDDLGEAFWKLVSEAGLAQDSDYDQFKRRLHPYGDKF
QPADSGAKLKFEADPPEPQAFHGRWYGAMSKRGNDAKELAAALYEHLHVDEKRIDGQPKR
NPKTDKFAPGLVVARALGIESSVLPRGMARLARNWGEEEIQTYFVVDVAASVKEVAKAAV
SAAQAFDPPRQVSGRSLSPKVGFALAEHLERVTGSKRCSFDPAAGPSVLALHDEVKKTYK
RLCARGKNAARAFPADKTELLALMRHTHENRVRNQMVRMGRVSEYRGQQAGDLAQSHYWT
SAGQTEIKESEIFVRLWVGAFALAGRSMKAWIDPMGKIVNTEKNDRDLTAAVNIRQVISN
KEMVAEAMARRGIYFGETPELDRLGAEGNEGFVFALLRYLRGCRNQTFHLGARAGFLKEI
RKELEKTRWGKAKEAEHVVLTDKTVAAIRAIIDNDAKALGARLLADLSGAFVAHYASKEH
FSTLYSEIVKAVKDAPEVSSGLPRLKLLLKRADGVRGYVHGLRDTRKHAFATKLPPPAP
RELDDPATKARYIALLRLYDGPFRAYASGITGTALAGPAARAKEAATALAQSVNVTKAYS
DVMEGRSSRLRPPNDGETLREYLSALTGETATEFRVQIGYESDSENARKQAEFIENYRRD
MLAFMFEDYIRAKGFDWILKIEPGATAMTRAPVLPEPIDTRGQYEHWQAALYLVMHFVPA
SDVSNLLHQLRKWEALQGKYELVQDGDATDQAADARREALDLVKRFRDVLVLFLKTGEARF
EGRAAPFDLKPFRALFANPATFDRLFMATPTTARPAEDDPEGDGASEPELRVARTLRGLR
QIARYNHMAVLSDLFAKHKVRDEEVARLAEIEDETQEKSQIVAAQELRTDLHDKVMKCHP
KTISPEERQSYAAAIKTIEEHRFLVGRVLGDHLRLHRLMMDVIGRLIDYAGAYERDTGT
FLINASKQLGAGADWAVTIAGAANTDARTQTRKDLAHFNVLDRADGTPDLTALVNRAREM
MAYDRKRKNAVPRSILDMLARLGLTIKWQMKDHLLQDATITQAAIKHLDKVRLTVGGPAA
VTEARFSQDYLQMVAAVFNGSVQNPKPRRRDGDAWHKPPKPATAQSQPDQKPPNKAPSA
GSRLPPPQVGEVYEGVVVKVIDTGSLGFLAVEGVAGNIGLHISRLRRIREDAIIVGRRYR
FRVEIYVPPKSNTSKLNAADLVRID (SEQ ID NO: 4)

FIG. 8E

>WP_034560163.1 WP_034560163.1 hypothetical protein [Carnobacterium gallinarum]
MRITKVKIKLDNKLYQVTMQKEEKYGTLKLNEESRKSTAEILRLKKASFNKSFHSKTINS
QKENKNATIKKNGDYISQIFEKLVGVDTNKNIRKPKMSLTDLKDLPKKDLALFIKRKFKN
DDIVEIKNLDLISLFYNALQKVPGEHFTDESWADFCQEMMPYREYKNKFIERKIILLANS
IEQNKGFSINPETFSKRKRVLHQWAIEVQERGDFSILDEKLSKLAEIYNFKKMCKRVQDE
LNDLEKSMKKGKNPEKEKEAYKKQKNFKIKTIWKDYPYKTHIGLIEKIKENEELNQFNIE
IGKYFEHYFPIKKERCTEDEPYYLNSETIATTVNYQLKNALISYLMQIGKYKQFGLENQV
LDSKKLQEIGIYEGFQTKFMDACVFATSSLKNIIEPMRSGDILGKREFKEAIATSSFVNY
HHFFPYFPFELKGMKDRESELIPFGEQTEAKQMQNIWALRGSVQQIRNEIFHSFDKNQKF
NLPQLDKSNEFFDASENSTGKSQSYIETDYKFLFEAEKNQLEQFFIERIKSSGALEYYPL
KSLEKLFAKKEMKFSLGSQVVAFAPSYKKLVKKGHSYQTATEGTANYLGLSYYNRYELKE
ESFQAQYYLLKLIYQYVFLPNFSQGNSPAFRETVKAILRINKDEARKKMKKNKFLRKYA
FEQVREMEFKETPDQYMSYLQSEMREEKVRKAEKNDKGFEKNITMNFEKLLMQIFVKGFD
VFLTTFAGKELLLSSEEKVIKETEISLSKKINEREKTLKASIQVEHQLVATNSAISYWLF
CKLLDSRHLNELRNEMIKFKQSRIKFNHTQHAELIQNLLPIVELTILSNDYDEKNDSQNV
DVSAYFEDKSLYETAPYVQTDDRTRVSFRPILKLEKYHTKSLIEALLKDNPQFRVAATDI
QEWMHKREEIGELVEKRKNLHTEWAEGQQTLGAEKREEYRDYCKKIDRFNWKANKVTLTY
LSQLHYLITDLLGRMVGFSALFERDLVYFSRSFSELGGETYHISDYKNLSGVLRLNAEVK
PIKIKNIKVIDNEENPYKGNEPEVKPFLDRLHAYLENVIGIKAVHGKIRNQTAHLSVLQL
ELSMIESMNNLRDLMAYDRKLKNAVTKSMIKILDKHGMILKLKIDENHKNFEIESLIPKE
IIHLKDKAIKTNQVSEEYCQLVLALLTTNPGNQLN   (SEQ ID NO: 5)

FIG. 8F

>CRZ35554.1 Herbinix hemicellulosilytica genome assembly TUM3/55, contig 02_T3/55T_contig26, whole genome shotgun sequence MKLTRRRISGNSVDQKITAAFYRDMSQGLLYDSEDNDCTDKVIESMDFERSWRGRILKN
GEDDKNPFYMFVKGLVGSNDKIVCEPIDVDSDPDNLDILINKNLTGFGRNLKAPDSNDTL
ENLIRKIQAGIPEEEVLPELKKIKEMIQKDIVNRKEQLLKSIKNNRIPFSLEGSKLVPST
KKMKWLFKLIDVPNKTFNEKMLEKYWEIYDYDKLKANITNRLDKTDKKARSISRAVSEEL
REYHKNLRTNYNRFVSGDRPAAGLDNGGSAKYNPDKEEFLLFLKEVEQYFKKYFPVKSKH
SNKSKDKSLVDKYKNYCSYKVKKEVNRSIINQLVAGLIQQGKLLYFYYNDTWQEDFLN
SYGLSYIQVEEAFKKSVMTSLSWGINRLTSFFIDDSNTVKFDDITTKKAKEAIESNYFNK
LRTCSRMQDHFKEKLAFFYPVYVKDKKDRPDDDIENLIVLVKNAIESVSYLRNRTFHFKE
SSLELLKELDDKNSGQNKIDYSVAAEFIKRDIENLYDVFREQIRSLGIAEYYKADMISD
CFKTCGLEFALYSPKNSLMPAFKNVYKRGANLNKAYIRDKGPKETGDQGQNSYKALEEYR
ELTWYIEVKNNDQSYNAYKNLLQLIYHAFLPEVRENEALITDFINRTKEWNRKETEERL
NTKNNKKHKNFDENDDITVNTYRYESIPDYQGESLDDYLKVLQRKQMARAKEVNEKEEGN
NNYIQFIRDVVVWAFGAYLENKLKNYKNELQPPLSKENIGINDTLIKELFPEEKVKSPFNI
KCRFSISTFIDNKGKSTDNTSAEAVKTDGKEDEKDKKNIKRKDLLCFYLFLRLLDENEIC
KLQHQFIKYRCSLKERRFPGNRTKLEKETELLAELEELMELVRFTMPSIPEISAKAESGY
DTMIKKYFKDFIEKKVFKNPKTSNLYYHSDSKTPVTRKYMALLMRSAPLHLYKDIFKGYY
LITKKECLEYIKLSNIIKDYQNSLNELHEQLERIKLKSEKQNGKDSLYLDKKDFYKVKEY
VENLEQVARYKHLQHKINFESLYRIFRIHVDIAARMVGYTQDWERDMHFLFKALVYNGVL
EERRFEAIFNNNDDNNDGRIVKKIQNNLNNKNRELVSMLCWNKKLNKNEFGAIIWKRNPI
AHLNHFTQTEQNSKSSLESLINSLRILLAYDRKRQNAVTKTINDLLINDYHIRIKWEGRV
DEGQIYFNIKEKEDIENEPIIHLKHLHKKDCYIYKNSYMFDKQKEWICNGIKEEVYDKSI
LKCIGNLFKFDYEDKNKSSANPKHT (SEQ ID NO: 6)

FIG. 9A
FIG. 9C
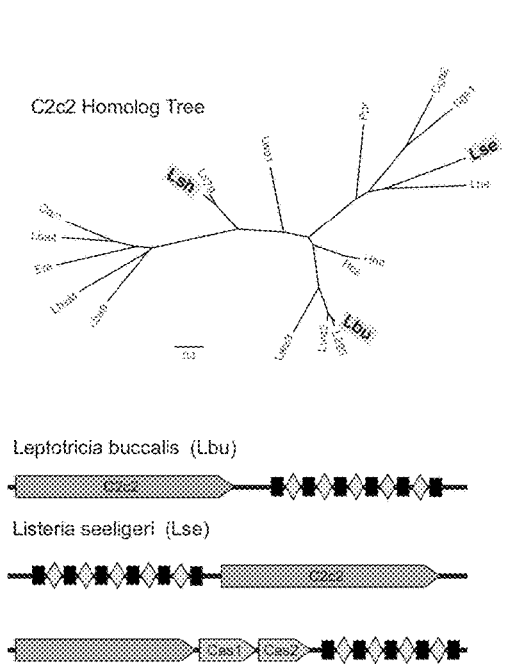
FIG. 9B
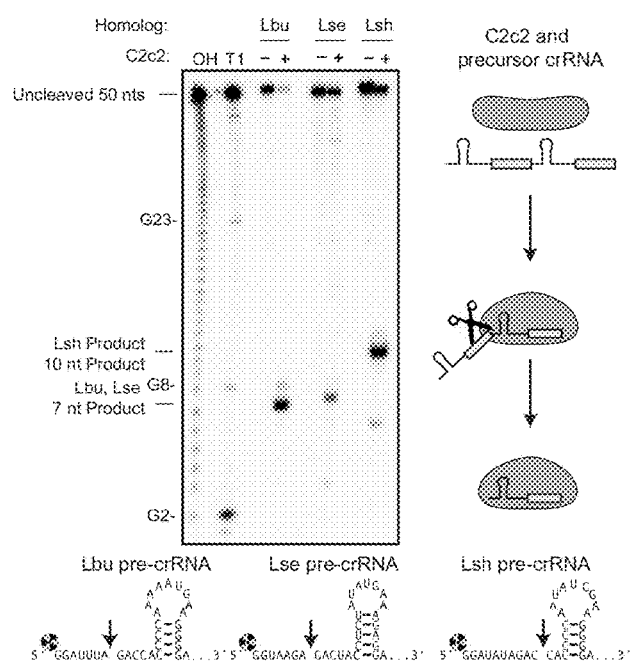

FIG. 10A
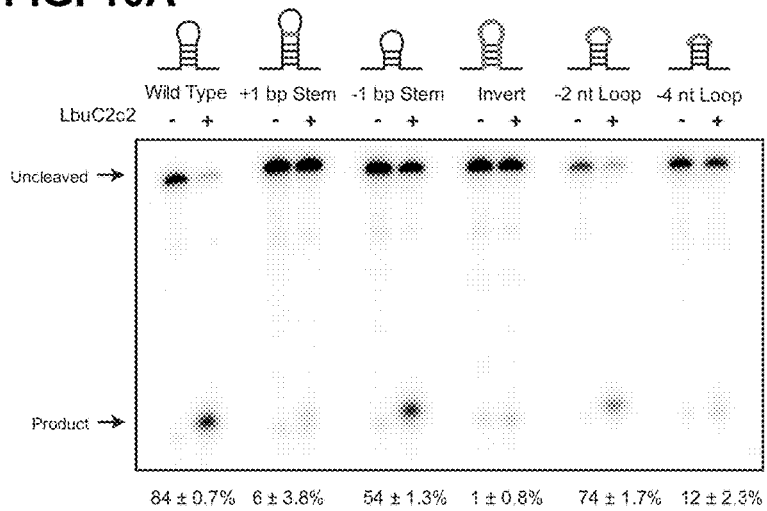
FIG. 10C
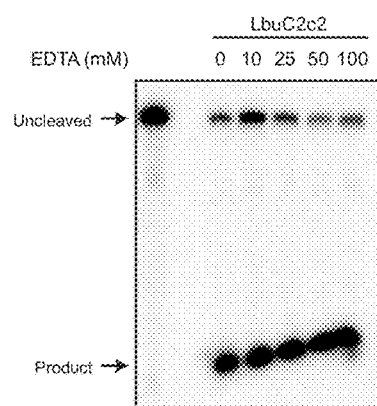
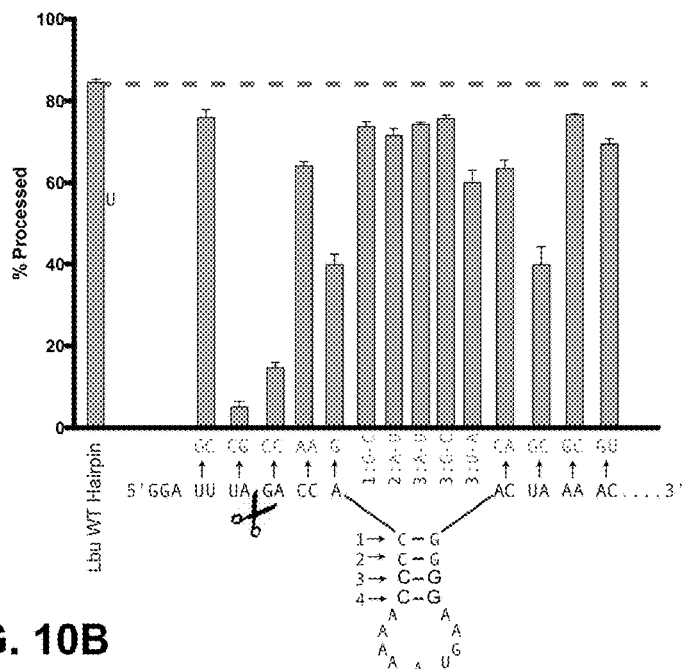
FIG. 10B

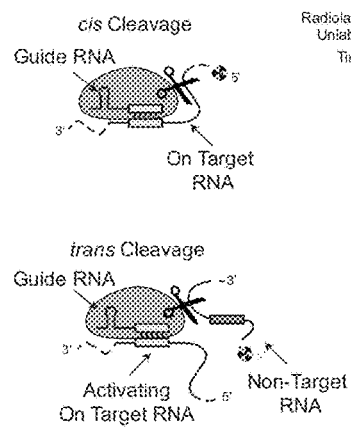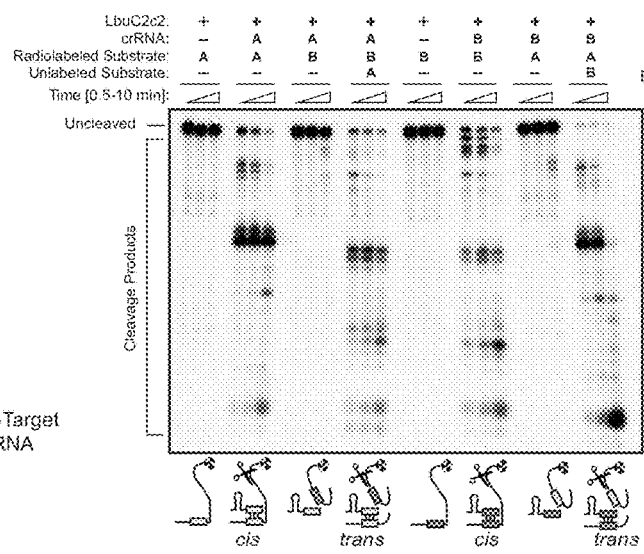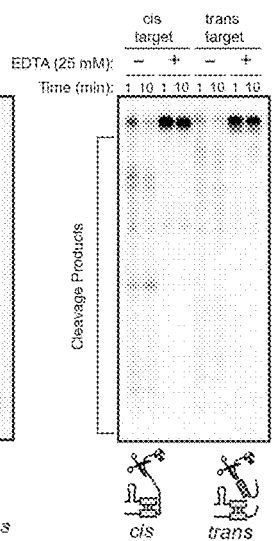
FIG. 11A  FIG. 11B  FIG. 11C

FIG. 12A
FIG. 12B
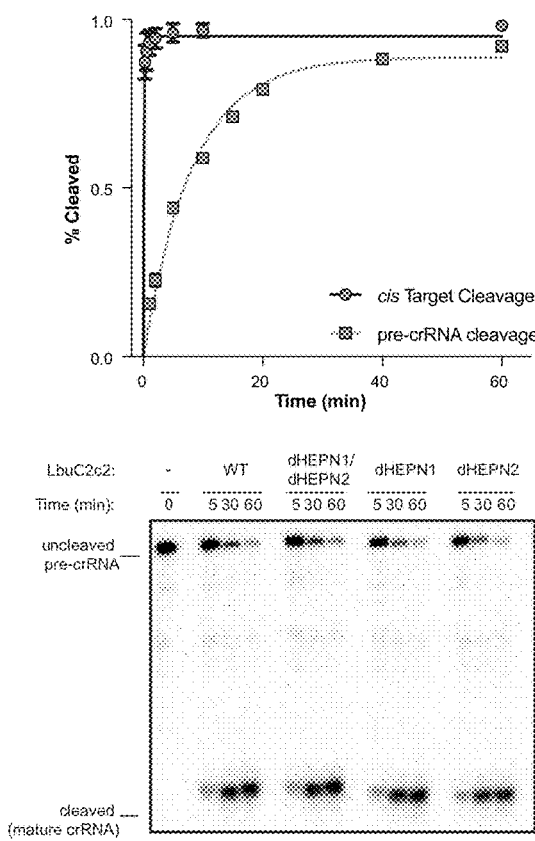
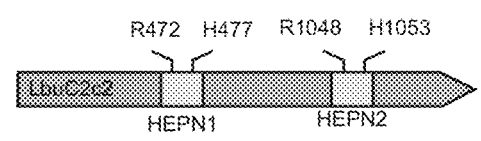
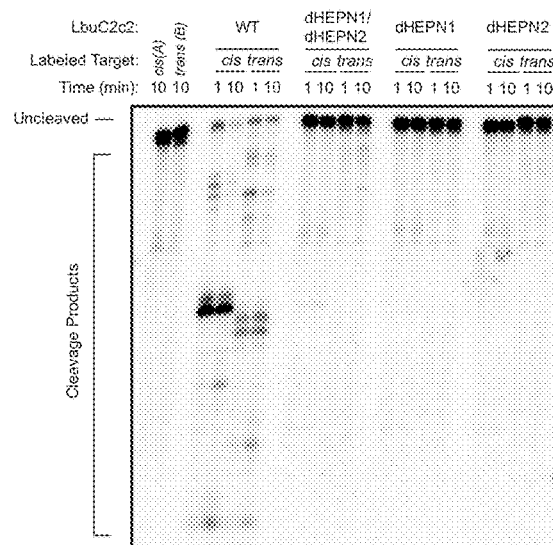
FIG. 12C
FIG. 12D

FIG. 14

Table 2: DNA oligonucleotides used in this study

| Name | Sequence |
|---|---|
| T7_forward_SCK337 | 5'-TAATACGACTCACTATAGG-3' |
| T7_forward_long_AES428 | 5'-CCAAGTAATACGACTCACTATAGG-3' |
| Lbu_R1048A_AES441 | 5'-TAATTAGCAATATAAAGGTCCTTCTTTTCTTGC-3' |
| Lbu_H1053A_AES442 | 5'-CATCGCCGCATTCAATTATATTCCTCACGCCG-3' |
| Lbu_R472A_AES443 | 5'-CCGTGAGCGATGGAAGAAATCGCCTCGTCG-3' |
| Lbu_H477A_AES444 | 5'-TATTGTCGCCTTCAACTTGGAATTAGAAGGTAAGGA-3' |

FIG. 15
Table 3: RNAs used in this study

| Name | Sequence[a] | Used in |
|---|---|---|
| Lbu_pre-crRNA_A_SCK314 | 5'- GGAUUUAGACCACCCCAAAAAUGAAGGGGACUAAAACAGGGGCAGAGAUGAUGACCCU -3' | FIG. 9C, 10A-10C, 12A, C, 16 |
| Lse_pre-crRNA_B_AES484 | 5'- GGUAAGAGACUACCUCUAUAUGAAAGAGGACUAAAACCAAACAUGAUCUGGGUCAUC -3' | FIG. 9C, 16 |
| Lsh_pre-crRNA_A_SCK339 | 5'- GGAUUUAGACCACCCCAAUAUCGAAGGGGACUAAAACAGGGGCAGAGAUGAUGACCCU -3' | FIG. 9C, 16 |
| Lbu_pre-crRNA_invert_SCK321 | 5'- GGAUUUAGACCAGGGGAAGUAAAAACCCCACUAAAACAGGGGCAGAGAUGAUGACCCU -3' | FIG. 10A |
| Lbu_pre-crRNA_5stem_SCK331 | 5'- GGAUUUAGACCACCCCAAAAAUGAAGGGGACUAAAACAGGGGCAGAGAUGAUGACCCU -3' | FIG. 10A |
| Lbu_pre-crRNA_7bubble_SCK334 | 5'- GGAUUUAGACCACCCCAUGAAGGGGACUAAAACAGGGGCAGAGAUGAUGACCCU -3' | FIG. 10A |
| Lbu_pre-crRNA_5bubble_SCK335 | 5'- GGAUUUAGACCACCCCAUGAAGGGGACUAAAACAGGGGCAGAGAUGAUGACCCU -3' | FIG. 10A |
| Lbu_pre-crRNA_3stem_SCK342 | 5'- GGAUUUAGACCACCCCAAAAAUGAAGGGCACUAAAACAGGGGCAGAGAUGAUGACCCU -3' | FIG. 10A |
| Lbu_pre-cr_5'_mut1_AES497 | 5'- GGCGUUAGACCACCCCAAAAAUGAAGGGGACUAAAACAGGGGCAGAGAUGAUGACCCU -3' | FIG. 10B, 17 |
| Lbu_pre-cr_5'_mut2_AES496 | 5'- GGAGCUAGACCACCCCAAAAAUGAAGGGGACUAAAACAGGGGCAGAGAUGAUGACCCU -3' | FIG. 10B, 17 |
| Lbu_pre-cr_5'_mut3_AES495 | 5'- GGAUCAGACCACCCCAAAAAUGAAGGGGACUAAAACAGGGGCAGAGAUGAUGACCCU -3' | FIG. 10B, 17 |
| Lbu_pre-cr_5'_mut4_AES477 | 5'- GGAUUCGACCACCCCAAAAAUGAAGGGGACUAAAACAGGGGCAGAGAUGAUGACCCU -3' | FIG. 10B, 17 |
| Lbu_pre-cr_5'_mut5_AES482 | 5'- GGAUUUACCCCACCCCAAAAAUGAAGGGGACUAAAACAGGGGCAGAGAUGAUGACCCU -3' | FIG. 10B, 17 |
| Lbu_pre-cr_5'_mut6_AES478 | 5'- GGAUUUAAUCCACCCCAAAAAUGAAGGGGACUAAAACAGGGGCAGAGAUGAUGACCCU -3' | FIG. 10B, 17 |
| Lbu_pre-cr_5'_mut7_AES480 | 5'- GGAUUUAGAAAACCCCAAAAAUGAAGGGGACUAAAACAGGGGCAGAGAUGAUGACCCU -3' | FIG. 10B, 17 |
| Lbu_pre-cr_5'_mut8_AES498 | 5'- GGAUUUAGACCGCCCCAAAAAUGAAGGGGACUAAAACAGGGGCAGAGAUGAUGACCCU -3' | FIG. 10B, 17 |
| Lbu_pre_stem_mut1_AES502 | 5'- GGAUUUAGACCAGCCCAAAAAUGAAGGGCACUAAAACAGGGGCAGAGAUGAUGACCCU -3' | FIG. 10B, 17 |
| Lbu_pre_stem_mut2_AES501 | 5'- GGAUUUAGACCACCGCAAAAAUGAAGGCGACUAAAACAGGGGCAGAGAUGAUGACCCU -3' | FIG. 10B, 17 |
| Lbu_pre_stem_mut3_AES500 | 5'- GGAUUUAGACCACACCACAAAAAUGAAGUGGACUAAAACAGGGGCAGAGAUGAUGACCCU -3' | FIG. 10B, 17 |
| Lbu_pre_stem_mut4_AES499 | 5'- GGAUUUAGACCACCCCAAAAAUGAAGGGGCUAAAACAGGGGCAGAGAUGAUGACCCU -3' | FIG. 10B, 17 |
| Lbu_pre_stem_mut5_AES504 | 5'- GGAUUUAGACCACUCCAAAAAUGAAGGAGACUAAAACAGGGGCAGAGAUGAUGACCCU -3' | FIG. 10B, 17 |
| Lbu_pre_cr_3'_mut1_AES505 | 5'- GGAUUUAGACCACCCCAAAAAUGAAGGGGCAUAAAACAGGGGCAGAGAUGAUGACCCU -3' | FIG. 10B, 17 |
| Lbu_pre_cr_3'_mut2_AES506 | 5'- GGAUUUAGACCACCCCAAAAAUGAAGGGGACGAAAACAGGGGCAGAGAUGAUGACCCU -3' | FIG. 10B, 17 |
| Lbu_pre_cr_3'_mut3_AES507 | 5'- GGAUUUAGACCACCCCAAAAAUGAAGGGGACUAGCACAGGGGCAGAGAUGAUGACCCU -3' | FIG. 10B, 17 |
| Lbu_pre_cr_3'_mut4_AES508 | 5'- GGAUUUAGACCACCCCAAAAAUGAAGGGGACUAAAGUAGGGCAGAGAUGAUGACCCU -3' | FIG. 10B, 17 |
| crLbu_A_GG_AES432 | 5'- GGCCACCCCAAAAAUGAAGGGGACUAAAACAGGGGCAGAGAUGAUGACCCU -3' | FIG. 11, 12, 18-20 |
| crLbu_B_AES451 | 5'- GGCCACCCCAAAAAUGAAGGGGACUAAAACACAAACAUGAUCUGGGUCAUC -3' | FIG. 11 |
| A.0_target_AES450 | 5'- GGCACACCCGCAGGGGGAGCAAAGGGUCAUCAUCUCUGCCCCUCACAGCAGAAGCCCC -3' | FIG. 11, 12, 20 |
| B_target_AES452 | 5'- GGGAACCCCAAGGCCAACCGCGAGAAGAUGACCCAGAUCAUGUUUGAGACUUCAACACCCC -3' | FIG. 11, 12, 20 |
| crLbu_Lambda2_AES453 | 5'- GGCCACCCCAAAAAUGAAGGGGACUAAAACAGUGAUAAGUGGAAUGCCAUG -3' | FIG. 13B-13C |
| crLbu_Lambda3_MOC410 | 5'- GGCCACCCCAAAAAUGAAGGGGACUAAAACACUGGUGAACUCCGAUAUG -3' | FIG. 13B |
| crLbu_Lambda4_MOC411 | 5'- GGCCACCCCAAAAAUGAAGGGGACUAAAACACAGAUAUAGCCUGGUGGUUC -3' | FIG. 13B |
| Lambda2_target_MOC28 | 5'- GGCUCAAUUUUGACAGCGGUCAUGGCAUUCCACUUAUUCACUGGCAUCCUUCCACUC -3' | FIG. 13B-C |
| Lambda3_target_MOC36 | 5'- GGAAAUCAUUCAACACCCGCACUAUCCGGAAGUUCACCAGCCAGCCGCAGCACGUU -3' | FIG. 13B |
| Lambda4_target_MOC37 | 5'- GGCAAUAAAAAUGCGCCUGAACCACCAGGCUAUAUCUGCCACUCAUUGUGUGA -3' | FIG. 13B |
| pre-crLbu_dimer_SCK324 | 5'- GGAUUUAGACCACCCCAAAAAUGAAGGGGACUAAAACAGGGGCAGAGAUGAUGACCCUAUUUAGACCACCCCAAAAAUGAAGGGGACUAAAACAGUGAUAAGUGGAAUGCCAUG -3' | FIG. 13C, 16A-16F |
| crLbu_lambda2_SCK315 | 5'- GGAUUUAGACCACCCCAAAAAUGAAGGGGACUAAAACAGUGAUAAGUGGAAUGCCAUG -3' | FIG. 16A-16F |
| Lbu_pre_cr_5'_4mer1_AES481 | 5'- GGAUUUAAUAACCCCAAAAAUGAAGGGGACUAAAACAGGGGCAGAGAUGAUGACCCU -3' | FIG. 16A-16F |
| Lbu_pre_cr_5'_4mer2_AES479 | 5'- GGAUUCGAUCCACCCCAAAAAUGAAGGGGACUAAAACAGGGGCAGAGAUGAUGACCCU -3' | FIG. 16A-16F |
| Lbu_pre_cr_5'_4mer3_SCK343 | 5'- GGAUUUAGGAAGCCCAAAAAUGAAGGGGACUAAAACAGGGGCAGAGAUGAUGACCCU -3' | FIG. 16A-16F |
| Lbu_pre_cr_5'_4mer4_AES503 | 5'- GGAUUUAGACCAGGCCAAAAAUGAAGGGGACUAAAACAGGGGCAGAGAUGAUGACCCU -3' | FIG. 16A-16F |
| crLbu_GuideWalk1_SCK302 | 5'- GGCCACCCCAAAAAUGAAGGGGACUAAAACAUUUGGCUCCCCCCUGCAAAGAG -3' | FIG. 18A-18B |
| crLbu_GuideWalk2_SCK303 | 5'- GGCCACCCCAAAAAUGAAGGGGACUAAAACAACCCUUUGGCUCCCCCCUGCAAA -3' | FIG. 18A-18B |
| crLbu_GuideWalk3_SCK304 | 5'- GGCCACCCCAAAAAUGAAGGGGACUAAAACAGAUGACCCUUUUGGCUCCCCCCUG -3' | FIG. 18A-18B |
| crLbu_GuideWalk4_SCK305 | 5'- GGCCACCCCAAAAAUGAAGGGGACUAAAACAAGAUGAUGACCCUUUUGGCUCCCC -3' | FIG. 18A-18B |
| crLbu_GuideWalk5_SCK306 | 5'- GGCCACCCCAAAAAUGAAGGGGACUAAAACAGCAGAGAUGAUGACCCUUUUGGCU -3' | FIG. 18A-18B |
| crLbu_GuideWalk6_SCK307 | 5'- GGCCACCCCAAAAAUGAAGGGGACUAAAACAGGGGCAGAGAUGAUGACCCUUUU -3' | FIG. 18A-18B |
| crLbu_GuideWalk7_SCK308 | 5'- GGCCACCCCAAAAAUGAAGGGGACUAAAACACAGAGGGGCAGAGAUGAUGACCC -3' | FIG. 18A-18B |
| crLbu_GuideWalk8_SCK309 | 5'- GGCCACCCCAAAAAUGAAGGGGACUAAAACAUCAGCAGAGGGGCAGAGAUGAUG -3' | FIG. 18A-18B |
| A.1_target_U_MOC279 | 5'- GGCCAUUUGCAGGGGGAGCAAAGGGUCAUCAUCUCUGCCCCUCUGCAUGCCCC -3' | FIG. 18A-18B |
| A.2_target_70nt_AES447 | 5'- GGCCUGACUGCUCUCAUUUGCAGUGGGAGCAAAGGGUCAUCAUCUCUGCCCCUCUGCUGAUGCCCC -3' | FIG. 18A-18B |
| A.3_target_80nt_AES448 | 5'- GGACCUGUGAAUCCUGACUGCUCUCAUUUGCAGUGGGAGCAAAGGGUCAUCAUCUCUGCCCCUCUGCUGAUGCCCC -3' | FIG. 18A-18B |
| A.4_5'_ts_shift_AES449 | 5'- GGCACACCCGCAGGGUUUAGCGGUCAUCAUCUCUGCCCCUCUGCUGAUGCCCC -3' | FIG. 18A-18B |
| crLbu_A_16nt_trunc_SCK282 | 5'- GGCCACCCCAAAAUGAAGGGGACUAAAACAGAGAUGAUGACCCU -3' | FIG. 19A-19C |
| crLbu_A_24nt_ext_SCK283 | 5'- GGCCACCCCAAAAAUGAAGGGGACUAAAACAAGAGGGGGCAGAGAUGAUGACCCU -3' | FIG. 19A-19C |
| crLbu_A_mature_GA_SCK340 | 5'- GACCACCCCAAAAAUGAAGGGGACUAAAACAGGGGCAGAGAUGAUGACCCU -3' | FIG. 19A-19C |
| crLbu_A_mature_GGGA_SCK341 | 5'- GGGACCACCCCAAAAAUGAAGGGGACUAAAACAGGGGCAGAGAUGAUGACCCU -3' | FIG. 19A-19C |
| crLbu_A_mature_CCA_AES461 | 5'- CCACCCCAAAAAUGAAGGGGACUAAAACAGGGGCAGAGAUGAUGACCCU -3' | FIG. 19A-19C |

[a] All RNAs were either ordered synthetically (Integrated DNA technologies) or transcribed from a complementary template as described in the Methods Percentage of hairpin cleavaged after 60 mins: 84 ± 1.3 %
Descriptive Name: pre-crRNA Lbu
In vitro transcription template ID: SCK314

| | | | | |
|---|---|---|---|---|
| | 68.1 ± 0.6 %<br>pre-crRNA 5' Flank Mut 1<br>AES497 | | 75.4 ± 0.8 %<br>pre-crRNA Stem Mut 1<br>AES501 | |
| | 75.6 ± 2.0 %<br>pre-crRNA 5' Flank Mut 2<br>AES496 | | 73.4 ± 1.2 %<br>pre-crRNA Stem Mut 2<br>AES502 | |
| | 75.0 ± 2.3 %<br>pre-crRNA 5' Flank Mut 3<br>AES495 | | 71.2 ± 1.7 %<br>pre-crRNA Stem Mut 3<br>AES499 | |
| | 4.8 ± 1.3 %<br>pre-crRNA 5' Flank Mut 4<br>AES477 | | 73.9 ± 0.5 %<br>pre-crRNA Stem Mut 4<br>AES500 | |
| | 14.4 ± 1.1 %<br>pre-crRNA 5' Flank Mut 5<br>AES482 | | 59.7 ± 3.1 %<br>pre-crRNA Stem Mut 5<br>AES504 | |
| | 18.5 ± 1.7 %<br>pre-crRNA 5' Flank Mut 6<br>AES478 | | 63.2 ± 2.1 %<br>pre-crRNA 3' Flank Mut 1<br>AES505 | |
| | 63.9 ± 1.0 %<br>pre-crRNA 5' Flank Mut 7<br>AES480 | | 39.5 ± 4.4 %<br>pre-crRNA 3' Flank Mut 2<br>AES506 | |
| | 39.1 ± 2.1 %<br>pre-crRNA 5' Flank Mut 8<br>AES498 | | 76.3 ± 0.2 %<br>pre-crRNA 3' Flank Mut 3<br>AES507 | |
| | | | 69.2 ± 1.3 %<br>pre-crRNA 3' Flank Mut 4<br>AES508 | |

FIG. 17

FIG. 19A
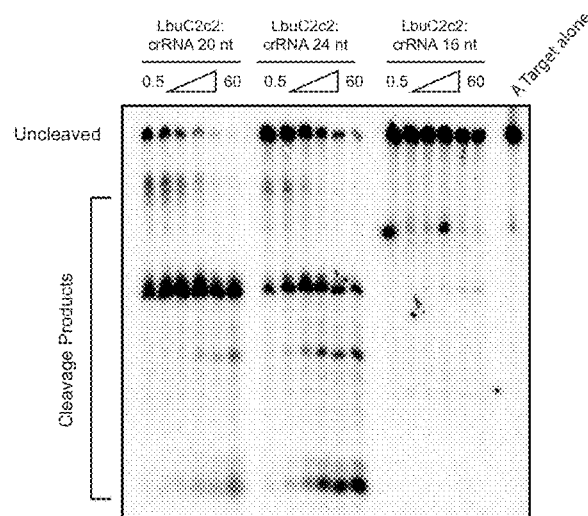
FIG. 19B
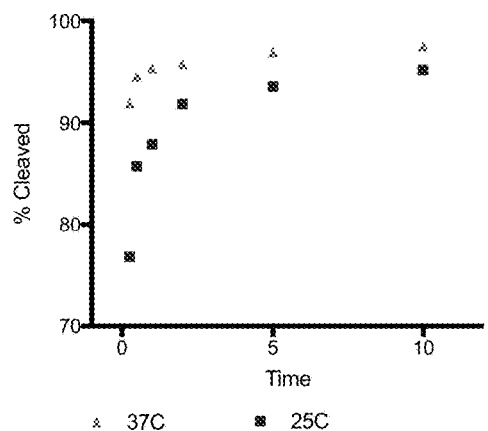
FIG. 19C
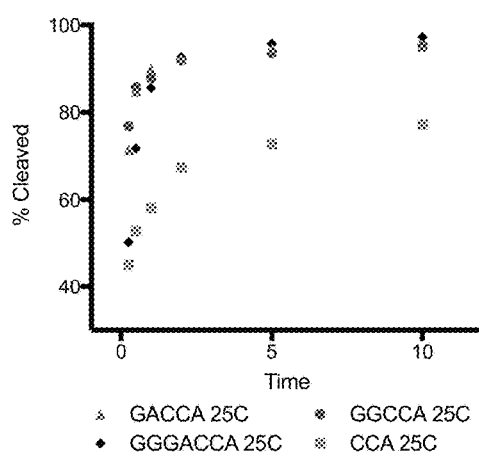
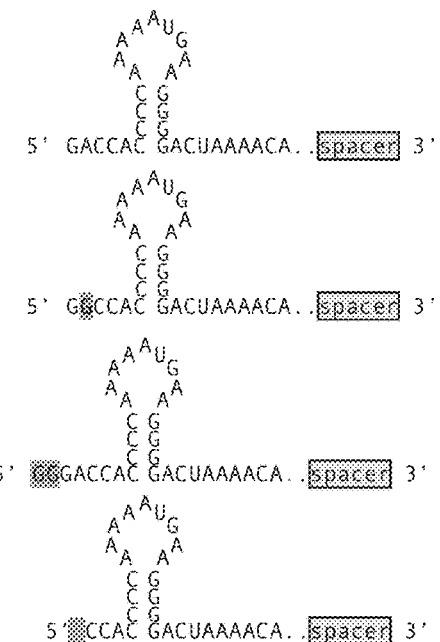

FIG. 23C
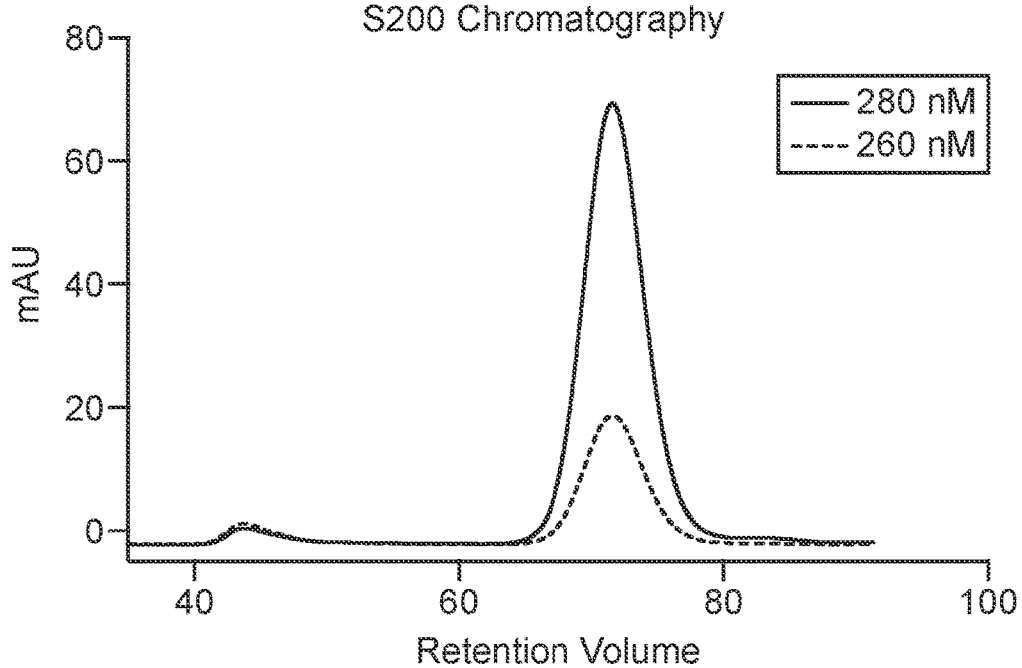
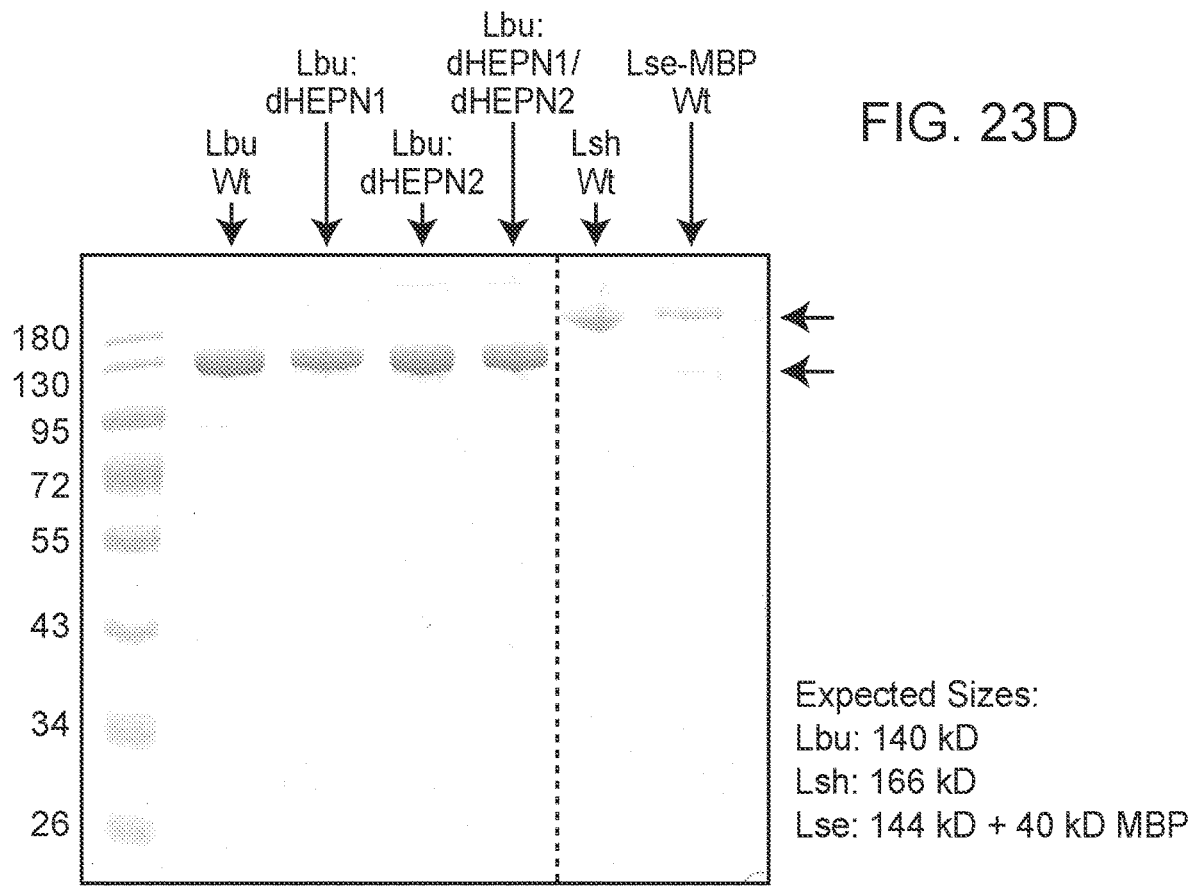
FIG. 23D

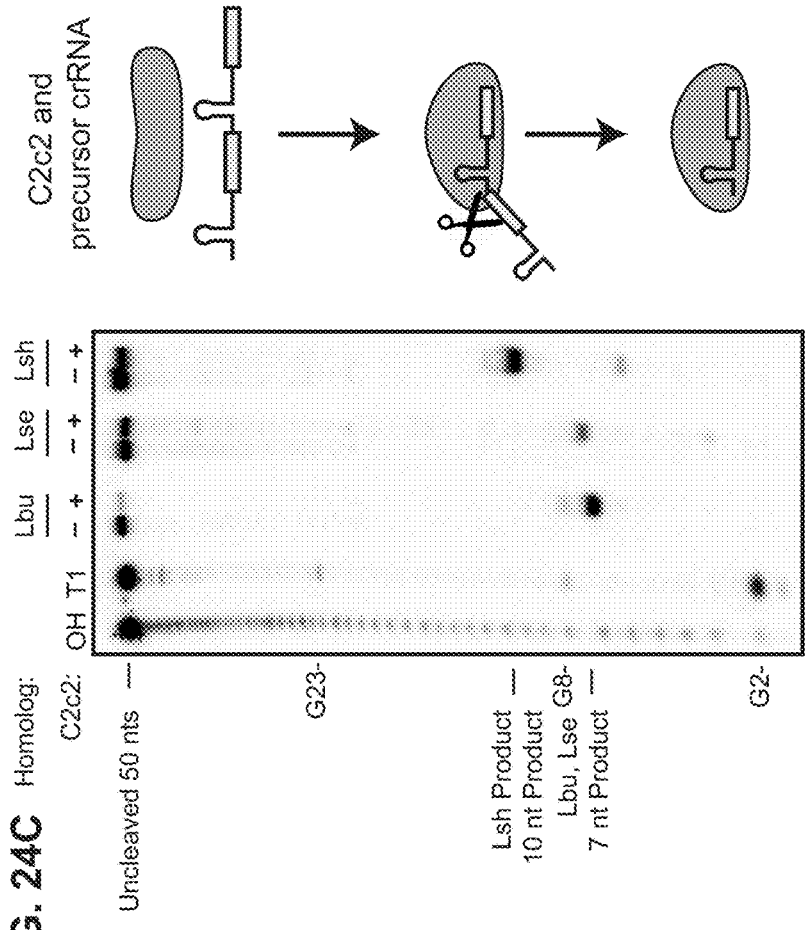
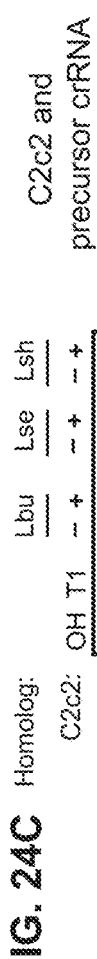
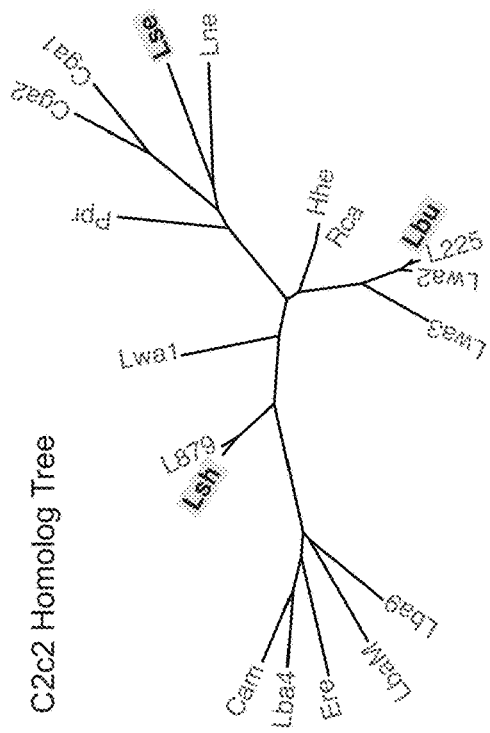
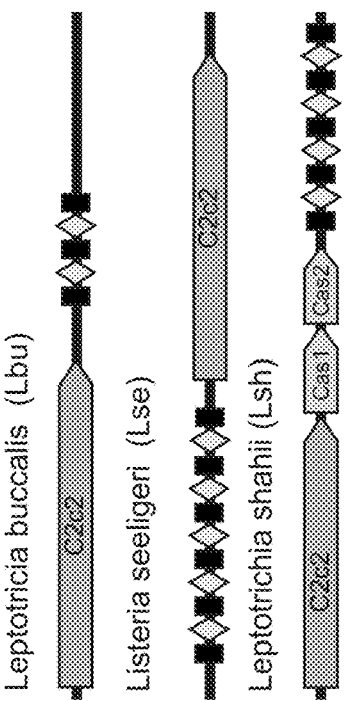
FIG. 24A
FIG. 24B
FIG. 24C

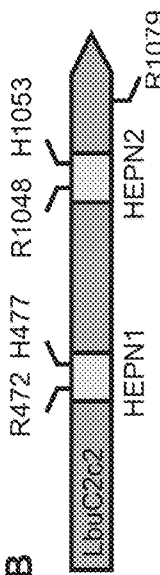
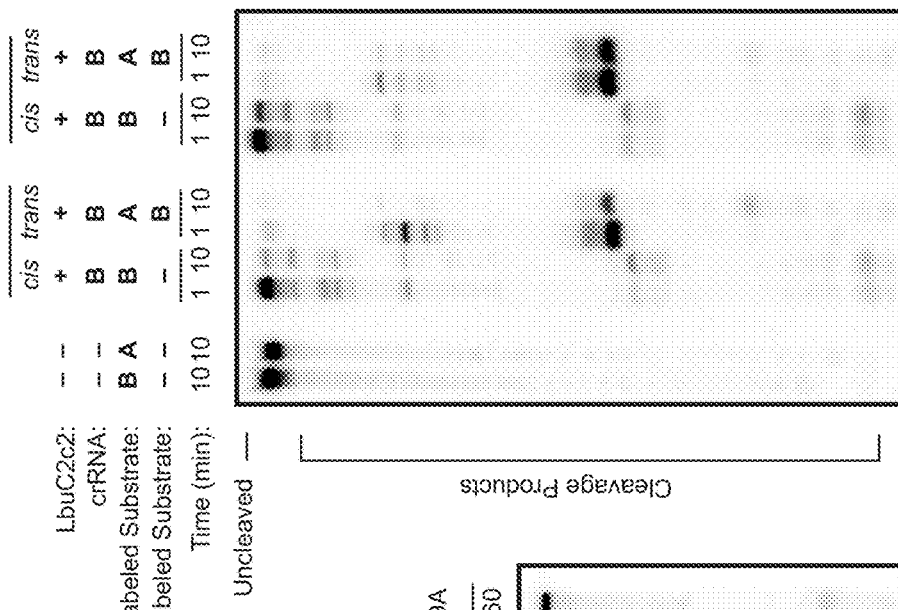
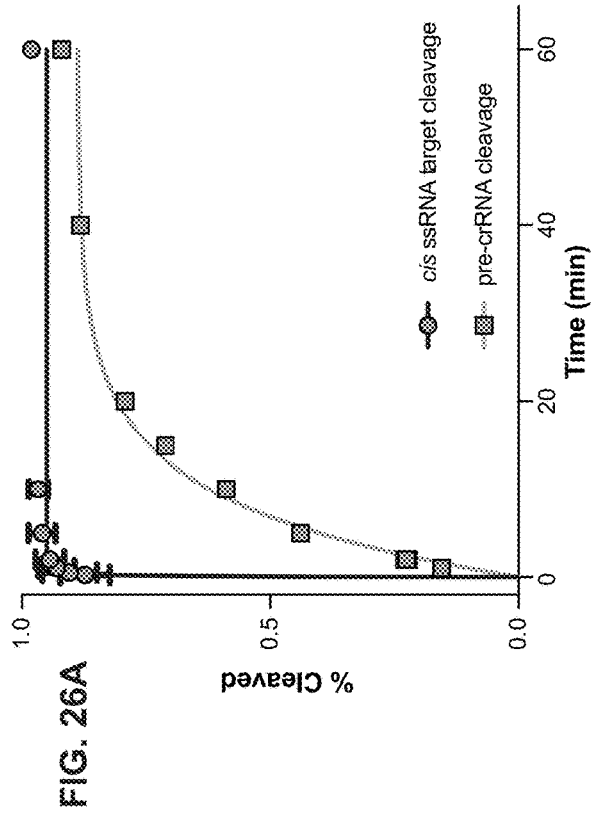
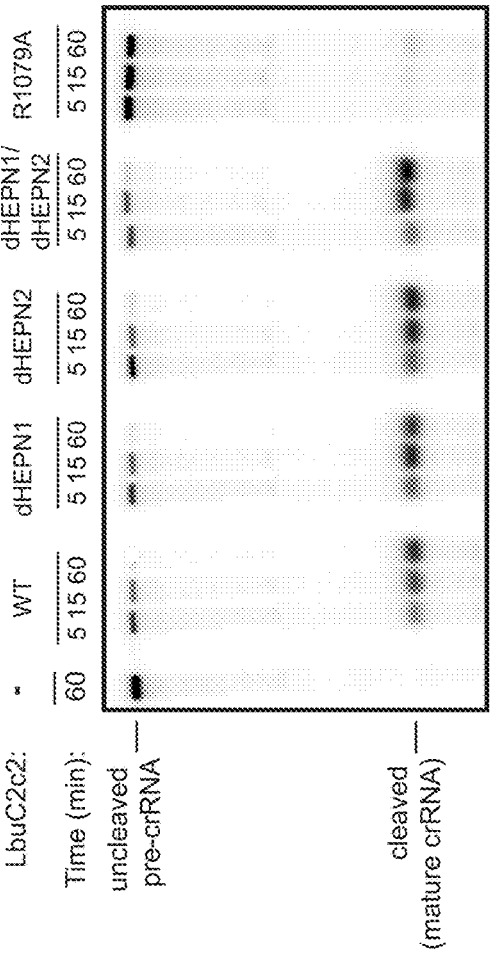
FIG. 26A
FIG. 26B
FIG. 26C
FIG. 26D

FIG. 29C
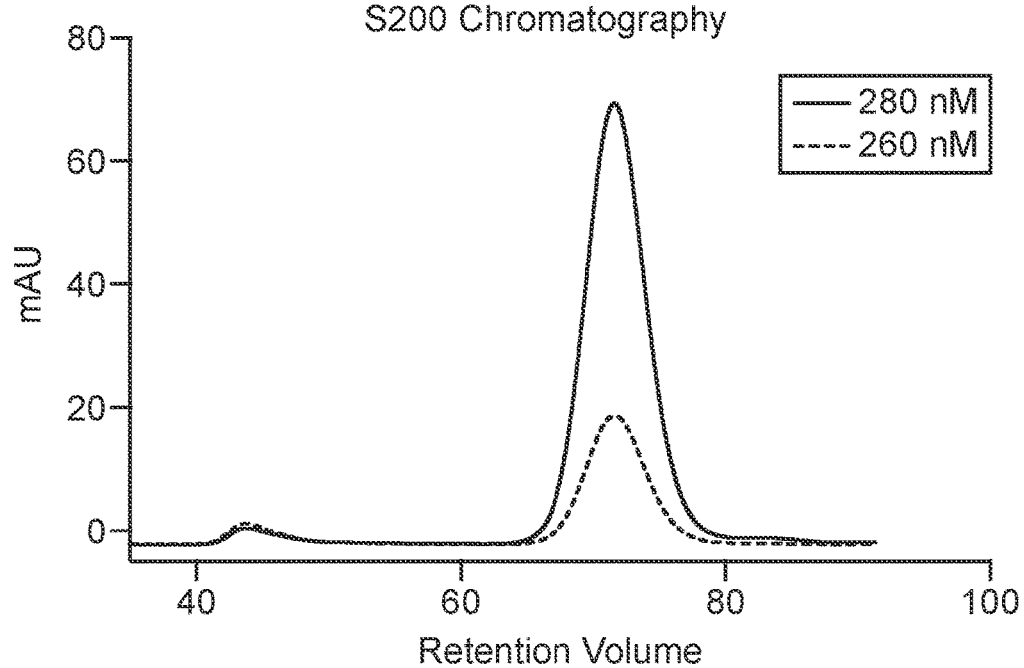
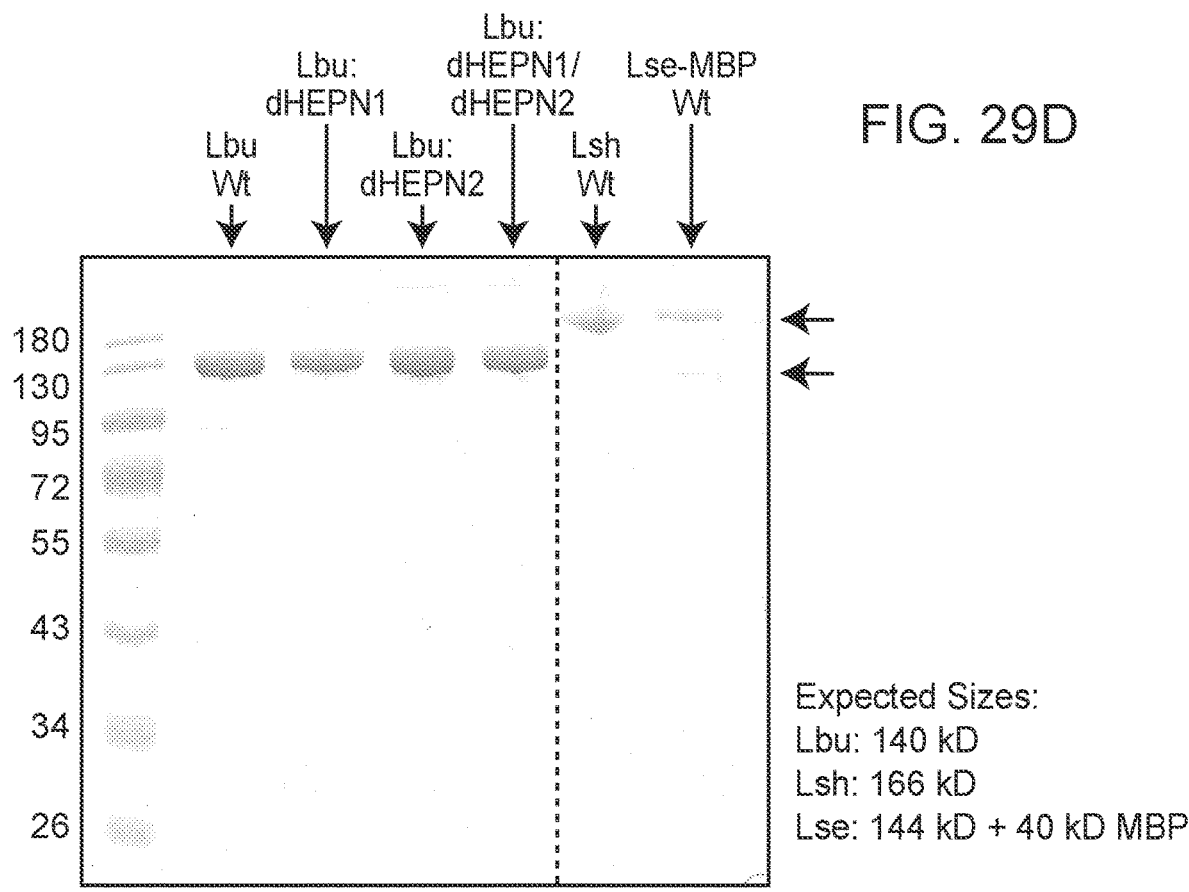
FIG. 29D

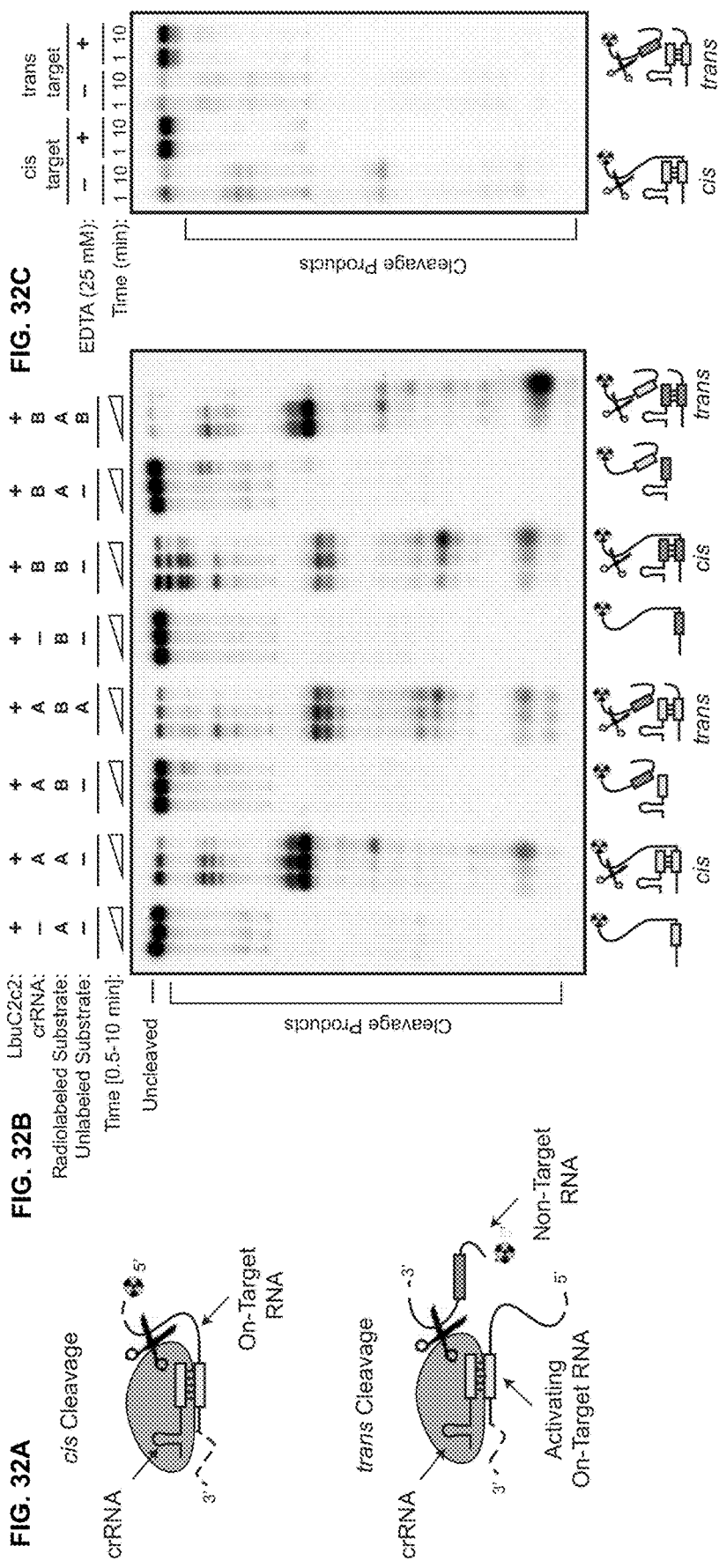

FIG. 33A
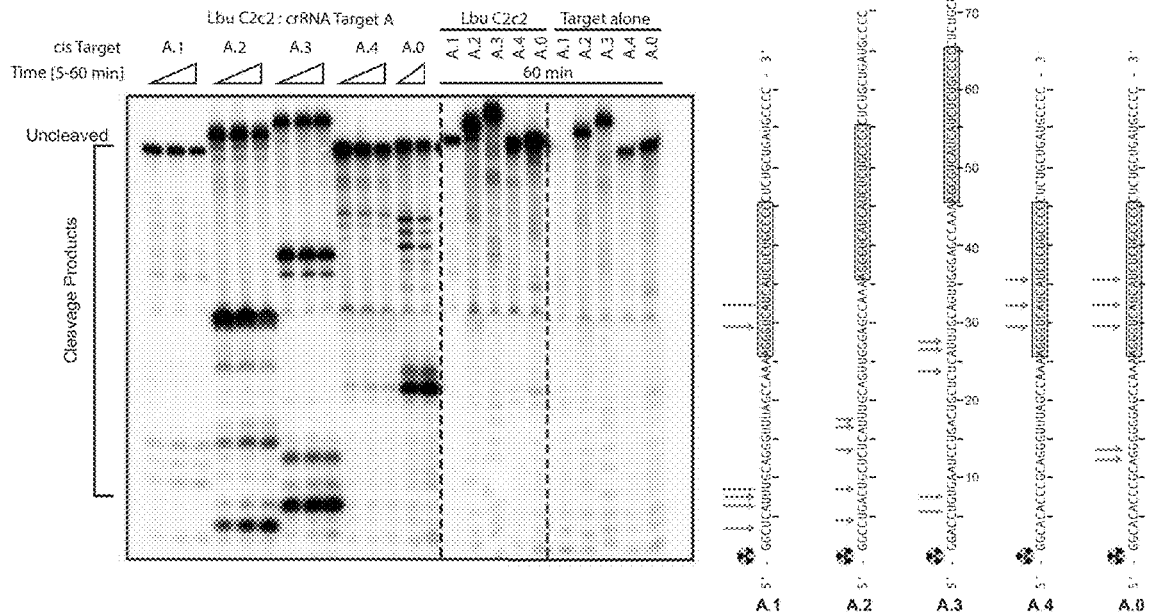
FIG. 33B
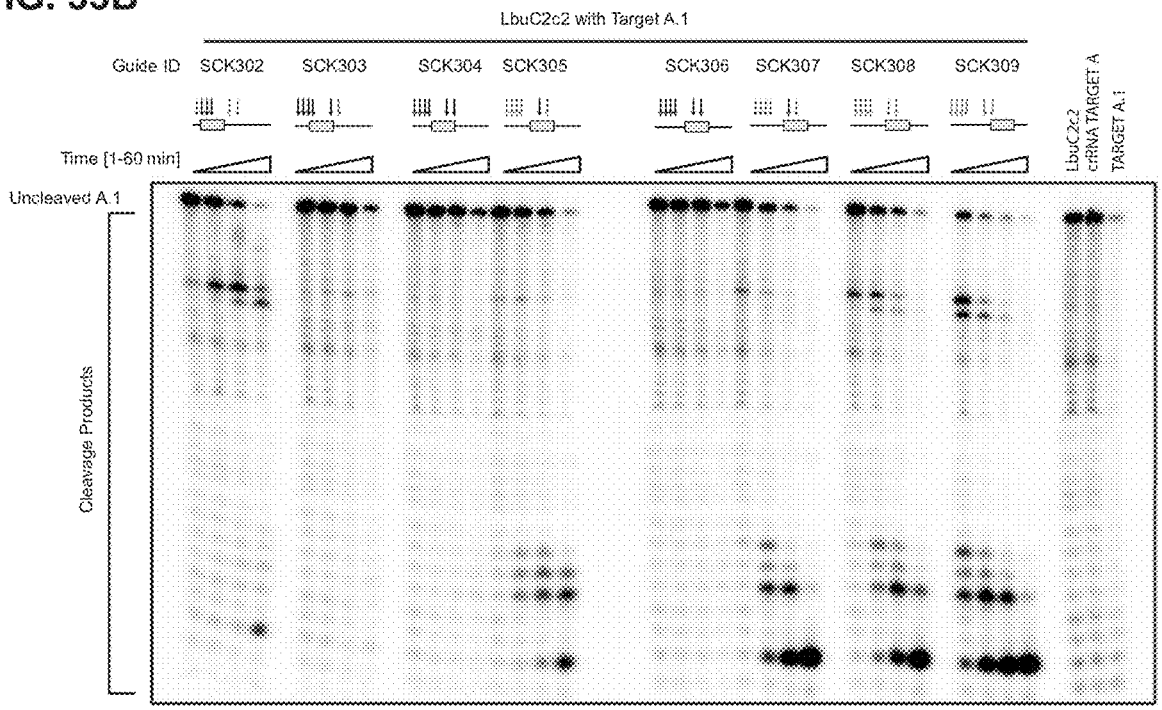
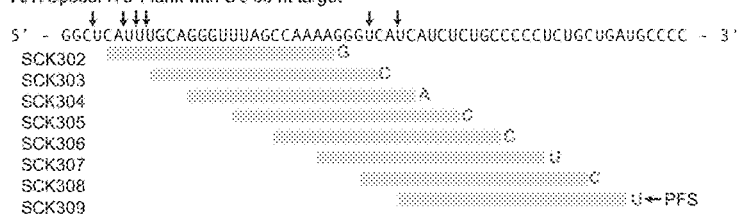

FIG. 38A FIG. 38B
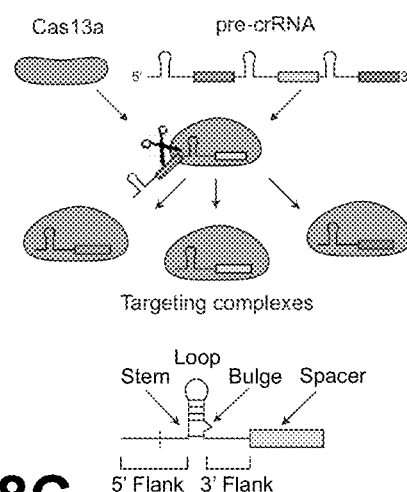
FIG. 38C
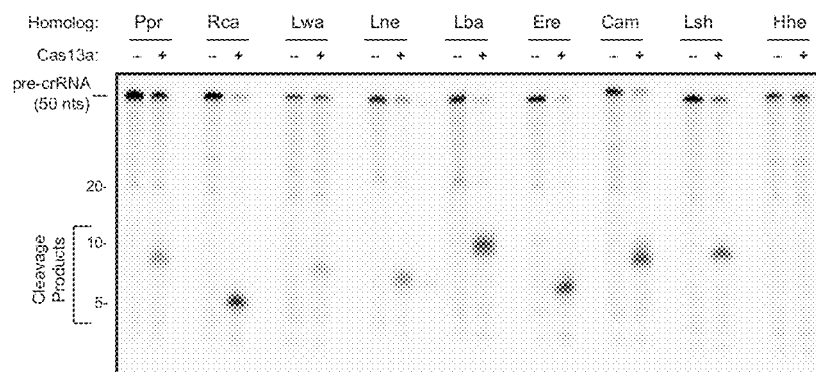

FIG. 39A

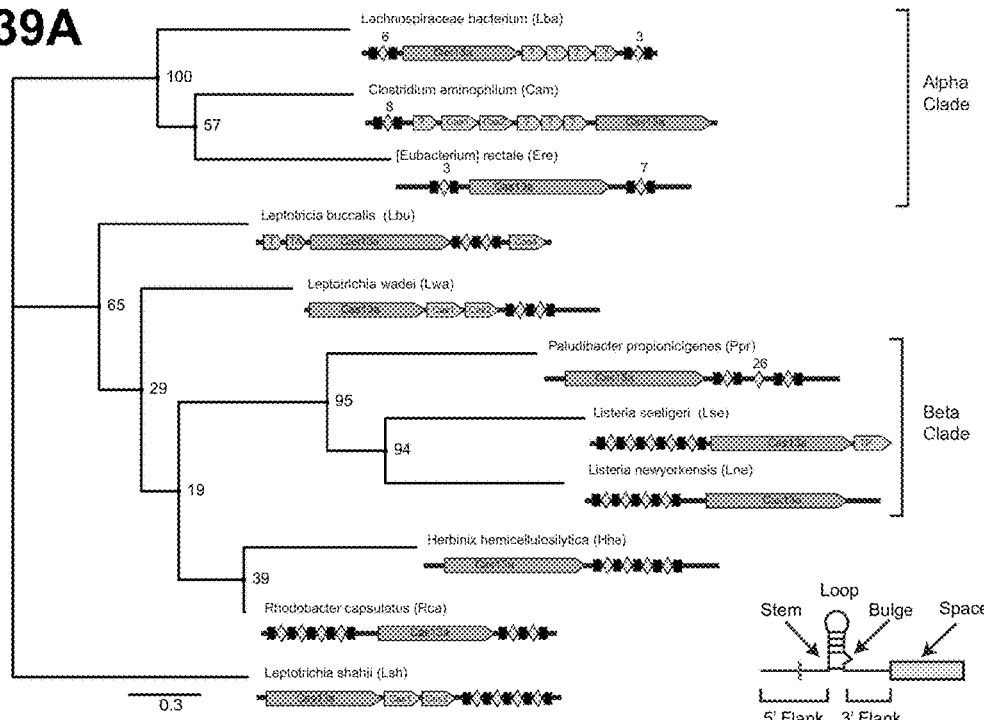

| | 5' Flank | Stem | Loop | Stem + Bulge | 3' Flank |
|---|---|---|---|---|---|
| Lbu: | gGAUUUA GACC | ACCCC | AAAAAUGAA | GGGG | ACU | AAAACA |
| Lse: | gCUAAGA GACU | ACCUCU | AUA-UGAA | ACACC | ACU | AAAAC |
| Ppr: | ggCUUGUG AAUU | AUCCC | AAAAUGAA | GGGA | ACU | ACAAC |
| Rca: | gGUCA CAUC | ACCGCC | AAGA-CGAC | GGCCC | ACU | GAACC |
| Lwa: | gCAUAUA GACC | ACCCC | AAUAUCGAA | GGGG | ACU | AAAACUU |
| Lne: | gCAUAUA GAGU | ACCUC | AAAACAAAA | GAGG | ACU | AAAAC |
| | | | | | | |
| Lba: | ggGCUGGAGA AGAU | AGCCC | AAGAAACA | GGGC | AAU | AAC |
| Ere: | ggGUGA AUAC | AGCUC | GAUAUACU | GAGC | AAU | AAG |
| Cam: | ggGUU GGA GAAC | AGCCC | GAUAUACA | GGGC | AAU | AGAC |
| | | | | | | |
| Lsh: | ggAUAUAGACIC | ACCCC | AAUUCGAA | GGGG | ACU | AAAAC |
| | | | | | | |
| Hhe: | gGUA -ACA | AUCCCC | GUAGAC-A | GGGCA | ACU | GUG |
| | ggtatgGUA -ACA | AUCCCC | GUAGAC-A | GGGCA | ACU | GUG |

FIG. 39B

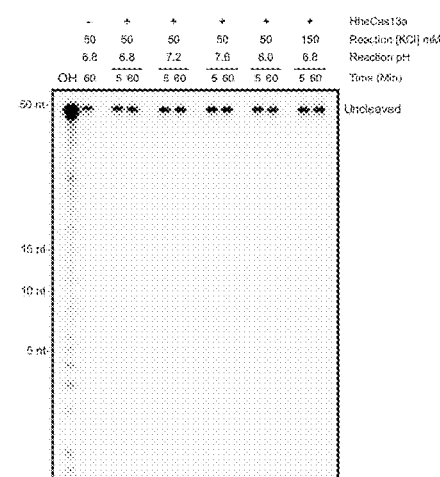

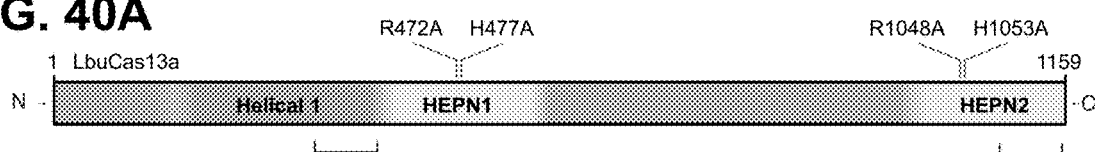

FIG. 40B

Mutants:
```
              300              310
Lbu  A F C H F Y E I E M S Q L L K N Y V Y - - K R L S N I
Lsh  I I Y R Y L K G R L E K I L V N E Q K - V R L K K M E
                   440              450
```
Mutants:

```
Hhe  - - - - L F L K E Y E Q Y F K K Y F P - V K S K H S N
Ere  Y W I H H I E N A V E R I L K N C K A - - - - - - - -
Lse  - - - - Q F N I E I R K H L E T Y F P - I K K T N R K
Ppr  - - - - I Y H L E V K Y L E H Y F P - I K T S K R R
Lwa  - - - - I Y N L E L K K Y I E N N F S - Y K K Q K S K
Lba  F F I H R I E Y G V E K I Y A N L K Q - - - - - - - -
Rca  - - - - A L H D E V K K T Y K R L C A - - - - - - - R
Cam  F W I H H I E S A V E R I L A S I N P - - - - - - - -
Lne  - - - - Q Y G I E V K K Y I Q R Y F P - I K R A P N R
```

Liu et al. crRNA processing region

FIG. 40C

Mutants:
```
              1070         1080              1090
Lbu  E N L  R K L L S D R L K N A V M K S V V D L L K
Lsh  D R V - S N L L S X S T Y N N S T Y A S V F E V F -
                   1310         1320
```
Mutants:

```
Hhe  N S L - R I L L A D R R Q N A Y T K T I N D L L L
Ere  S E V F D R F F T D I K Y Q K N V L N L L Q N L L L
Lse  D D A - R D V L S D R L K N A V S K S L K E I L S
Ppr  N E L - R E L L H D R L K N A V S K A F I D L F D
Lwa  N L L - I K L F S D K K V Q N H I L K S T K T L L E
Lba  S E V F D R F F T Y G L Y R K N V P T I L Y N I L L
Rca  N R A - R E M M A Y D R L R K N A V P R S I L D M L A
Cam  S E I H D R F F T Y D M F Y Q K N V A N M L E N I L L
Lne  E R L - R E L F K Y D R L K N A V S K S L I D L L D
```

East-Seletsky et al. crRNA processing region

FIG. 40D   FIG. 40E   FIG. 40F

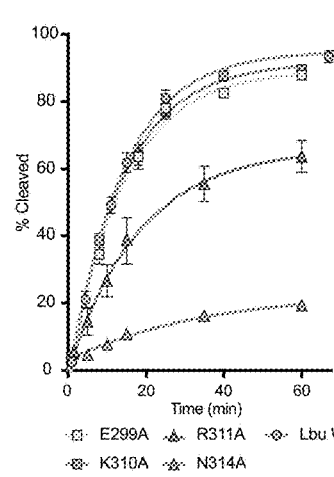
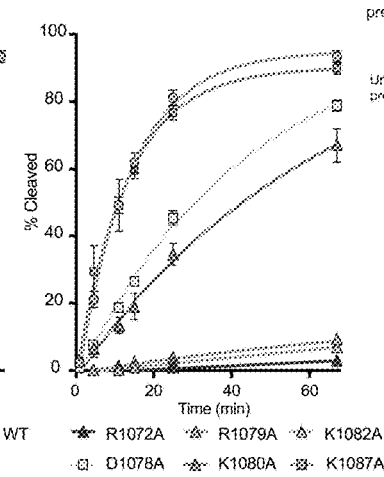
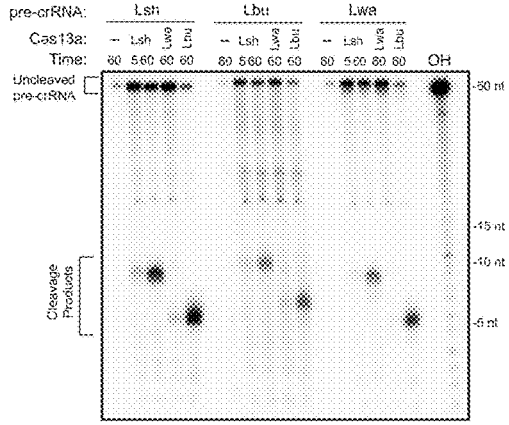

FIG. 40D legend: E299A, R311A, Lbu WT, K310A, N314A

FIG. 40E legend: R1072A, R1079A, K1082A, D1078A, K1080A, K1087A

FIG. 41A

| | |
|---|---|
| 506250229_Leptotrichia_buccalis | YAFCHFVEIEMSQLLKNYVY--KRLSNISND |
| 517262777_Leptotrichia_shahii | -IIYRYLKGRIEKILVNEQK-VRLKKMEK-- |

| | |
|---|---|
| 912591537_Herbinix_hemicellulosilytica | -----LFLKEVEQYFKKYFP-VKSKHSNKSK |
| 937566624_Eubacterium_rectale | -YWIHHIENAVERILKNCKA---------- |
| 502750493_Listeria_seeligeri | -----QFNIEIRKHLETYFP-IKKTNRKV-- |
| 503209049_Paludibacter_propionicigenes | -----IYHLEVVKYLEHYFP-IKTSKRRNTA |
| 544240864_Leptotrichia_wadei | -----IYNLELKKYIENNFS-YKKQKSKSKN |
| 545620493_Leptotrichia_oral_taxon_879 | -IIYRYLKGRIEKILVNEQK-VRLKKMEK-- |
| 545623306_Leptotrichia_wadei | YAFCHFVEIEMSQLLKNYVY--KRLSNISND |
| 545623740_Leptotrichia_wadei | FAFCYFVEIEVNNLLKENVYKIKRFNESNKK |
| 551041827_Lachnospiraceae_bacterium_NK4A179 | -FFIHRIEYGVEKIYANLKQ---------- |
| 564875111_Rhodobacter_capsulatus_R121 | -----ALHDEVKKTYKRLCA-------RGKN |
| 652829192_Lachnospiraceae_bacterium_NK4A144 | -FWIHRIENAVERILGSIND---------- |
| 671463495_Clostridium_aminophilum | -FWIHMIESAVERILASINP---------- |
| 736546968_Carnobacterium_gallinarum | -----QFNIEIGKYFEHYFP-IKKERCTE-- |
| 736550717_Carnobacterium_gallinarum | -----QFNIEIGKYFEHYFP--KTGKKES-- |
| 738133341_Listeria_newyorkensis | -----QYGIEVKKYIQRYFP-IKRAPNRSKH |
| 769144435_Lachnospiraceae_bacterium_MA2020 | -FWIHLIENEVERLYNGIEN---------- |
| 545661797_Leptotrichia_oral_taxon_225_PARTIAL_ | YVFCHFVEIEMSKLLKNYVY--KKPSNISND |

Conservation

FIG. 41B

| | |
|---|---|
| 506250229_Leptotrichia_buccalis | ENL-RKLLSYDRKLKNAVMKSVVDILK |
| 517262777_Leptotrichia_shahii | DRV-SNLLSKSTRYNNSTYASVFEVF- |

| | |
|---|---|
| 912591537_Herbinix_hemicellulosilytica | NSL-RILLAYDRKRQNAVTKTINDLLL |
| 937566624_Eubacterium_rectale | SEVFDRFFTYDIRYQKNVLNLLQNILL |
| 502750493_Listeria_seeligeri | DDA-RDVLSYDRKLKNAVSKSLKEILS |
| 503209049_Paludibacter_propionicigenes | NEL-RELLHYDRKLKNAVSKAFIDLFD |
| 544240864_Leptotrichia_wadei | NLL-IKLFSYDRKVQNHILKSTKTLLE |
| 545620493_Leptotrichia_oral_taxon_879 | DRV-SNLLSKSTRYNNSTYASVFEVF- |
| 545623306_Leptotrichia_wadei | ENL-RKLLSYDRKLKNAIMKSIVDILK |
| 545623740_Leptotrichia_wadei | EEL-RNLLKYDRKLKNAVMKSIKDIFK |
| 551041827_Lachnospiraceae_bacterium_NK4A179 | SEVFDRFFTYDLKYRKNVPTILYNILL |
| 564875111_Rhodobacter_capsulatus_R121 | NRA-REMMAYDRKRKNAVPRSILDMLA |
| 652829192_Lachnospiraceae_bacterium_NK4A144 | SEFFDRFFTYDMKYQKNVVNVLENILL |
| 671463495_Clostridium_aminophilum | SEIHDRFFTYDMKYQKNVANMLENILL |
| 736546968_Carnobacterium_gallinarum | NNL-RDLMAYDRKLKNAVTKSMIKILD |
| 736550717_Carnobacterium_gallinarum | NDL-RKLMSYDRKLKNAVTKAIIKILD |
| 738133341_Listeria_newyorkensis | ERL-REIFKYDRKLKNAVSKSLIDILD |
| 769144435_Lachnospiraceae_bacterium_MA2020 | SEVFDRFFTYDMLRKNVVNMLYNILL |
| 545661797_Leptotrichia_oral_taxon_225_PARTIAL_ | ENL-RKLLSYDRKLKNAIMKSIVDILK |

Conservation

FIG. 42A FIG. 42B
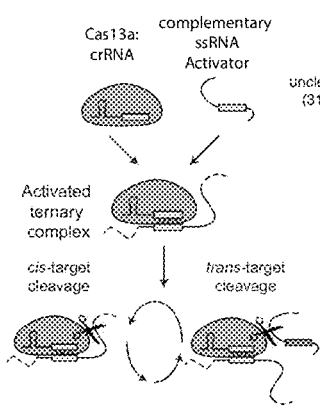 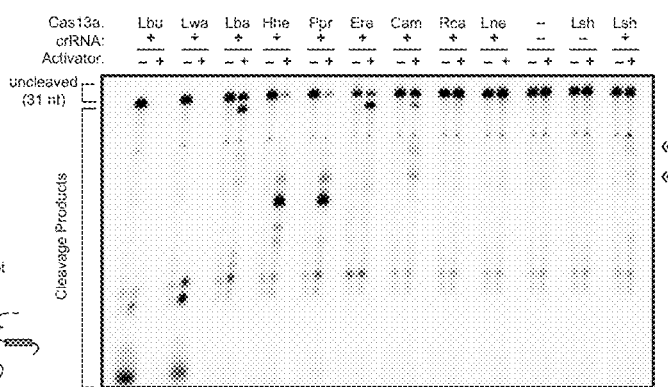
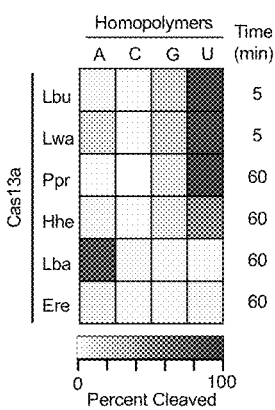 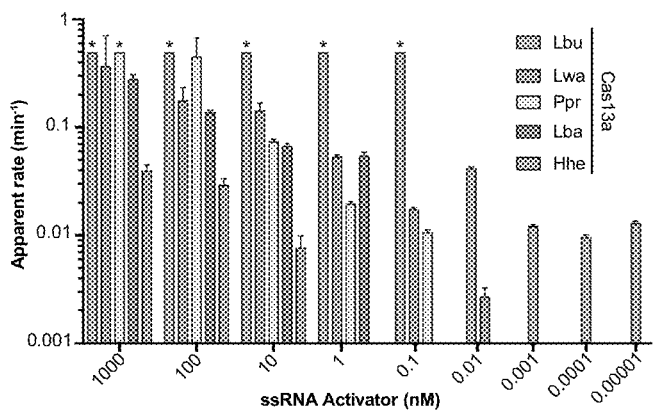
FIG. 42C FIG. 42D

FIG. 43A
FIG. 43B
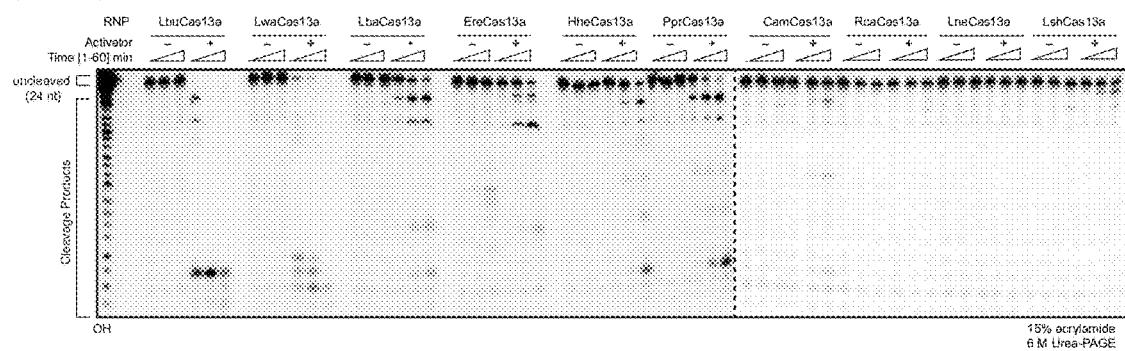
FIG. 43C
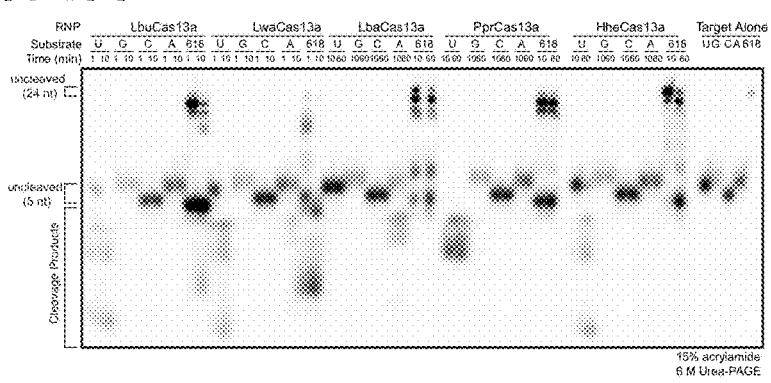
FIG. 43D
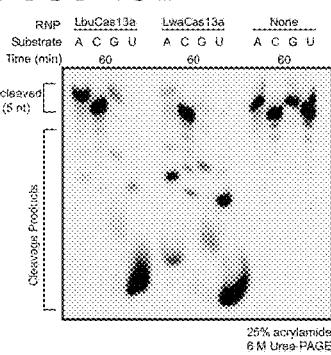

Table 4

| Prefix | Species | Strain | Cas13a Accession | Genome Accession | CRISPR array start | CRISPR array stop | CRISPR Repeat Consensus | Mature crRNA handle | Use in Study |
|---|---|---|---|---|---|---|---|---|---|
| Lwa | Leptotrichia wadei | F0279 | ERK53440.1 | AWVM01000026.1 | 24602 | 24774 | GATATAGACCACCCCAATATCGAAGGGGACTAAAACTT | GACCACCCCAAUAUCGAAGGGGACUAAAACUU | Yes |
| Rca | Rhodobacter capsulatus | R121 | ETD76934.1 | AYQC01000019.1 | 321133 | 321440 | TCACATCACCGCCAACACCACCGCGGACTGAACC | CAUCACCGCCAACACCACCGCGGACUGAACC | Yes |
| Hhe | Herbinix hemicellulosilytica | T3/55T | CRZ35554.1 | CVTD020000026.1 | 325840 | 326009 | CACATCACCGCCAA·A·GACGGCGGACTGAACCT | not tested | No |
| Lbu | Leptotrichia buccalis | DSM 1135 | WP_015770004.1 | NC_013192.1 | 59561 | 59859 | GTAACAATCCCCGTAGACAGGGAACTGCAAC | not cleaved | No |
| Lse | Listeria seeligeri | SLCC3954 | WP_012985477.1 | NC_013891.1 | 1880132 | 1880237 | GATTTAGACCACCCAAAATGAAGGGGACTAAAACA | GACCACCCCAAAAUGAAGGGGACUAAAACA | Yes |
| Ppr | Paludibacter propionicigenes | WB4 | WP_013443710.1 | NC_014734.1 | 1174057 | 1174422 | GTAAGAGACTACCTCTATATGAAAGAGGACTAAAAC | GACUACCUCUAUAUGAAAGAGGACUAAAAC | Yes |
|  |  |  |  |  | 223912 | 225653 | CTTGTGAATTATCCCAAAATTGAAGGGAACTACAAC | AAUUAUCCCAAAAUUGAAGGGAACUACAAC | Yes |
|  |  |  |  |  |  |  | CTTGTG·ATTATCC·CAA··ATTGAAGGAACTA·CAAC | not tested | No |
| Lba | Lachnospiraceae bacterium | NK4A179 | WP_022785443.1 |  | 10469 | 109913 | GCTGGAGAAGATAGCCCAAGAAAGAGGGCAATAAC | AGAUAGCCCAAGAAAGAGGGCAAUAAC | Yes |
|  |  |  |  |  | 49 | 290 | G·TG·A·GA·A·AGCCCAAGA·AGAGGGCAATAAC | GAAGAGCCCAAGAUAGAGGGCAAUAAC | No |
| Ere | [Eubacterium] rectale | T1-815 | WP_055061018.1 | NZ_CVRQ01000308.1 | 63967 | 64487 | GTGAAAGTAGCCGATATAGAGGGCAATAAC | AAGUAGCCGAUAUAGAGGGCAAUAAC | Yes |
|  |  |  |  |  | 58872 | 59187 | GTGAA·A·AGC·CGATATAG·G·GCAATAAG | AUACAGCUCGAUAUACUGAGGCAAUAAG | No |
| Lny | Listeria newyorkensis | FSL M6-0635 | WP_036091002.1 | NZ_JNFB01000012.1 | 169592 | 169890 | GATTTAGAGTACCTCAAAACAAAAGAGGACTAAAAC | GACUACCUCAAAACAAAAGAGGACUAAAAC | Yes |
| Cam | Clostridium aminophilum | DSM 10710 | WP_031473346.1 | NZ_JONJ01000012.1 | 1521 | 2181 | GTTTTGGAGAACACCCATATACGAGGACTAATAGAC | GAACACCCCAUAUAGAGGCAAUAGAC | Yes |
| Lsh | Leptotrichia shahii | DSM 19757 | WP_018451595.1 | NZ_KB890278.1 | 34127 | 34365 | GATATAGACCACCCCAATATCGAAGGGGACTAAAAC | CACCCCAAUAUCGAAGGGGACUAAAAC | Yes |

FIG. 49

Table 5

| Oligo ID | Type | Source | Description | Sequence |
|---|---|---|---|---|
| AES559 | pre-crRNA | SS | Cam pre-crRNA L4 | GGGUUUCGAGAACAGCCCGAUAUAGAGGGCAAUAGACCAGAUAUAGCCUGGUGGUUCAGGC |
| AES557 | pre-crRNA | SS | Ere pre-crRNA2 L4 | GGGUGAAUACAGCUCGAUAUAGUGAGCAAUAAGCAGAUAUAGCCUGGUGGUUCAGGC |
| AES620 | pre-crRNA | SS | Hhe pre-crRNA L4 | GGUAUGUAACAAUCCCCGUAGACAGGGGAACUGCAACCAGAUAUAGCCUGGUGGUUCAGGC |
| AES556 | pre-crRNA | SS | Lba pre-crRNA2 L4 | GGGCUGGAGAAGAUAGCCCAAGAAAGAGGGCAAUAACCAGAUAUAGCCUGGUGGUUCAGGC |
| AES634 | pre-crRNA | SS | Lbu pre-crRNA L4 | GGAUUUAGACCACCCCAAAAAUGAAGGGGACUAAAACACAGAUAUAGCCUGGUGGUUCAGGC |
| AES619 | pre-crRNA | SS | Lne pre-crRNA L4 | GCAUUUAGAGUACCUCAAAACAAAAGAGGACUAAAACCAGAUAUAGCCUGGUGGUUCAGGC |
| AES625 | pre-crRNA | SS | Lse pre-crRNA L4 | GGUAAGAGACUACCUCUAUAUGAAAGAGGACUAAAACCAGAUAUAGCCUGGUGGUUCAGGC |
| AES566 | pre-crRNA | SS | Lsh pre-crRNA L4 | GGAUAUAGACCACCCCAAUAUCGAAGGGGACUAAAACCAGAUAUAGCCUGGUGGUUCAGGC |
| AES553 | pre-crRNA | SS | Lwa pre-crRNA L4 | GGGAUAUAGACCACCCCAAUAUCGAAGGGACUAAAACUUCAGAUAUAGCCUGGUGGUUCAGGC |
| AES597 | pre-crRNA | SS | Ppr pre-crRNA L4 | GGCUUGUGAAUUAUCCCAAAAUUGAAGGGAACUACAACCAGAUAUAGCCUGGUGGUUCAGGC |
| AES568 | pre-crRNA | SS | Rca pre-crRNA L4 | GGUCACAUCACCGCCAAGACGACGGCGGACUGAACCCAGAUAUAGCCUGGUGGUUCAGGC |
| AES614 | crRNA | HH PCR | HH-Cam crRNA uncleaved | GGUGUUCUCUGAUGAGGCCUUCGGGCCGAAACGGUGAAAGCCGUAAGAACAGCCCGAUAUAGAGGG CAAUAGACCAGAUAUAGCCUGGUGGUUCAGGC |
|  |  |  | Cam crRNA L4 | GAACAGCCCGAUAUAGAGGGCAAUAGACCAGAUAUAGCCUGGUGGUUCAGGC |
| AES610 | crRNA | HH PCR | HH-Ere crRNA uncleaved | GGUGUAUUCUGAUGAGGCCUUCGGGCCGAAACGGUGAAAGCCGUAAAUACAGCUCGAUAUAGUGAG CAAUAAGCAGAUAUAGCCUGGUGGUUCAGGC |
|  |  |  | Ere crRNA L4 | AAGUAGCCCGAUAUAGAGGGCAAUAACCAGAUAUAGCCUGGUGGUUCAGGC |
| AES612 | crRNA | HH PCR | HH-Lba crRNA uncleaved | GGUAUCUUCUGAUGAGGCCUUCGGGCCGAAACGGUGAAAGCCGUAAAGAUAGCCCAAGAAAGAGGG CAAUAACCAGAUAUAGCCUGGUGGUUCAGGC |
|  |  |  | Lba crRNA L4 | AGAUAGCCCAAGAAAGAGGGCAAUAACCAGAUAUAGCCUGGUGGUUCAGGC |
| MOC410 | crRNA | SS | Lbu crRNA L3 | GGCCACCCCAAAAAUGAAGGGGACUAAAACACUGGUGAACUUCCGAUAGUG |
| MOC411 | crRNA | SS | Lbu crRNA L4 | GGCCACCCCAAAAAUGAAGGGGACUAAAACACAGAUAUAGCCUGGUGGUUC |
| SCK340 | crRNA | SS | Lbu crRNA Sp3 | GACCACCCCAAAAAUGAAGGGGACUAAAACAGGGGCAGAGAUGAUGACCCU |
| AES641 | crRNA | SS | Lne crRNA L4 | GAGUACCUCAAAACAAAAGAGGACUAAAACCAGAUAUAGCCUGGUGGUUCAGGC |
| AES646 | crRNA | SS | Lsh crRNA (gggc) L4 | GGGCCACCCCAAUAUCGAAGGGGACUAAAACCAGAUAUAGCCUGGUGGUUCAGGC |
| AES647 | crRNA | SS | Lwa crRNA L4 | GACCACCCCAAUAUCGAAGGGGACUAAAACUUCAGAUAUAGCCUGGUGGUUCAGGC |
| AES639 | crRNA | HH PCR | HH-Ppr crRNA uncleaved | GGAUAUUCUGAUGAGGCCUUCGGGCCGAAACGGUGAAAGCCGUAAAUUAUCCCAAAAUUGAAGGG AACUACAACCAGAUAUAGCCUGGUGGUUCAGGC |
|  |  |  | Ppr crRNA L4 | AAUUAUCCCAAAAUUGAAGGGAACUACAACCAGAUAUAGCCUGGUGGUUCAGGC |
| AES642 | crRNA | HH PCR | HH-Rca crRNA uncleaved | GGGUGAUGCUCUGAUGAGGCCUUCGGGCCGAAACGGUGAAAGCCGUACAUCACCGCCAAGACGACGGC GGACUGAACCAGAUAUAGCCUGGUGGUUCAGGC |
|  |  |  | Rca-crRNA L4 | CATCACCGCCAAGACGACGGCGGACTGAACCAGATATAGCCTGGTGGTTCAGGC |
| AES618 | Target | SS | 18-mer Random | GGCAUGACUAGUCGUACUGCAUCG |
| MOC36 | Target | SS | Sp1/L3 Target | GGAAAUCAUUCAACACCCGCACUAUCGGAAGUUCACCAGCCAGCCGCAGCACGUU |
| MOC37 | Target | SS | Sp2/L4 Target | GGCAAUAAAAAUGCGCCGCCUGAACCACCAGGCUAUAUCUGCCACUCAUUGUUGUGA |
| AES532 | Target | SS | Sp3 Target- 31 mer | GGUCCAAGGGUCAUCAUCUCUGCCCCCACAG |
| AES450 | Target | SS | Sp3 Target- 60 mer | GGCACACCCGCAGGGGGGAGCCAAAAGGGUCAUCAUCUCUGCCCCCACAGCAGAAGCCCC |
| AES653 | Target | SS | Sp4 Target | GGACCAUAUAUCGAAAGUUAAGCUAGAAUGUGUCAUAUGGCAG |
| AES452 | Target | SS | Sp5 Target | GGGAACCCCAAGGCCAACCGCGAGAAGAUGACCCAGAUCAUGUUUGAGACCUUCAACACCCC |
| MOC28 | Target | SS | Sp6/L2 Target | GGCUCAAUUUUGACAGCCGGUCAUGGCAUUCCACUUAUCACUGGCAUCCUUCCACUC |
| AES652 | Target | IDT | FQ A5 | /56-FAM/rArArArArA/3IABkFQ/ |
| MOC533 | Target | IDT | FQ U5 | /56-FAM/rUrUrUrUrU/3IABkFQ/ |
| AES626 | Target | IDT | Homo A | rArArArArA |
| AES627 | Target | IDT | Homo C | rCrCrCrCrC |
| AES628 | Target | IDT | Homo G | rGrGrGrGrG |
| AES629 | Target | IDT | Homo U | rUrUrUrUrU |
| Lbu-CRISPR Array | pre-crRNA array | PCR | Six-mer Array Leader-Sp1-Sp2-Sp3-Sp4-Sp5-Sp6 | GGGCGAAUUGAAGGAAGCCCGUCAAGGCCGCAUGCCAUUAAUACGACUCACUAUAGGAUUUAGACC ACCCCAAAAAUGAAGGGGACUAAAACACUGGUGAACUUCCGAUAGUGCGGGUGUUGAAUGAUUUAG ACCACCCCAAAAAUGAAGGGGACUAAAACACAGAUAUAGCCUGGUGGUUCAGGCGGCCGCAUUGAUUU AGACCACCCCAAAAAUGAAGGGGACUAAAACAGGGGCAGAGAUGAUGACCCUUUGGCUCCCCCGAU UUAGACCACCCCAAAAAUGAAGGGGACUAAAACAAUGACACAUUCUAGCUUAACUUUCGAUAUAG AUUUAGACCACCCCAAAAAUGAAGGGGACUAAAACACAAACAUGAUCUGGGUCAUCUUCUCGCGGUU GGAUUUAGACCACCCCAAAAAUGAAGGGGACUAAAACAAUGCCAGUGAUAAGUGGAAUGCCAUGACC GCU |

Table 6

| Cas13a Homolog | rArArArArA Avg | SD | rCrCrCrCrC Avg | SD | rGrGrGrGrG Avg | SD | rUrUrUrUrU Avg | SD |
|---|---|---|---|---|---|---|---|---|
| Lbu | 2.66 | 0.15 | 0.96 | 0.09 | 17.83 | 0.79 | 92.69 | 2.10 |
| Lwa | 13.67 | 0.92 | 0.87 | 0.10 | 18.97 | 1.31 | 90.87 | 1.76 |
| Lba | 82.34 | 5.35 | 3.01 | 1.16 | 2.23 | 0.75 | 1.73 | 0.70 |
| Ppr | 1.19 | 0.26 | 0.50 | 0.14 | 10.21 | 6.63 | 93.20 | 4.78 |
| Hhe | 3.56 | 0.51 | 1.01 | 0.12 | 10.34 | 8.55 | 48.04 | 9.07 |
| Ere | 6.32 | 0.18 | 2.42 | 0.03 | 2.37 | 1.58 | 4.25 | 1.99 |

FIG. 52

Table 7

| Descriptive ID | RNA ID | Lbu WT Avg | SD | CamCas13a Avg | SD | EreCas13a Avg | SD | LbaCas13a Avg | SD | LwaCas13a Avg | SD | RcaCas13a Avg | SD | HheCas13a Avg | SD | PprCas13a Avg | SD | LshCas13a Avg | SD | LnyCas13a Avg | SD |
|---|---|---|---|---|---|---|---|---|---|---|---|---|---|---|---|---|---|---|---|---|---|
| pre-crLbu | AES634 | 82.0 | 3.1 | 0.0 | 3.2 | 0.3 | 0.7 | 0.2 | 0.7 | 3.6 | 2.1 | 44.0 | 29.7 | 4.7 | 3.1 | 78.5 | 5.5 | 40.8 | 9.7 | 58.8 | 38.5 |
| pre-crLse | AES625 | 29.1 | 11.9 | 0.8 | 1.3 | 0.3 | 1.7 | 74.7 | 7.6 | 0.9 | 0.9 | 49.3 | 28.4 | -0.5 | 2.2 | 27.0 | 4.7 | 39.9 | 7.8 | 55.9 | 21.1 |
| pre-crLba1 | AES555 | 1.7 | 2.7 | 15.3 | 6.8 | 2.5 | 1.6 | 75.9 | 7.0 | 2.5 | 3.1 | 2.5 | 2.6 | 0.8 | 2.0 | 1.3 | 3.0 | -0.2 | 1.8 | 2.8 | 2.2 |
| pre-crLba2 | AES556 | 0.1 | 1.9 | 7.6 | 2.5 | -0.1 | 3.7 | 75.4 | 7.1 | 0.4 | 3.4 | -0.7 | 4.1 | -1.9 | 5.0 | -2.2 | 5.5 | -2.5 | 4.1 | 0.3 | 7.3 |
| pre-crEre2 | AES557 | 1.6 | 1.4 | 63.9 | 6.0 | 69.7 | 1.7 | 76.2 | 6.4 | 0.7 | 1.4 | -1.4 | 3.8 | -2.2 | 3.7 | -1.4 | 3.5 | -2.7 | 8.3 | -1.8 | 6.3 |
| pre-crEre1 | AES558 | -0.9 | 2.3 | 68.5 | 9.5 | 66.4 | 6.8 | 74.5 | 9.7 | -0.3 | 2.7 | 0.4 | 3.4 | -1.7 | 5.1 | 0.2 | 4.9 | -0.5 | 7.1 | 2.5 | 3.2 |
| pre-crCam | AES559 | -0.1 | 1.2 | 72.1 | 4.4 | 33.6 | 5.9 | 77.7 | 3.4 | 0.7 | 0.9 | -0.2 | 0.4 | -1.2 | 0.6 | -1.3 | 1.1 | -0.6 | 0.7 | 0.6 | 0.3 |
| pre-crLwa | AES553 | 78.4 | 9.4 | 2.8 | 1.8 | 1.1 | 2.6 | 2.6 | 2.0 | 32.7 | 10.1 | 29.4 | 8.6 | 3.5 | 2.3 | 74.4 | 9.3 | 59.9 | 9.5 | 56.6 | 5.8 |
| pre-crLsh | AES566 | 79.0 | 7.0 | 1.3 | 2.7 | 0.8 | 1.7 | 1.9 | 2.4 | 24.0 | 9.4 | 6.1 | 1.8 | 5.4 | 8.1 | 69.0 | 11.5 | 59.9 | 9.6 | 60.9 | 16.6 |
| pre-crRca | AES568 | 1.6 | 1.4 | 0.8 | 2.0 | 1.5 | 2.8 | 2.1 | 2.3 | 4.6 | 2.7 | 80.7 | 3.4 | 5.4 | 3.6 | 4.4 | 2.0 | 5.4 | 5.0 | 4.4 | 3.5 |
| pre-crPpr | AES597 | -1.0 | 2.2 | -0.8 | 1.2 | -1.0 | 1.8 | 2.1 | 2.3 | -1.0 | 2.2 | -0.2 | 2.8 | -1.5 | 2.3 | 41.3 | 4.9 | -1.0 | 2.5 | 1.5 | 1.9 |
| pre-crHhe | AES620 | 5.8 | 4.5 | 3.9 | 14.3 | 1.9 | 10.4 | -1.0 | 6.9 | 0.5 | 4.4 | -2.8 | 9.7 | -6.6 | 5.2 | 3.5 | 9.4 | -6.5 | 6.6 | 3.8 | 10.6 |
| pre-crLne | AES619 | 48.6 | 1.7 | 0.7 | 2.3 | -0.5 | 1.3 | -0.1 | 0.3 | -0.9 | 3.2 | 5.6 | 3.6 | -2.4 | 1.5 | 50.6 | 4.4 | 1.3 | 2.9 | 61.4 | 1.1 |

FIG. 53

Table 8

| Guide | LwaCas13a slope | SE | LbaCas13a slope | SE | LbuCas13a slope | SE | PprCas13a slope | SE | HheCas13a slope | SE |
|---|---|---|---|---|---|---|---|---|---|---|
| Lwa pre-crRNA | 100.0 | 4.2 | 124.5 | 37.4 | 35.6 | 1.9 | 31.5 | 6.4 | 1.5 | 0.2 |
| Lba pre-crRNA | -0.3 | 0.0 | 0.0 | 0.0 | 1.8 | 0.1 | -0.6 | -0.1 | 100.0 | 15.8 |
| Ere pre-crRNA | -0.2 | 0.0 | -0.1 | 0.0 | 3.2 | 0.2 | 0.0 | 0.0 | 152.5 | 27.3 |
| Cam pre-crRNA | -0.3 | 0.0 | 0.0 | 0.0 | 2.7 | 0.2 | 0.0 | 0.0 | 77.8 | 10.0 |
| Lsh pre-crRNA | 120.7 | 7.7 | 166.0 | 49.8 | 71.7 | 4.8 | 30.7 | 6.3 | 2.4 | 0.3 |
| Rca pre-crRNA | 0.0 | 0.0 | 0.0 | -0.7 | 26.6 | 1.4 | 0.1 | 0.0 | 0.8 | 0.1 |
| Ppr pre-crRNA | 37.4 | 1.4 | 100.0 | 42.4 | 66.4 | 4.3 | 86.7 | 22.8 | 1.5 | 0.2 |
| Lne pre-crRNA | -0.2 | 0.0 | 104.6 | 31.4 | 29.8 | 1.6 | 7.1 | 1.6 | 1.3 | 0.2 |
| Hhe pre-crRNA | 0.0 | 0.0 | 16.2 | 4.9 | 100.0 | 7.3 | -0.1 | 0.0 | 0.8 | 0.1 |
| Lse pre-crRNA | 1.5 | 0.0 | 170.2 | 51.1 | 63.7 | 3.6 | 6.6 | 1.8 | 51.5 | 6.0 |
| Lbu pre-crRNA | 140.0 | 12.0 | 90.0 | 27.0 | 42.6 | 2.2 | 100.0 | 28.0 | 7.8 | 0.9 |

FIG. 54

Table 9

| Guide | LwaCas13a slope | SE | LbaCas13a slope | SE | LbuCas13a slope | SE | PprCas13a slope | SE | HheCas13a slope | SE |
|---|---|---|---|---|---|---|---|---|---|---|
| Cam crRNA | 0.0 | 0.1 | 174.8 | 50.9 | -0.2 | 0.0 | -0.9 | -0.1 | 7.4 | 0.4 |
| Lba crRNA | -0.4 | -0.1 | 100.0 | 22.3 | 0.0 | 0.0 | -1.2 | -0.1 | 12.6 | 0.7 |
| Ere crRNA | -0.5 | -0.1 | 81.7 | 23.5 | 0.1 | 0.0 | -0.8 | 0.0 | 6.5 | 0.4 |
| Ppr crRNA | 77.8 | 14.3 | 1.5 | 0.2 | 11.6 | 0.7 | 100.0 | 2.6 | 100.0 | 7.5 |
| Lne crRNA | 0.1 | 0.0 | 1.6 | 0.3 | 0.1 | 0.0 | -0.2 | -0.1 | 54.7 | 3.0 |
| Rca crRNA | -0.1 | -0.1 | 3.9 | 0.6 | -0.8 | 0.0 | -0.1 | -0.1 | 50.4 | 2.7 |
| Lsh crRNA | 93.3 | 21.5 | 0.9 | 0.2 | 10.0 | 0.5 | 27.2 | 1.1 | 75.9 | 4.5 |
| Lwa crRNA | 100.0 | 24.3 | 10.6 | 1.7 | 75.7 | 5.5 | 12.8 | 0.4 | 60.4 | 3.7 |
| Lbu crRNA | 98.2 | 18.2 | 21.1 | 3.4 | 100.0 | 6.1 | 398.3 | 20.8 | 92.6 | 7.0 |

FIG. 56A

>WP_012985477.1 WP_012985477.1 hypothetical protein [Listeria seeligeri]
MWISIKTLIHHLGVLFFCDYMYNRREKKIIEVKTMRITKVEVDRKKVLISRDKNGGKLVY
ENEMQDNTEQIMHHKKSSFYKSVVNKTICRPEQKQMKKLVHGLLQENSQEKIKVSDVTKL
NISNFLNHRFKKSLYYFPENSPDKSEEYRIEINLSQLLEDSLKKQQGTFICWESFSKDME
LYINWAENYISSKTKLIKKSIRNNRIQSTESRSGQLMDRYMKDILNKNKPFDIQSVSEKY
QLEKLTSALKATFKEAKKNDKEINYKLKSTLQNHERQIIEELKENSELNQFNIEIRKHLE
TYFPIKKTNRKVGDIRNLEIGEIQKIVNHRLKNKIVQRILQEGKLASYEIESTVNSNSLQ
KIKIEEAFALKFINACLFASNNLRNMVYPVCKKDILMIGEFKNSFKEIKHKKFIRQWSQF
FSQEITVDDIELASWGLRGAIAPIRNEIIHLKKHSWKKFFNNPTFKVKKSKIINGKTKDV
TSEFLYKETLFKDYFYSELDSVPELIINKMESSKILDYYSSDQLNQVFTIPNFELSLLTS
AVPFAPSFKRVYLKGFDYQNQDEAQPDYNLKLNIYNEKAFNSEAFQAQYSLFKMVYYQVF
LPQFTTNNDLFKSSVDFILTLNKERKGYAKAFQDIRKMNKDEKPSEYMSYIQSQLMLYQK
KQEEKEKINHFEKFINQVFIKGFNSFIEKNRLTYICHPTKNTVPENDNIEIPFHTDMDDS
NIAFWLMCKLLDAKQLSELRNEMIKFSCSLQSTEEISTFTKAREVIGLALLNGEKGCNDW
KELFDDKEAWKKNMSLYVSEELLQSLPYTQEDGQTPVINRSIDLVKKYGTETILEKLFSS
SDDYKVSAKDIAKLHEYDVTEKIAQQESLHKQWIEKPGLARDSAWTKKYQNVINDISNYQ
WAKTKVELTQVRHLHQLTIDLLSRLAGYMSIADRDFQFSSNYILERENSEYRVTSWILLS
ENKNKNKYNDYELYNLKNASIKVSSKNDPQLKVDLKQLRLTLEYLELFDNRLKEKRNNIS
HFNYLNGQLGNSILELFDDARDVLSYDRKLKNAVSKSLKEILSSHGMEVTFKPLYQTNHH
LKIDKLQPKKIHHLGEKSTVSSNQVSNEYCQLVRTLLTMK

FIG. 56B
>WP_013443710.1 WP_013443710.1 hypothetical protein [Paludibacter propionicigenes]
MRVSKVKVKDGGKDKMVLVHRKTTGAQLVYSGQPVSNETSNILPEKKRQSFDLSTLNKTI
IKFDTAKKQKLNVDQYKIVEKIFKYPKQELPKQIKAEEILPFLNHKFQEPVKYWKNGKEE
SFNLTLLIVEAVQAQDKRKLQPYYDWKTWYIQTKSDLLKKSIENNRIDLTENLSKRKKAL
LAWETEFTASGSIDLTHYHKVYMTDVLCKMLQDVKPLTDDKGKINTNAYHRGLKKALQNH
QPAIFGTREVPNEANRADNQLSIYHLEVVKYLEHYFPIKTSKRRNTADDIAHYLKAQTLK
TTIEKQLVNAIRANIIQQGKTNHHELKADTTSNDLIRIKTNEAFVLNLTGTCAFAANNIR
NMVDNEQTNDILGKGDFIKSLLKDNTNSQLYSFFFGEGLSTNKAEKETQLWGIRGAVQQI
RNNVNHYKKDALKTVFNISNFENPTITDPKQQTNYADTIYKARFINELEKIPEAFAQQLK
TGGAVSYYTIENLKSLLTTFQFSLCRSTIPFAPGFKKVFNGGINYQNAKQDESFYELMLE
QYLRKENFAEESYNARYFMLKLIYNNLFLPGFTTDRKAFADSVGFVQMQNKKQAEKVNPR
KKEAYAFEAVRPMTAADSIADYMAYVQSELMQEQNKKEEKVAEETRINFEKFVLQVFIKG
FDSFLRAKEFDFVQMPQPQLTATASNQQKADKLNQLEASITADCKLTPQYAKADDATHIA
FYVFCKLLDAAHLSNLRNELIKFRESVNEFKFHHLLEIIEICLLSADVVPTDYRDLYSSE
ADCLARLRPFIEQGADITNWSDLFVQSDKHSPVIHANIELSVKYGTTKLLEQIINKDTQF
KTTEANFTAWNTAQKSIEQLIKQREDHHEQWVKAKNADDKEKQERKREKSNFAQKFIEKH
GDDYLDICDYINTYNWLDNKMHFVHLNRLHGLTIELLGRMAGFVALFDRDFQFFDEQQIA
DEFKLHGFVNLHSIDKKLNEVPTKKIKEIYDIRNKIIQINGNKINESVRANLIQFISSKR
NYYNNAFLHVSNDEIKEKQMYDIRNHIAHFNYLTKDAADFSLIDLINELRELLHYDRKLK
NAVSKAFIDLFDKHGMILKLKLNADHKLKVESLEPKKIYHLGSSAKDKPEYQYCTNQVMM
AYCNMCRSLLEMKK

FIG. 56C
>WP_015770004.1 WP_015770004.1 hypothetical protein [Leptotrichia buccalis]
MKVTKVGGISHKKYTSEGRLVKSESEENRTDERLSALLNMRLDMYIKNPSSTETKENQKR
IGKLKKFFSNKMVYLKDNTLSLKNGKKENIDREYSETDILESDVRDKKNFAVLKKIYLNE
NVNSEELEVFRNDIKKKLNKINSLKYSFEKNKANYQKINENNIEKVEGKSKRNIIYDYYR
ESAKRDAYVSNVKEAFDKLYKEEDIAKLVLEIENLTKLEKYKIREFYHEIIGRKNDKENF
AKIIYEEIQNVNNMKELIEKVPDMSELKKSQVFYKYYLDKEELNDKNIKYAFCHFVEIEM
SQLLKNYVYKRLSNISNDKIKRIFEYQNLKKLIENKLLNKLDTYVRNCGKYNYYLQDGEI
ATSDFIARNRQNEAFLRNIIGVSSVAYFSLRNILETENENDITGRMRGKTVKNNKGEEKY
VSGEVDKIYNENKKNEVKENLKMFYSYDFNMDNKNEIEDFFANIDEAISSIRHGIVHFNL
ELEGKDIFAFKNIAPSEISKKMFQNEINEKKLKLKIFRQLNSANVFRYLEKYKILNYLKR
TRFEFVNKNIPFVPSFTKLYSRIDDLKNSLGIYWKTPKTNDDNKTKEIIDAQIYLLKNIY
YGEFLNYFMSNNGNFFEISKEIIELNKNDKRNLKTGFYKLQKFEDIQEKIPKEYLANIQS
LYMINAGNQDEEEKDTYIDFIQKIFLKGFMTYLANNGRLSLIYIGSDEETNTSLAEKKQE
FDKFLKKYEQNNNIKIPYEINEFLREIKLGNILKYTERLNMFYLILKLLNHKELTNLKGS
LEKYQSANKEEAFSDQLELINLLNLDNNRVTEDFELEADEIGKFLDFNGNKVKDNKELKK
FDTNKIYFDGENIIKHRAFYNIKKYGMLNLLEKIADKAGYKISIEELKKYSNKKNEIEKN
HKMQENLHRKYARPRKDEKFTDEDYESYKQAIENIEEYTHLKNKVEFNELNLLQGLLLRI
LHRLVGYTSIWERDLRFRLKGEFPENQYIEEIFNFENKKNVKYKGGQIVEKYIKFYKELH
QNDEVKINKYSSANIKVLKQEKKDLYIRNYIAHFNYIPHAEISLLEVLENLRKLLSYDRK
LKNAVMKSVVDILKEYGFVATFKIGADKKIGIQTLESEKIVHLKNLKKKKLMTDRNSEEL
CKLVKIMFEYKMEEKKSEN

FIG. 56D

>WP_018451595.1 WP_018451595.1 hypothetical protein [Leptotrichia shahii]
MGNLFGHKRWYEVRDKKDFKIKRKVKVKRNYDGNKYILNINENNNKEKIDNNKFIRKYIN
YKKNDNILKEFTRKFHAGNILFKLKGKEGIIRIENNDDFLETEEVVLYIEAYGKSEKLKA
LGITKKKIIDEAIRQGITKDDKKIEIKRQENEEEIEIDIRDEYTNKTLNDCSIILRIIEN
DELETKKSIYEIFKNINMSLYKIIEKIIENETEKVFENRYYEEHLREKLLKDDKIDVILT
NFMEIREKIKSNLEILGFVKFYLNVGGDKKKSKNKKMLVEKILNINVDLTVEDIADFVIK
ELEFWNITKRIEKVKKVNNEFLEKRRNRTYIKSYVLLDKHEKFKIERENKKDKIVKFFVE
NIKNNSIKEKIEKILAEFKIDELIKKLEKELKKGNCDTEIFGIFKKHYKVNFDSKKFSKK
SDEEKELYKIIYRYLKGRIEKILVNEQKVRLKKMEKIEIEKILNESILSEKILKRVKQYT
LEHIMYLGKLRHNDIDMTTVNTDDFSRLHAKEELDLELITFFASTNMELNKIFSRENINN
DENIDFFGGDREKNYVLDKKILNSKIKIIRDLDFIDNKNNITNNFIRKFTKIGTNERNRI
LHAISKERDLQGTQDDYNKVINIIQNLKISDEEVSKALNLDVVFKDKKNIITKINDIKIS
EENNNDIKYLPSFSKVLPEILNLYRNNPKNEPFDTIETEKIVLNALIYVNKELYKKLILE
DDLEENESKNIFLQELKKTLGNIDEIDENIIENYYKNAQISASKGNNKAIKKYQKKVIEC
YIGYLRKNYEELFDFSDFKMNIQEIKKQIKDINDNKTYERITVKTSDKTIVINDDFEYII
SIFALLNSNAVINKIRNRFFATSVWLNTSEYQNIIDILDEIMQLNTLRNECITENWNLNL
EEFIQKMKEIEKDFDDFKIQTKKEIFNNYYEDIKNNILTEFKDDINGCDVLEKKLEKIVI
FDDETKFEIDKKSNILQDEQRKLSNINKKDLKKKVDQYIKDKDQEIKSKILCRIIFNSDF
LKKYKKEIDNLIEDMESENENKFQEIYYPKERKNELYIYKKNLFLNIGNPNFDKIYGLIS
NDIKMADAKFLFNIDGKNIRKNKISEIDAILKNLNDKLNGYSKEYKEKYIKKLKENDDFF
AKNIQNKNYKSFEKDYNRVSEYKKIRDLVEFNYLNKIESYLIDINWKLAIQMARFERDMH
YIVNGLRELGIIKLSGYNTGISRAYPKRNGSDGFYTTTAYYKFFDEESYKKFEKICYGFG
IDLSENSEINKPENESIRNYISHFYIVRNPFADYSIAEQIDRVSNLLSYSTRYNNSTYAS
VFEVFKKDVNLDYDELKKKFKLIGNNDILERLMKPKKVSVLELESYNSDYIKNLIIELLT
KIENTNDTL

FIG. 56E

```
>ERK53440.1 ERK53440.1 hypothetical protein HMPREF9015_00520
[Leptotrichia wadei F0279]
MYMKITKIDGVSHYKKQDKGILKKKWKDLDERKQREKIEARYNKQIESKIYKEFFRLKNK
KRIEKEEDQNIKSLYFFIKELYLNEKNEEWELKNINLEILDDKERVIKGYKFKEDVYFFK
EGYKEYYLRILFNNLIEKVQNENREKVRKNKEFLDLKEIFKKYKNRKIDLLLKSINNNKI
NLEYKKENVNEEIYGINPTNDREMTFYELLKEIIEKKDEQKSILEEKLDNFDITNFLENI
EKIFNEETEINIIKGKVLNELREYIKEKEENNSDNKLKQIYNLELKKYIENNFSYKKQKS
KSKNGKNDYLYLNFLKKIMFIEEVDEKKEINKEKFKNKINSNFKNLFVQHILDYGKLLYY
KENDEYIKNTGQLETKDLEYIKTKETLIRKMAVLVSFAANSYYNLFGRVSGDILGTEVVK
SSKTNVIKVGSHIFKEKMLNYFFDFEIFDANKIVEILESISYSIYNVRNGVGHFNKLILG
KYKKKDINTNKRIEEDLNNNEEIKGYFIKKRGEIERKVKEKFLSNNLQYYYSKEKIENYF
EVYEFEILKRKIPFAPNFKRIIKKGEDLFNNKNNKKYEYFKNFDKNSAEEKKEFLKTRNF
LLKELYYNNFYKEFLSKKEEFEKIVLEVKEEKKSRGNINNKKSGVSFQSIDDYDTKINIS
DYIASIHKKEMERVEKYNEEKQKDTAKYIRDFVEEIFLTGFINYLEKDKRLHFLKEEFSI
LCNNNNNVVDFNININEEKIKEFLKENDSKTLNLYFFNMIDSKRISEFRNELVKYKQFT
KKRLDEEKEFLGIKIELYETLIEFVILTREKLDTKKSEEIDAWLVDKLYVKDSNEYKEYE
EILKLFVDEKILSSKEAPYYATDNKTPILLSNFEKTRKYGTQSFLSEIQSNYKYSKVEKE
NIEDYNKKEEIEQKKKSNIEKLQDLKVELHKKWEQNKITEKEIEKYNNTTRKINEYNYLK
NKEELQNVYLLHEMLSDLLARNVAFFNKWERDFKFIVIAIKQFLRENDKEKVNEFLNPPD
NSKGKKVYFSVSKYKNTVENIDGIHKNFMNLIFLNNKFMNRKIDKMNCAIWVYFRNYIAH
FLHLHTKNEKISLISQMNLLIKLFSYDKKVQNHILKSTKTLLEKYNIQINFEISNDKNEV
FKYKIKNRLYSKKGKMLGKNNKFEILENEFLENVKAMLEYSE
```

FIG. 56F

```
>WP_022785443.1 WP_022785443.1 hypothetical protein
[Lachnospiraceae bacterium NK4A179]
MKISKVREENRGAKLTVNAKTAVVSENRSQEGILYNDPSRYGKSRKNDEDRDRYIESRLK
SSGKLYRIFNEDKNKRETDELQWFLSEIVKKINRRNGLVLSDMLSVDDRAFEKAFEKYAE
LSYTNRRNKVSGSPAFETCGVDAATAERLKGIISETNFINRIKNNIDNKVSEDIIDRIIA
KYLKKSLCRERVKRGLKKLLMNAFDLPYSDPDIDVQRDFIDYVLEDFYHVRAKSQVSRSI
KNMNMPVQPEGDGKFAITVSKGGTESGNKRSAEKEAFKKFLSDYASLDERVRDDMLRRMR
RLVVLYFYGSDDSKLSDVNEKFDVWEDHAARRVDNREFIKLPLENKLANGKTDKDAERIR
KNTVKELYRNQNIGCYRQAVKAVEEDNNGRYFDDKMLNMFFIHRIEYGVEKIYANLKQVT
EFKARTGYLSEKIWKDLINYISIKYIAMGKAVYNYAMDELNASDKKEIELGKISEEYLSG
ISSFDYELIKAEEMLQRETAVYVAFAARHLSSQTVELDSENSDFLLLKPKGTMDKNDKNK
LASNNILNFLKDKETLRDTILQYFGGHSLWTDPFDKYLAGGKDDVDFLTDLKDVIYSMR
NDSFHYATENHNNGKWNKELISAMFEHETERMTVVMKDKFYSNNLPMFYKNDDLKKLLID
LYKDNVERASQVPSFNKVFVRKNFPALVRDKDNLGIELDLKADADKGENELKFYNALYYM
FKEIYYNAFLNDKNVRERFITKATKVADNYDRNKERNLKDRIKSAGSDEKKKLREQLQNY
IAENDFGQRIKNIVQVNPDYTLAQICQLIMTEYNQQNNGCMQKKSAARKDINKDSYQHYK
MLLLVNLRKAFLEFIKENYAFVLKPYKHDLCDKADFVPDFAKYVKPYAGLISRVAGSSEL
QKWYIVSRFLSPAQANHMLGFLHSYKQYVWDIYRRASETGTEINHSIAEDKIAGVDITDV
DAVIDLSVKLCGTISSEISDYFKDDEVYAEYISSYLDFEYDGGNYKDSLNRFCNSDAVND
QKVALYYDGEHPKLNRNIILSKLYGERRFLEKITDRVSRSDIVEYYKLKKETSQYQTKGI
FDSEDEQKNIKKFQEMKNIVEFRDLMDYSEIADELQGQLINWIYLRERDLMNFQLGYHYA
CLNNDSNKQATYVTLDYQGKKNRKINGAILYQICAMYINGLPLYYVDKDSSEWTVSDGKE
STGAKIGEFYRYAKSFENTSDCYASGLEIFENISEHDNITELRNYIEHFRYYSSFDRSFL
GIYSEVFDRFFTYDLKYRKNVPTILYNILLQHFVNRFEFVSGKKMIGIDKKDRKIAKEK
ECARITIREKNGVYSEQFTYKLKNGTVYVDARDKRYLQSIIRLLFYPEKVNMDEMIEVKE
KKKPSDNNTGKGYSKRDRQQDRKEYDKYKEKKKKEGNFLSGMGGNINWDEINAQLKN
```

FIG. 56G

```
>ETD76934.1 ETD76934.1 hypothetical protein U717_11515
[Rhodobacter capsulatus R121]
MQIGKVQGRTISEFGDPAGGLKRKISTDGKNRKELPAHLSSDPKALIGQWISGIDKIYRK
PDSRKSDGKAIHSPTPSKMQFDARDDLGEAFWKLVSEAGLAQDSDYDQFKRRLHPYGDKF
QPADSGAKLKFEADPPEPQAFHGRWYGAMSKRGNDAKELAAALYEHLHVDEKRIDGQPKR
NPKTDKFAPGLVVARALGIESSVLPRGMARLARNWGEEEIQTYFVVDVAASVKEVAKAAV
SAAQAFDPPRQVSGRSLSPKVGFALAEHLERVTGSKRCSFDPAAGPSVLALHDEVKKTYK
RLCARGKNAARAFPADKTELLALMRHTHENRVRNQMVRMGRVSEYRGQQAGDLAQSHYWT
SAGQTEIKESEIFVRLWVGAFALAGRSMKAWIDPMGKIVNTEKNDRDLTAAVNIRQVISN
KEMVAEAMARRGIYFGETPELDRLGAEGNEGFVFALLRYLRGCRNQTFHLGARAGFLKEI
RKELEKTRWGKAKEAEHVVLTDKTVAAIRAIIDNDAKALGARLLADLSGAFVAHYASKEH
FSTLYSEIVKAVKDAPEVSSGLPRLKLLLKRADGVRGYVHGLRDTRKHAFATKLPPPPAP
RELDDPATKARYIALLRLYDGPFRAYASGITGTALAGPAARAKEAATALAQSVNVTKAYS
DVMEGRSSRLRPPNDGETLREYLSALTGETATEFRVQIGYESDSENARKQAEFIENYRRD
MLAFMFEDYIRAKGFDWILKIEPGATAMTRAPVLPEPIDTRGQYEHWQAALYLVMHFVPA
SDVSNLLHQLRKWEALQGKYELVQDGDATQADARREALDLVKRFRDVLVLFLKTGEARF
EGRAAPFDLKPFRALFANPATFDRLFMATPTTARPAEDDPEGDGASEPELRVARTLRGLR
QIARYNHMAVLSDLFAKHKVRDEEVARLAEIEDETQEKSQIVAAQELRTDLHDKVMKCHP
KTISPEERQSYAAAIKTIEEHRFLVGRVYLGDHLRLHRLMMDVIGRLIDYAGAYERDTGT
FLINASKQLGAGADWAVTIAGAANTDARTQTRKDLAHFNVLDRADGTPDLTALVNRAREM
MAYDRKRKNAVPRSILDMLARLGLTLKWQMKDHLLQDATITQAAIKHLDKVRLTVGGPAA
VTEARFSQDYLQMVAAVFNGSVQNPKPRRRDDGDAWHKPPKPATAQSQPDQKPPNKAPSA
GSRLPPPQVGEVYEGVVVKVIDTGSLGFLAVEGVAGNIGLHISRLRRIREDAIIVGRRYR
FRVEIYVPPKSNTSKLNAADLVRID
```

FIG. 56H

```
>WP_031473346.1 WP_031473346.1 hypothetical protein
[[Clostridium] aminophilum]
MKFSKVDHTRSAVGIQKATDSVHGMLYTDPKKQEVNDLDKRFDQLNVKAKRLYNVFNQSK
AEEDDDEKRFGKVVKKLNRELKDLLFHREVSRYNSIGNAKYNYYGIKSNPEEIVSNLGMV
ESLKGERDPQKVISKLLLYYLRKGLKPGTDGLRMILEASCGLRKLSGDEKELKVFLQTLD
EDFEKKTFKKNLIRSIENQNMAVQPSNEGDPIIGITQGRFNSQKNEEKSAIERMMSMYAD
LNEDHREDVLRKLRRLNVLYFNVDTEKTEEPTLPGEVDTNPVFEVWHDHEKGKENDRQFA
TFAKILTEDRETRKKEKLAVKEALNDLKSAIRDHNIMAYRCSIKVTEQDKDGLFFEDQRI
NRFWIHHIESAVERILASINPEKLYKLRIGYLGEKVWKDLLNYLSIKYIAVGKAVFHFAM
EDLGKTGQDIELGKLSNSVSGGLTSFDYEQIRADETLQRQLSVEVAFAANNLFRAVVGQT
GKKIEQSKSEENEEDFLLWKAEKIAESIKKEGEGNTLKSILQFFGGASSWDLNHFCAAYG
NESSALGYETKFADDLRKAIYSLRNETFHFTTLNKGSFDWNAKLIGDMFSHEAATGIAVE
RTRFYSNNLPMFYRESDLKRIMDHLYNTYHPRASQVPSFNSVFVRKNFRLFLSNTLNTNT
SFDTEVYQKWESGVYYLFKEIYYNSFLPSGDAHHLFFEGLRRIRKEADNLPIVGKEAKKR
NAVQDFGRRCDELKNLSLSAICQMIMTEYNEQNNGNRKVKSTREDKRKPDIFQHYKMLLL
RTLQEAFAIYIRREEFKFIFDLPKTLYVMKPVEEFLPNWKSGMFDSLVERVKQSPDLQRW
YVLCKFLNGRLLNQLSGVIRSYIQFAGDIQRRAKANHNRLYMDNTQRVEYYSNVLEVVDF
CIKGTSRFSNVFSDYFRDEDAYADYLDNYLQFKDEKIAEVSSFAALKTFCNEEEVKAGIY
MDGENPVMQRNIVMAKLFGPDEVLKNVVPKVTREEIEEYYQLEKQIAPYRQNGYCKSEED
QKKLLRFQRIKNRVEFQTITEFSEIINELLGQLISWSFLRERDLLYFQLGFHYLCLHNDT
EKPAEYKEISREDGTVIRNAILHQVAAMYVGGLPVYTLADKKLAAFEKGEADCKLSISKD
TAGAGKKIKDFFRYSKYVLIKDRMLTDQNQKYTIYLAGLELFENTDEHDNITDVRKYVDH
FKYYATSDENAMSILDLYSEIHDRFFTYDMKYQKNVANMLENILLRHFVLIRPEFFTGSK
KVGEGKKITCKARAQIEIAENGMRSEDFTYKLSDGKKNISTCMIAARDQKYLNTVARLLY
YPHEAKKSIVDTREKKNNKKTNRGDGTFNKQKGTARKEKDNGPREFNDTGFSNTPFAGFD
PFRNS
```

FIG. 56I

>WP_036091002.1 WP_036091002.1 hypothetical protein [Listeria newyorkensis]
MKITKMRVDGRTIVMERTSKEGQLGYEGIDGNKTTEIIFDKKKESFYKSILNKTVRKPDE
KEKNRRKQAINKAINKEITELMLAVLHQEVPSQKLHNLKSLNTESLTKLFKPKFQNMISY
PPSKGAEHVQFCLTDIAVPAIRDLDEIKPDWGIFFEKLKPYTDWAESYIHYKQTTIQKSI
EQNKIQSPDSPRKLVLQKYVTAFLNGEPLGLDLVAKKYKLADLAESFKLVDLNEDKSANY
KIKACLQQHQRNILDELKEDPELNQYGIEVKKYIQRYFPIKRAPNRSKHARADFLKKELI
ESTVEQQFKNAVYHYVLEQGKMEAYELTDPKTKDLQDIRSGEAFSFKFINACAFASNNLK
MILNPECEKDILGKGNFKKNLPNSTTRSDVVKKMIPFFSDELQNVNFDEAIWAIRGSIQQ
IRNEVYHCKKHSWKSILKIKGFEFEPNNMKYADSDMQKLMDKDIAKIPEFIEEKLKSSGV
VRFYRHDELQSIWEMKQGFSLLTTNAPFVPSFKRVYAKGHDYQTSKNRYYNLDLTTFDIL
EYGEEDFRARYFLTKLVYYQQFMPWFTADNNAFRDAANFVLRLNKNRQQDAKAFINIREV
EEGEMPRDYMGYVQGQIAIHEDSIEDTPNHFEKFISQVFIKGFDRHMRSANLKFIKNPRN
QGLEQSEIEEMSFDIKVEPSFLKNKDDYIAFWIFCKMLDARHLSELRNEMIKYDGHLTGE
QEIIGLALLGVDSRENDWKQFFSSEREYEKIMGYVVEELYQREPYRQSDGKTPILFRGV
EQARKYGTETVIQRLFDANPEFKVSKCNLAEWERQKETIEETIKRRKELHNEWAKNPKKP
QNNAFFKEYKECCDAIDAYNWHKNKTTLAYVNELHHLLIEILGRYVGYVAIADRDFQCMA
NQYFKHSGITERVEYWGDNRLKSIKKLDTFLKKEGLFVSEKNARNHIAHLNYLSLKSECT
LLYLSERLREIFKYDRKLKNAVSKSLIDILDRHGMSVVFANLKENKHRLVIKSLEPKKLR
HLGGKKIDGGYIETNQVSEEYCGIVKRLLEM

FIG. 56J

>WP_055061018.1 Eubacterium rectale genome assembly T1815, contig T1815_16, whole genome shotgun sequence
MLRRDKEVKKLYNVFNQIQVGTKPKKWNNDEKLSPEENERRAQQKNIKMKNYKWREACSK
YVESSQRIINDVIFYSYRKAKNKLRYMRKNEDILKKMQEAEKLSKFSGGKLEDFVAYTLR
KSLVVSKYDTQEFDSLAAMVVFLECIGKNNISDHEREIVCKLLELIRKDFSKLDPNVKGS
QGANIVRSVRNQNMIVQPQGDRFLFPQVYAKENETVTNKNVEKEGLNEFLLNYANLDDEK
RAESLRKLRRILDVYFSAPNHYEKDMDITLSDNIEKEKFNVWEKHECGKKETGLFVDIPD
VLMEAEAENIKLDAVVEKRERKVLNDRVRKQNIICYRYTRAVVEKYNSNEPLFFENNAIN
QYWIHHIENAVERILKNCKAGKLFKLRKGYLAEKVWKDAINLISIKYIALGKAVYNFALD
DIWKDKKNKELGIVDERIRNGITSFDYEMIKAHENLQRELAVDIAFSVNNLARAVCDMSN
LGNKESDFLLWKRNDIADKLKNKDDMASVSAVLQFFGGKSSWDINIFKDAYKGKKKYNYE
VRFIDDLRKAIYCARNENFHFKTALVNDEKWNTELFGKIFERETEFCLNVEKDRFYSNNL
YMFYQVSELRNMLDHLYSRSVSRAAQVPSYNSVIVRTAFPEYITNVLGYQKPSYDADTLG
KWYSACYYLLKEIYYNSFLQSDRALQLFEKSVKTLSWDDKKQQRAVDNFKDHFSDIKSAC
TSLAQVCQIYMTEYNQQNNQIKKVRSSNDSIFDQPVYQHYKVLLKKAIANAFADYLKNNK
DLFGFIGKPFKANEIREIDKEQFLPDWTSRKYEALCIEVSGSQELQKWYIVGKFLNARSL
NLMVGSMRSYIQYVTDIKRRAASIGNELHVSVHDVEKVEKWVQVIEVCSLLASRTSNQFE
DYFNDKDDYARYLKSYVDFSNVDMPSEYSALVDFSNEEQSDLYVDPKNPKVNRNIVHSKL
FAADHILRDIVEPVSKDNIEEFYSQKAEIAYCKIKGKEITAEEQKAVLKYQKLKNRVELR
DIVEYGEIINELLGQLINWSFMRERDLLYFQLGFHYDCLRNDSKKPEGYKNIKVDENSIK
DAILYQIIGMYVNGVTVYAPEKDGDKLKEQCVKGGVGVKVSAFHRYSKYLGLNEKTLYNA
GLEIFEVVAEHEDIINLRNGIDHFKYYLGDYRSMLSIYSEVFDRFFTYDIKYQKNVLNLL
QNILLRHNVIVEPILESGFKTIGEQTKPGAKLSIRSIKSDTFQYKVKGGTLITDAKDERY
LETIRKILYYAENEEDNLKKSVVVTNADKYEKNKESDDQNKQKEKKNKDNKGKKNEETKS
DAEKNNNERLSYNPFANLNFKLSN

FIG. 56K

```
>CRZ35554.1 Herbinix hemicellulosilytica genome assembly TUM3/55,
contig 02_T3/55T_contig26, whole genome shotgun sequence
MKLTRRRISGNSVDQKITAAFYRDMSQGLLYYDSEDNDCTDKVIESMDFERSWRGRILKN
GEDDKNPFYMFVKGLVGSNDKIVCEPIDVDSDPDNLDILINKNLTGFGRNLKAPDSNDTL
ENLIRKIQAGIPEEEVLPELKKIKEMIQKDIVNRKEQLLKSIKNNRIPFSLEGSKLVPST
KKMKWLFKLIDVPNKTFNEKMLEKYWEIYDYDKLKANITNRLDKTDKKARSISRAVSEEL
REYHKNLRTNYNRFVSGDRPAAGLDNGGSAKYNPDKEEFLLFLKEVEQYFKKYFPVKSKH
SNKSKDKSLVDKYKNYCSYKVVKKEVNRSIINQLVAGLIQQGKLLYYFYYNDTWQEDFLN
SYGLSYIQVEEAFKKSVMTSLSWGINRLTSFFIDDSNTVKFDDITTKKAKEAIESNYFNK
LRTCSRMQDHFKEKLAFFYPVYVKDKKDRPDDDIENLIVLVKNAIESVSYLRNRTFHFKE
SSLLELLKELDDKNSGQNKIDYSVAAEFIKRDIENLYDVFREQIRSLGIAEYYKADMISD
CFKTCGLEFALYSPKNSLMPAFKNVYKRGANLNKAYIRDKGPKETGDQGQNSYKALEEYR
ELTWYIEVKNNDQSYNAYKNLLQLIYYHAFLPEVRENEALITDFINRTKEWNRKETEERL
NTKNNKKHKNFDENDDITVNTYRYESIPDYQGESLDDYLKVLQRKQMARAKEVNEKEEGN
NNYIQFIRDVVVWAFGAYLENKLKNYKNELQPPLSKENIGLNDTLKELFPEEKVKSPFNI
KCRFSISTFIDNKGKSTDNTSAEAVKTDGKEDEKDKKNIKRKDLLCFYLFLRLLDENEIC
KLQHQFIKYRCSLKERRFPGNRTKLEKETELLAELEELMELVRFTMPSIPEISAKAESGY
DTMIKKYFKDFIEKKVFKNPKTSNLYYHSDSKTPVTRKYMALLMRSAPLHLYKDIFKGYY
LITKKECLEYIKLSNIIKDYQNSLNELHEQLERIKLKSEKQNGKDSLYLDKKDFYKVKEY
VENLEQVARYKHLQHKINFESLYRIFRIHVDIAARMVGYTQDWERDMHFLFKALVYNGVL
EERRFEAIFNNNDDNNDGRIVKKIQNNLNNKNRELVSMLCWNKKLNKNEFGAIIWKRNPI
AHLNHFTQTEQNSKSSLESLINSLRILLAYDRKRQNAVTKTINDLLLNDYHIRIKWEGRV
DEGQIYFNIKEKEDIENEPIIHLKHLHKKDCYIYKNSYMFDKQKEWICNGIKEEVYDKSI
LKCIGNLFKFDYEDKNKSSANPKHT
```

```
 3 502750493_Listeria_seeligeri                    11.1%
 4 503209049_Paludibacter_propionicigenes          11.3%
 5 506250229_Leptotrichia_buccalis                 11.6%
 6 517262777_Leptotrichia_shahii                    9.2%
 7 544240864_Leptotrichia_wadei                    11.8%
 8 545620493_Leptotrichia_oral_taxon_879            8.8%
 9 545623306_Leptotrichia_wadei                    12.3%
10 545623740_Leptotrichia_wadei                    11.0%
11 551041827_Lachnospiraceae_bacterium_NK4A179     32.0%
12 564875111_Rhodobacter_capsulatus_R121            7.2%
13 652829192_Lachnospiraceae_bacterium_NK4A144     36.5%
14 671463495_Clostridium_aminophilum               35.3%
15 736546968_Carnobacterium_gallinarum              9.7%
16 736550717_Carnobacterium_gallinarum             10.3%
17 738133341_Listeria_newyorkensis                 10.9%
18 769144435_Lachnospiraceae_bacterium_MA2020      33.7%
19 545661797_Leptotrichia_oral_taxon_225_PARTIAL   13.5%
   consensus/100%
   consensus/90%
   consensus/80%
   consensus/70%

2161    ] 2164
 1 937566624_Eubacterium_rectale                  100.0%
 2 912591537_Herbinix_hemicellulosilytica          10.6%
 3 502750493_Listeria_seeligeri                    11.1%
 4 503209049_Paludibacter_propionicigenes          11.3%
 5 506250229_Leptotrichia_buccalis                 11.6%
 6 517262777_Leptotrichia_shahii                    9.2%
 7 544240864_Leptotrichia_wadei                    11.8%
 8 545620493_Leptotrichia_oral_taxon_879            8.8%
 9 545623306_Leptotrichia_wadei                    12.3%
10 545623740_Leptotrichia_wadei                    11.0%
11 551041827_Lachnospiraceae_bacterium_NK4A179     32.0%
12 564875111_Rhodobacter_capsulatus_R121            7.2%
13 652829192_Lachnospiraceae_bacterium_NK4A144     36.5%
14 671463495_Clostridium_aminophilum               35.3%
15 736546968_Carnobacterium_gallinarum              9.7%
16 736550717_Carnobacterium_gallinarum             10.3%
17 738133341_Listeria_newyorkensis                 10.9%
18 769144435_Lachnospiraceae_bacterium_MA2020      33.7%
19 545661797_Leptotrichia_oral_taxon_225_PARTIAL   13.5%
   consensus/100%
   consensus/90%
   consensus/80%
   consensus/70%
```

METHODS AND COMPOSITIONS FOR DETECTING A TARGET RNA

CROSS-REFERENCE

This application is a continuation of U.S. patent application Ser. No. 15/920,222, filed Mar. 13, 2018, issued as U.S. Pat. No. 10,494,664, which application is a divisional of U.S. patent application Ser. No. 15/467,922, filed Mar. 23, 2017, issued as U.S. Pat. No. 10,337,051, which application claims the benefit of U.S. Provisional Patent Application No. 62/351,172, filed Jun. 16, 2016, and U.S. Provisional Patent Application No. 62/378,156, filed Aug. 22, 2016, which applications are incorporated herein by reference in their entirety.

STATEMENT REGARDING FEDERALLY SPONSORED RESEARCH

This invention was made with government support under Grant No. GM102706 awarded by the National Institutes of Health and under Grant No. 1244557 awarded by the National Science Foundation. The government has certain rights in the invention.

INCORPORATION BY REFERENCE OF SEQUENCE LISTING PROVIDED AS A TEXT FILE

A Sequence Listing is provided herewith as a text file, "08_BERK-337CON2_SeqList_ST25" created on Feb. 21, 2019 and having a size of 68,038 bytes. The contents of the text file are incorporated by reference herein in their entirety.

INTRODUCTION

Bacterial adaptive immune systems employ CRISPRs (clustered regularly interspaced short palindromic repeats) and CRISPR-associated (Cas) proteins for RNA-guided nucleic acid cleavage. Although generally targeted to DNA substrates, the Type III and Type VI CRISPR systems direct interference complexes against single-stranded RNA (ssRNA) substrates. In Type VI CRISPR systems, the single-subunit C2c2 protein functions as an RNA-guided RNA endonuclease.

CRISPR-Cas systems confer adaptive immunity in bacteria and archaea via RNA-guided nucleic acid interference. Among the diverse CRISPR types, only the relatively rare Type VI CRISPR systems are believed to target single-stranded RNA substrates exclusively, an activity conferred by the large effector protein C2c2. The Type VI operons share common features of other CRISPR-Cas genomic loci, including CRISPR sequence arrays that serve as repositories of short viral DNA segments. To provide anti-viral immunity, processed CRISPR array transcripts (crRNAs) assemble with Cas protein-containing surveillance complexes that recognize nucleic acids bearing sequence complementarity to the virus derived segment of the crRNAs, known as the spacer.

The first step of immune surveillance requires processing of precursor crRNAs (pre-crRNAs), consisting of repeat sequences flanking viral spacer sequences, into individual functional crRNAs that each contain a single virally-derived sequence segment. CRISPR systems employ a variety of mechanisms to produce mature crRNAs, including the use of dedicated endonucleases (e.g., Cas6 or Cas5d in Type I and III systems), coupling of a host endonuclease (e.g., RNase III) with a trans-activating crRNA (tracrRNA, Type II systems), or a ribonuclease activity endogenous to the effector enzyme itself (e.g., Cpf1, from Type V systems).

SUMMARY

The present disclosure provides methods for detecting a single-stranded target RNA. The present disclosure provides methods of cleaving a precursor C2c2 guide RNA array into two or more C2c2 guide RNAs. The present disclosure provides a kit for detecting a target RNA in a sample.

Provided are compositions and methods for detecting a single stranded target RNA, where the methods include (i) contacting a sample having a plurality of RNAs with (a) a C2c2 guide RNA that hybridizes with the single stranded target RNA, and (b) a C2c2 protein that cleaves RNAs of the sample; and (ii) measuring a detectable signal produced by the cleavage. Once a subject C2c2 protein is activated by a C2c2 guide RNA, which occurs when the sample includes a single stranded target RNA to which the guide RNA hybridizes (i.e., the sample includes the targeted single stranded target RNA), the C2c2 protein becomes an endoribonuclease that cleaves RNAs of the sample. Thus, when the targeted single stranded target RNA is present in the sample (e.g., in some cases above a threshold amount), the result is cleavage of RNA in the sample, which can be detected using any convenient detection method (e.g., using a labeled detector RNA).

In some cases, two or more C2c2 guide RNAs can be provided by using a precursor C2c2 guide RNA array, which can be cleaved by the C2c2 protein into individual guide RNAs, and this is independent of whether the C2c2 protein has intact HEPN1 and/or HEPN2 domains. Thus, also provided are methods of cleaving a precursor C2c2 guide RNA array into two or more C2c2 guide RNAs. In some cases, the C2c2 protein lacks a catalytically active HEPN1 domain and/or lacks a catalytically active HEPN2 domain.

BRIEF DESCRIPTION OF THE DRAWINGS

FIG. 7A-7B depict a schematic and sequences of example C2c2 guide RNAs. FIG. 7A: Top is SEQ ID NO: 27, Bottom is SEQ ID NO: 28. FIG. 7B: Top to bottom: SEQ ID NOs: 29-34.

FIG. 8A-8F provides amino acid sequences of various C2c2 polypeptides.

FIG. 9A-9C depict C2c2 family processing of precursor crRNA transcripts to generate mature crRNAs. FIG. 9C: left to right: SEQ ID NOs: 35-37.

FIG. 10A-10C depict the effect of structure and sequence of CRISPR repeats on LbuC2c2 mediated crRNA biogenesis. FIG. 10B: SEQ ID NO: 38.

FIG. 11A-11C depict guide-dependent ssRNA degradation of cis and trans targets by LbuC2c2.

FIG. 12A-12D depict two distinct ribonuclease activities of LbuC2c2.

FIG. 14 provides Table 2: various DNA substrates used in the studies described in Examples 8-12 and shown in FIG. 12A-12D.Top to bottom: SEQ ID NOs: 39-44.

FIG. 15 provides Table 3: various RNA substrates used in the studies described in Examples 8-12. Top to bottom: SEQ ID NOs: 45-102.

FIG. 16E: top to bottom: SEQ ID NOs: 103-106.

FIG. 17 provides a summary of the effect of pre-crRNA double mutations on pre-crRNA processing activity. top to bottom left: SEQ ID NOs: 107-115; top to bottom right: SEQ ID NOs: 116-124.

FIG. 18A: A.1 (SEQ ID NO: 125); A.4 (SEQ ID NO: 126); A.0 (SEQ ID NO: 127); B.0 (SEQ ID NO: 128); A.2 (SEQ ID NO: 129); and A.3 (SEQ ID NO: 130). FIG. 18B: SEQ ID NO: 131.

FIG. 19A-19C depict dependence of crRNA spacer length, reaction temperature, and 5'-end sequence of crRNA on target RNA cleavage efficiency. FIG. 19B, top to bottom: SEQ ID NOs: 132-135.

FIG. 23A-23D depict purification and production of C2c2.

FIG. 24A-24C depict data showing that C2c2 proteins process precursor crRNA transcripts to generate mature crRNAs. a, Maximum-likelihood phylogenetic tree of C2c2 proteins. Homologs used in this study are highlighted in yellow. b, Diagram of the three Type VI CRISPR loci used in this study. Black rectangles denote repeat elements, yellow diamonds denote spacer sequences. Cas1 and Cas2 are only found in the genomic vicinity of LshC2c2. left to right: SEQ ID NOs: 136-138. c, C2c2-mediated cleavage of pre-crRNA derived from the LbuC2c2, LseC2c2 and LshC2c2 CRISPR repeat loci. OH: alkaline hydrolysis ladder; T1: RNase T1 hydrolysis ladder; processing cleavage reactions were performed with 100 nM C2c2 and <1 nM pre-crRNA. Schematic of cleavage is depicted on right, and predicted pre-crRNA secondary structures are diagrammed below, with arrows indicating the mapped C2c2 cleavage sites.

FIG. 26A-26D depict data showing that that LbuC2c2 contains two distinct ribonuclease activities. a, Quantified time-course data of cis ssRNA target (black) and pre-crRNA (teal) cleavage by LbuC2c2 performed at 37° C. Exponential fits are shown as solid lines (n=3), and the calculated pseudo-first-order rate constants ($k_{obs}$) (mean±s.d.) are 9.74±1.15 $min^{-1}$ and 0.12±0.02 $min^{-1}$ for cis ssRNA target and pre-crRNA cleavage, respectively. b, LbuC2c2 architecture depicting the location of HEPN motifs and processing deficient point mutant c,d Ribonuclease activity of LbuC2c2 mutants for pre-crRNA processing in c and ssRNA targeting in d and Extended Data FIG. 6d.

FIG. 29A-29D depict data related to purification and production of C2c2. All C2c2 homologs were expressed in *E. coli* as His-MBP fusions and purified by a combination of affinity, ion exchange and size exclusion chromatography. The $Ni^+$ affinity tag was removed by incubation with TEV protease. Representative SDS-PAGE gels of chromatography fractions are shown in (a, b). c, The chromatogram from Superdex 200 (16/60) column demonstrating that C2c2 elutes as a single peak, devoid of nucleic acid. d, SDS PAGE analysis of purified proteins used in this manuscript.

FIG. 32A-32C show that LbuC2c2 catalyzes guide-dependent ssRNA degradation on cis and trans targets. a, Schematic of the two modes of C2c2, guide-dependent ssRNA degradation. b, Cleavage of two distinct radiolabeled ssRNA substrates, A and B, by LbuC2c2. Complexes of 100 nM C2c2 and 50 nM crRNA were pre-formed at 37° C., and reaction was initiated upon addition of <1 nM 5'-labeled target RNA at 25° C. Trans cleavage reactions contained equimolar (<1 nM) concentrations of radiolabeled non-guide-complementary substrate, and unlabeled on-target ssRNA. For multiple ssRNA substrates, we observed that LbuC2c2 catalyzed efficient cleavage only when bound to the complementary crRNA, indicating that LbuC2c2:crRNA cleaves ssRNA in an RNA-guided fashion This activity is hereafter referred to as on-target or cis-target cleavage. LbuC2c2-mediated cis cleavage resulted in a laddering of multiple products, with cleavage preferentially occurring before uracil residues, analogous to LshC2c2[9]. We repeated non-target cleavage reactions in the presence of unlabeled, on-target (crRNA-complementary) ssRNA. In contrast to non-target cleavage experiments performed in cis, we observed rapid degradation of non-target RNA in trans. The similar RNA cleavage rates and near identical cleavage products observed for both cis on-target cleavage and trans non-target cleavage implicate the same nuclease center in both activities. c, LbuC2c2 loaded with crRNA targeting spacer A was tested for cleavage activity under both cis (target A labeled) and trans (target B labeled in the presence of unlabeled target A) cleavage conditions in the presence of 25 mM EDTA.

FIG. 33A-33B show LbuC2c2 ssRNA target cleavage site mapping a, ssRNA target cleavage assay conducted per Methods demonstrating LbuC2c2-mediated 'cis'-cleavage of several radiolabeled ssRNA substrates with identical spacer-complementary sequences but distinct 5' flanking sequences of variable length and nucleotide composition. Sequences of ssRNA substrates are shown to the right with spacer-complementary sequences for crRNA-A highlighted in yellow. Arrows indicate detected cleavage sites. Gel was cropped for clarity. It should be noted that the pattern of cleavage products produced on different substrates (e.g. A.1 vs. A.2 vs. A.3) indicates that the cleavage site choice is primarily driven by a uracil preference and exhibits an apparent lack of exclusive cleavage mechanism within the crRNA-complementary target sequence, which is in contrast to what is observed for other Class II CRISPR single effector complexes such as Cas9 and Cpf1[1,21]. Interestingly, the cleavage pattern observed for substrate A.0 hints at a secondary preference for polyG sequences. A.1 (SEQ ID NO: 125); A.2 (SEQ ID NO: 129); A.3 (SEQ ID NO: 130); A.4 (SEQ ID NO: 126); and A.0 (SEQ ID NO: 127). b, LbuC2c2 ssRNA target cleavage assay as per Methods, using a range of crRNAs that tile the length of the ssRNA target. The sequence of the ssRNA substrates used in this experiment is shown below the gel with spacer-complementary sequences for each crRNA highlighted in yellow. Arrows indicate predicted cleavage sites. Above each set of lanes, a small diagram indicates the location of the spacer sequence along the target (yellow box) and the cleavage products observed (red arrows) or absent (black arrows). Likewise, it should be noted that for every crRNA the cleavage product length distribution is very similar, again indicating an apparent lack of exclusive cleavage within the crRNA-bound sequence. The absence of a several cleavage products in a subset of the reactions might be explained by the presence of bound C2c2:crRNA on the ssRNA target, which could sterically occlude access to uracils by any cis (intramolecular) or trans (intermolecular) LbuC2c2 active sites. While proper analysis for protospacer flanking site (PFS) preference for LbuC2c2 is beyond the scope of this study, minimal impact of the 3' flanking nucleotide was observed. Expected PFS base is noted in diagram next to each guide tested in red. (SEQ ID NO: 131).

FIG. 38A-38C depict conservation of pre-crRNA processing within the Cas13a family. FIG. 38B: Flank-stem, top-bottom: SEQ ID NOs: 150-160.

FIG. 39A-39C depict CRISPR loci and crRNA repeat architecture for Cas13a homologs. FIG. 39B: top to bottom: SEQ ID NOs: 161-172.

FIG. 40A-40F depict residues important for pre-crRNA cleavage by LbuCas13a. FIG. 40B: top to bottom: SEQ ID NOs: 173-183. FIG. 40C: top to bottom: SEQ ID NOs: 184-194.

FIG. 41A-41B depict alignments of Helical 1 and HEPN domains of Cas13a family members. (Top to bottom: SEQ ID NOs: 195-232).

FIG. 42A-42D depict efficiencies of ssRNA by members of the Cas13a family.

FIG. 43A-43D depict trans-ssRNA cleavage by Cas13a homologs. FIG. 43B: top to bottom: SEQ ID NOs: 233-234.

FIG. 48A-48B depict features of the LbuCas13a R1079A/K1080A double mutant relative to wild-type LbuCas13a.

FIG. 49 provides Table 4. "CRISPR Repeat Consensus": top to bottom: SEQ ID NOs: 235-250. "Mature crRNA handle": top to bottom: SEQ ID NOs: 251-262.

FIG. 50 provides Table 5. Top to bottom: SEQ ID NOs: 253-298.

FIG. 51 provides Table 6.
FIG. 52 provides Table 7.
FIG. 53 provides Table 8.
FIG. 54 provides Table 9.

FIG. 56A-56K provide amino acid sequences of various Cas13a polypeptides. *Listeria seeligeri* (SEQ ID NO: 1); *Paludibacter propionicigenes* (SEQ ID NO: 299); *Leptotrichia buccalis* (SEQ ID NO: 2); *Leptotrichia shahii* (SEQ ID NO: 3); *Leptotrichia wadei* F0279 (SEQ ID NO: 300); Lachnospiraceae *bacterium* NK4A179 (SEQ ID NO: 301); *Rhodobacter capsulatus* R121 (SEQ ID NO: 4); *Clostridium aminophilum* (SEQ ID NO: 302); *Listeria newyorkensis* (SEQ ID NO: 303); *Eubacterium* rectale genome assembly T1815 (SEQ ID NO: 304); Herbinix hemicellulosilytica (SEQ ID NO: 6).

Figure 57A:
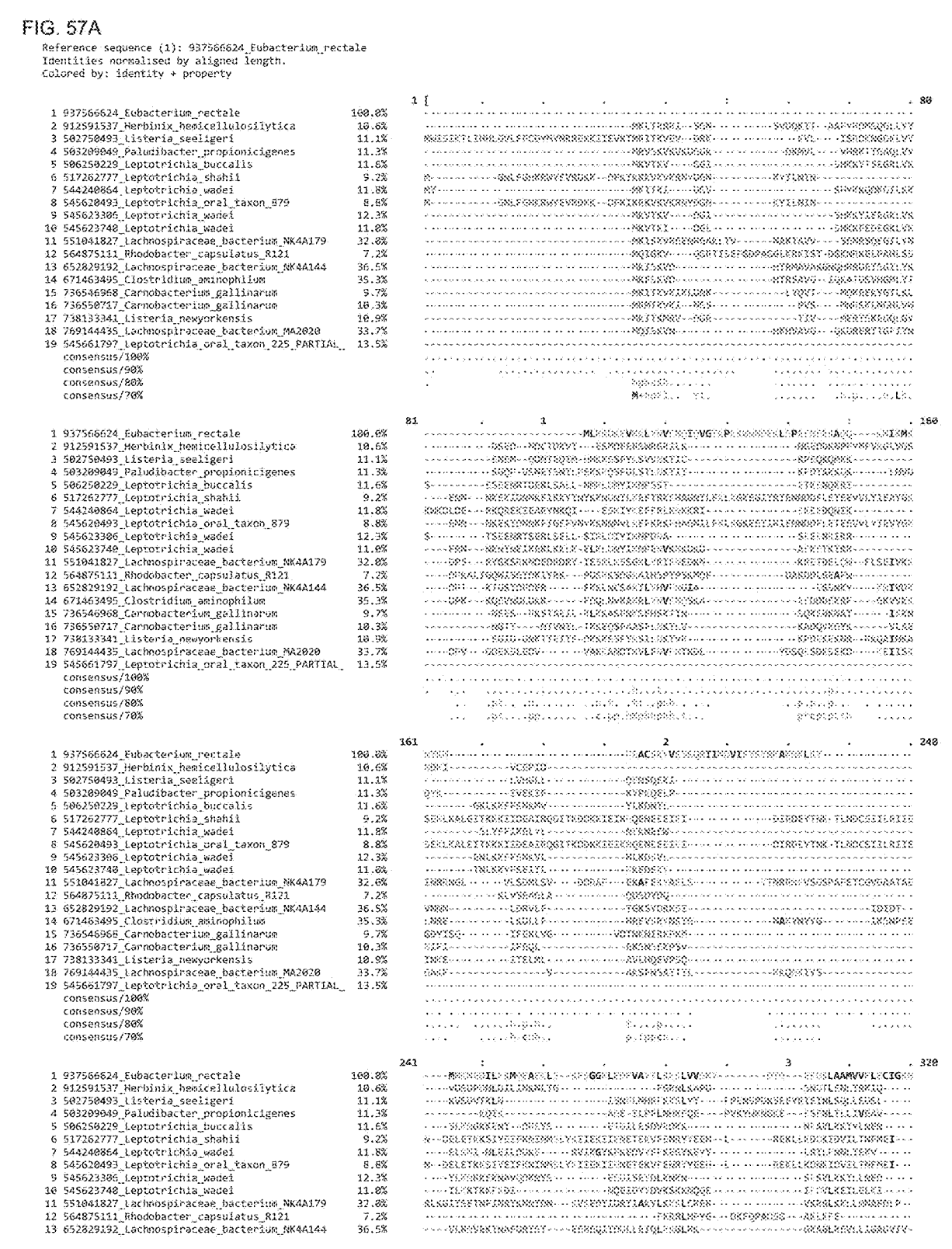
Figure 57B:
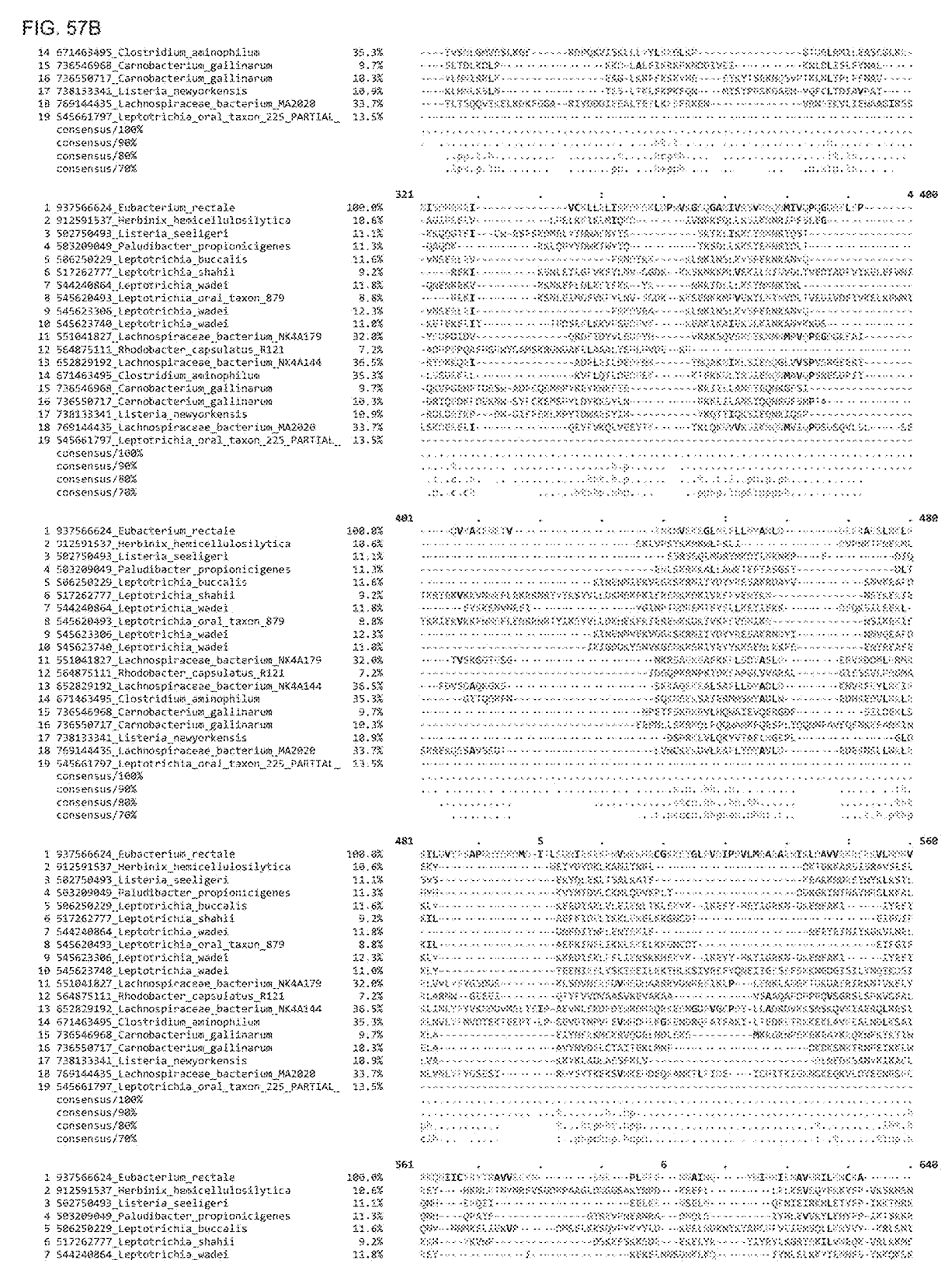
Figure 57C:
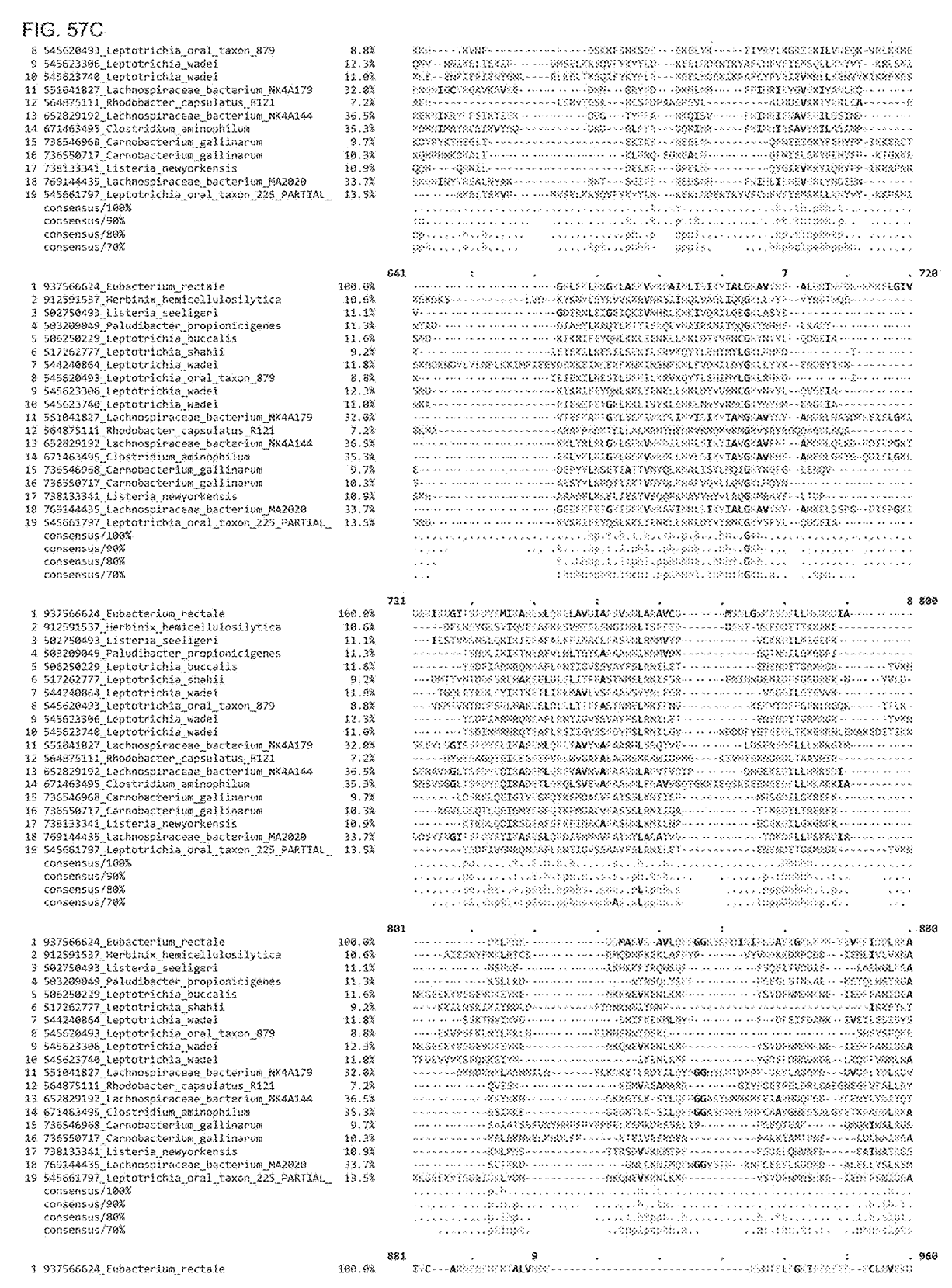
Figure 57D:
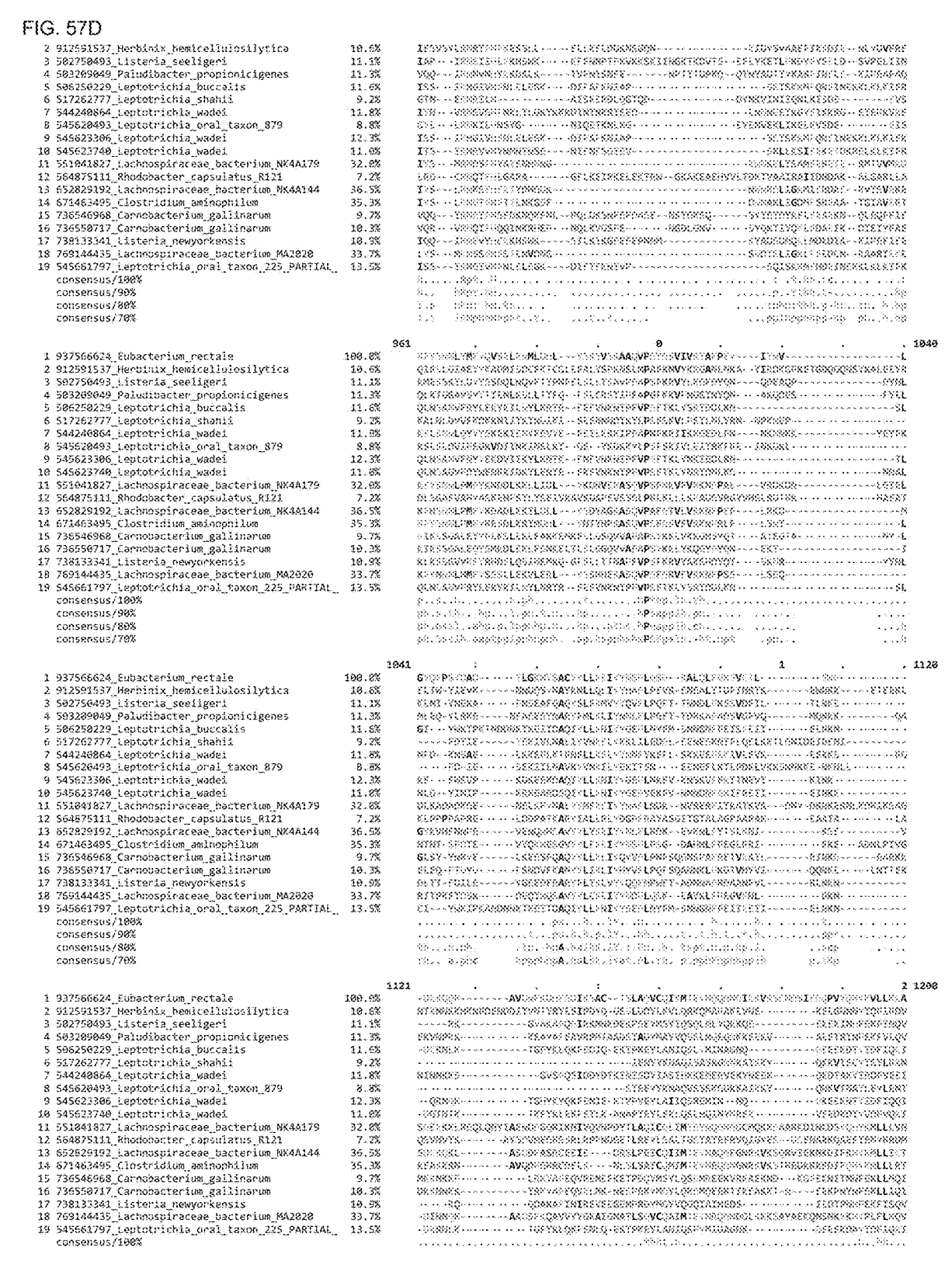
Figure 57E:
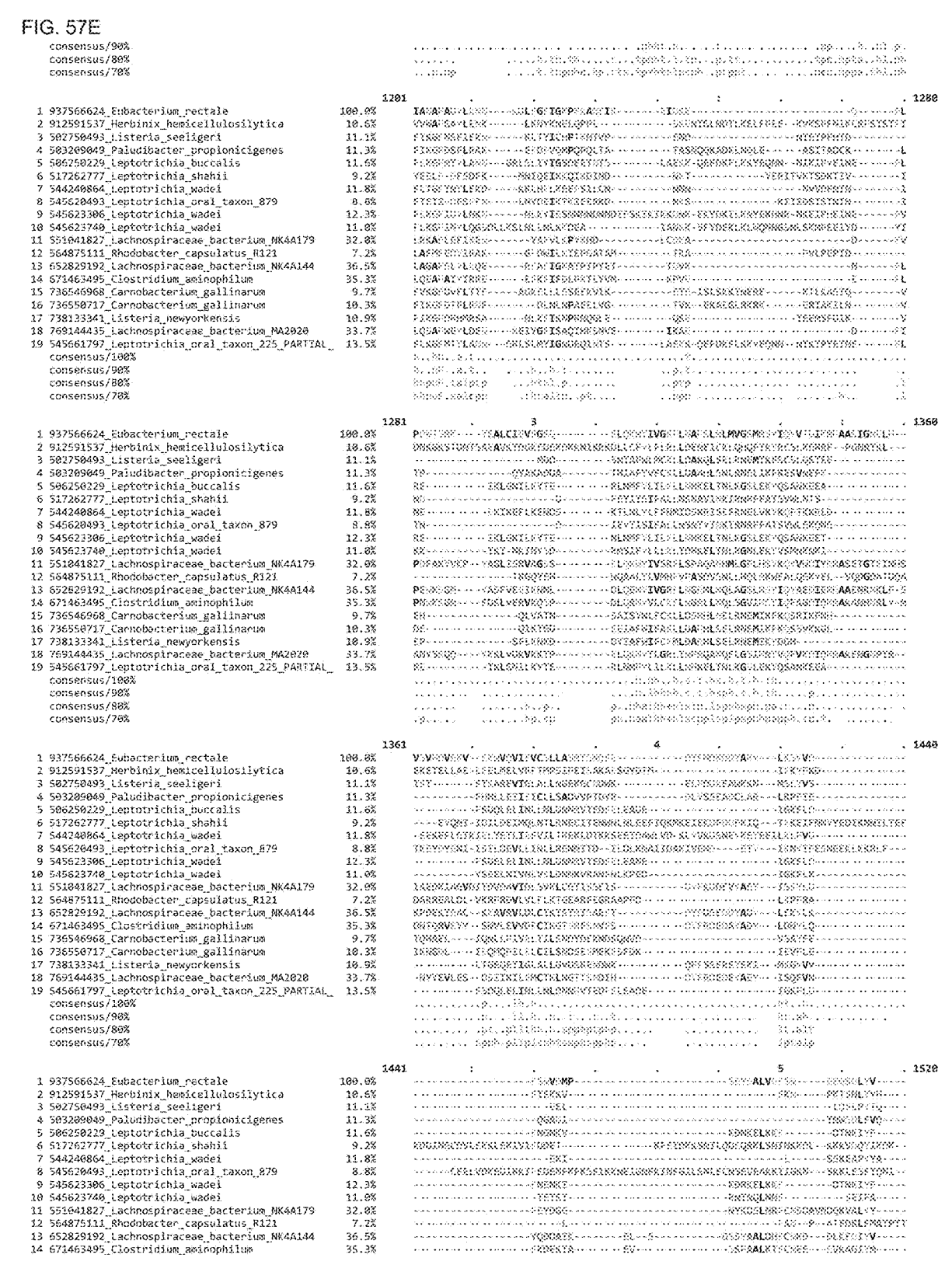
Figure 57F:
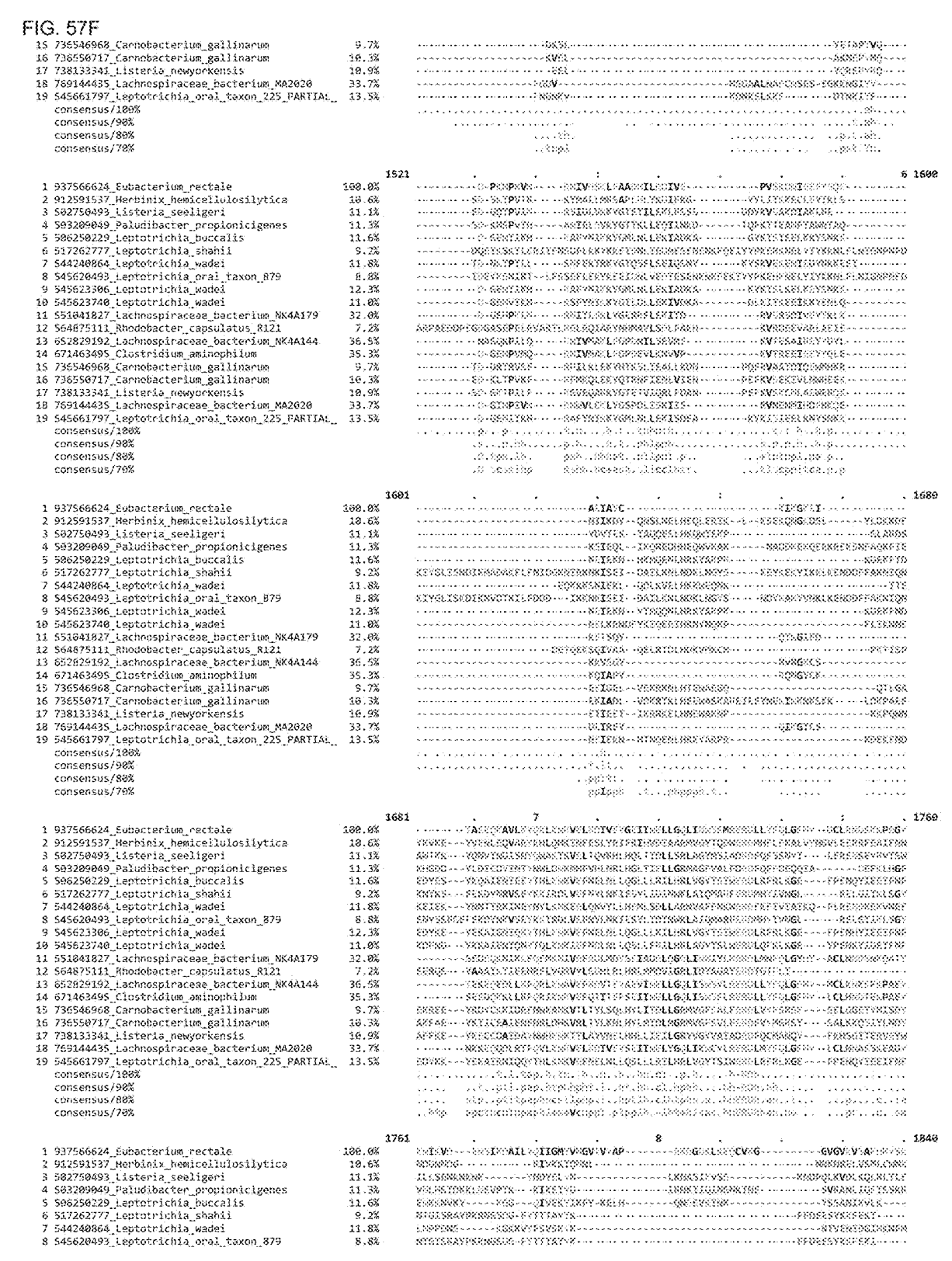
Figure 57G:
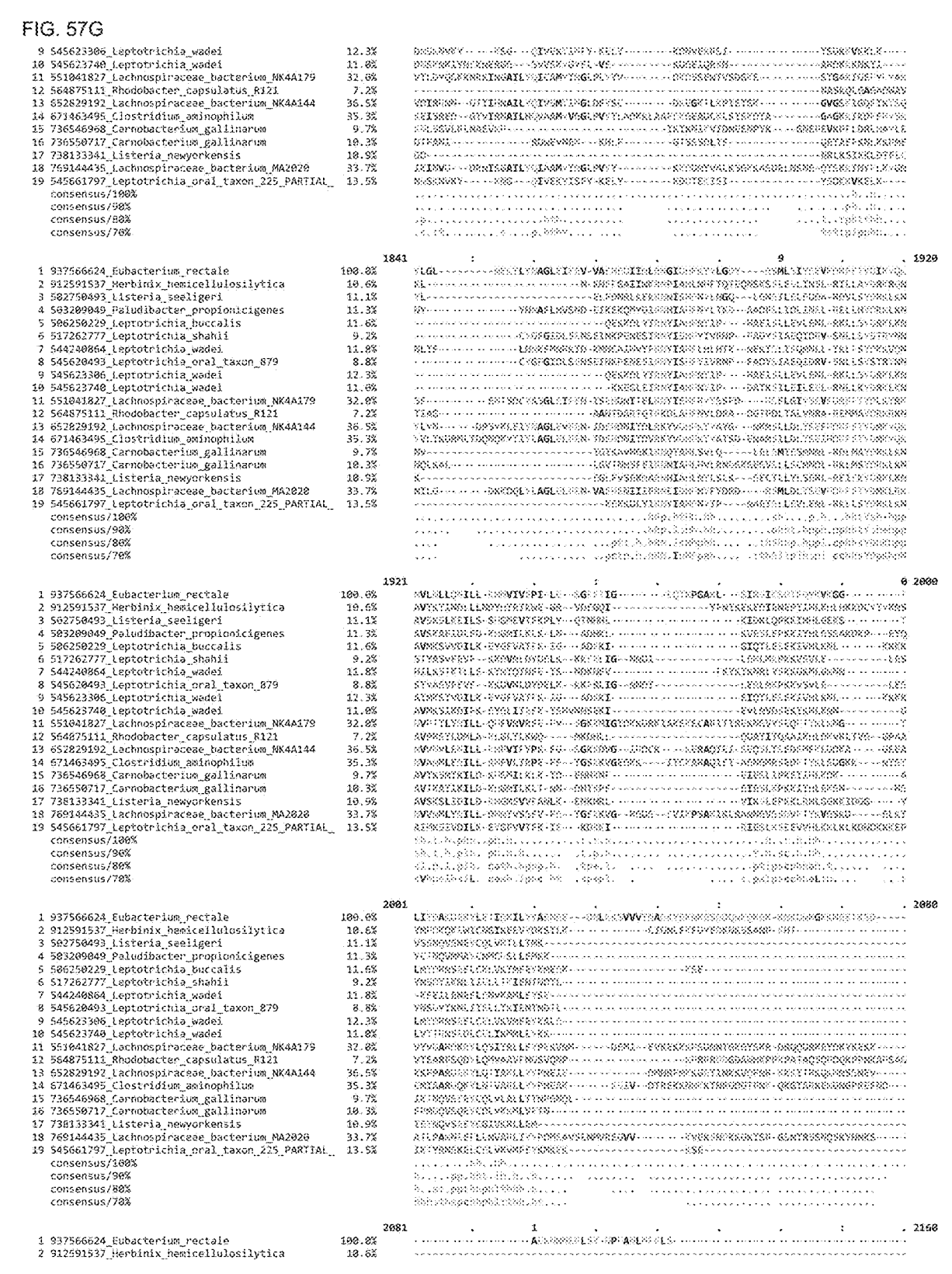

FIG. 57A-57H provides an alignment of amino acid sequences of various Cas13a polypeptides. Sequences labeled 1-19 are SEQ ID NOs: 304-322, respectively.

DEFINITIONS

Figure 1A:
FIG. 1A-1E present schematics related to an endogenous C2c2 locus and experiments demonstrating heterologous expression and purification of recombinant C2c2 protein.

The terms "polynucleotide" and "nucleic acid," used interchangeably herein, refer to a polymeric form of nucleotides of any length, either ribonucleotides or deoxyribonucleotides. Thus, terms "polynucleotide" and "nucleic acid" encompass single-stranded DNA; double-stranded DNA; multi-stranded DNA; single-stranded RNA; double-stranded RNA; multi-stranded RNA; genomic DNA; cDNA; DNA-RNA hybrids; and a polymer comprising purine and pyrimidine bases or other natural, chemically or biochemically modified, non-natural, or derivatized nucleotide bases.

The term "oligonucleotide" refers to a polynucleotide of between 3 and 100 nucleotides of single- or double-stranded nucleic acid (e.g., DNA, RNA, or a modified nucleic acid). However, for the purposes of this disclosure, there is no upper limit to the length of an oligonucleotide. Oligonucleotides are also known as "oligomers" or "oligos" and can be isolated from genes, transcribed (in vitro and/or in vivo), or chemically synthesized. The terms "polynucleotide" and "nucleic acid" should be understood to include, as applicable to the embodiments being described, single-stranded (such as sense or antisense) and double-stranded polynucleotides.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine/adenosine) (A) pairing with thymidine/thymidine (T), A pairing with uracil/uridine (U), and guanine/guanosine) (G) pairing with cytosine/cytidine (C). In addition, for hybridization between two RNA molecules (e.g., dsRNA), and for hybridization of a DNA molecule with an RNA molecule (e.g., when a DNA target nucleic acid base pairs with a C2c2 guide RNA, etc.): G can also base pair with U. For example, G/U base-pairing is partially responsible for the degeneracy (i.e., redundancy) of the genetic code in the context of tRNA anti-codon base-pairing with codons in mRNA. Thus, in the context of this disclosure, a G (e.g., of a protein-binding segment (dsRNA duplex) of a C2c2 guide RNA molecule; of a target nucleic acid base pairing with a C2c2 guide RNA) is considered complementary to both a U and to C. For example, when a G/U base-pair can be made at a given nucleotide position of a protein-binding segment (e.g., dsRNA duplex) of a C2c2 guide RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches can become important (see Sambrook et al., supra, 11.7-11.8). Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more). The temperature and wash solution salt concentration may be adjusted as necessary according to factors such as length of the region of complementation and the degree of complementation.

It is understood that the sequence of a polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Exemplary methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to an RNA-binding domain of a polypeptide, binding to a target nucleic acid, and the like) refers to a non-covalent interaction between macromolecules (e.g., between a protein and a nucleic acid; between a C2c2 guide RNA complex and a target nucleic acid; and the like). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant ($K_d$) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower $K_d$.

By "binding domain" it is meant a protein domain that is able to bind non-covalently to another molecule. A binding domain can bind to, for example, an RNA molecule (an RNA-binding domain) and/or a protein molecule (a protein-binding domain). In the case of a protein having a protein-binding domain, it can in some cases bind to itself (to form homodimers, homotrimers, etc.) and/or it can bind to one or more regions of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various methods and computer programs (e.g., BLAST, T-COFFEE, MUSCLE, MAFFT, Phyre2, etc.), available over the world wide web at sites including ncbi.nlm.followed by nili.gov/ followed by BLAST, ebi.ac followed by .uk followed by/Tools/followed by msa followed by /tcoffee/, ebi. followed by ac.uk followed by /Tools/followed by msa/followed by muscle/, mafft. followed by cbrc. followed by jp/ followed by alignment followed by /software/, http followed by:// followed by www followed by.sbg. followed by bio. followed by ic. followed by ac. followed by uk/ followed by ~phyre2/. See, e.g., Altschul et al. (1990), J. Mol. Bioi. 215:403-10.

A DNA sequence that "encodes" a particular RNA is a DNA nucleic acid sequence that is transcribed into RNA. A DNA polynucleotide may encode an RNA (mRNA) that is translated into protein, or a DNA polynucleotide may encode an RNA that is not translated into protein (e.g. tRNA, rRNA, microRNA (miRNA), a "non-coding" RNA (ncRNA), a C2c2 guide RNA, etc.).

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., Cas9 guide RNA) or a coding sequence (e.g., Cas9 protein) and/or regulate translation of an encoded polypeptide.

As used herein, a "promoter sequence" is a DNA regulatory region capable of binding RNA polymerase and initiating transcription of a downstream (3' direction) coding or non-coding sequence. For purposes of the present disclosure, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present disclosure.

The term "naturally-occurring" or "unmodified" or "wild type" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is wild type (and naturally occurring).

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA (e.g., C2c2 guide RNA) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

Any given component, or combination of components can be unlabeled, or can be detectably labeled with a label moiety. In some cases, when two or more components are labeled, they can be labeled with label moieties that are distinguishable from one another.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a protein" includes a plurality of such proteins and reference to "the guide RNA" includes reference to one or more such guide RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods for detecting a single-stranded target RNA. The present disclosure provides methods of cleaving a precursor C2c2 guide RNA array into two or more C2c2 guide RNAs. The present disclosure provides a kit for detecting a target RNA in a sample. The term "C2c2 guide RNA" is used herein interchangeably with "Cas13a guide RNA" and in some cases a guide RNA is referred to as a crRNA (e.g., "Cas13a crRNA"); the term "C2c2 protein" (or "C2c2 polypeptide") is used herein interchangeably with "Cas13a protein" (or "Cas13a polypeptide").

Methods of Detecting a Single-Stranded RNA

Provided are compositions and methods for detecting a single stranded target RNA, where the methods include (i) contacting a sample having a plurality of RNAs with (a) a C2c2 guide RNA that hybridizes with the single stranded target RNA, and (b) a C2c2 protein that cleaves RNAs present in the sample; and (ii) measuring a detectable signal produced by the cleavage. Once a subject C2c2 protein is activated by a C2c2 guide RNA, which occurs when the sample includes a single stranded target RNA to which the guide RNA hybridizes (i.e., the sample includes the targeted single stranded target RNA), the C2c2 protein is activated and functions as an endoribonuclease that non-specifically cleaves RNAs (including non-target RNAs) present in the sample. Thus, when the targeted single stranded target RNA is present in the sample (e.g., in some cases above a threshold amount), the result is cleavage of RNA (including non-target RNA) in the sample, which can be detected using any convenient detection method (e.g., using a labeled detector RNA). The contacting step is generally carried out in a composition comprising divalent metal ions. The contacting step can be carried out in an acellular environment, e.g., outside of a cell. The contacting step can be carried out inside a cell. The contacting step can be carried out in a cell in vitro. The contacting step can be carried out in a cell ex vivo. The contacting step can be carried out in a cell in vivo. In some cases, the C2c2 guide RNA is provided as RNA; and the C2c2 protein is provided as protein per se. In some cases, the C2c2 guide RNA is provided as DNA encoding the guide RNA; and the C2c2 protein is provided as protein per se. In some cases, the C2c2 guide RNA is provided as RNA; and the C2c2 protein is provided as RNA encoding the C2c2 protein. In some cases, the C2c2 guide RNA is provided as DNA encoding the guide RNA; and C2c2 protein is provided as RNA encoding the C2c2 protein. In some cases, the C2c2 guide RNA is provided as RNA; and the C2c2 protein is provided as DNA comprising a nucleotide sequence encoding the C2c2 protein. In some cases, the C2c2 guide RNA is provided as DNA encoding the guide RNA; and the C2c2 protein is provided as DNA comprising a nucleotide sequence encoding the C2c2 protein. In some cases, a method of the present disclosure provides for substantially simultaneous detection of two different target RNAs (a first single-stranded target RNA and a second single-stranded target RNA) in a sample.

In some cases, two or more (e.g., 3 or more, 4 or more, 5 or more, or 6 or more) C2c2 guide RNAs can be provided by using a precursor C2c2 guide RNA array, which can be cleaved by the C2c2 protein into individual ("mature") guide RNAs; cleavage of a precursor C2c2 guide RNA is independent of whether the C2c2 protein has intact HEPN1 and/or HEPN2 domains. Thus, also provided are methods of cleaving a precursor C2c2 guide RNA array into two or more C2c2 guide RNAs. Thus a C2c2 guide RNA array can include more than one guide sequence. In some cases, a subject C2c2 guide RNA can include a handle from a precursor crRNA but does not necessarily have to include multiple guide sequences. In some cases, the C2c2 protein lacks a catalytically active HEPN1 domain and/or lacks a catalytically active HEPN2 domain. The contacting step can be carried out in an acellular environment, e.g., outside of a cell. The contacting step can be carried out inside a cell. The contacting step can be carried out in a cell in vitro. The contacting step can be carried out in a cell ex vivo. The contacting step can be carried out in a cell in vivo.

In some cases (e.g., when contacting with a C2c2 guide RNA and a C2c2 protein, when contacting with a precursor C2c2 guide RNA array and a C2c2 protein, and the like), the sample is contacted for 2 hours or less (e.g., 1.5 hours or less, 1 hour or less, 40 minutes or less, 30 minutes or less, 20 minutes or less, 10 minutes or less, or 5 minutes or less, or 1 minute or less) prior to the measuring step. For example, in some cases the sample is contacted for 40 minutes or less prior to the measuring step. In some cases the sample is contacted for 20 minutes or less prior to the measuring step. In some cases the sample is contacted for 10 minutes or less prior to the measuring step. In some cases the sample is contacted for 5 minutes or less prior to the measuring step. In some cases the sample is contacted for 1 minute or less prior to the measuring step. In some cases the sample is contacted for from 50 seconds to 60 seconds prior to the measuring step. In some cases the sample is contacted for from 40 seconds to 50 seconds prior to the measuring step. In some cases the sample is contacted for from 30 seconds to 40 seconds prior to the measuring step. In some cases the sample is contacted for from 20 seconds to 30 seconds prior to the measuring step. In some cases the sample is contacted for from 10 seconds to 20 seconds prior to the measuring step.

The present disclosure provides methods of detecting a single-stranded RNA in a sample comprising a plurality of RNAs (e.g., comprising a target RNA and a plurality of non-target RNAs). In some cases, the methods comprise: a) contacting the sample with: (i) a C2c2 guide RNA that hybridizes with the single stranded target RNA, and (ii) a C2c2 protein that cleaves RNAs present in the sample; and b) measuring a detectable signal produced by C2c2 protein-mediated RNA cleavage. In some cases, the methods comprise: a) contacting the sample with: i) a precursor C2c2 guide RNA array comprising two or more C2c2 guide RNAs each of which has a different guide sequence; and (ii) a C2c2 protein that cleaves the precursor C2c2 guide RNA array into individual C2c2 guide RNAs, and also cleaves RNAs of the sample; and b) measuring a detectable signal produced by C2c2 protein-mediated RNA cleavage. In some cases, a method of the present disclosure provides for substantially simultaneous detection of two different target RNAs (a first single-stranded target RNA and a second single-stranded target RNA) in a sample.

A method of the present disclosure for detecting a single-stranded RNA (a single-stranded target RNA) in a sample comprising a plurality of RNAs (including the single stranded target RNA and a plurality of non-target RNAs) can detect a single-stranded target RNA with a high degree of sensitivity. In some cases, a method of the present disclosure can be used to detect a target single-stranded RNA present in a sample comprising a plurality of RNAs (including the single stranded target RNA and a plurality of non-target RNAs), where the target single-stranded RNA is present at one or more copies per $10^7$ non-target RNAs (e.g., one or more copies per $10^6$ non-target RNAs, one or more copies per $10^5$ non-target RNAs, one or more copies per $10^4$ non-target RNAs, one or more copies per $10^3$ non-target RNAs, one or more copies per $10^2$ non-target RNAs, one or more copies per 50 non-target RNAs, one or more copies per 20 non-target RNAs, one or more copies per 10 non-target RNAs, or one or more copies per 5 non-target RNAs).

In some cases, a method of the present disclosure can detect a target single-stranded RNA present in a sample comprising a plurality of RNAs (including the single stranded target RNA and a plurality of non-target RNAs), where the target single-stranded RNA is present at from one copy per $10^7$ non-target RNAs to one copy per 10 non-target RNAs (e.g., from 1 copy per $10^7$ non-target RNAs to 1 copy per $10^2$ non-target RNAs, from 1 copy per $10^7$ non-target RNAs to 1 copy per $10^3$ non-target RNAs, from 1 copy per $10^7$ non-target RNAs to 1 copy per $10^4$ non-target RNAs, from 1 copy per $10^7$ non-target RNAs to 1 copy per $10^5$ non-target RNAs, from 1 copy per $10^7$ non-target RNAs to 1 copy per $10^6$ non-target RNAs, from 1 copy per $10^6$ non-target RNAs to 1 copy per 10 non-target RNAs, from 1 copy per $10^6$ non-target RNAs to 1 copy per $10^2$ non-target RNAs, from 1 copy per $10^6$ non-target RNAs to 1 copy per $10^3$ non-target RNAs, from 1 copy per $10^6$ non-target RNAs to 1 copy per $10^4$ non-target RNAs, from 1 copy per $10^6$ non-target RNAs to 1 copy per $10^5$ non-target RNAs, from 1 copy per $10^5$ non-target RNAs to 1 copy per 10 non-target RNAs, from 1 copy per $10^5$ non-target RNAs to 1 copy per $10^2$ non-target RNAs, from 1 copy per $10^5$ non-target RNAs to 1 copy per $10^3$ non-target RNAs, or from 1 copy per $10^5$ non-target RNAs to 1 copy per $10^4$ non-target RNAs).

In some cases, a method of the present disclosure can detect a target single-stranded RNA present in a sample comprising a plurality of RNAs (including the single stranded target RNA and a plurality of non-target RNAs), where the target single-stranded RNA is present at from one copy per $10^7$ non-target RNAs to one copy per 100 non-target RNAs (e.g., from 1 copy per $10^7$ non-target RNAs to 1 copy per $10^2$ non-target RNAs, from 1 copy per $10^7$ non-target RNAs to 1 copy per $10^3$ non-target RNAs, from 1 copy per $10^7$ non-target RNAs to 1 copy per $10^4$ non-target RNAs, from 1 copy per $10^7$ non-target RNAs to 1 copy per $10^5$ non-target RNAs, from 1 copy per $10^7$ non-target RNAs to 1 copy per $10^6$ non-target RNAs, from 1 copy per $10^6$ non-target RNAs to 1 copy per 100 non-target RNAs, from 1 copy per $10^6$ non-target RNAs to 1 copy per $10^2$ non-target RNAs, from 1 copy per $10^6$ non-target RNAs to 1 copy per $10^3$ non-target RNAs, from 1 copy per $10^6$ non-target RNAs to 1 copy per $10^4$ non-target RNAs, from 1 copy per $10^6$ non-target RNAs to 1 copy per $10^5$ non-target RNAs, from 1 copy per $10^5$ non-target RNAs to 1 copy per 100 non-target RNAs, from 1 copy per $10^5$ non-target RNAs to 1 copy per $10^2$ non-target RNAs, from 1 copy per $10^5$ non-target RNAs to 1 copy per $10^3$ non-target RNAs, or from 1 copy per $10^5$ non-target RNAs to 1 copy per $10^4$ non-target RNAs).

In some cases, the threshold of detection, for a subject method of detecting a single stranded target RNA in a sample, is 10 nM or less. The term "threshold of detection" is used herein to describe the minimal amount of target RNA that must be present in a sample in order for detection to occur. Thus, as an illustrative example, when a threshold of detection is 10 nM, then a signal can be detected when a target RNA is present in the sample at a concentration of 10 nM or more. In some cases, a method of the present disclosure has a threshold of detection of 5 nM or less. In some cases, a method of the present disclosure has a threshold of detection of 1 nM or less. In some cases, a method of the present disclosure has a threshold of detection of 0.5 nM or less. In some cases, a method of the present disclosure has a threshold of detection of 0.1 nM or less. In some cases, a method of the present disclosure has a threshold of detection of 0.05 nM or less. In some cases, a method of the present disclosure has a threshold of detection of 0.01 nM or less. In some cases, a method of the present disclosure has a threshold of detection of 0.005 nM or less. In some cases, a method of the present disclosure has a threshold of detection of 0.001 nM or less. In some cases, a method of the present disclosure has a threshold of detection of 0.0005 nM or less. In some cases, a method of the present disclosure has a threshold of detection of 0.0001 nM or less. In some cases, a method of the present disclosure has a threshold of detection of 0.00005 nM or less. In some cases, a method of the present disclosure has a threshold of detection of 0.00001 nM or less. In some cases, a method of the present disclosure has a threshold of detection of 10 pM or less. In some cases, a method of the present disclosure has a threshold of detection of 1 pM or less. In some cases, a method of the present disclosure has a threshold of detection of 500 fM or less. In some cases, a method of the present disclosure has a threshold of detection of 250 fM or less. In some cases, a method of the present disclosure has a threshold of detection of 100 fM or less. In some cases, a method of the present disclosure has a threshold of detection of 50 fM or less.

In some cases, the threshold of detection (for detecting the single stranded target RNA in a subject method), is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM) (where the concentration refers to the threshold concentration of target RNA at which the target RNA can be detected). In some cases, a method of the present disclosure has a threshold of detection in a range of from 800 fM to 100 pM. In some cases, a method of the present disclosure has a threshold of detection in a range of from 1 pM to 10 pM. In some cases, a method of the present disclosure has a threshold of detection in a range of from 10 fM to 500 fM, e.g., from 10 fM to 50 fM, from 50 fM to 100 fM, from 100 fM to 250 fM, or from 250 fM to 500 fM.

In some cases, the minimum concentration at which a single stranded target RNA can be detected in a sample is in a range of from 500 fM to 1 nM (e.g., from 500 fM to 500 pM, from 500 fM to 200 pM, from 500 fM to 100 pM, from 500 fM to 10 pM, from 500 fM to 1 pM, from 800 fM to 1 nM, from 800 fM to 500 pM, from 800 fM to 200 pM, from 800 fM to 100 pM, from 800 fM to 10 pM, from 800 fM to 1 pM, from 1 pM to 1 nM, from 1 pM to 500 pM, from 1 pM to 200 pM, from 1 pM to 100 pM, or from 1 pM to 10 pM). In some cases, the minimum concentration at which a single stranded target RNA can be detected in a sample is in a range of from 800 fM to 100 pM. In some cases, the minimum concentration at which a single stranded target RNA can be detected in a sample is in a range of from 1 pM to 10 pM.

In some cases, a method of the present disclosure can detect a target single-stranded RNA present in a sample comprising a plurality of RNAs (including the single stranded target RNA and a plurality of non-target RNAs), where the target single-stranded RNA is present at a concentration as low as 500 fM (e.g., as low as 800 fM, as low as 1 pM, as low as 10 pM or as low as 100 pM). In some cases, a method of the present disclosure can detect a target single-stranded RNA present in a sample comprising a plurality of RNAs (including the single stranded target RNA and a plurality of non-target RNAs), where the target single-stranded RNA is present at a concentration as low as 1 pM.

In some cases, a method of the present disclosure can detect a target single-stranded RNA present in a sample comprising a plurality of RNAs (including the single stranded target RNA and a plurality of non-target RNAs), where the target single-stranded RNA is present at a concentration as low as 500 fM (e.g., as low as 800 fM, as low as 1 pM, as low as 10 pM or as low as 100 pM), and where the sample is contacted for 60 minutes or less prior to the measuring step (e.g., in some cases 40 minutes or less). In some cases, a method of the present disclosure can detect a target single-stranded RNA present in a sample comprising a plurality of RNAs (including the single stranded target RNA and a plurality of non-target RNAs), where the target single-stranded RNA is present at a concentration as low as 1 pM, and where the sample is contacted for 60 minutes or less prior to the measuring step (e.g., in some cases 40 minutes or less).

For example, in some cases, a method of the present disclosure provides for detection of a target RNA present in a sample at a concentration of 500 fM or more (e.g., 800 fM or more, 1 pM or more, 5 pM or more, 10 pM or more). In some cases, a method of the present disclosure provides for detection of a target RNA present in a sample at a concentration of 1 pM or more (e.g., 2 pM or more 5 pM or more, or 8 pM or more). In some cases, a method of the present disclosure provides for detection of a target RNA present in a sample at a concentration of 500 fM or more (e.g., 1 pM or more, 5 pM or more, 10 pM or more), where the sample is contacted for 60 minutes or less prior to the measuring step (e.g., in some cases 40 minutes or less). In some cases, a method of the present disclosure provides for detection of a target RNA present in a sample at a concentration of 1 pM or more (e.g., 2 pM or more 5 pM or more, or 8 pM or more) where the sample is contacted for 60 minutes or less prior to the measuring step (e.g., in some cases 40 minutes or less).

In some cases, a method of the present disclosure provides for detection of a target RNA present in a sample at a concentration of 10 nM or less. In some cases, a method of the present disclosure provides for detection of a target RNA present in a sample at a concentration of 5 nM or less. In some cases, a method of the present disclosure provides for detection of a target RNA present in a sample at a concentration of 1 nM or less. In some cases, a method of the present disclosure provides for detection of a target RNA present in a sample at a concentration of 0.5 nM or less. In some cases, a method of the present disclosure provides for detection of a target RNA present in a sample at a concentration of 0.1 nM or less. In some cases, a method of the present disclosure provides for detection of a target RNA present in a sample at a concentration of 0.05 nM or less. In some cases, a method of the present disclosure provides for detection of a target RNA present in a sample at a concentration of 0.01 nM or less. In some cases, a method of the present disclosure provides for detection of a target RNA present in a sample at a concentration of 0.005 nM or less. In some cases, a method of the present disclosure provides for detection of a target RNA present in a sample at a concentration of 0.001 nM or less. In some cases, a method of the present disclosure provides for detection of a target RNA present in a sample at a concentration of 0.0005 nM or less. In some cases, a method of the present disclosure provides for detection of a target RNA present in a sample at a concentration of 0.0001 nM or less. In some cases, a method of the present disclosure provides for detection of a target RNA present in a sample at a concentration of 0.00005 nM or less. In some cases, a method of the present disclosure provides for detection of a target RNA present in a sample at a concentration of 0.00001 nM or less.

In some cases, a method of the present disclosure provides for detection of a target RNA present in a sample at a concentration of from $10^{-6}$ nM to 1 nM, e.g., from $10^{-6}$ nM to $5\times10^{-6}$ nM, from $5\times10^{-6}$ nM to $10^{-5}$ nM, from $10^{-5}$ nM to $5\times10^{-5}$ nM, from $5\times10^{-5}$ nM to $10^{-4}$ nM, from $10^{-4}$ nM to $5\times10^{-4}$ nM, from $5\times10^{-4}$ nM to $10^{-3}$ nM, from $10^{-3}$ nM to $5\times10^{-3}$ nM, from $5\times10^{-3}$ nM to $10^{-2}$ nM, from $10^{-2}$ nM to $5\times10^{-2}$ nM, from $5\times10^{-2}$ nM to 0.1 nM, from 0.1 nM to 0.5 nM, from 0.5 nM to 1 nM, from 1 nM to 5 nM, or from 5 nM to 10 nM.

In some cases, a method of the present disclosure provides for detection of a target RNA present in a sample at a concentration of less than 10 nM. In some cases, a method of the present disclosure provides for detection of a target RNA present in a sample at a concentration of less than 5 nM. In some cases, a method of the present disclosure provides for detection of a target RNA present in a sample at a concentration of less than 1 nM. In some cases, a method of the present disclosure provides for detection of a target RNA present in a sample at a concentration of less than 0.5 nM. In some cases, a method of the present disclosure provides for detection of a target RNA present in a sample at a concentration of less than 0.1 nM. In some cases, a method of the present disclosure provides for detection of a target RNA present in a sample at a concentration of less than 0.05 nM. In some cases, a method of the present disclosure provides for detection of a target RNA present in a sample at a concentration of less than 0.01 nM. In some cases, a method of the present disclosure provides for detection of a target RNA present in a sample at a concentration of less than 0.005 nM. In some cases, a method of the present disclosure provides for detection of a target RNA present in a sample at a concentration of less than 0.001 nM. In some cases, a method of the present disclosure provides for detection of a target RNA present in a sample at a concentration of less than 0.0005 nM. In some cases, a method of the present disclosure provides for detection of a target RNA present in a sample at a concentration of less than 0.0001 nM. In some cases, a method of the present disclosure provides for detection of a target RNA present in a sample at a concentration of less than 0.00005 nM. In some cases, a method of the present disclosure provides for detection of a target RNA present in a sample at a concentration of less than 0.00001 nM.

In some cases, a method of the present disclosure can be used to determine the amount of a target RNA in a sample (e.g., a sample comprising the target RNA and a plurality of non-target RNAs). Determining the amount of a target RNA in a sample can comprise comparing the amount of detectable signal generated from a test sample to the amount of detectable signal generated from a reference sample. Determining the amount of a target RNA in a sample can comprise: measuring the detectable signal to generate a test measurement; measuring a detectable signal produced by a reference sample to generate a reference measurement; and comparing the test measurement to the reference measurement to determine an amount of target RNA present in the sample.

For example, in some cases, a method of the present disclosure for determining the amount of a target RNA in a sample comprises: a) contacting the sample (e.g., a sample comprising the target RNA and a plurality of non-target RNAs) with: (i) a C2c2 guide RNA that hybridizes with the single stranded target RNA, and (ii) a C2c2 protein that cleaves RNAs present in the sample; b) measuring a detectable signal produced by C2c2 protein-mediated RNA cleavage, generating a test measurement; c) measuring a detectable signal produced by a reference sample to generate a reference measurement; and d) comparing the test measurement to the reference measurement to determine an amount of target RNA present in the sample.

As another example, in some cases, a method of the present disclosure for determining the amount of a target RNA in a sample comprises: a) contacting the sample (e.g., a sample comprising the target RNA and a plurality of non-target RNAs) with: i) a precursor C2c2 guide RNA array comprising two or more C2c2 guide RNAs each of which has a different guide sequence; and (ii) a C2c2 protein that cleaves the precursor C2c2 guide RNA array into individual C2c2 guide RNAs, and also cleaves RNAs of the sample; b) measuring a detectable signal produced by C2c2 protein-mediated RNA cleavage, generating a test measurement; c) measuring a detectable signal produced by each of two or more reference samples to generate two or more reference measurements; and d) comparing the test measurement to the reference measurements to determine an amount of target RNA present in the sample.

Samples

A subject sample includes a plurality of target RNAs. The term "plurality" is used herein to mean two or more. Thus, in some cases a sample includes two or more (e.g., 3 or more, 5 or more, 10 or more, 20 or more, 50 or more, 100 or more, 500 or more, 1,000 or more, or 5,000 or more) RNAs. A subject method can be used as a very sensitive way to detect a single stranded target RNA present in a complex mixture of RNAs. Thus, in some cases the sample includes 5 or more RNAs (e.g., 10 or more, 20 or more, 50 or more, 100 or more, 500 or more, 1,000 or more, or 5,000 or more RNAs) that differ from one another in sequence. In some cases, the sample includes 10 or more, 20 or more, 50 or more, 100 or more, 500 or more, $10^3$ or more, $5 \times 10^3$ or more, $10^4$ or more, $5 \times 10^4$ or more, $10^5$ or more, $5 \times 10^5$ or more, $10^6$ or more $5 \times 10^6$ or more, or $10^7$ or more, RNAs that differ from one another in sequence. In some cases, the sample comprises from 10 to 20, from 20 to 50, from 50 to 100, from 100 to 500, from 500 to $10^3$, from $10^3$ to $5 \times 10^3$, from $5 \times 10^3$ to $10^4$, from $10^4$ to $5 \times 10^4$, from $5 \times 10^4$ to $10^5$, from $10^5$ to $5 \times 10^5$, from $5 \times 10^5$ to $10^6$, from $10^6$ to $5 \times 10^6$, or from $5 \times 10^6$ to $10^7$, or more than $10^7$, RNAs that differ from one another in sequence. In some cases, the sample comprises from 5 to $10^7$ RNAs that differ from one another in sequence (e.g., from 5 to $10^6$, from 5 to $10^5$, from 5 to 50,000, from 5 to 30,000, from 10 to $10^6$, from 10 to $10^5$, from 10 to 50,000, from 10 to 30,000, from 20 to $10^6$, from 20 to $10^5$, from 20 to 50,000, or from 20 to 30,000 RNAs that differ from one another in sequence). In some cases, the sample comprises from 5 to 50,000 RNAs that differ from one another in sequence (e.g., from 5 to 30,000, from 10 to 50,000, or from 10 to 30,000) RNAs that differ from one another in sequence). In some cases the sample includes 20 or more RNAs that differ from one another in sequence. In some cases, the sample includes RNAs from a cell lysate (e.g., a eukaryotic cell lysate, a mammalian cell lysate, a human cell lysate, a prokaryotic cell lysate, a plant cell lysate, and the like). For example, in some cases the sample includes expressed RNAs from a cell such as a eukaryotic cell, e.g., a mammalian cell such as a human cell.

The term "sample" is used herein to mean any sample that includes single stranded RNA. The sample can be derived from any source, e.g., the sample can be a synthetic combination of purified RNAs; the sample can be a cell lysate, an RNA-enriched cell lysate, or RNAs isolated and/or purified from a cell lysate. The sample can be from a patient (e.g., for the purpose of diagnosis). The sample can be from permeabilized cells. The sample can be from crosslinked cells. The sample can be in tissue sections. The sample can be from tissues prepared by crosslinking followed by delipidation and adjustment to make a uniform refractive index. Examples of tissue preparation by crosslinking followed by delipidation and adjustment to make a uniform refractive index have been described in, for example, Shah et al., Development (2016) 143, 2862-2867 doi:10.1242/dev.138560.

A "sample" can include a single stranded target RNA and a plurality of non-target RNAs. In some cases, the target single-stranded RNA is present in the sample at one copy per 10 non-target RNAs, one copy per 20 non-target RNAs, one copy per 25 non-target RNAs, one copy per 50 non-target RNAs, one copy per 100 non-target RNAs, one copy per 500 non-target RNAs, one copy per $10^3$ non-target RNAs, one copy per $5 \times 10^3$ non-target RNAs, one copy per $10^4$ non-target RNAs, one copy per $5 \times 10^4$ non-target RNAs, one copy per $10^5$ non-target RNAs, one copy per $5 \times 10^5$ non-target RNAs, one copy per $10^6$ non-target RNAs, or less than one copy per $10^6$ non-target RNAs. In some cases, the target single-stranded RNA is present in the sample at from one copy per 10 non-target RNAs to 1 copy per 20 non-target RNAs, from 1 copy per 20 non-target RNAs to 1 copy per 50 non-target RNAs, from 1 copy per 50 non-target RNAs to 1 copy per 100 non-target RNAs, from 1 copy per 100 non-target RNAs to 1 copy per 500 non-target RNAs, from 1 copy per 500 non-target RNAs to 1 copy per $10^3$ non-target RNAs, from 1 copy per $10^3$ non-target RNAs to 1 copy per $5 \times 10^3$ non-target RNAs, from 1 copy per $5 \times 10^3$ non-target RNAs to 1 copy per $10^4$ non-target RNAs, from 1 copy per $10^4$ non-target RNAs to 1 copy per $10^5$ non-target RNAs, from 1 copy per $10^5$ non-target RNAs to 1 copy per $10^6$ non-target RNAs, or from 1 copy per $10^6$ non-target RNAs to 1 copy per $10^7$ non-target RNAs.

Suitable samples include but are not limited to blood, serum, plasma, urine, aspirate, and biopsy samples. Thus, the term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., RNAs. The term "sample" encompasses biological samples such as a clinical sample such as blood, plasma, serum, aspirate, cerebral spinal fluid (CSF), and also includes tissue obtained by surgical resection, tissue obtained by biopsy, cells in culture, cell supernatants, cell lysates, tissue samples, organs, bone marrow, and the like. A "biological sample" includes biological fluids derived therefrom (e.g., cancerous cell, infected cell, etc.), e.g., a sample comprising RNAs that is obtained from such cells (e.g., a cell lysate or other cell extract comprising RNAs).

A sample can comprise, or can be obtained from, any of a variety of cells, tissues, organs, or acellular fluids. Suitable sample sources include eukaryotic cells, bacterial cells, and archaeal cells. Suitable sample sources include single-celled organisms and multi-cellular organisms. Suitable sample sources include single-cell eukaryotic organisms; a plant or a plant cell; an algal cell, e.g., *Botryococcus braunii, Chlamydomonas reinhardtii, Nannochloropsis gaditana, Chlorella pyrenoidosa, Sargassum patens*, C. agardh, and the like; a fungal cell (e.g., a yeast cell); an animal cell, tissue, or organ; a cell, tissue, or organ from an invertebrate animal (e.g. fruit fly, cnidarian, echinoderm, nematode, an insect, an arachnid, etc.); a cell, tissue, fluid, or organ from a vertebrate animal (e.g., fish, amphibian, reptile, bird, mammal); a cell, tissue, fluid, or organ from a mammal (e.g., a human; a non-human primate; an ungulate; a feline; a bovine; an ovine; a caprine; etc.). Suitable sample sources include nematodes, protozoans, and the like. Suitable sample sources include parasites such as helminths, malarial parasites, etc.

Suitable sample sources include a cell, tissue, or organism of any of the six kingdoms, e.g., Bacteria (e.g., Eubacteria); Archaebacteria; Protista; Fungi; Plantae; and Animalia. Suitable sample sources include plant-like members of the kingdom Protista, including, but not limited to, algae (e.g., green algae, red algae, glaucophytes, cyanobacteria); fungus-like members of Protista, e.g., slime molds, water molds, etc.; animal-like members of Protista, e.g., *flagellates* (e.g., *Euglena*), amoeboids (e.g., amoeba), sporozoans (e.g, Apicomplexa, Myxozoa, Microsporidia), and ciliates (e.g., Paramecium). Suitable sample sources include members of the kingdom Fungi, including, but not limited to, members of any of the phyla: Basidiomycota (club fungi; e.g., members of *Agaricus, Amanita, Boletus*, Cantherellus, etc.); Ascomycota (sac fungi, including, e.g., *Saccharomyces*); Mycophycophyta (lichens); Zygomycota (conjugation fungi); and Deuteromycota. Suitable sample sources include members of the kingdom Plantae, including, but not limited to, members of any of the following divisions: *Bryophyta* (e.g., mosses), Anthocerotophyta (e.g., hornworts), Hepaticophyta (e.g., liverworts), Lycophyta (e.g., club mosses), Sphenophyta (e.g., horsetails), Psilophyta (e.g., whisk ferns), Ophioglossophyta, Pterophyta (e.g., ferns), Cycadophyta, Gingkophyta, Pinophyta, Gnetophyta, and Magnoliophyta (e.g., flowering plants). Suitable sample sources include members of the kingdom Animalia, including, but not limited to, members of any of the following phyla: Porifera (sponges); Placozoa; Orthonectida (parasites of marine invertebrates); Rhombozoa; Cnidaria (corals, anemones, jellyfish, sea pens, sea pansies, sea wasps); Ctenophora (comb jellies); Platyhelminthes (flatworms); Nemertina (ribbon worms); Ngathostomulida (jawed worms)p Gastrotricha; Rotifera; Priapulida; Kinorhyncha; Loricifera; Acanthocephala; Entoprocta; Nemotoda; Nematomorpha; Cycliophora; Mollusca (mollusks); Sipuncula (peanut worms); Annelida (segmented worms); Tardigrada (water bears); Onychophora (velvet worms); Arthropoda (including the subphyla: Chelicerata, Myriapoda, Hexapoda, and Crustacea, where the Chelicerata include, e.g., arachnids, Merostomata, and Pycnogonida, where the Myriapoda include, e.g., Chilopoda (centipedes), Diplopoda (millipedes), Paropoda, and Symphyla, where the Hexapoda include insects, and where the Crustacea include shrimp, krill, barnacles, etc.; Phoronida; Ectoprocta (moss animals); Brachiopoda; Echinodermata (e.g. starfish, sea daisies, feather stars, sea urchins, sea cucumbers, brittle stars, brittle baskets, etc.); Chaetognatha (arrow worms); Hemichordata (acorn worms); and Chordata. Suitable members of Chordata include any member of the following subphyla: Urochordata (sea squirts; including Ascidiacea, Thaliacea, and Larvacea); Cephalochordata (lancelets); Myxini (hagfish); and Vertebrata, where members of Vertebrata include, e.g., members of Petromyzontida (lampreys), Chondrichthyces (cartilaginous fish), Actinopterygii (ray-finned fish), Actinista (coelocanths), Dipnoi (lungfish), Reptilia (reptiles, e.g., snakes, alligators, crocodiles, lizards, etc.), Aves (birds); and Mammalian (mammals). Suitable plants include any monocotyledon and any dicotyledon.

Suitable sources of a sample include cells, fluid, tissue, or organ taken from an organism; from a particular cell or group of cells isolated from an organism; etc. For example, where the organism is a plant, suitable sources include xylem, the phloem, the cambium layer, leaves, roots, etc. Where the organism is an animal, suitable sources include particular tissues (e.g., lung, liver, heart, kidney, brain, spleen, skin, fetal tissue, etc.), or a particular cell type (e.g., neuronal cells, epithelial cells, endothelial cells, astrocytes, macrophages, glial cells, islet cells, T lymphocytes, B lymphocytes, etc.).

In some cases, the source of the sample is a diseased cell, fluid, tissue, or organ. In some cases, the source of the sample is a normal (non-diseased) cell, fluid, tissue, or organ. In some cases, the source of the sample is a pathogen-infected cell, tissue, or organ. Pathogens include viruses, fungi, helminths, protozoa, malarial parasites, *Plasmodium* parasites, *Toxoplasma* parasites, *Schistosoma* parasites, and the like. "Helminths" include roundworms, heartworms, and phytophagous nematodes (Nematoda), flukes (Tematoda), Acanthocephala, and tapeworms (Cestoda). Protozoan infections include infections from Giardia spp., *Trichomonas* spp., African trypanosomiasis, amoebic dysentery, babesiosis, balantidial dysentery, Chaga's disease, coccidiosis, malaria and toxoplasmosis. Examples of pathogens such as parasitic/protozoan pathogens include, but are not limited to: *Plasmodium falciparum, Plasmodium vivax, Trypanosoma cruzi* and *Toxoplasma gondii*. Fungal pathogens include, but are not limited to: *Cryptococcus neoformans, Histoplasma capsulatum, Coccidioides immitis, Blastomyces dermatitidis, Chlamydia trachomatis*, and *Candida albicans*. Pathogenic viruses include, e.g., immunodeficiency virus (e.g., HIV); influenza virus; dengue; West Nile virus; herpes virus; yellow fever virus; Hepatitis Virus C; Hepatitis Virus A; Hepatitis Virus B; papillomavirus; and the like. Pathogens include, e.g., HIV virus, *Mycobacterium tuberculosis, Streptococcus agalactiae*, methicillin-resistant *Staphylococcus aureus, Legionella pneumophila, Streptococcus pyogenes, Escherichia coli, Neisseria gonorrhoeae, Neisseria meningitidis*, Pneumococcus, *Cryptococcus neoformans, Histoplasma capsulatum, Hemophilus influenzae* B, *Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, Sendai virus, feline leukemia virus, Reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiense, Trypanosoma brucei, Schistosoma mansoni, Schistosoma japonicum, Babesia bovis, Eimeria tenella, Onchocerca volvulus, Leishmania tropica, Mycobacterium tuberculosis, Trichinella spiralis, Theileria parva, Taenia hydatigena, Taenia ovis, Taenia saginata, Echinococcus granulosus, Mesocestoides corti, Mycoplasma arthritidis, M. hyorhinis, M. orale, M. arginini, Acholeplasma laidlawii, M. salivarium* and *M. pneumoniae*.

Target RNA

A target RNA can be any single stranded RNA (ssRNA). Examples include but are not limited to mRNA, rRNA, tRNA, non-coding RNA (ncRNA), long non-coding RNA (lncRNA), and microRNA (miRNA). In some cases, the target ssRNA is mRNA. In some cases, the single stranded target nucleic acid is ssRNA from a virus (e.g., Zika virus, human immunodeficiency virus, influenza virus, and the like). In some cases, the single-stranded target nucleic acid is ssRNA of a parasite. In some cases, the single-stranded target nucleic acid is ssRNA of a *bacterium*, e.g., a pathogenic *bacterium*. The source of the target RNA can be the same as the source of the RNA sample, as described above.

Measuring a Detectable Signal

In some cases, a subject method includes a step of measuring (e.g., measuring a detectable signal produced by C2c2 protein-mediated RNA cleavage). Because a C2c2 protein cleaves non-targeted RNA once activated, which occurs when a C2c2 guide RNA hybridizes with a target RNA in the presence of a C2c2 protein, a detectable signal can be any signal that is produced when RNA is cleaved. For example, in some cases the step of measuring can include one or more of: gold nanoparticle based detection (e.g., see Xu et al., Angew Chem Int Ed Engl. 2007; 46(19):3468-70; and Xia et. al., Proc Natl Acad Sci USA. 2010 Jun. 15; 107(24):10837-41), fluorescence polarization, colloid phase transition/dispersion (e.g., Baksh et. al., Nature. 2004 Jan. 8; 427(6970):139-41), electrochemical detection, semiconductor-based sensing (e.g., Rothberg et. al., Nature. 2011 Jul. 20; 475(7356):348-52; e.g., one could use a phosphatase to generate a pH change after RNA cleavage reactions, by opening 2'-3' cyclic phosphates, and by releasing inorganic phosphate into solution), and detection of a labeled detector RNA (see below for more details). The readout of such detection methods can be any convenient readout. Examples of possible readouts include but are not limited to: a measured amount of detectable fluorescent signal; a visual analysis of bands on a gel (e.g., bands that represent cleaved product versus uncleaved substrate), a visual or sensor based detection of the presence or absence of a color (i.e., color detection method), and the presence or absence of (or a particular amount of) an electrical signal.

The measuring can in some cases be quantitative, e.g., in the sense that the amount of signal detected can be used to determine the amount of target RNA present in the sample. The measuring can in some cases be qualitative, e.g., in the sense that the presence or absence of detectable signal can indicate the presence or absence of targeted RNA. In some cases, a detectable signal will not be present (e.g., above a given threshold level) unless the targeted RNA(s) is present above a particular threshold concentration (e.g., see FIG. 5). In some cases, the threshold of detection can be titrated by modifying the amount of C2c2 protein, guide RNA, sample volume, and/or detector RNA (if one is used). As such, for example, as would be understood by one of ordinary skill in the art, a number of controls can be used if desired in order to set up one or more reactions, each set up to detect a different threshold level of target RNA, and thus such a series of reactions could be used to determine the amount of target RNA present in a sample (e.g., one could use such a series of reactions to determine that a target RNA is present in the sample 'at a concentration of at least X').

Labeled Detector RNA

In some cases, a subject method includes contacting a sample (e.g., a sample comprising a target RNA and a plurality of non-target RNAs) with: i) a labeled detector RNA; ii) a C2c2 protein; and iii) a C2c2 guide RNA (or precursor C2c2 guide RNA array). For example, in some cases, a subject method includes contacting a sample with a labeled detector RNA comprising a fluorescence-emitting dye pair; the C2c2 protein cleaves the labeled detector RNA after it is activated (by binding to the C2c2 guide RNA in the context of the guide RNA hybridizing to a target RNA); and the detectable signal that is measured is produced by the fluorescence-emitting dye pair. For example, in some cases, a subject method includes contacting a sample with a labeled detector RNA comprising a fluorescence resonance energy transfer (FRET) pair or a quencher/fluor pair, or both. In some cases, a subject method includes contacting a sample with a labeled detector RNA comprising a FRET pair. In some cases, a subject method includes contacting a sample with a labeled detector RNA comprising a fluor/quencher pair. Fluorescence-emitting dye pairs comprise a FRET pair or a quencher/fluor pair. In both cases of a FRET pair and a quencher/fluor pair, the emission spectrum of one of the dyes overlaps a region of the absorption spectrum of the other dye in the pair. As used herein, the term "fluorescence-emitting dye pair" is a generic term used to encompass both a "fluorescence resonance energy transfer (FRET) pair" and a "quencher/fluor pair," both of which terms are discussed in more detail below. The term "fluorescence-emitting dye pair" is used interchangeably with the phrase "a FRET pair and/or a quencher/fluor pair."

In some cases (e.g., when the detector RNA includes a FRET pair) the labeled detector RNA produces an amount of detectable signal prior to being cleaved, and the amount of detectable signal that is measured is reduced when the labeled detector RNA is cleaved. In some cases, the labeled detector RNA produces a first detectable signal prior to being cleaved (e.g., from a FRET pair) and a second detectable signal when the labeled detector RNA is cleaved (e.g., from a quencher/fluor pair). As such, in some cases, the labeled detector RNA comprises a FRET pair and a quencher/fluor pair.

In some cases, the labeled detector RNA comprises a FRET pair. FRET is a process by which radiationless transfer of energy occurs from an excited state fluorophore to a second chromophore in close proximity. The range over which the energy transfer can take place is limited to approximately 10 nanometers (100 angstroms), and the efficiency of transfer is extremely sensitive to the separation distance between fluorophores. Thus, as used herein, the term "FRET" ("fluorescence resonance energy transfer"; also known as "Förster resonance energy transfer") refers to a physical phenomenon involving a donor fluorophore and a matching acceptor fluorophore selected so that the emission spectrum of the donor overlaps the excitation spectrum of the acceptor, and further selected so that when donor and acceptor are in close proximity (usually 10 nm or less) to one another, excitation of the donor will cause excitation of and emission from the acceptor, as some of the energy passes from donor to acceptor via a quantum coupling effect. Thus, a FRET signal serves as a proximity gauge of the donor and acceptor; only when they are in close proximity to one another is a signal generated. The FRET donor moiety (e.g., donor fluorophore) and FRET acceptor moiety (e.g., acceptor fluorophore) are collectively referred to herein as a "FRET pair".

The donor-acceptor pair (a FRET donor moiety and a FRET acceptor moiety) is referred to herein as a "FRET pair" or a "signal FRET pair." Thus, in some cases, a subject labeled detector RNA includes two signal partners (a signal pair), when one signal partner is a FRET donor moiety and the other signal partner is a FRET acceptor moiety. A subject labeled detector RNA that includes such a FRET pair (a FRET donor moiety and a FRET acceptor moiety) will thus exhibit a detectable signal (a FRET signal) when the signal partners are in close proximity (e.g., while on the same RNA molecule), but the signal will be reduced (or absent) when the partners are separated (e.g., after cleavage of the RNA molecule by a C2c2 protein).

FRET donor and acceptor moieties (FRET pairs) will be known to one of ordinary skill in the art and any convenient FRET pair (e.g., any convenient donor and acceptor moiety pair) can be used. Examples of suitable FRET pairs include but are not limited to those presented in Table 1. See also: Bajar et al. Sensors (Basel). 2016 Sep. 14; 16(9); and Abraham et al. PLoS One. 2015 Aug. 3; 10(8):e0134436.

TABLE 1

Examples of FRET pairs (donor and acceptor FRET moieties)

| Donor | Acceptor |
|---|---|
| Tryptophan | Dansyl |
| IAEDANS (1) | DDPM (2) |
| BFP | DsRFP |
| Dansyl | Fluorescein isothiocyanate (FITC) |
| Dansyl | Octadecylrhodamine |
| Cyan fluorescent protein (CFP) | Green fluorescent protein (GFP) |
| CF (3) | Texas Red |
| Fluorescein | Tetramethylrhodamine |
| Cy3 | Cy5 |
| GFP | Yellow fluorescent protein (YFP) |
| BODIPY FL (4) | BODIPY FL (4) |
| Rhodamine 110 | Cy3 |

TABLE 1-continued

Examples of FRET pairs (donor and acceptor FRET moieties)

| Donor | Acceptor |
| --- | --- |
| Rhodamine 6G | Malachite Green |
| FITC | Eosin Thiosemicarbazide |
| B-Phycoerythrin | Cy5 |
| Cy5 | Cy5.5 |

(1) 5-(2-iodoacetylaminoethyl)aminonaphthalene-1-sulfonic acid
(2) N-(4-dimethylamino-3,5-dinitrophenyl)maleimide
(3) carboxyfluorescein succinimidyl ester
(4) 4,4-difluoro-4-bora-3a,4a-diaza-s-indacene In some cases, a detectable signal is produced when the labeled detector RNA is cleaved (e.g., in some cases, the labeled detector RNA comprises a quencher/fluor pair. One signal partner of a signal quenching pair produces a detectable signal and the other signal partner is a quencher moiety that quenches the detectable signal of the first signal partner (i.e., the quencher moiety quenches the signal of the signal moiety such that the signal from the signal moiety is reduced (quenched) when the signal partners are in proximity to one another, e.g., when the signal partners of the signal pair are in close proximity).

For example, in some cases, an amount of detectable signal increases when the labeled detector RNA is cleaved. For example, in some cases, the signal exhibited by one signal partner (a signal moiety) is quenched by the other signal partner (a quencher signal moiety), e.g., when both are present on the same RNA molecule prior to cleavage by a C2c2 protein. Such a signal pair is referred to herein as a "quencher/fluor pair", "quenching pair", or "signal quenching pair." For example, in some cases, one signal partner (e.g., the first signal partner) is a signal moiety that produces a detectable signal that is quenched by the second signal partner (e.g., a quencher moiety). The signal partners of such a quencher/fluor pair will thus produce a detectable signal when the partners are separated (e.g., after cleavage of the detector RNA by a C2c2 protein), but the signal will be quenched when the partners are in close proximity (e.g., prior to cleavage of the detector RNA by a C2c2 protein).

A quencher moiety can quench a signal from the signal moiety (e.g., prior to cleave of the detector RNA by a C2c2 protein) to various degrees. In some cases, a quencher moiety quenches the signal from the signal moiety where the signal detected in the presence of the quencher moiety (when the signal partners are in proximity to one another) is 95% or less of the signal detected in the absence of the quencher moiety (when the signal partners are separated). For example, in some cases, the signal detected in the presence of the quencher moiety can be 90% or less, 80% or less, 70% or less, 60% or less, 50% or less, 40% or less, 30% or less, 20% or less, 15% or less, 10% or less, or 5% or less of the signal detected in the absence of the quencher moiety. In some cases, no signal (e.g., above background) is detected in the presence of the quencher moiety.

In some cases, the signal detected in the absence of the quencher moiety (when the signal partners are separated) is at least 1.2 fold greater (e.g., at least 1.3fold, at least 1.5 fold, at least 1.7 fold, at least 2 fold, at least 2.5 fold, at least 3 fold, at least 3.5 fold, at least 4 fold, at least 5 fold, at least 7 fold, at least 10 fold, at least 20 fold, or at least 50 fold greater) than the signal detected in the presence of the quencher moiety (when the signal partners are in proximity to one another).

In some cases, the signal moiety is a fluorescent label. In some such cases, the quencher moiety quenches the signal (the light signal) from the fluorescent label (e.g., by absorbing energy in the emission spectra of the label). Thus, when the quencher moiety is not in proximity with the signal moiety, the emission (the signal) from the fluorescent label is detectable because the signal is not absorbed by the quencher moiety. Any convenient donor acceptor pair (signal moiety/quencher moiety pair) can be used and many suitable pairs are known in the art.

In some cases the quencher moiety absorbs energy from the signal moiety (also referred to herein as a "detectable label") and then emits a signal (e.g., light at a different wavelength). Thus, in some cases, the quencher moiety is itself a signal moiety (e.g., a signal moiety can be 6-carboxyfluorescein while the quencher moiety can be 6-carboxy-tetramethylrhodamine), and in some such cases, the pair could also be a FRET pair. In some cases, a quencher moiety is a dark quencher. A dark quencher can absorb excitation energy and dissipate the energy in a different way (e.g., as heat). Thus, a dark quencher has minimal to no fluorescence of its own (does not emit fluorescence). Examples of dark quenchers are further described in U.S. Pat. Nos. 8,822,673 and 8,586,718; U.S. patent publications 20140378330, 20140349295, and 20140194611; and international patent applications: WO200142505 and WO200186001, all if which are hereby incorporated by reference in their entirety.

Examples of fluorescent labels include, but are not limited to: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein isothiocyanate (FITC), tetramethylrhodamine (TRITC), Texas Red, Oregon Green, Pacific Blue, Pacific Green, Pacific Orange, quantum dots, and a tethered fluorescent protein.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, and Pacific Orange.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, a quantum dot, and a tethered fluorescent protein.

Examples of ATTO dyes include, but are not limited to: ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, and ATTO 740.

Examples of AlexaFluor dyes include, but are not limited to: Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, Alexa Fluor® 790, and the like.

Examples of quencher moieties include, but are not limited to: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and metal clusters such as gold nanoparticles, and the like.

In some cases, a quencher moiety is selected from: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and a metal cluster.

Examples of an ATTO quencher include, but are not limited to: ATTO 540Q, ATTO 580Q, and ATTO 612Q. Examples of a Black Hole Quencher® (BHQ®) include, but are not limited to: BHQ-0 (493 nm), BHQ-1 (534 nm), BHQ-2 (579 nm) and BHQ-3 (672 nm).

For examples of some detectable labels (e.g., fluorescent dyes) and/or quencher moieties, see, e.g., Bao et al., Annu Rev Biomed Eng. 2009; 11:25-47; as well as U.S. Pat. Nos. 8,822,673 and 8,586,718; U.S. patent publications 20140378330, 20140349295, 20140194611, 20130323851, 20130224871, 20110223677, 20110190486, 20110172420, 20060179585 and 20030003486; and international patent applications: WO200142505 and WO200186001, all of which are hereby incorporated by reference in their entirety.

In some cases, cleavage of a labeled detector RNA can be detected by measuring a colorimetric read-out. For example, the liberation of a fluorophore (e.g., liberation from a FRET pair, liberation from a quencher/fluor pair, and the like) can result in a wavelength shift (and thus color shift) of a detectable signal. Thus, in some cases, cleavage of a subject labeled detector RNA can be detected by a color-shift. Such a shift can be expressed as a loss of an amount of signal of one color (wavelength), a gain in the amount of another color, a change in the ration of one color to another, and the like.

Nucleic Acid Modifications

In some cases, a labeled detector RNA comprises one or more modifications, e.g., a base modification, a backbone modification, a sugar modification, etc., to provide the nucleic acid with a new or enhanced feature (e.g., improved stability). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Backbones and Modified Internucleoside Linkages

Examples of suitable modifications include modified nucleic acid backbones and non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some cases, a labeled detector RNA comprises one or more phosphorothioate and/or heteroatom internucleoside linkages, in particular —CH$_2$—NH—O—CH$_2$—, —CH$_2$—N(CH$_3$)—O—CH$_2$-(known as a methylene(methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677. Suitable amide internucleoside linkages are disclosed in t U.S. Pat. No. 5,602,240.

Also suitable are nucleic acids having morpholino backbone structures as described in, e.g., U.S. Pat. No. 5,034,506. For example, in some cases, a labeled detector RNA comprises a 6-membered morpholino ring in place of a ribose ring. In some cases, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Mimetics

A labeled detector RNA can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene ($-CH_2-$), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (Wahlestedt et al., Proc. Natl. Acad. Sci. U.S.A., 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Modified Sugar Moieties

A labeled detector RNA can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O-$CH_2$ $CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a $O(CH_2)_2O$ $N(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O-$CH_2$-O-$CH_2$-N$(CH_3)_2$.

Other suitable sugar substituent groups include methoxy ($-O-CH_3$), aminopropoxy ($-O$ $CH_2$ $CH_2$ $CH_2NH_2$), allyl (—CH$_2$—CH═CH$_2$), —O-allyl (—O—CH$_2$—CH═CH$_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A labeled detector RNA may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

Detection of Two Different Target RNAs

As noted above, in some cases, a method of the present disclosure provides for substantially simultaneous detection of two different target RNAs (a first single-stranded target RNA and a second single-stranded target RNA) in a sample.

In some cases, the method comprises: a) contacting a sample (e.g., a sample comprising the two different target RNAs and a plurality of non-target RNAs) with: (i) a first C2c2 protein that cleaves adenine$^+$ RNAs (i.e., RNAs that include A, but not RNAs that lack A such as a polyU RNA) present in the sample; (ii); a second C2c2 protein that cleaves uracil$^+$ RNAs (i.e., RNAs that include U, but not RNAs that lack U such as a polyA RNA); (iii) a first C2c2 guide RNA that comprises a first nucleotide sequence that hybridizes with the first single stranded target RNA and a second nucleotide sequence that binds to the first C2c2 protein; and (iv) a second C2c2 guide RNA that comprises a first nucleotide sequence that hybridizes with the second single stranded target RNA and a second nucleotide sequence that binds to the second C2c2 protein; and b) measuring a detectable signal produced by RNA cleavage mediated by the first and the second C2c2 proteins, wherein a first detectable signal is produced by the first C2c2 protein and a second detectable signal is produced by the second C2c2 protein, where the first detectable signal and the second detectable signal are distinguishable from one another. In some cases, the first C2c2 protein is not activated by the second C2c2 guide RNA, and the first C2c2 protein cleaves ssRNA that includes A (e.g., does not cleave ssRNA that lacks A); and the second C2c2 protein is not activated by the first C2c2 guide RNA, and the second C2c2 protein cleaves ssRNA that includes U (e.g., does not cleave ssRNA that lacks U). In some cases, the first C2c2 protein is not activated by the second C2c2 guide RNA, and the first C2c2 protein cleaves ssRNA that includes U (e.g., does not cleave ssRNA that lacks U); and the second C2c2 protein is not activated by the first C2c2 guide RNA, and the second C2c2 protein cleaves ssRNA that includes A (e.g., does not cleave ssRNA that lacks A).

In some cases, the method also comprises contacting the sample with: i) a first labeled detector RNA comprising a first FRET pair and/or a first quencher/fluor pair (example FRET pairs and quencher/fluor pairs are described above); and ii) a second labeled detector RNA comprising a second FRET pair and/or a second quencher/fluor pair (example FRET pairs and quencher/fluor pairs are described above). In some cases, the first labelled detector RNA comprises at least one A and does not comprise U; while the second labelled detector RNA comprises at least one U and does not comprise A. In some cases, the first labelled detector RNA comprises at least one U and does not comprise A; while the second labelled detector RNA comprises at least one A and does not comprise U. The first C2c2 protein cleaves the first labelled detector RNA, and the first detectable signal is produced by the first FRET pair and/or the first quencher/fluor pair, and the second C2c2 protein cleaves the second labelled detector RNA, and the second detectable signal is produced by the second FRET pair and/or the second quencher/fluor pair. Detection of the first detectable signal indicates the presence in the sample of the first target RNA; and detection of the second detectable signal indicates the presence in the sample of the second target RNA. In some cases, the relative amounts of detected first and second signal indicate the ratio of the first target RNA to the second target RNA in the sample.

In some cases, the first labelled detector RNA comprises a label that is distinguishable from the label of the second labelled detector RNA. For example, the first labelled detector RNA can comprise a first FRET pair and/or a first quencher/fluor pair; and the second labelled detector RNA can comprise a second FRET pair and/or a second quencher/fluor pair. As one non-limiting example, the first labelled detector RNA can comprise a donor comprising tryptophan and an acceptor comprising dansyl; and the second labelled detector RNA can comprise a donor comprising IAEDANS and an acceptor comprising DDPM. As another non-limiting example, the first labelled detector RNA comprises a donor comprising dansyl and an acceptor comprising FITC; and the second labelled detector RNA comprises a donor comprising Cy3 and an acceptor comprising Cy5. In some cases, the first labelled detector RNA comprises a 5' FAM (Fluorescein)-3' IBFQ (Iowa Black® FQ) quencher/fluor pair, and in some cases the second labelled detector RNA comprises a 5'FAM (Fluorescein)-3' IBFQ (Iowa Black® FQ) quencher/fluor pair.

In some cases, the first and second labelled detector RNAs are added to the sample at the same time (substantially simultaneous contact). In some such cases, the signals produced by the first and second labelled detector RNAs are detected at the same time (substantially simultaneous contact), e.g., because in such cases the first and second labelled detector RNAs can be distinguishably labeled.

"Substantially simultaneous" refers to within about 5 minutes, within about 3 minutes, within about 2 minutes, within about 1 minute, within about 30 seconds, within about 15 seconds, within about 10 seconds, within about 5 seconds, or within about 1 second.

However, in some cases, the signals produced by the first and second labelled detector RNAs are not detected at the same time and are instead detected sequentially (one before the other). For example, in some cases, the first and second labelled detector RNAs are not added to the sample at the same time and are instead added sequentially (e.g., the second labelled detector RNA can be added after the first labelled detector RNA is added), and in some such cases the second labelled detector RNA is not added until after the signal produced by the first labelled detector RNA is detected. Thus, in some cases, the first and second labelled detector RNAs do not need to be distinguishably labeled (e.g, they can in some cases produce the same detectable signal, e.g., can flouresce at the same wavelength) because the signals are to be detected sequentially.

As an illustrative example, in some cases: (i) the first and second labelled detector RNAs are not distinguishably labeled; (ii) the sample is contacted with one labelled detector RNA and the signal produced by that labelled detector RNA is detected (e.g., measured); and (iii) the sample is then contacted with the other labelled detector RNA and the signal produced by the second added labelled detector RNA is detected—thus, when both target ssRNAs are present in the sample, addition of the second labelled detector RNA can result in a boost of signal (e.g., if the signal increases with increased cleavage, e.g., Flour/Quencher pair) or can result in a detectable decrease in signal following addition of the second labelled detector RNA (e.g., if the signal decreases with increased cleavage, e.g., FRET pair).

The first and the second C2c2 proteins can be orthogonal to one another with respect to C2c2 guide RNA binding. In such cases, the first C2c2 protein does not bind to the second C2c2 guide RNA; and the second C2c2 protein does not bind to the first guide RNA. The first C2c2 protein and the second C2c2 protein can also differ from one another in their ssRNA cleavage preference, such that one of the C2c2 proteins cleaves ssRNA at As and the other C2c2 protein cleaves ssRNA at Us.

Figure 44A:
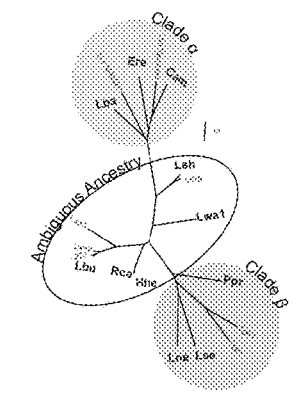
FIG. 44A-44F depict crRNA exchangeability within the Cas13a family.
Figure 44B:
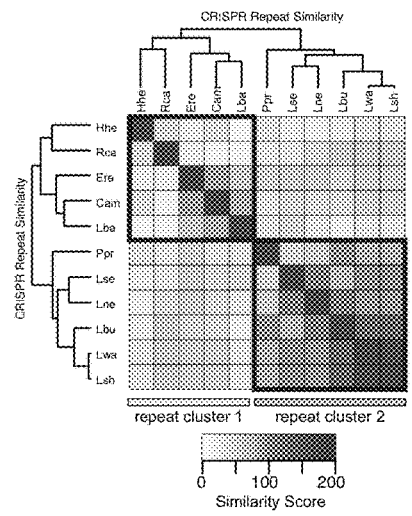
Figure 44C:
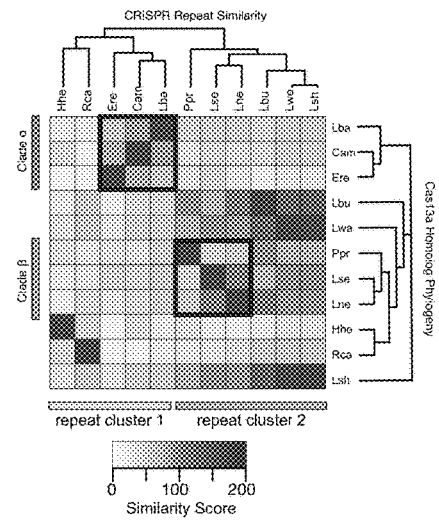
Figure 44D:
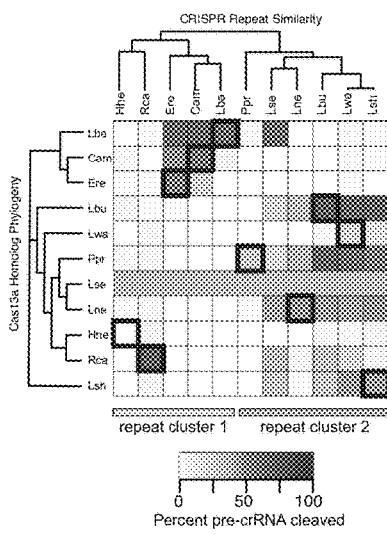
Figure 44E:
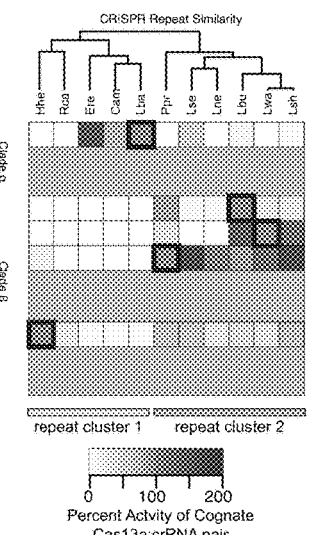

Guidance for orthogonal pairs of C2c2 proteins can be found in FIG. 44E.

Non-limiting examples of orthogonal pairs of C2c2 proteins suitable for use in a method of the present disclosure include those depicted below in Table 10. The cleavage preference is presented in parenthesis following the name of the Cas13a protein. For example, "Lba (A)" refers to an Lba Cas13a protein, which cleaves ssRNA at A; and "Lbu (U)" refers to an Lbu Cas13a protein, which cleaves ssRNA at U. IDC-22 T1

TABLE 10

| C2c2 protein #1 | C2c2 protein #2 |
| --- | --- |
| Lba (A) | Hhe (U) |
| Lba (A) | Rca (U) |
| Lba (A) | Ppr (U) |
| Lba (A) | Lne (U) |
| Lba (A) | Lbu (U) |
| Lba (A) | Lwa (U) |
| Lba (A) | Lsh (U) |
| Ere (A) | Hhe (U) |
| Ere (A) | Rca (U) |
| Ere (A) | Ppr (U) |
| Ere (A) | Lne (U) |
| Ere (A) | Lbu (U) |
| Ere (A) | Lwa (U) |
| Ere (A) | Lsh (U) |
| Ere (A) | Lse (U) |
| Cam (A) | Hhe (U) |
| Cam (A) | Rca (U) |
| Cam (A) | Ppr (U) |
| Cam (A) | Lne (U) |
| Cam (A) | Lbu (U) |
| Cam (A) | Lwa (U) |
| Cam (A) | Lsh (U) |
| Cam (A) | Lse (U) |

The first and the second labelled detector RNAs can each independently have a length of from 2 to 100 ribonucleotides (e.g., from 2 to 80, 2 to 60, 2 to 50, 2 to 40, 2 to 30, 2 to 20, 2 to 15, or 2 to 10 ribonucleotides). The first and the second labelled detector RNAs can each independently have a length of from 2 ribonucleotides to 100 ribonucleotides, e.g., from 2 ribonucleotides to 5 ribonucleotides, from 5 ribonucleotides to 7 ribonucleotides, from 7 ribonucleotides to 10 ribonucleotides, from 10 ribonucleotides to 15 ribonucleotides, from 15 ribonucleotides to 20 ribonucleotides, from 20 ribonucleotides to 25 ribonucleotides, from 25 ribonucleotides to 30 ribonucleotides, from 30 ribonucleotides to 35 ribonucleotides, from 35 ribonucleotides to 40 ribonucleotides, from 40 ribonucleotides to 45 ribonucleotides, or from 45 ribonucleotides to 50 ribonucleotides.

In some cases, the first labelled detector RNA comprises at least one A (e.g., at least 2, at least 3, or at least 4 As) and lacks U; and the second labelled detector RNA comprises at least one U (e.g., at least 2, at least 3, or at least 4 Us) and lacks A.

In some cases, the first labelled detector RNA lacks U and includes a stretch of from 2 to 15 consecutive As (e.g., from 2 to 12, 2 to 10, 2 to 8, 2 to 6, 2 to 4, 3 to 15, 3 to 12, 3 to 10, 3 to 8, 3 to 6, 3 to 5, 4 to 15, 4 to 12, 4 to 10, 4 to 8, or 4 to 6 consecutive As). In some cases, the first labelled detector RNA lacks U and includes a stretch of at least 2 consecutive As (e.g., at least 3, at least 4, or at least 5 consecutive As). In some cases, the second labelled detector RNA lacks A and includes a stretch of from 2 to 15 consecutive Us (e.g., from 2 to 12, 2 to 10, 2 to 8, 2 to 6, 2 to 4, 3 to 15, 3 to 12, 3 to 10, 3 to 8, 3 to 6, 3 to 5, 4 to 15, 4 to 12, 4 to 10, 4 to 8, or 4 to 6 consecutive Us). In some cases, the second labelled detector RNA lacks A and includes a stretch of at least 2 consecutive Us (e.g., at least 3, at least 4, or at least 5 consecutive Us).

In some cases, the first labelled detector RNA lacks A and includes a stretch of from 2 to 15 consecutive Us (e.g., from 2 to 12, 2 to 10, 2 to 8, 2 to 6, 2 to 4, 3 to 15, 3 to 12, 3 to 10, 3 to 8, 3 to 6, 3 to 5, 4 to 15, 4 to 12, 4 to 10, 4 to 8, or 4 to 6 consecutive Us). In some cases, the first labelled detector RNA lacks A and includes a stretch of at least 2 consecutive Us (e.g., at least 3, at least 4, or at least 5 consecutive Us). In some cases, the second labelled detector RNA lacks U and includes a stretch of from 2 to 15 consecutive As (e.g., from 2 to 12, 2 to 10, 2 to 8, 2 to 6, 2 to 4, 3 to 15, 3 to 12, 3 to 10, 3 to 8, 3 to 6, 3 to 5, 4 to 15, 4 to 12, 4 to 10, 4 to 8, or 4 to 6 consecutive As). In some cases, the second labelled detector RNA lacks U and includes a stretch of at least 2 consecutive As (e.g., at least 3, at least 4, or at least 5 consecutive As).

In some cases, the first labelled detector RNA comprises at least one U and lacks A; and the second labelled detector RNA comprises at least one A and lacks U.

In some cases, the first labelled detector RNA comprises at least one A and lacks U. For example, in some cases, the first labelled detector RNA is a homoadenosine polymer (a polyA RNA). As another example, the first labelled detector RNA: i) comprises at least one A; ii) lacks U; and iii) comprises one or more C and/or Gs. In some cases, the second labelled detector RNA comprises at least one U and lacks A. For example, in some cases, the second labelled detector RNA is a homouridine polymer (a polyU RNA). As another example, the second labelled detector RNA: i) comprises at least one U; ii) lacks A; and iii) comprises one or more C and/or Gs.

In some cases, the first labelled detector RNA comprises at least one U and lacks A. For example, in some cases, the first labelled detector RNA is a homouridine polymer (polyU RNA). As another example, the second labelled detector RNA: i) comprises at least one U; ii) lacks A; and iii) comprises one or more Cs and/or Gs. In some cases, the second labelled detector RNA comprises at least one A and lacks U. For example, in some cases, the second labelled detector RNA is a homoadenosine polymer (polyA RNA). As another example, the second labelled detector RNA: i) comprises at least one A; ii) lacks U; and iii) comprises one or more Cs and/or Gs.

As noted above, a method of the present disclosure can comprise contacting a sample with: a first C2c2 protein; a second C2c2 protein; a first C2c2 guide RNA that comprises a first nucleotide sequence that hybridizes with the first single stranded target RNA and a second nucleotide sequence also referred to herein as a 'constant region' or 'handle' that binds to the first C2c2 protein; and a second C2c2 guide RNA that comprises a first nucleotide sequence that hybridizes with the second single stranded target RNA and a second nucleotide sequence (a handle) that binds to the second C2c2 protein.

For example, in some cases, the first C2c2 protein is a Cas13a polypeptide comprising an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the first C2c2 guide RNA comprises a constant region (a 'handle'—a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence AGAUAGCCCAAGAAAGAGGGCAAUAAC (SEQ ID NO: 16), where the crRNA has a length of about 25 nt, 26 nt, 27 nt, 28 nt, 29 nt, or 30 nt. In some cases, the crRNA has the nucleotide sequence AGAUAGCC-CAAGAAAGAGGGCAAUAAC (SEQ ID NO: 16); and has a length of 27 nt. In some cases, the second C2c2 protein comprises an amino acid sequence having at least 75%, at least 80%, at least 85%, at least 90%, at least 95%, at least 98%, at least 99%, or 100%, amino acid sequence identity to the Hhe Cas13a amino acid sequence depicted in FIG. 56K; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GUAACAAUCCCCGUA-GACAGGGGAACUGCAAC (SEQ ID NO: 17). In some cases, the second C2c2 protein comprises an amino acid sequence having at least 75%, at least 80%, at least 85%, at least 90%, at least 95%, at least 98%, at least 99%, or 100%, amino acid sequence identity to the Rca Cas13a amino acid sequence depicted in FIG. 56G; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence CAU-CACCCGCCAAGACGACGGCGGACUGAACC (SEQ ID NO: 18). In some cases, the second C2c2 protein comprises an amino acid sequence having at least 75%, at least 80%, at least 85%, at least 90%, at least 95%, at least 98%, at least 99%, or 100%, amino acid sequence identity to the Ppr Cas13a amino acid sequence depicted in FIG. 56B; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence AAUUAUCCCAAAAUUGAAGGGAACUA-CAAC (SEQ ID NO: 19); where the handle has a length of about 28 nt, 29 nt, 30 nt, 31 nt, or 32 nt. In some cases, the second C2c2 guide RNA comprises a handle comprising the nucleotide sequence AAUUAUCCCAAAAUUGAAGG-GAACUACAAC (SEQ ID NO: 19); and the handle has a length of 30 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lne Cas13a amino acid sequence depicted in FIG. 56I; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GAGUACCU-CAAAACAAAAGAGGACUAAAAC (SEQ ID NO: 20) (e.g., comprising a nucleotide sequence having only 1 nt, 2 nt, 3 nt, 4 nt, or 5 nt, differences from the nucleotide sequence GAGUACCUCAAAACAAAAGAGGAC-UAAAAC (SEQ ID NO: 20)); where the handle has a length of about 28 nt, 29 nt, 30 nt, 31 nt, or 32 nt. In some cases, the second guide RNA comprises a handle comprising the nucleotide sequence GAGUACCU-CAAAACAAAAGAGGACUAAAAC (SEQ ID NO: 20); where the handle has a length of 30 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lbu Cas13a amino acid sequence depicted in FIG. 56C; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GACCACCC-CAAAAAUGAAGGGGACUAAAACA (SEQ ID NO: 9) (e.g., comprising a nucleotide sequence having only 1 nt, 2 nt, 3 nt, 4 nt, or 5 nt, differences from the nucleotide sequence GACCACCCCAAAAAUGAAGGGGAC-UAAAACA (SEQ ID NO: 9)); where the handle has a length of about 28 nt, 29 nt, 30 nt, 31 nt, or 32 nt. In some cases, the second guide RNA comprises a handle comprising the nucleotide sequence GACCACCC-CAAAAAUGAAGGGGACUAAAACA (SEQ ID NO: 9); where the handle has a length of 31 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lwa Cas13a amino acid sequence depicted in FIG. 56E; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GACCACCC-CAAUAUCGAAGGGGACUAAAACUU (SEQ ID NO: 21) (e.g., comprising a nucleotide sequence having only 1 nt, 2 nt, 3 nt, 4 nt, or 5 nt, differences from the nucleotide sequence GACCACCCCAAUAUCGAAGGGGAC-UAAAACUU (SEQ ID NO: 21); where the handle has a length of about 28 nt, 29 nt, 30 nt, 31 nt, or 32 nt. In some cases, the second guide RNA comprises a handle comprising the nucleotide sequence GACCACCC-CAAUAUCGAAGGGGACUAAAACUU (SEQ ID NO: 21); where the handle has a length of 32 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lsh Cas13a amino acid sequence depicted in FIG. 56D; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence CACCC-CAAUAUCGAAGGGGACUAAAAC (SEQ ID NO: 22) (e.g., comprising a nucleotide sequence having only 1 nt, 2 nt, 3 nt, 4 nt, or 5 nt, differences from the nucleotide sequence CACCCCAAUAUCGAAGGGGACUAAAAC (SEQ ID NO: 22); where the handle has a length of 25 nt, 26 nt, 27 nt, 28 nt, or 29 nt. In some cases, the second guide RNA comprises a handle comprising the nucleotide sequence CACCCCAAUAUCGAAGGGGACUAAAAC (SEQ ID NO: 22); where the handle has a length of 27 nt.

As another example, in some cases, the first C2c2 protein is a Cas13a polypeptide comprising an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the first C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence AAGUAGCCCGAUAUAGAGGGCAAUAAC (SEQ ID NO: 23), where the handle has a length of about 25 nt, 26 nt, 27 nt, 28 nt, 29 nt, or 30 nt. In some cases, the handle has the nucleotide sequence AAGUAGCCCGAUAUA-GAGGGCAAUAAC (SEQ ID NO: 23); and has a length of 27 nt. in some cases, the first C2c2 protein is a Cas13a polypeptide comprising an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the first C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence AUACAG-CUCGAUAUAGUGAGCAAUAAG (SEQ ID NO: 24), where the handle has a length of about 25 nt, 26 nt, 27 nt, 28 nt, 29 nt, or 30 nt. In some cases, the handle has the nucleotide sequence AUACAG-CUCGAUAUAGUGAGCAAUAAG (SEQ ID NO: 24); and has a length of 27 nt. In some cases, the second C2c2 protein comprises an amino acid sequence having at least 75%, at least 80%, at least 85%, at least 90%, at least 95%, at least 98%, at least 99%, or 100%, amino acid sequence identity to the Hhe Cas13a amino acid sequence depicted in FIG. 56K; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GUAACAAUCCCCGUA-GACAGGGGAACUGCAAC (SEQ ID NO: 17); where the handle has a length of about 30 nt, 31 nt, 32 nt, 33 nt, 34 nt, or 35 nt. In some cases, the second C2c2 guide RNA comprises a handle comprising the nucleotide sequence GUAACAAUCCCCGUAGACAGGGGAACUGCAAC (SEQ ID NO: 17); and the handle has a length of 32 nt. In some cases, the second C2c2 protein comprises an amino acid sequence having at least 75%, at least 80%, at least 85%, at least 90%, at least 95%, at least 98%, at least 99%, or 100%, amino acid sequence identity to the Rca Cas13a amino acid sequence depicted in FIG. 56G; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence UCACAUCACCGCCAAGACGACGGCGGACUGAACC (SEQ ID NO: 25); where the handle has a length of about 32 nt, 33 nt, 34 nt, 35 nt, 36 nt, or 37 nt. In some cases, the second C2c2 guide RNA comprises a handle comprising the nucleotide sequence UCACAUCACCGCCAA-GACGACGGCGGACUGAACC (SEQ ID NO: 25); and the handle has a length of 34 nt. In some cases, the second C2c2 protein comprises an amino acid sequence having at least 75%, at least 80%, at least 85%, at least 90%, at least 95%, at least 98%, at least 99%, or 100%, amino acid sequence identity to the Ppr Cas13a amino acid sequence depicted in FIG. 56B; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence AAUUAUCC-CAAAAUUGAAGGGAACUACAAC (SEQ ID NO: 19); where the handle has a length of about 28 nt, 29 nt, 30 nt, 31 nt, or 32 nt. In some cases, the second C2c2 guide RNA comprises a handle comprising the nucleotide sequence AAUUAUCCCAAAAUUGAAGGGAACUACAAC (SEQ ID NO: 19); and the handle has a length of 30 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lne Cas13a amino acid sequence depicted in FIG. 56I; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GAGUACCUCAAAACAAAAGAGGACUAAAAC (SEQ ID NO: 20) (e.g., comprising a nucleotide sequence having only 1 nt, 2 nt, 3 nt, 4 nt, or 5 nt, differences from the nucleotide sequence GAGUACCUCAAAACAAAAGAGGACUAAAAC (SEQ ID NO: 20)); where the handle has a length of about 28 nt, 29 nt, 30 nt, 31 nt, or 32 nt. In some cases, the second guide RNA comprises a handle comprising the nucleotide sequence GAGUACCUCAAAACAAAAGAGGACUAAAAC (SEQ ID NO: 20); where the handle has a length of 30 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lbu Cas13a amino acid sequence depicted in FIG. 56C; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GACCACCCCAAAAAUGAAGGGGACUAAAACA (SEQ ID NO: 9) (e.g., comprising a nucleotide sequence having only 1 nt, 2 nt, 3 nt, 4 nt, or 5 nt, differences from the nucleotide sequence GACCACCCCAAAAAUGAAGGGGACUAAAACA (SEQ ID NO: 9)); where the handle has a length of about 28 nt, 29 nt, 30 nt, 31 nt, or 32 nt. In some cases, the second guide RNA comprises a handle comprising the nucleotide sequence GACCACCCCAAAAAUGAAGGGGACUAAAACA (SEQ ID NO: 9); where the handle has a length of 31 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lwa Cas13a amino acid sequence depicted in FIG. 56E; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GACCACCCCAAUAUCGAAGGGGACUAAAACUU (SEQ ID NO: 21) (e.g., comprising a nucleotide sequence having only 1 nt, 2 nt, 3 nt, 4 nt, or 5 nt, differences from the nucleotide sequence GACCACCCCAAUAUCGAAGGGGACUAAAACUU (SEQ ID NO: 21)); where the handle has a length of about 28 nt, 29 nt, 30 nt, 31 nt, or 32 nt. In some cases, the second guide RNA comprises a handle comprising the nucleotide sequence GACCACCCCAAUAUCGAAGGGGACUAAAACUU (SEQ ID NO: 21); where the handle has a length of 32 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lsh Cas13a amino acid sequence depicted in FIG. 56D; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence CACCCCAAUAUCGAAGGGGACUAAAAC (SEQ ID NO: 22) (e.g., comprising a nucleotide sequence having only 1 nt, 2 nt, 3 nt, 4 nt, or 5 nt, differences from the nucleotide sequence CACCCCAAUAUCGAAGGGGACUAAAAC (SEQ ID NO: 22); where the handle has a length of 25 nt, 26 nt, 27 nt, 28 nt, or 29 nt. In some cases, the second guide RNA comprises a handle comprising the nucleotide sequence CACCCCAAUAUCGAAGGGGACUAAAAC (SEQ ID NO: 22); where the handle has a length of 27 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lse Cas13a amino acid sequence depicted in FIG. 56A; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GACUACCUCUAUAUGAAAGAGGACUAAAAC (SEQ ID NO: 7); where the handle has a length of about 28 nt, 29 nt, 30 nt, 31 nt, or 32 nt. In some cases, the second C2c2 guide RNA comprises a handle comprising the nucleotide sequence GACUACCUCUAUAUGAAAGAGGACUAAAAC (SEQ ID NO: 7); and the handle has a length of 30 nt.

As another example, in some cases, the first C2c2 protein is a Cas13a polypeptide comprising an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the first C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GAACAGCCCGAUAUAGAGGGCAAUAGAC (SEQ ID NO: 26), where the handle has a length of about 26 nt, 27 nt, 28 nt, 29 nt, or 30 nt. In some cases, the handle has the nucleotide sequence GAACAGCCCGAUAUAGAGGGCAAUAGAC (SEQ ID NO: 26); and has a length of 28 nt. In some cases, the second C2c2 protein comprises an amino acid sequence having at least 75%, at least 80%, at least 85%, at least 90%, at least 95%, at least 98%, at least 99%, or 100%, amino acid sequence identity to the Hhe Cas13a amino acid sequence depicted in FIG. 56K; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GUAACAAUCCCCGUAGACAGGGGAACUGCAAC (SEQ ID NO: 17); where the handle has a length of about 30 nt, 31 nt, 32 nt, 33 nt, 34 nt, or 35 nt. In some cases, the second C2c2 guide RNA comprises a handle comprising the nucleotide sequence GUAACAAUCCCCGUAGACAGGGGAACUGCAAC (SEQ ID NO: 17); and the handle has a length of 32 nt. In some cases, the second C2c2 protein comprises an amino acid sequence having at least 75%, at least 80%, at least 85%, at least 90%, at least 95%, at least 98%, at least 99%, or 100%, amino acid sequence identity to the Rca Cas13a amino acid sequence depicted in FIG. 56G; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence UCACAUCACCGCCAAGACGACGGCGGACUGAACC (SEQ ID NO: 25); where the handle has a length of about 32 nt, 33 nt, 34 nt, 35 nt, 36 nt, or 37 nt. In some cases, the second C2c2 guide RNA comprises a handle comprising the nucleotide sequence UCACAUCACCGCCAAGACGACGGCGGACUGAACC (SEQ ID NO: 25); and the handle has a length of 34 nt. In some cases, the second C2c2 protein comprises an amino acid sequence having at least 75%, at least 80%, at least 85%, at least 90%, at least 95%, at least 98%, at least 99%, or 100%, amino acid sequence identity to the Ppr Cas13a amino acid sequence depicted in FIG. 56B; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence AAUUAUCCCAAAAUUGAAGGGAACUACAAC (SEQ ID NO: 19); where the handle has a length of about 28 nt, 29 nt, 30 nt, 31 nt, or 32 nt. In some cases, the second C2c2 guide RNA comprises a handle comprising the nucleotide sequence AAUUAUCCCAAAAUUGAAGGGAACUACAAC (SEQ ID NO: 19); and the handle has a length of 30 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lne Cas13a amino acid sequence depicted in FIG. 56I; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GAGUACCUCAAAACAAAAGAGGACUAAAAC (SEQ ID NO: 20) (e.g., comprising a nucleotide sequence having only 1 nt, 2 nt, 3 nt, 4 nt, or 5 nt, differences from the nucleotide sequence GAGUACCUCAAAACAAAAGAGGACUAAAAC (SEQ ID NO: 20)); where the handle has a length of about 28 nt, 29 nt, 30 nt, 31 nt, or 32 nt. In some cases, the second guide RNA comprises a handle comprising the nucleotide sequence GAGUACCUCAAAACAAAAGAGGACUAAAAC (SEQ ID NO: 20); where the handle has a length of 30 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lbu Cas13a amino acid sequence depicted in FIG. 56C; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GACCACCCCAAAAAUGAAGGGGACUAAAACA (SEQ ID NO: 9) (e.g., comprising a nucleotide sequence having only 1 nt, 2 nt, 3 nt, 4 nt, or 5 nt, differences from the nucleotide sequence GACCACCCCAAAAAUGAAGGGGACUAAAACA (SEQ ID NO: 9)); where the handle has a length of about 28 nt, 29 nt, 30 nt, 31 nt, or 32 nt. In some cases, the second guide RNA comprises a handle comprising the nucleotide sequence GACCACCCCAAAAAUGAAGGGGACUAAAACA (SEQ ID NO: 9); where the handle has a length of 31 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lwa Cas13a amino acid sequence depicted in FIG. 56E; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GACCACCCCAAUAUCGAAGGGGACUAAAACUU (SEQ ID NO: 21) (e.g., comprising a nucleotide sequence having only 1 nt, 2 nt, 3 nt, 4 nt, or 5 nt, differences from the nucleotide sequence GACCACCCCAAUAUCGAAGGGGACUAAAACUU (SEQ ID NO: 21); where the handle has a length of about 28 nt, 29 nt, 30 nt, 31 nt, or 32 nt. In some cases, the second guide RNA comprises a handle comprising the nucleotide sequence GACCACCCCAAUAUCGAAGGGGACUAAAACUU (SEQ ID NO: 21); where the handle has a length of 32 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lsh Cas13a amino acid sequence depicted in FIG. 56D; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence CACCCCAAUAUCGAAGGGGACUAAAAC (SEQ ID NO: 22) (e.g., comprising a nucleotide sequence having only 1 nt, 2 nt, 3 nt, 4 nt, or 5 nt, differences from the nucleotide sequence CACCCCAAUAUCGAAGGGGACUAAAAC (SEQ ID NO: 22); where the handle has a length of 25 nt, 26 nt, 27 nt, 28 nt, or 29 nt. In some cases, the second guide RNA comprises a handle comprising the nucleotide sequence CACCCCAAUAUCGAAGGGGACUAAAAC (SEQ ID NO: 22); where the handle has a length of 27 nt. In some cases, the second C2c2 protein comprises an amino acid sequence having at least 75%, at least 80%, at least 85%, at least 90%, at least 95%, at least 98%, at least 99%, or 100%, amino acid sequence identity to the Lse Cas13a amino acid sequence depicted in FIG. 56A; and the second C2c2 guide RNA comprises a handle (a stretch of nucleotides that binds to the Cas13a polypeptide) comprising a nucleotide sequence having no more than 1 nucleotide (nt), no more than 2 nt, no more than 3 nt, no more than 4 nt, or no more than 5 nt differences from the nucleotide sequence GACUACCUCUAUAUGAAAGAGGACUAAAAC (SEQ ID NO: 7); where the handle has a length of about 28 nt, 29 nt, 30 nt, 31 nt, or 32 nt. In some cases, the second C2c2 guide RNA comprises a handle comprising the nucleotide sequence GACUACCUCUAUAUGAAAGAGGACUAAAAC (SEQ ID NO: 7); and the handle has a length of 30 nt.

Multiplexing

As noted above, in some cases, a method of the present disclosure comprises: a) contacting a sample (e.g., a sample comprising a target RNA and a plurality of non-target RNAs) with: i) a precursor C2c2 guide RNA array comprising two or more C2c2 guide RNAs each of which has a different guide sequence; and (ii) a C2c2 protein that cleaves the precursor C2c2 guide RNA array into individual C2c2 guide RNAs, and also cleaves RNAs of the sample; and b) measuring a detectable signal produced by C2c2 protein-mediated RNA cleavage.

In some cases, two or more C2c2 guide RNAs can be present on an array (a precursor C2c2 guide RNA array). A C2c2 protein can cleave the precursor C2c2 guide RNA array into individual C2c2 guide RNAs (e.g., see FIG. 4 and FIG. 6).

In some cases a subject C2c2 guide RNA array includes 2 or more C2c2 guide RNAs (e.g., 3 or more, 4 or more, 5 or more, 6 or more, or 7 or more, C2c2 guide RNAs). The C2c2 guide RNAs of a given array can target (i.e., can include guide sequences that hybridize to) different target sites of the same target RNA (e.g., which can increase sensitivity of detection) and/or can target different target RNA molecules (e.g., a family of transcripts, e.g., based on variation such as single-nucleotide polymorphisms, single nucleotide polymorphisms (SNPs), etc., and such could be used for example to detect multiple strains of a virus such as influenza virus variants, Zika virus variants, HIV variants, and the like).

C2c2 Protein

A C2c2 protein binds to a C2c2 guide RNA, is guided to a single stranded target RNA by the guide RNA (which hybridizes to the target RNA), and is thereby 'activated.' If the HEPN1 and HEPN2 domains of the C2c2 protein are intact, once activated, the C2c2 protein cleaves the target RNA, but also cleaves non-target RNAs.

Example naturally existing C2c2 proteins are depicted in FIG. 8 and are set forth as SEQ ID NOs: 1-6. In some cases, a subject C2c2 protein includes an amino acid sequence having 80% or more (e.g., 85% or more, 90% or more, 95% or more, 98% or more, 99% or more, 99.5% or more, or 100%) amino acid sequence identity with the amino acid sequence set forth in any one of SEQ ID NOs: 1-6. In some cases, a suitable C2c2 polypeptide comprises an amino acid sequence having at least 80%, at least 85%, at least 90%, at least 95%, at least 98%, at least 99%, or 100%, amino acid sequence identity to the *Listeria seeligeri* C2c2 amino acid sequence set forth in SEQ ID NO:1. In some cases, a suitable C2c2 polypeptide comprises an amino acid sequence having at least 80%, at least 85%, at least 90%, at least 95%, at least 98%, at least 99%, or 100%, amino acid sequence identity to the *Leptotrichia buccalis* C2c2 amino acid sequence set forth in SEQ ID NO:2. In some cases, a suitable C2c2 polypeptide comprises an amino acid sequence having at least 80%, at least 85%, at least 90%, at least 95%, at least 98%, at least 99%, or 100%, amino acid sequence identity to the *Rhodobacter capsulatus* C2c2 amino acid sequence set forth in SEQ ID NO:4. In some cases, a suitable C2c2 polypeptide comprises an amino acid sequence having at least 80%, at least 85%, at least 90%, at least 95%, at least 98%, at least 99%, or 100%, amino acid sequence identity to the *Carnobacterium gallinarum* C2c2 amino acid sequence set forth in SEQ ID NO:5. In some cases, a suitable C2c2 polypeptide comprises an amino acid sequence having at least 80%, at least 85%, at least 90%, at least 95%, at least 98%, at least 99%, or 100%, amino acid sequence identity to the Herbinix hemicellulosilytica C2c2 amino acid sequence set forth in SEQ ID NO:6. In some cases, the C2c2 protein includes an amino acid sequence having 80% or more amino acid sequence identity with the *Leptotrichia buccalis* (Lbu) C2c2 amino acid sequence set forth in SEQ ID NO: 2. In some cases, the C2c2 protein is a *Leptotrichia buccalis* (Lbu) C2c2 protein (e.g., see SEQ ID NO: 2). In some cases, the C2c2 protein includes the amino acid sequence set forth in any one of SEQ ID NOs: 1-2 and 4-6.

In some cases, a C2c2 protein used in a method of the present disclosure is not a *Leptotrichia shahii* (Lsh) C2c2 protein. In some cases, a C2c2 protein used in a method of the present disclosure is not a C2c2 polypeptide having at least 80%, at least 85%, at least 90%, at least 95%, at least 98%, at least 99%, or 100%, amino acid sequence identity to the Lsh C2c2 polypeptide set forth in SEQ ID NO:3.

In some cases, the C2c2 protein is more efficient, by a factor of 1.2-fold or more, than a *Leptotrichia shahii* (Lsh) C2c2 protein at cleaving RNA that is not targeted by a C2c2 guide RNA of the method. In some cases, the C2c2 protein is more efficient, by a factor of 1.5-fold or more, than a *Leptotrichia shahii* (Lsh) C2c2 protein at cleaving RNA that is not targeted by a C2c2 guide RNA of the method. In some cases, the C2c2 polypeptide used in a method of the present disclosure, when activated, cleaves non-target RNA at least 1.2-fold, at least 1.5-fold, at least 2-fold, at least 2.5-fold, at least 3-fold, at least 4-fold, at least 5-fold, at least 6-fold, at least 7-fold, at least 8-fold, at least 9-fold, at least 10-fold, at least 15-fold, at least 20-fold, at least 30-fold, or more than 30-fold, more efficiently than Lsh C2c2.

In some cases, the C2c2 protein exhibits at least a 50% RNA cleavage efficiency within 1 hour of said contacting (e.g., 55% or more, 60% or more, 65% or more, 70% or more, or 75% or more cleavage efficiency). In some cases, the C2c2 protein exhibits at least a 50% RNA cleavage efficiency within 40 minutes of said contacting (e.g., 55% or more, 60% or more, 65% or more, 70% or more, or 75% or more cleavage efficiency). In some cases, the C2c2 protein exhibits at least a 50% RNA cleavage efficiency within 30 minutes of said contacting (e.g., 55% or more, 60% or more, 65% or more, 70% or more, or 75% or more cleavage efficiency).

In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 30 seconds to 60 minutes, e.g., from 1 minute to 60 minutes, from 30 seconds to 5 minutes, from 1 minute to 5 minutes, from 1 minute to 10 minutes, from 5 minutes to 10 minutes, from 10 minutes to 15 minutes, from 15 minutes to 20 minutes, from 20 minutes to 25 minutes, from 25 minutes to 30 minutes, from 30 minutes to 35 minutes, from 35 minutes to 40 minutes, from 40 minutes to 45 minutes, from 45 minutes to 50 minutes, from 50 minutes to 55 minutes, or from 55 minutes to 60 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 30 seconds to 5 minutes (e.g., from 1 minute to 5 minutes, e.g., in a time period of 1 minute, 2 minutes, 3 minutes, 4 minutes, or 5 minutes). In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 5 minutes to 10 minutes (e.g., in a time period of 5 minutes, 6 minutes, 7 minutes, 8 minutes, 9 minutes, or 10 minutes). In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 10 minutes to 15 minutes (e.g., 10 minutes, 11 minutes, 12 minutes, 13 minutes, 14 minutes, or 15 minutes). In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 15 minutes to 20 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 20 minutes to 25 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 25 minutes to 30 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 30 minutes to 35 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 35 minutes to 40 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 40 minutes to 45 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 45 minutes to 50 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 50 minutes to 55 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of from 55 minutes to 60 minutes. In some cases, a C2c2 protein suitable for use in a method of the present disclosure cleaves at least 50%, at least 60%, at least 70%, at least 80%, at least 90%, at least 95%, at least 98%, at least 99%, or more than 99%, of the RNA present in a sample in a time period of less than 1 minute, e.g., in a time period of from 50 seconds to 59 seconds, from 40 seconds to 49 seconds, from 30 seconds to 39 seconds, or from 20 seconds to 29 seconds. In some cases, the cleavage takes place under physiological conditions. In some cases, the cleavage takes place at a temperature of from 15° C. to 20° C., from 20° C. to 25° C., from 25° C. to 30° C., from 30° C. to 35° C., or from 35° C. to 40° C. In some cases, the cleavage takes place at about 37° C. In some cases, the cleavage takes place at about 37° C. and the reaction conditions include divalent metal ions. In some cases, the divalent metal ion is $Mg^{2+}$. In some cases, the divalent metal ion is $Mn^{2+}$. In some cases the pH of the reaction conditions is between pH 5 and pH 6. In some cases the pH of the reaction conditions is between pH 6 and pH 7. In some cases the pH of the reaction conditions is between pH 6.5 and pH 7.5. In some cases the pH of reaction conditions is above pH 7.5.

The term "cleavage efficiency" is used herein to refer to the ability of the C2c2 protein to rapidly cleave RNA in sample once the C2c2 protein has been activated by an appropriate C2c2 guide RNA/target RNA hybridization. "Cleavage efficiency" refers to the amount of RNA the protein can cleave within a given period of time. For example, 50% cleavage efficiency would indicate that 50% of a given RNA is cleaved within a specified period of time. For example, if an RNA is present in a sample at a starting concentration of 100 μM, 50% cleavage has been achieved when 50 μM of the RNA has been cleaved. As another example, if a plurality of RNA molecules is present in the sample, 50% cleavage has been achieved when 50% of the RNA molecules have been cleaved; efficiency is an expression of the amount of time that is required for a certain percent of the total RNA to be cleaved. This can be measured by any convenient method and many such methods will be known to one of ordinary skill in the art. For example, a labeled detector RNA can be used. In some cases, the RNA species (cleaved versus uncleaved) can be separated on a gel and the amount of cleaved RNA can be compared to the amount of uncleaved RNA, e.g., see FIG. 3.

When the phrase "wherein the C2c2 protein cleaves at least X % of the RNAs present in the sample" (e.g., within a specified time period) is used, it is meant that X % of the 'signal-producing' RNAs present in the sample is cleaved within the specified time period. Which RNAs are 'signal-producing' RNAs can depend on the detection method used. For example, when a labeled detector RNA is used, the labeled detector RNA might be the only 'signal-producing RNA.' However, the labeled detector RNA is used to represent the RNAs of the sample and thus, what one observes for the labeled detector RNA is assumed to be representative of what is happening to the non-target RNAs of the sample. As such, when 50% of the labeled detector RNA is cleaved, this will generally be assumed to represent when 50% of the 'RNAs present in the sample' are cleaved. In some cases, RNA cleavage in general is being measured and as such, all cleavable RNAs of the sample are 'signal-producing RNAs'. Thus, when referring to the % of RNAs present in the sample being cleaved, this value can be measured using any convenient method, and whatever the method being used, the value is generally meant herein to mean when the enzyme has cleaved half of the cleavable targets in the sample.

In some cases, the C2c2 protein is not a *Leptotrichia shahii* (Lsh) C2c2 protein. In some cases, the C2c2 protein is more efficient than a *Leptotrichia shahii* (Lsh) C2c2 protein (e.g., at cleaving non-target RNA) by a factor of 1.2-fold or more (e.g., 1.5-fold or more, 1.7-fold or more, or 2-fold or more). As such, in some cases, a subject C2c2 protein is more efficient, by a factor of 1.2-fold or more (e.g., 1.5-fold or more, 1.7-fold or more, or 2-fold or more), than a *Leptotrichia shahii* (Lsh) C2c2 protein at cleaving RNA that is not targeted by the C2c2 guide RNA of the method. In some cases, the C2c2 polypeptide used in a method of the present disclosure, when activated, cleaves non-target RNA at least 1.2-fold, at least 1.5-fold, at least 2-fold, at least 2.5-fold, at least 3-fold, at least 4-fold, at least 5-fold, at least 6-fold, at least 7-fold, at least 8-fold, at least 9-fold, at least 10-fold, at least 15-fold, at least 20-fold, at least 30-fold, or more than 30-fold, more efficiently than Lsh C2c2.

Variant C2c2 Polypeptides

Variant C2c2 polypeptides include variants of any one of SEQ ID NOs:1, 2, and 4-6, where the variant C2c2 polypeptide exhibits reduced (or undetectable) nuclease activity. For example, in some cases, a variant C2c2 protein lacks a catalytically active HEPN1 domain. As another example, a variant C2c2 protein lacks a catalytically active HEPN2 domain. In some cases, a variant C2c2 protein lacks a catalytically active HEPN1 domain and lacks a catalytically active HEPN2 domain.

In some cases, a variant C2c2 polypeptide comprises amino acid substitutions of 1, 2, 3, or 4 of amino acids R472, H477, R1048, and H1053 of the amino acid sequence set forth in SEQ ID NO:2 (*Leptotrichia buccalis* C2c2), or a corresponding amino acid of a C2c2 amino acid sequence depicted in SEQ ID NO:1, SEQ ID NO:4, SEQ ID NO:5, or SEQ ID NO:6. Corresponding amino acids in SEQ ID NO:1, SEQ ID NO:4, SEQ ID NO:5, and SEQ ID NO:6 are readily identified; see, e.g., FIG. 22B. For example, amino positions in SEQ ID NO:1 (*Listeria seeligeri* C2c2) that correspond to R472, H477, R1048, and H1053 of SEQ ID NO:2 are R445, H450, R1016, and H1021, respectively. As another example, amino acid positions in SEQ ID NO:4 (*Rhodobacter capsulatus* C2c2) that correspond to R472, H477, R1048, and H1053 of SEQ ID NO:2 are R464, H469, R1052, and H1057, respectively. As another example, amino acid positions in SEQ ID NO:5 (*Carnobacterium gallinarum* C2c2) that correspond to R472, H477, R1048, and H1053 of SEQ ID NO:2 are R467, H472, R1069, and H1074, respectively. As another example, amino acid positions in SEQ ID NO:6 (*Herbinix hemicellulosilytica* C2c2) that correspond to R472, H477, R1048, and H1053 of SEQ ID NO:2 are R472, H477, R1044, and H1049, respectively.

In some cases, a variant C2c2 polypeptide comprises amino acid substitutions of amino acids R472 and H477 of the amino acid sequence set forth in SEQ ID NO:2, or corresponding amino acids of a C2c2 amino acid sequence depicted in SEQ ID NO:1, SEQ ID NO:4, SEQ ID NO:5, or SEQ ID NO:6. In some cases, a variant C2c2 polypeptide comprises amino acid substitutions of amino acids R1048 and H1053 of the amino acid sequence set forth in SEQ ID NO:2, or corresponding amino acids of a C2c2 amino acid sequence depicted in SEQ ID NO:1, SEQ ID NO:4, SEQ ID NO:5, or SEQ ID NO:6. In some cases, a variant C2c2 polypeptide comprises amino acid substitutions of amino acids R472, H477, R1048, and H1053 of the amino acid sequence set forth in SEQ ID NO:2, or corresponding amino acids of a C2c2 amino acid sequence depicted in SEQ ID NO:1, SEQ ID NO:4, SEQ ID NO:5, or SEQ ID NO:6.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R472 and H477. In some cases, the amino acid at position 472 is any amino acid other than Arg; and the amino acid at position 477 is any amino acid other than His. In some cases, the substitutions are R472A and H477A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R1048 and H1053. In some cases, the amino acid at position 1048 is any amino acid other than Arg; and the amino acid at position 1053 is any amino acid other than His. In some cases, the substitutions are R1048A and H1053A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R472, H477, R1048, and H1053. In some cases, the amino acid at positions 472 and 1048 is any amino acid other than Arg; and the amino acid at positions 477 and 1053 is any amino acid other than His. In some cases, the substitutions are R472A, H477A, R1048A, and H1053A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R445 and H450. In some cases, the amino acid at position 445 is any amino acid other than Arg; and the amino acid at position 450 is any amino acid other than His. In some cases, the substitutions are R445A and H450A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R1016 and H1021. In some cases, the amino acid at position 1016 is any amino acid other than Arg; and the amino acid at position 1021 is any amino acid other than His. In some cases, the substitutions are R1016A and H1021A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R445, H450, R1016, and H1021. In some cases, the amino acid at positions 445 and 1016 is any amino acid other than Arg; and the amino acid at positions 450 and 1016 is any amino acid other than His. In some cases, the substitutions are R445A, H450A, R1016A, and H1021A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4 (*Rhodobacter capsulatus* C2c2), and comprises substitution of amino acids R464 and H469. In some cases, the amino acid at position 464 is any amino acid other than Arg; and the amino acid at position 469 is any amino acid other than His. In some cases, the substitutions are R464A and H469A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises substitution of amino acids R1052 and H1057. In some cases, the amino acid at position 1052 is any amino acid other than Arg; and the amino acid at position 1057 is any amino acid other than His. In some cases, the substitutions are R1052A and H1057A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises substitution of amino acids R464, H469, R1052, and H1057. In some cases, the amino acid at positions 464 and 1052 is any amino acid other than Arg; and the amino acid at positions 469 and 1057 is any amino acid other than His. In some cases, the substitutions are R464A, H469A, R1052A, and H1057A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5 (*Carnobacterium gallinarum* C2c2), and comprises substitution of amino acids R467 and H472. In some cases, the amino acid at position 467 is any amino acid other than Arg; and the amino acid at position 472 is any amino acid other than His. In some cases, the substitutions are R469A and H472A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises substitution of amino acids R1069 and H1074. In some cases, the amino acid at position 1069 is any amino acid other than Arg; and the amino acid at position 1074 is any amino acid other than His. In some cases, the substitutions are R1069A and H1074A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises substitution of amino acids R467, H472, R1069, and H1074. In some cases, the amino acid at positions 467 and 1069 is any amino acid other than Arg; and the amino acid at positions 472 and 1074 is any amino acid other than His. In some cases, the substitutions are R469A, H472A, R1069A, and H1074A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6 (Herbinix hemicellulosilytica C2c2), and comprises substitution of amino acids R472 and H477. In some cases, the amino acid at position 472 is any amino acid other than Arg; and the amino acid at position 477 is any amino acid other than His. In some cases, the substitutions are R472A and H477A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises substitution of amino acids R1044 and H1049. In some cases, the amino acid at position 1044 is any amino acid other than Arg; and the amino acid at position 1049 is any amino acid other than His. In some cases, the substitutions are R1044A and H1049A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises substitution of amino acids R472, H477, R1044, and H1049. In some cases, the amino acid at positions 472 and 1044 is any amino acid other than Arg; and the amino acid at positions 477 and 1049 is any amino acid other than His. In some cases, the substitutions are R472A, H477A, R1044A, and H1049A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of 1, 2, 3, or 4 of amino acids R472, H477, R1048, and H1053, such that the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. For example, in some cases, the variant C2c2 polypeptide exhibits less than 50%, less than 40%, less than 30%, less than 20%, less than 10%, less than 5%, less than 1%, or less than 0.1%, of the RNA-guided cleavage of a non-target RNA exhibited by a C2c2 polypeptide having the amino acid sequence set forth in SEQ ID NO:2. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

Any of the above variant C2c2 polypeptides can also include a mutation (e.g., at any one of positions R1079, R1072, and K1082, as described in further detail below) that results in reduced ability (e.g., loss of ability) to cleave precursor C2c2 guide RNA.

In some cases, a variant C2c2 polypeptide has reduced ability to cleave precursor C2c2 guide RNA (e.g., see examples below and related FIGS. 26C-26D, 35D, and 37). For example, in some cases, a variant C2c2 polypeptide comprises amino acid substitutions of 1, 2, or 3 of amino acids R1079, R1072, and K1082 of the amino acid sequence set forth in SEQ ID NO:2 (*Leptotrichia buccalis* C2c2), or a corresponding amino acid of any C2c2 amino acid sequence (e.g., the C2c2 amino acid sequence depicted in SEQ ID NO:1, SEQ ID NO:4, SEQ ID NO:5, or SEQ ID NO:6). Corresponding amino acids in SEQ ID NO:1, SEQ ID NO:4, SEQ ID NO:5, and SEQ ID NO:6 are readily identified. For example, amino positions in SEQ ID NO:1 (*Listeria seeligeri* C2c2) that correspond to R1079, R1072, and K1082 of SEQ ID NO:2 are R1048, R1041, and R1051, respectively. As another example, amino acid positions in SEQ ID NO:4 (*Rhodobacter capsulatus* C2c2) that correspond to R1079, R1072, and K1082 of SEQ ID NO:2 are R1085, R1078, and K1088, respectively. As another example, amino acid positions in SEQ ID NO:5 (*Carnobacterium gallinarum* C2c2) that correspond to R1079, R1072, and K1082 of SEQ ID NO:2 are R1099, R1092, and K1102, respectively. As another example, amino acid positions in SEQ ID NO:6 (*Herbinix hemicellulosilytica* C2c2) that correspond to R1079 and R1072 of SEQ ID NO:2 are R1172 and R1165, respectively.

In some cases, a variant C2c2 polypeptide comprises an amino acid substitution of amino acid R1079 (e.g., R1079A) of the amino acid sequence set forth in SEQ ID NO:2, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:6). In some cases, a variant C2c2 polypeptide comprises an amino acid substitution of amino acid R1072 (e.g., R1072A) of the amino acid sequence set forth in SEQ ID NO:2, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:6). In some cases, a variant C2c2 polypeptide comprises an amino acid substitution of amino acid K1082 (e.g., K1082A) of the amino acid sequence set forth in SEQ ID NO:2, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:6). In some cases, a variant C2c2 polypeptide comprises one or more (e.g, two or more, or all three) amino acid substitutions at positions selected from R1079 (e.g., R1079A). R1072 (e.g., R1072A), and K1082 (e.g., K1082A) of the amino acid sequence set forth in SEQ ID NO:2, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:6).

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises an amino acid substitution of amino acid R1079 (e.g., R1079A) of the amino acid sequence set forth in SEQ ID NO:2, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises an amino acid substitution of amino acid R1072 (e.g., R1072A) of the amino acid sequence set forth in SEQ ID NO:2, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises an amino acid substitution of amino acid K1082 (e.g., K1082A) of the amino acid sequence set forth in SEQ ID NO:2, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises one or more (e.g, two or more, or all three) amino acid substitutions at positions selected from R1079 (e.g., R1079A). R1072 (e.g., R1072A), and K1082 (e.g., K1082A) of the amino acid sequence set forth in SEQ ID NO:2, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:6).

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises an amino acid substitution of amino acid R1041 (e.g., R1041A) of the amino acid sequence set forth in SEQ ID NO:1, or the corresponding amino acid of any C2c2 amino acid sequence (e.g., a C2c2 amino acid sequence depicted in SEQ ID NO:2, SEQ ID NO:4, SEQ ID NO:5, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises an amino acid substitution of amino acid R1048 (e.g., R1048A) of the amino acid sequence set forth in SEQ ID NO:1, or the corresponding amino acid of any C2c2 amino acid sequence (e.g., a C2c2 amino acid sequence depicted in SEQ ID NO:2, SEQ ID NO:4, SEQ ID NO:5, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises an amino acid substitution of amino acid K1051 (e.g., K1051A) of the amino acid sequence set forth in SEQ ID NO:1, or the corresponding amino acid of any C2c2 amino acid sequence (e.g., a C2c2 amino acid sequence depicted in SEQ ID NO:2, SEQ ID NO:4, SEQ ID NO:5, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises one or more (e.g, two or more, or all three) amino acid substitutions at positions selected from R1048 (e.g., R1048A). R1041 (e.g., R1041A), and K1051 (e.g., K1051A) of the amino acid sequence set forth in SEQ ID NO:1, or the corresponding amino acid of any C2c2 amino acid sequence (e.g., a C2c2 amino acid sequence depicted in SEQ ID NO:2, SEQ ID NO:4, SEQ ID NO:5, or SEQ ID NO:6).

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises an amino acid substitution of amino acid R1085 (e.g., R1085A) of the amino acid sequence set forth in SEQ ID NO:4, or the corresponding amino acid of any C2c2 amino acid sequence (e.g., a C2c2 amino acid sequence depicted in SEQ ID NO:1, SEQ ID NO:2, SEQ ID NO:5, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises an amino acid substitution of amino acid R1078 (e.g., R1078A) of the amino acid sequence set forth in SEQ ID NO:4, or the corresponding amino acid of any C2c2 amino acid sequence (e.g., a C2c2 amino acid sequence depicted in SEQ ID NO:1, SEQ ID NO:2, SEQ ID NO:5, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises an amino acid substitution of amino acid K1088 (e.g., K1088A) of the amino acid sequence set forth in SEQ ID NO:4, or the corresponding amino acid of any C2c2 amino acid sequence (e.g., a C2c2 amino acid sequence depicted in SEQ ID NO:1, SEQ ID NO:2, SEQ ID NO:5, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises one or more (e.g, two or more, or all three) amino acid substitutions at positions selected from R1085 (e.g., R1085A). R1078 (e.g., R1078A), and K1088 (e.g., K1088A) of the amino acid sequence set forth in SEQ ID NO:4, or the corresponding amino acid of any C2c2 amino acid sequence (e.g., a C2c2 amino acid sequence depicted in SEQ ID NO:1, SEQ ID NO:2, SEQ ID NO:5, or SEQ ID NO:6).

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises an amino acid substitution of amino acid R1099 (e.g., R1099A) of the amino acid sequence set forth in SEQ ID NO:5, or the corresponding amino acid of any C2c2 amino acid sequence (e.g., a C2c2 amino acid sequence depicted in SEQ ID NO:1, SEQ ID NO:4, SEQ ID NO:2, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises an amino acid substitution of amino acid R1092 (e.g., R1092A) of the amino acid sequence set forth in SEQ ID NO:5, or the corresponding amino acid of any C2c2 amino acid sequence (e.g., a C2c2 amino acid sequence depicted in SEQ ID NO:1, SEQ ID NO:4, SEQ ID NO:2, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises an amino acid substitution of amino acid K1102 (e.g., K1102A) of the amino acid sequence set forth in SEQ ID NO:5, or the corresponding amino acid of any C2c2 amino acid sequence (e.g., a C2c2 amino acid sequence depicted in SEQ ID NO:1, SEQ ID NO:4, SEQ ID NO:2, or SEQ ID NO:6). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises one or more (e.g, two or more, or all three) amino acid substitutions at positions selected from R1099 (e.g., R1099A). R1092 (e.g., R1092A), and K1102 (e.g., K1102A) of the amino acid sequence set forth in SEQ ID NO:5, or the corresponding amino acid of any C2c2 amino acid sequence (e.g., a C2c2 amino acid sequence depicted in SEQ ID NO:1, SEQ ID NO:4, SEQ ID NO:2, or SEQ ID NO:6).

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises an amino acid substitution of amino acid R1172 (e.g., R1172A) of the amino acid sequence set forth in SEQ ID NO:6, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:2. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises an amino acid substitution of amino acid R1165 (e.g., R1165A) of the amino acid sequence set forth in SEQ ID NO:6, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:2). In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises one or more (e.g, both) amino acid substitutions at positions selected from R1172 (e.g., R1172A) and R1165 (e.g., R1165A) of the amino acid sequence set forth in SEQ ID NO:6, or the corresponding amino acid of any C2c2 amino acid sequence (e.g., a C2c2 amino acid sequence depicted in SEQ ID NO:1, SEQ ID NO:4, SEQ ID NO:5, or SEQ ID NO:2).

C2c2 Guide RNA

A subject C2c2 guide RNA (e.g., a C2c2 crRNA) includes a guide sequence and a constant region (e.g., a region that is 5' of the guide sequence). The region that is 5' of the guide sequence binds to the C2c2 protein (and can be considered a protein-binding region) while the guide sequence hybridizes to a target sequence of the target RNA.

Guide Sequence

The guide sequence has complementarity with (hybridizes to) a target sequence of the single stranded target RNA. In some cases, the base of the target RNA that is immediately 3' of the target sequence (protospacer) is not a G. In some cases, the guide sequence is 16-28 nucleotides (nt) in length (e.g., 16-26, 16-24, 16-22, 16-20, 16-18, 17-26, 17-24, 17-22, 17-20, 17-18, 18-26, 18-24, or 18-22 nt in length). In some cases, the guide sequence is 18-24 nucleotides (nt) in length. In some cases, the guide sequence is at least 16 nt long (e.g., at least 18, 20, or 22 nt long). In some cases, the guide sequence is at least 17 nt long. In some cases, the guide sequence is at least 18 nt long. In some cases, the guide sequence is at least 20 nt long.

In some cases, the guide sequence has 80% or more (e.g., 85% or more, 90% or more, 95% or more, or 100% complementarity) with the target sequence of the single stranded target RNA. In some cases, the guide sequence is 100% complementary to the target sequence of the single stranded target RNA.

Constant Region

The following 3 sequences are each an example of a constant region of a naturally existing C2c2 guide RNA (e.g., a region that is 5' of the guide sequence):

GACUACCUCUAUAUGAAAGAGGACUAAAAC (SEQ ID NO: 7)
(*Listeria seeligeri*) ("Lse")

CCACCCCAAUAUCGAAGGGGACUAAAACA (SEQ ID NO: 8)
(*Leptotrichia shahii*) ("Lsh")

GACCACCCCAAAAAUGAAGGGGACUAAAACA (SEQ ID NO: 9)
(*Leptotrichia buccalis*) ("Lbu")

In some embodiments, a subject C2c2 guide RNA includes a nucleotide sequence having 70% or more identity (e.g., 80% or more, 85% or more, 90% or more, 95% or more, 98% or more, 99% or more, or 100% identity) with the sequence set forth in any one of SEQ ID NOs: 7-9. In some embodiments, a subject C2c2 guide RNA includes a nucleotide sequence having 90% or more identity (e.g., 95% or more, 98% or more, 99% or more, or 100% identity) with the sequence set forth in any one of SEQ ID NOs: 7-9. In some embodiments, a subject C2c2 guide RNA includes the nucleotide sequence set forth in any one of SEQ ID NOs: 7-9.

In some embodiments, a subject C2c2 guide RNA includes a nucleotide sequence having 70% or more identity (e.g., 80% or more, 85% or more, 90% or more, 95% or more, 98% or more, 99% or more, or 100% identity) with the sequence set forth in SEQ ID NO: 9. In some embodiments, a subject C2c2 guide RNA includes a nucleotide sequence having 90% or more identity (e.g., 95% or more, 98% or more, 99% or more, or 100% identity) with the sequence set forth in SEQ ID NO: 9. In some embodiments, a subject C2c2 guide RNA includes the nucleotide sequence set forth in SEQ ID NO: 9.

In some embodiments, a subject C2c2 guide RNA does not include a nucleotide sequence of a *Leptotrichia shahii* (LsH) C2c2 guide RNA. For example, in some cases, the C2c2 protein that is used is not a C2c2 from *Leptotrichia shahii* (e.g., is not an Lsh C2c2 protein), and in some such cases the C2c2 guide RNA that is used is also not from *Leptotrichia shahii* (e.g., the guide RNA used does not include the constant region of an Lsh C2c2 guide RNA). Therefore, in some cases a subject C2c2 guide RNA does not include the sequence set forth in SEQ ID NO: 8.

In some cases, the C2c2 guide RNA includes a double stranded RNA duplex (dsRNA duplex). For example, see FIG. 7A which illustrates a C2c2 guide RNA from Lbu hybridized to a single stranded target RNA, where the C2c2 guide RNA includes a dsRNA duplex that is 4 base pairs (bp) in length. In some cases, a C2c2 guide RNA includes a dsRNA duplex with a length of from 2 to 12 bp (e.g., from 2 to 10 bp, 2 to 8 bp, 2 to 6 bp, 2 to 5 bp, 2 to 4 bp, 3 to 12 bp, 3 to 10 bp, 3 to 8 bp, 3 to 6 bp, 3 to 5 bp, 3 to 4 bp, 4 to 12 bp, 4 to 10 bp, 4 to 8 bp, 4 to 6 bp, or 4 to 5 bp). In some cases, a C2c2 guide RNA includes a dsRNA duplex that is 2 or more bp in length (e.g., 3 or more, 4 or more, 5 or more, 6 or more, or 7 or more bp in length). In some cases, a C2c2 guide RNA includes a dsRNA duplex that is longer than the dsRNA duplex of a corresponding wild type C2c2 guide RNA. For example, see FIG. 7A, which illustrates a C2c2 guide RNA from Lbu hybridized to a single stranded target RNA, where the C2c2 guide RNA includes a dsRNA duplex that is 4 base pairs (bp) in length. As such, a C2c2 guide RNA can in some cases include a dsRNA duplex that is 5 or more bp in length (e.g., 6 or more, 7 or more, or 8 or more bp in length). In some cases, a C2c2 guide RNA includes a dsRNA duplex that is shorter than the dsRNA duplex of a corresponding wild type C2c2 guide RNA. As such in some cases, a C2c2 guide RNA includes a dsRNA duplex that is less than 4 bp in length. In some cases, a C2c2 guide RNA includes a dsRNA duplex having a length of 2 or 3 bp in length.

In some cases, the region of a C2c2 guide RNA that is 5' of the guide sequence is 15 or more nucleotides (nt) in length (e.g., 18 or more, 20 or more, 21 or more, 22 or more, 23 or more, 24 or more, 25 or more, 26 or more, 27 or more, 28 or more, 29 or more, 30 or more, 31 or more nt, 32 or more, 33 or more, 34 or more, or 35 or more nt in length). In some cases, the region of a C2c2 guide RNA that is 5' of the guide sequence is 29 or more nt in length.

In some cases, the region of a C2c2 guide RNA that is 5' of the guide sequence has a length in a range of from 12 to 100 nt (e.g., from 12 to 90, 12 to 80, 12 to 70, 12 to 60, 12 to 50, 12 to 40, 15 to 100, 15 to 90, 15 to 80, 15 to 70, 15 to 60, 15 to 50, 15 to 40, 20 to 100, 20 to 90, 20 to 80, 20 to 70, 20 to 60, 20 to 50, 20 to 40, 25 to 100, 25 to 90, 25 to 80, 25 to 70, 25 to 60, 25 to 50, 25 to 40, 28 to 100, 28 to 90, 28 to 80, 28 to 70, 28 to 60, 28 to 50, 28 to 40, 29 to 100, 29 to 90, 29 to 80, 29 to 70, 29 to 60, 29 to 50, or 29 to 40 nt). In some cases, the region of a C2c2 guide RNA that is 5' of the guide sequence has a length in a range of from 28 to 100 nt. In some cases, the region of a C2c2 guide RNA that is 5' of the guide sequence has a length in a range of from 28 to 40 nt.

In some cases, the region of the C2c2 guide RNA that is 5' of the guide sequence is truncated relative to (shorter than) the corresponding region of a corresponding wild type C2c2 guide RNA. For example, the mature Lse C2c2 guide RNA includes a region 5' of the guide sequence that is 30 nucleotides (nt) in length, and a subject truncated C2c2 guide RNA (relative to the Lse C2c2 guide RNA) can therefore have a region 5' of the guide sequence that is less than 30 nt in length (e.g., less than 29, 28, 27, 26, 25, 22, or 20 nt in length). In some cases, a truncated C2c2 guide RNA includes a region 5' of the guide sequence that has a length in a range of from 12 to 29 nt (e.g., from 12 to 28, 12 to 27, 12 to 26, 12 to 25, 12 to 22, 12 to 20, 12 to 18 nt). In some cases, the truncated C2c2 guide RNA is truncated by one or more nt (e.g., 2 or more, 3 or more, 4 or more, 5 or more, or 10 or more nt), e.g., relative to a corresponding wild type C2c2 guide).

In some cases, the region of the C2c2 guide RNA that is 5' of the guide sequence is extended relative to (longer than) the corresponding region of a corresponding wild type C2c2 guide RNA. For example, the mature Lse C2c2 guide RNA includes a region 5' of the guide sequence that is 30 nucleotides (nt) in length, and an extended C2c2 guide RNA (relative to the Lse C2c2 guide RNA) can therefore have a region 5' of the guide sequence that is longer than 30 nt (e.g., longer than 31, longer than 32, longer than 33, longer than 34, or longer than 35 nt). In some cases, an extended C2c2 guide RNA includes a region 5' of the guide sequence that has a length in a range of from 30 to 100 nt (e.g., from 30 to 90, 30 to 80, 30 to 70, 30 to 60, 30 to 50, or 30 to 40 nt). In some cases, the extended C2c2 guide RNA includes a region 5' of the guide sequence that is extended (e.g., relative to the corresponding region of a corresponding wild type C2c2 guide RNA) by one or more nt (e.g., 2 or more, 3 or more, 4 or more, 5 or more, or 10 or more nt).

In some cases, a subject C2c2 guide RNA is 30 or more nucleotides (nt) in length (e.g., 34 or more, 40 or more, 45 or more, 50 or more, 55 or more, 60 or more, 65 or more, 70 or more, or 80 or more nt in length). In some cases, the C2c2 guide RNA is 35 or more nt in length.

In some cases, a subject C2c2 guide RNA has a length in a range of from 30 to 120 nt (e.g., from 30 to 110, 30 to 100, 30 to 90, 30 to 80, 30 to 70, 30 to 60, 35 to 120, 35 to 110, 35 to 100, 35 to 90, 35 to 80, 35 to 70, 35 to 60, 40 to 120, 40 to 110, 40 to 100, 40 to 90, 40 to 80, 40 to 70, 40 to 60, 50 to 120, 50 to 110, 50 to 100, 50 to 90, 50 to 80, or 50 to 70 nt). In some cases, the C2c2 guide RNA has a length in a range of from 33 to 80 nt. In some cases, the C2c2 guide RNA has a length in a range of from 35 to 60 nt.

In some cases, a subject C2c2 guide RNA is truncated relative to (shorter than) a corresponding wild type C2c2 guide RNA. For example, a mature Lse C2c2 guide RNA can be 50 nucleotides (nt) in length, and a truncated C2c2 guide RNA (relative to the Lse C2c2 guide RNA) can therefore in some cases be less than 50 nt in length (e.g., less than 49, 48, 47, 46, 45, 42, or 40 nt in length). In some cases, a truncated C2c2 guide RNA has a length in a range of from 30 to 49 nt (e.g., from 30 to 48, 30 to 47, 30 to 46, 30 to 45, 30 to 42, 30 to 40, 35 to 49, 35 to 48, 35 to 47, 35 to 46, 35 to 45, 35 to 42, or 35 to 40 nt). In some cases, the truncated C2c2 guide RNA is truncated by one or more nt (e.g., 2 or more, 3 or more, 4 or more, 5 or more, or 10 or more nt), e.g., relative to a corresponding wild type C2c2 guide).

In some cases, a subject C2c2 guide RNA is extended relative to (longer than) a corresponding wild type C2c2 guide RNA. For example, a mature Lse C2c2 guide RNA can be 50 nucleotides (nt) in length, and an extended C2c2 guide RNA (relative to the Lse C2c2 guide RNA) can therefore in some cases be longer than 50 nt (e.g., longer than 51, longer than 52, longer than 53, longer than 54, or longer than 55 nt). In some cases, an extended C2c2 guide RNA has a length in a range of from 51 to 100 nt (e.g., from 51 to 90, 51 to 80, 51 to 70, 51 to 60, 53 to 100, 53 to 90, 53 to 80, 53 to 70, 53 to 60, 55 to 100, 55 to 90, 55 to 80, 55 to 70, or 55 to 60 nt). In some cases, the extended C2c2 guide RNA is extended (e.g., relative to a corresponding wild type C2c2 guide RNA) by one or more nt (e.g., 2 or more, 3 or more, 4 or more, 5 or more, or 10 or more nt).

Methods of Cleaving a Precursor C2c2 Guide RNA Array

The present disclosure provides a method of cleaving a precursor C2c2 guide RNA array into two or more C2c2 guide RNAs. The method comprises contacting a precursor C2c2 guide RNA array with a C2c2 protein. The precursor C2c2 guide RNA array comprises two or more (e.g., 2, 3, 4, 5, or more) C2c2 guide RNAs, each of which can have a different guide sequence. The C2c2 protein cleaves the precursor C2c2 guide RNA array into individual C2c2 guide RNAs. In some cases, the contant region (also referred to as a 'handle') of a C2c2 guide RNA includes nucleotide sequence from the precursor guide RNA (e.g., sequence that is normally present prior to cleavage of the guide RNA array). In other words, in some cases the constant region of a subject C2c2 guide RNA includes a precursor crRNA handle.

In some cases, the contacting step does not take place inside a cell, e.g., inside a living cell. In some cases, the contacting step takes place inside of a cell (e.g., a cell in vitro (in culture), a cell ex vivo, a cell in vivo). Any cell is suitable. Examples of cells in which contacting can take place include but are not limited to: a eukaryotic cell; a prokaryotic cell (e.g., a bacterial cell, an archaeal cell); a single-cell eukaryotic organism; a plant cell; an algal cell, e.g., *Botryococcus braunii*, *Chlamydomonas reinhardtii*, *Nannochloropsis gaditana*, *Chlorella pyrenoidosa*, *Sargassum patens*, *C. agardh*, and the like; a fungal cell (e.g., a yeast cell); an animal cell; an invertebrate cell (e.g. fruit fly, cnidarian, echinoderm, nematode, an insect, an arachnid, etc.); a vertebrate cell (e.g., fish, amphibian, reptile, bird, mammal); a mammal cell (e.g., a human; a non-human primate; an ungulate; a feline; a bovine; an ovine; a caprine; a rat; a mouse; a rodent; a pig; a sheep; a cow; etc.); a parasite cell (e.g., helminths, malarial parasites, etc.).

C2c2 Protein

When a C2c2 protein has intact HEPN domains, it can cleave RNA (target RNA as well as non-target RNA) after it is 'activated'. However, C2c2 protein can also cleave precursor C2c2 guide RNAs into mature C2c2 guide RNAs in a HEPN-independent fashion. For example, when a C2c2 protein lacks a catalytically active HEPN1 domain and also lacks a catalytically active HEPN2 domain, it can still cleave precursor guide RNA into mature guide RNA. As such, when used in a method that includes a precursor C2c2 guide RNA and/or a precursor C2c2 guide RNA array, the C2c2 protein can (and will in some cases) lack a catalytically active HEPN1 domain and/or catalytically active HEPN2 domain. In some cases, the C2c2 protein lacks a catalytically active HEPN1 domain and lacks a catalytically active HEPN2 domain.

A C2c2 protein that lacks a catalytically active HEPN1 domain and lacks a catalytically active HEPN2 domain can in some cases be used in methods of binding (e.g. imaging methods). For example, in some cases, a method of binding (and/or imaging) includes contacting a sample with a precursor C2c2 guide RNA array and a C2c2 protein that lacks a catalytically active HEPN1 domain and lacks a catalytically active HEPN2 domain. In such cases, the C2c2 protein can be detectably labeled (e.g., fused an epitope tag, fused to a fluorophore, fused to a fluorescent protein such as a green fluorescent protein, etc.).

A C2c2 protein suitable for use in a method of the present disclosure for cleaving a precursor C2c2 guide RNA array can have intact HEPN1 and HEPN2 domains. However, in some cases, the C2c2 protein lacks a catalytically active HEPN1 domain and/or lacks a catalytically active HEPN2 domain.

In some cases, a C2c2 protein suitable for use in a method of the present disclosure for cleaving a precursor C2c2 guide RNA array includes an amino acid sequence having 80% or more (e.g., 85% or more, 90% or more, 95% or more, 98% or more, 99% or more, 99.5% or more, or 100%) amino acid sequence identity with the amino acid sequence set forth in any one of SEQ ID NOs: 1-6. In some cases, a C2c2 protein suitable for use in a method of the present disclosure for cleaving a precursor C2c2 guide RNA array comprises an amino acid sequence having at least 80%, at least 85%, at least 90%, at least 95%, at least 98%, at least 99%, or 100%, amino acid sequence identity to the *Listeria seeligeri* C2c2 amino acid sequence set forth in SEQ ID NO:1. In some cases, a C2c2 protein suitable for use in a method of the present disclosure for cleaving a precursor C2c2 guide RNA array comprises an amino acid sequence having at least 80%, at least 85%, at least 90%, at least 95%, at least 98%, at least 99%, or 100%, amino acid sequence identity to the *Leptotrichia buccalis* C2c2 amino acid sequence set forth in SEQ ID NO:2. In some cases, a C2c2 protein suitable for use in a method of the present disclosure for cleaving a precursor C2c2 guide RNA array comprises an amino acid sequence having at least 80%, at least 85%, at least 90%, at least 95%, at least 98%, at least 99%, or 100%, amino acid sequence identity to the *Rhodobacter capsulatus* C2c2 amino acid sequence set forth in SEQ ID NO:4. In some cases, a C2c2 protein suitable for use in a method of the present disclosure for cleaving a precursor C2c2 guide RNA array comprises an amino acid sequence having at least 80%, at least 85%, at least 90%, at least 95%, at least 98%, at least 99%, or 100%, amino acid sequence identity to the *Carnobacterium gallinarum* C2c2 amino acid sequence set forth in SEQ ID NO:5. In some cases, a C2c2 protein suitable for use in a method of the present disclosure for cleaving a precursor C2c2 guide RNA array comprises an amino acid sequence having at least 80%, at least 85%, at least 90%, at least 95%, at least 98%, at least 99%, or 100%, amino acid sequence identity to the Herbinix hemicellulosilytica C2c2 amino acid sequence set forth in SEQ ID NO:6. In some cases, a C2c2 protein suitable for use in a method of the present disclosure for cleaving a precursor C2c2 guide RNA array includes an amino acid sequence having 80% or more amino acid sequence identity with the *Leptotrichia buccalis* (Lbu) C2c2 amino acid sequence set forth in SEQ ID NO: 2. In some cases, a C2c2 protein suitable for inclusion in a kit of the present disclosure is a *Leptotrichia buccalis* (Lbu) C2c2 protein (e.g., see SEQ ID NO: 2). In some cases, a C2c2 protein suitable for use in a method of the present disclosure for cleaving a precursor C2c2 guide RNA array includes the amino acid sequence set forth in any one of SEQ ID NOs: 1-2 and 4-6.

In some cases, a C2c2 protein used in a method of the present disclosure for cleaving a precursor C2c2 guide RNA array is not a *Leptotrichia shahii* (Lsh) C2c2 protein. In some cases, a C2c2 protein used in a method of the present disclosure for cleaving a precursor C2c2 guide RNA array is not a C2c2 polypeptide having at least 80%, at least 85%, at least 90%, at least 95%, at least 98%, at least 99%, or 100%, amino acid sequence identity to the Lsh C2c2 polypeptide set forth in SEQ ID NO:3.

In some cases, a C2c2 polypeptide suitable for use in a method of the present disclosure for cleaving a precursor C2c2 guide RNA array is a variant C2c2 polypeptide. Variant C2c2 polypeptides suitable for use in a method of the present disclosure for cleaving a precursor C2c2 guide RNA array include variants of any one of SEQ ID NOs:1, 2, and 4-6, where the variant C2c2 polypeptide exhibits reduced (or undetectable) nuclease activity. For example, in some cases, a variant C2c2 protein lacks a catalytically active HEPN1 domain. As another example, a variant C2c2 protein lacks a catalytically active HEPN2 domain. In some cases, a variant C2c2 protein lacks a catalytically active HEPN1 domain and lacks a catalytically active HEPN2 domain.

In some cases, a variant C2c2 polypeptide comprises amino acid substitutions of 1, 2, 3, or 4 of amino acids R472, H477, R1048, and H1053 of the amino acid sequence set forth in SEQ ID NO:2 (*Leptotrichia buccalis* C2c2), or a corresponding amino acid of a C2c2 amino acid sequence depicted in SEQ ID NO:1, SEQ ID NO:4, SEQ ID NO:5, or SEQ ID NO:6. Corresponding amino acids in SEQ ID NO:1, SEQ ID NO:4, SEQ ID NO:5, and SEQ ID NO:6 are readily identified; see, e.g., FIG. 22B. For example, amino positions in SEQ ID NO:1 (*Listeria seeligeri* C2c2) that correspond to R472, H477, R1048, and H1053 of SEQ ID NO:2 are R445, H450, R1016, and H1021, respectively.

In some cases, a variant C2c2 polypeptide comprises amino acid substitutions of amino acids R472 and H477 of the amino acid sequence set forth in SEQ ID NO:2, or a corresponding amino acid of a C2c2 amino acid sequence depicted in SEQ ID NO:1, SEQ ID NO:4, SEQ ID NO:5, or SEQ ID NO:6. In some cases, a variant C2c2 polypeptide comprises amino acid substitutions of amino acids R1048 and H1053 of the amino acid sequence set forth in SEQ ID NO:2, or a corresponding amino acid of a C2c2 amino acid sequence depicted in SEQ ID NO:1, SEQ ID NO:4, SEQ ID NO:5, or SEQ ID NO:6. In some cases, a variant C2c2 polypeptide comprises amino acid substitutions of amino acids R472, H477, R1048, and H1053 of the amino acid sequence set forth in SEQ ID NO:2, or a corresponding amino acid of a C2c2 amino acid sequence depicted in SEQ ID NO:1, SEQ ID NO:4, SEQ ID NO:5, or SEQ ID NO:6.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R472 and H477. In some cases, the amino acid at position 472 is any amino acid other than Arg; and the amino acid at position 477 is any amino acid other than His. In some cases, the substitutions are R472A and H477A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R1048 and H1053. In some cases, the amino acid at position 1048 is any amino acid other than Arg; and the amino acid at position 1053 is any amino acid other than His. In some cases, the substitutions are R1048A and H1053A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R472, H477, R1048, and H1053. In some cases, the amino acid at positions 472 and 1048 is any amino acid other than Arg; and the amino acid at positions 477 and 1053 is any amino acid other than His. In some cases, the substitutions are R472A, H477A, R1048A, and H1053A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R445 and H450. In some cases, the amino acid at position 445 is any amino acid other than Arg; and the amino acid at position 450 is any amino acid other than His. In some cases, the substitutions are R445A and H450A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R1016 and H1021. In some cases, the amino acid at position 1016 is any amino acid other than Arg; and the amino acid at position 1021 is any amino acid other than His. In some cases, the substitutions are R1016A and H1021A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R445, H450, R1016, and H1021. In some cases, the amino acid at positions 445 and 1016 is any amino acid other than Arg; and the amino acid at positions 450 and 1016 is any amino acid other than His. In some cases, the substitutions are R445A, H450A, R1016A, and H1021A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4 (*Rhodobacter capsulatus* C2c2), and comprises substitution of amino acids R464 and H469. In some cases, the amino acid at position 464 is any amino acid other than Arg; and the amino acid at position 469 is any amino acid other than His. In some cases, the substitutions are R464A and H469A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises substitution of amino acids R1052 and H1057. In some cases, the amino acid at position 1052 is any amino acid other than Arg; and the amino acid at position 1057 is any amino acid other than His. In some cases, the substitutions are R1052A and H1057A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises substitution of amino acids R464, H469, R1052, and H1057. In some cases, the amino acid at positions 464 and 1052 is any amino acid other than Arg; and the amino acid at positions 469 and 1057 is any amino acid other than His. In some cases, the substitutions are R464A, H469A, R1052A, and H1057A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5 (*Carnobacterium gallinarum* C2c2), and comprises substitution of amino acids R467 and H472. In some cases, the amino acid at position 467 is any amino acid other than Arg; and the amino acid at position 472 is any amino acid other than His. In some cases, the substitutions are R469A and H472A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises substitution of amino acids R1069 and H1074. In some cases, the amino acid at position 1069 is any amino acid other than Arg; and the amino acid at position 1074 is any amino acid other than His. In some cases, the substitutions are R1069A and H1074A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises substitution of amino acids R467, H472, R1069, and H1074. In some cases, the amino acid at positions 467 and 1069 is any amino acid other than Arg; and the amino acid at positions 472 and 1074 is any amino acid other than His. In some cases, the substitutions are R469A, H472A, R1069A, and H1074A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6 (Herbinix hemicellulosilytica C2c2), and comprises substitution of amino acids R472 and H477. In some cases, the amino acid at position 472 is any amino acid other than Arg; and the amino acid at position 477 is any amino acid other than His. In some cases, the substitutions are R472A and H477A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises substitution of amino acids R1044 and H1049. In some cases, the amino acid at position 1044 is any amino acid other than Arg; and the amino acid at position 1049 is any amino acid other than His. In some cases, the substitutions are R1044A and H1049A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises substitution of amino acids R472, H477, R1044, and H1049. In some cases, the amino acid at positions 472 and 1044 is any amino acid other than Arg; and the amino acid at positions 477 and 1049 is any amino acid other than His. In some cases, the substitutions are R472A, H477A, R1044A, and H1049A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

Precursor C2c2 Guide RNA Array

As demonstrated in the working examples below, a C2c2 protein can cleave a precursor C2c2 guide RNA into a mature guide RNA, e.g., by endoribonucleolytic cleavage of the precursor. Also as demonstrated in the working examples below, a C2c2 protein can cleave a precursor C2c2 guide RNA array (that includes more than one C2c2 guide RNA arrayed in tandem) into two or more individual C2c2 guide RNAs. Thus, in some cases a precursor C2c2 guide RNA array comprises two or more (e.g., 3 or more, 4 or more, 5 or more, 2, 3, 4, or 5) C2c2 guide RNAs (e.g., arrayed in tandem as precursor molecules). In some cases, each guide RNA of a precursor C2c2 guide RNA array has a different guide sequence. In some cases, two or more guide RNAs of a precursor C2c2 guide RNA array have the same guide sequence.

In some cases, the precursor C2c2 guide RNA array comprises two or more C2c2 guide RNAs that target different target sites within the same target RNA molecule. For example, such a scenario can in some cases increase sensitivity of detection by activating C2c2 protein when either one hybridizes to the target RNA molecule.

In some cases, the precursor C2c2 guide RNA array comprises two or more C2c2 guide RNAs that target different target RNA molecules. For example, such a scenario can result in a positive signal when any one of a family of potential target RNAs is present. Such an array could be used for targeting a family of transcripts, e.g., based on variation such as single nucleotide polymorphisms (SNPs) (e.g., for diagnostic purposes). Such could also be useful for detecting whether any one of a number of different strains of virus is present (e.g., influenza virus variants, Zika virus variants, HIV variants, and the like). Such could also be useful for detecting whether any one of a number of different species, strains, isolates, or variants of a *bacterium* is present (e.g., different species, strains, isolates, or variants of *Mycobacterium*, different species, strains, isolates, or variants of *Neisseria*, different species, strains, isolates, or variants of *Staphylococcus aureus*; different species, strains, isolates, or variants of *E. coli*; etc.)

Variant C2c2 Polypeptides

The present disclosure provides a variant C2c2 polypeptide, as well as a nucleic acid (e.g., a recombinant expression vector) comprising a nucleotide sequence encoding the variant C2c2 polypeptide.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R472 and H477. In some cases, the amino acid at position 472 is any amino acid other than Arg; and the amino acid at position 477 is any amino acid other than His. In some cases, the substitutions are R472A and H477A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R1048 and H1053. In some cases, the amino acid at position 1048 is any amino acid other than Arg; and the amino acid at position 1053 is any amino acid other than His. In some cases, the substitutions are R1048A and H1053A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R472, H477, R1048, and H1053. In some cases, the amino acid at positions 472 and 1048 is any amino acid other than Arg; and the amino acid at positions 477 and 1053 is any amino acid other than His. In some cases, the substitutions are R472A, H477A, R1048A, and H1053A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R445 and H450. In some cases, the amino acid at position 445 is any amino acid other than Arg; and the amino acid at position 450 is any amino acid other than His. In some cases, the substitutions are R445A and H450A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R1016 and H1021. In some cases, the amino acid at position 1016 is any amino acid other than Arg; and the amino acid at position 1021 is any amino acid other than His. In some cases, the substitutions are R1016A and H1021A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R445, H450, R1016, and H1021. In some cases, the amino acid at positions 445 and 1016 is any amino acid other than Arg; and the amino acid at positions 450 and 1016 is any amino acid other than His. In some cases, the substitutions are R445A, H450A, R1016A, and H1021A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4 (*Rhodobacter capsulatus* C2c2), and comprises substitution of amino acids R464 and H469. In some cases, the amino acid at position 464 is any amino acid other than Arg; and the amino acid at position 469 is any amino acid other than His. In some cases, the substitutions are R464A and H469A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises substitution of amino acids R1052 and H1057. In some cases, the amino acid at position 1052 is any amino acid other than Arg; and the amino acid at position 1057 is any amino acid other than His. In some cases, the substitutions are R1052A and H1057A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises substitution of amino acids R464, H469, R1052, and H1057. In some cases, the amino acid at positions 464 and 1052 is any amino acid other than Arg; and the amino acid at positions 469 and 1057 is any amino acid other than His. In some cases, the substitutions are R464A, H469A, R1052A, and H1057A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5 (Carnobacterium gallinarum C2c2), and comprises substitution of amino acids R467 and H472. In some cases, the amino acid at position 467 is any amino acid other than Arg; and the amino acid at position 472 is any amino acid other than His. In some cases, the substitutions are R469A and H472A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises substitution of amino acids R1069 and H1074. In some cases, the amino acid at position 1069 is any amino acid other than Arg; and the amino acid at position 1074 is any amino acid other than His. In some cases, the substitutions are R1069A and H1074A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises substitution of amino acids R467, H472, R1069, and H1074. In some cases, the amino acid at positions 467 and 1069 is any amino acid other than Arg; and the amino acid at positions 472 and 1074 is any amino acid other than His. In some cases, the substitutions are R469A, H472A, R1069A, and H1074A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6 (Herbinix hemicellulosilytica C2c2), and comprises substitution of amino acids R472 and H477. In some cases, the amino acid at position 472 is any amino acid other than Arg; and the amino acid at position 477 is any amino acid other than His. In some cases, the substitutions are R472A and H477A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises substitution of amino acids R1044 and H1049. In some cases, the amino acid at position 1044 is any amino acid other than Arg; and the amino acid at position 1049 is any amino acid other than His. In some cases, the substitutions are R1044A and H1049A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises substitution of amino acids R472, H477, R1044, and H1049. In some cases, the amino acid at positions 472 and 1044 is any amino acid other than Arg; and the amino acid at positions 477 and 1049 is any amino acid other than His. In some cases, the substitutions are R472A, H477A, R1044A, and H1049A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of 1, 2, 3, or 4 of amino acids R472, H477, R1048, and H1053, such that the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. For example, in some cases, the variant C2c2 polypeptide exhibits less than 50%, less than 40%, less than 30%, less than 20%, less than 10%, less than 5%, less than 1%, or less than 0.1%, of the RNA-guided cleavage of a non-target RNA exhibited by a C2c2 polypeptide having the amino acid sequence set forth in SEQ ID NO:2. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

The present disclosure provides a nucleic acid (e.g., an isolated nucleic acid) comprising a nucleotide sequence encoding a variant C2c2 polypeptide of the present disclosure. In some cases, the nucleotide sequence is operably linked to a transcriptional control element, e.g., a promoter. In some cases, the promoter is a constitutive promoter. In some cases, the promoter is a regulatable promoter. In some cases, the promoter is an inducible promoter. In some cases, the promoter is functional in a eukaryotic cell. In some cases, the promoter is functional in a prokaryotic cell.

The present disclosure provides a recombinant expression vector comprising a nucleic acid of the present disclosure, e.g., a nucleic acid comprising a nucleotide sequence encoding a variant C2c2 polypeptide of the present disclosure.

The present disclosure provides a host cell that is genetically modified with a nucleic acid of the present disclosure, e.g., a nucleic acid comprising a nucleotide sequence encoding a variant C2c2 polypeptide of the present disclosure. The present disclosure provides a host cell that is genetically modified with a recombinant expression vector comprising a nucleic acid of the present disclosure, e.g., a nucleic acid comprising a nucleotide sequence encoding a variant C2c2 polypeptide of the present disclosure. In some cases, the host cell is a prokaryotic cell. In some cases, the host cell is a eukaryotic cell. In some cases, the host cell is in vitro. In some cases, the host cell is ex vivo. In some cases, the host cell is in vivo. In some cases, the host cell is a bacterial cell. In some cases, the host cell is a yeast cell. In some cases, the host cell is a plant cell. In some cases, the host cell is a mammalian cell. In some cases, the host cell is human cell. In some cases, the host cell is a non-human mammalian cell. In some cases, the host cell is an insect cell. In some cases, the host cell is an arthropod cell. In some cases, the host cell is a fungal cell. In some cases, the host cell is an algal cell.

Kits

The present disclosure provides a kit for detecting a target RNA in a sample comprising a plurality of RNAs. In some cases, the kit comprises: (a) a precursor C2c2 guide RNA array comprising two or more C2c2 guide RNAs each of which has a different guide sequence; and (b) a C2c2 protein, and/or a nucleic acid encoding said C2c2 protein. In some cases, such a kit further includes a labeled detector RNA (e.g., a labeled detector RNA comprising a fluorescence-emitting dye pair, i.e., a FRET pair and/or a quencher/fluor pair). In some cases, two or more C2c2 guide RNAs (e.g., in some cases each of the C2c2 guide RNAs) of a given precursor C2c2 guide RNA array include the same guide sequence.

In some cases, a subject kit comprises: (a) a labeled detector RNA comprising a fluorescence-emitting dye pair, i.e., a FRET pair and/or a quencher/fluor pair; and (b) a C2c2 protein, and/or a nucleic acid encoding said C2c2 protein. In some cases, such a kit further includes (c) a C2c2 guide RNA (and/or a nucleic acid encoding a C2c2 guide RNA), and/or (d) a precursor C2c2 guide RNA (and/or a nucleic acid encoding a precursor C2c2 guide RNA) and/or (e) a precursor C2c2 guide RNA array (and/or a nucleic acid encoding a precursor C2c2 guide RNA array, e.g., a nucleic acid encoding a precursor C2c2 guide RNA array that includes sequence insertion sites for the insertion of guide sequences by a user).

1) Kit Comprising a Precursor C2c2 Guide RNA Array and a C2c2 Protein

In some cases, the kit comprises: (a) a precursor C2c2 guide RNA array comprising two or more C2c2 guide RNAs each of which has a different guide sequence; and (b) a C2c2 protein, and/or a nucleic acid encoding said C2c2 protein. As noted above, in some cases such a kit further includes a labeled detector RNA (e.g., a labeled detector RNA comprising a fluorescence-emitting dye pair, i.e., a FRET pair and/or a quencher/fluor pair).

C2c2 Protein

A C2c2 protein suitable for inclusion in a kit of the present disclosure binds to a C2c2 guide RNA, is guided to a single stranded target RNA by the guide RNA (which hybridizes to the target RNA), and is thereby 'activated.' If the HEPN1 and HEPN2 domains of the C2c2 protein are intact, once activated, the C2c2 protein cleaves the target RNA, but also cleaves non-target RNAs.

In some cases, a C2c2 protein suitable for inclusion in a kit of the present disclosure includes an amino acid sequence having 80% or more (e.g., 85% or more, 90% or more, 95% or more, 98% or more, 99% or more, 99.5% or more, or 100%) amino acid sequence identity with the amino acid sequence set forth in any one of SEQ ID NOs: 1-6. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the Listeria seeligeri C2c2 amino acid sequence set forth in SEQ ID NO:1. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the Leptotrichia buccalis C2c2 amino acid sequence set forth in SEQ ID NO:2. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the Rhodobacter capsulatus C2c2 amino acid sequence set forth in SEQ ID NO:4. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the Carnobacterium gallinarum C2c2 amino acid sequence set forth in SEQ ID NO:5. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the Herbinix hemicellulosilytica C2c2 amino acid sequence set forth in SEQ ID NO:6. In some cases, a C2c2 protein suitable for inclusion in a kit of the present disclosure includes an amino acid sequence having 80% or more amino acid sequence identity with the Leptotrichia buccalis (Lbu) C2c2 amino acid sequence set forth in SEQ ID NO: 2. In some cases, a C2c2 protein suitable for inclusion in a kit of the present disclosure is a Leptotrichia buccalis (Lbu) C2c2 protein (e.g., see SEQ ID NO: 2). In some cases, a C2c2 protein suitable for inclusion in a kit of the present disclosure includes the amino acid sequence set forth in any one of SEQ ID NOs: 1-2 and 4-6.

In some cases, a C2c2 protein included in a kit of the present disclosure is not a Leptotrichia shahii (Lsh) C2c2 protein. In some cases, a C2c2 protein included in a kit of the present disclosure is not a C2c2 polypeptide having at least 80%, at least 85%, at least 90%, at least 95%, at least 98%, at least 99%, or 100%, amino acid sequence identity to the Lsh C2c2 polypeptide set forth in SEQ ID NO:3.

In some cases, a C2c2 polypeptide included in a kit of the present disclosure is a variant C2c2 polypeptide. Variant C2c2 polypeptides suitable for inclusion in a kit of the present disclosure include variants of any one of SEQ ID NOs:1, 2, and 4-6, where the variant C2c2 polypeptide exhibits reduced (or undetectable) nuclease activity. For example, in some cases, a variant C2c2 protein lacks a catalytically active HEPN1 domain. As another example, a variant C2c2 protein lacks a catalytically active HEPN2 domain. In some cases, a variant C2c2 protein lacks a catalytically active HEPN1 domain and lacks a catalytically active HEPN2 domain.

In some cases, a variant C2c2 polypeptide comprises amino acid substitutions of 1, 2, 3, or 4 of amino acids R472, H477, R1048, and H1053 of the amino acid sequence set forth in SEQ ID NO:2 (Leptotrichia buccalis C2c2), or a corresponding amino acid of a C2c2 amino acid sequence depicted in SEQ ID NO:1, SEQ ID NO:4, SEQ ID NO:5, or SEQ ID NO:6. Corresponding amino acids in SEQ ID NO:1, SEQ ID NO:4, SEQ ID NO:5, and SEQ ID NO:6 are readily identified; see, e.g., FIG. 22B. For example, amino positions in SEQ ID NO:1 (Listeria seeligeri C2c2) that correspond to R472, H477, R1048, and H1053 of SEQ ID NO:2 are R445, H450, R1016, and H1021, respectively.

In some cases, a variant C2c2 polypeptide comprises amino acid substitutions of amino acids R472 and H477 of the amino acid sequence set forth in SEQ ID NO:2, or corresponding amino acids of a C2c2 amino acid sequence depicted in SEQ ID NO:1, SEQ ID NO:4, SEQ ID NO:5, or SEQ ID NO:6. In some cases, a variant C2c2 polypeptide comprises amino acid substitutions of amino acids R1048 and H1053 of the amino acid sequence set forth in SEQ ID NO:2, or corresponding amino acids of a C2c2 amino acid sequence depicted in SEQ ID NO:1, SEQ ID NO:4, SEQ ID NO:5, or SEQ ID NO:6. In some cases, a variant C2c2 polypeptide comprises amino acid substitutions of amino acids R472, H477, R1048, and H1053 of the amino acid sequence set forth in SEQ ID NO:2, or corresponding amino acids of a C2c2 amino acid sequence depicted in SEQ ID NO:1, SEQ ID NO:4, SEQ ID NO:5, or SEQ ID NO:6.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R472 and H477. In some cases, the amino acid at position 472 is any amino acid other than Arg; and the amino acid at position 477 is any amino acid other than His. In some cases, the substitutions are R472A and H477A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R1048 and H1053. In some cases, the amino acid at position 1048 is any amino acid other than Arg; and the amino acid at position 1053 is any amino acid other than His. In some cases, the substitutions are R1048A and H1053A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:2, and comprises substitution of amino acids R472, H477, R1048, and H1053. In some cases, the amino acid at positions 472 and 1048 is any amino acid other than Arg; and the amino acid at positions 477 and 1053 is any amino acid other than His. In some cases, the substitutions are R472A, H477A, R1048A, and H1053A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R445 and H450. In some cases, the amino acid at position 445 is any amino acid other than Arg; and the amino acid at position 450 is any amino acid other than His. In some cases, the substitutions are R445A and H450A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R1016 and H1021. In some cases, the amino acid at position 1016 is any amino acid other than Arg; and the amino acid at position 1021 is any amino acid other than His. In some cases, the substitutions are R1016A and H1021A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:1, and comprises substitution of amino acids R445, H450, R1016, and H1021. In some cases, the amino acid at positions 445 and 1016 is any amino acid other than Arg; and the amino acid at positions 450 and 1016 is any amino acid other than His. In some cases, the substitutions are R445A, H450A, R1016A, and H1021A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4 (*Rhodobacter capsulatus* C2c2), and comprises substitution of amino acids R464 and H469. In some cases, the amino acid at position 464 is any amino acid other than Arg; and the amino acid at position 469 is any amino acid other than His. In some cases, the substitutions are R464A and H469A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises substitution of amino acids R1052 and H1057. In some cases, the amino acid at position 1052 is any amino acid other than Arg; and the amino acid at position 1057 is any amino acid other than His. In some cases, the substitutions are R1052A and H1057A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:4, and comprises substitution of amino acids R464, H469, R1052, and H1057. In some cases, the amino acid at positions 464 and 1052 is any amino acid other than Arg; and the amino acid at positions 469 and 1057 is any amino acid other than His. In some cases, the substitutions are R464A, H469A, R1052A, and H1057A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5 (*Carnobacterium gallinarum* C2c2), and comprises substitution of amino acids R467 and H472. In some cases, the amino acid at position 467 is any amino acid other than Arg; and the amino acid at position 472 is any amino acid other than His. In some cases, the substitutions are R469A and H472A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises substitution of amino acids R1069 and H1074. In some cases, the amino acid at position 1069 is any amino acid other than Arg; and the amino acid at position 1074 is any amino acid other than His. In some cases, the substitutions are R1069A and H1074A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:5, and comprises substitution of amino acids R467, H472, R1069, and H1074. In some cases, the amino acid at positions 467 and 1069 is any amino acid other than Arg; and the amino acid at positions 472 and 1074 is any amino acid other than His. In some cases, the substitutions are R469A, H472A, R1069A, and H1074A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6 (Herbinix hemicellulosilytica C2c2), and comprises substitution of amino acids R472 and H477. In some cases, the amino acid at position 472 is any amino acid other than Arg; and the amino acid at position 477 is any amino acid other than His. In some cases, the substitutions are R472A and H477A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises substitution of amino acids R1044 and H1049. In some cases, the amino acid at position 1044 is any amino acid other than Arg; and the amino acid at position 1049 is any amino acid other than His. In some cases, the substitutions are R1044A and H1049A. In some cases, a variant C2c2 polypeptide comprises an amino acid sequence having at least 80%, at least 85%, at least 90%, at least 95%, at least 98%, or at least 99%, amino acid sequence identity to the amino acid sequence set forth in SEQ ID NO:6, and comprises substitution of amino acids R472, H477, R1044, and H1049. In some cases, the amino acid at positions 472 and 1044 is any amino acid other than Arg; and the amino acid at positions 477 and 1049 is any amino acid other than His. In some cases, the substitutions are R472A, H477A, R1044A, and H1049A. In some cases, the variant C2c2 polypeptide has reduced or undetectable cleavage of ss RNA (e.g., RNA-guided cleavage activity), and retains the ability to bind C2c2 guide RNA and ss RNA. In some cases, the variant C2c2 polypeptide retains the ability to cleave precursor C2c2 guide RNA. In some cases, the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

2) Kit Comprising a Labeled Detector RNA and a C2c2 Protein

In some cases, the kit comprises: (a) a labeled detector RNA comprising a fluorescence-emitting dye pair, i.e., a FRET pair and/or a quencher/fluor pair; and (b) a C2c2 protein, and/or a nucleic acid encoding said C2c2 protein. In some cases, a kit further includes a C2c2 guide RNA, precursor C2c2 guide RNA array, and/or a nucleic acid encoding a constant region of a C2c2 guide RNA. As noted above, in some cases such a kit further includes (c) a C2c2 guide RNA (and/or a nucleic acid encoding a C2c2 guide RNA), and/or (d) a precursor C2c2 guide RNA (and/or a nucleic acid encoding a precursor C2c2 guide RNA), and/or (e) a precursor C2c2 guide RNA array (and/or a nucleic acid encoding a precursor C2c2 guide RNA array, e.g., a nucleic acid encoding a precursor C2c2 guide RNA array that includes sequence insertion sites for the insertion of guide sequences by a user).

Labeled Detector RNA

In some cases, a kit of the present disclosure comprises a labeled detector RNA comprising a fluorescence-emitting dye pair, i.e., a FRET pair and/or a quencher/fluor pair. The labeled detector RNA produces an amount of detectable signal prior to being cleaved, and the amount of detectable signal that is measured is reduced when the labeled detector RNA is cleaved. In some cases, the labeled detector RNA produces a first detectable signal prior to being cleaved (e.g., from a FRET pair) and a second detectable signal when the labeled detector RNA is cleaved (e.g., from a quencher/fluor pair). As such, in some cases, the labeled detector RNA comprises a FRET pair and a quencher/fluor pair.

In some cases, the labeled detector RNA comprises a FRET pair. FRET is a process by which radiationless transfer of energy occurs from an excited state fluorophore to a second chromophore in close proximity. The range over which the energy transfer can take place is limited to approximately 10 nanometers (100 angstroms), and the efficiency of transfer is extremely sensitive to the separation distance between fluorophores. The donor-acceptor pair (a FRET donor moiety and a FRET acceptor moiety) is referred to herein as a "FRET pair" or a "signal FRET pair." Thus, in some cases, a subject labeled detector RNA includes two signal partners (a signal pair), when one signal partner is a FRET donor moiety and the other signal partner is a FRET acceptor moiety. A subject labeled detector RNA that includes such a FRET pair (a FRET donor moiety and a FRET acceptor moiety) will thus exhibit a detectable signal (a FRET signal) when the signal partners are in close proximity (e.g., while on the same RNA molecule), but the signal will be reduced (or absent) when the partners are separated (e.g., after cleavage of the RNA molecule by a C2c2 protein).

FRET donor and acceptor moieties (FRET pairs) will be known to one of ordinary skill in the art and any convenient FRET pair (e.g., any convenient donor and acceptor moiety pair) can be used. Examples of suitable FRET pairs include but are not limited to those presented in Table 1, above.

In some cases, a detectable signal is produced when the labeled detector RNA is cleaved (e.g., in some cases, the labeled detector RNA comprises a quencher/fluor pair. One signal partner of a signal quenching pair produces a detectable signal and the other signal partner is a quencher moiety that quenches the detectable signal of the first signal partner (i.e., the quencher moiety quenches the signal of the signal moiety such that the signal from the signal moiety is reduced (quenched) when the signal partners are in proximity to one another, e.g., when the signal partners of the signal pair are in close proximity).

For example, in some cases, an amount of detectable signal increases when the labeled detector RNA is cleaved. For example, in some cases, the signal exhibited by one signal partner (a signal moiety) is quenched by the other signal partner (a quencher signal moiety), e.g., when both are present on the same RNA molecule prior to cleavage by a C2c2 protein. Such a signal pair is referred to herein as a "quencher/fluor pair", "quenching pair", or "signal quenching pair." For example, in some cases, one signal partner (e.g., the first signal partner) is a signal moiety that produces a detectable signal that is quenched by the second signal partner (e.g., a quencher moiety). The signal partners of such a quencher/fluor pair will thus produce a detectable signal when the partners are separated (e.g., after cleavage of the detector RNA by a C2c2 protein), but the signal will be quenched when the partners are in close proximity (e.g., prior to cleavage of the detector RNA by a C2c2 protein).

A quencher moiety can quench a signal from the signal moiety (e.g., prior to cleave of the detector RNA by a C2c2 protein) to various degrees. In some cases, a quencher moiety quenches the signal from the signal moiety where the signal detected in the presence of the quencher moiety (when the signal partners are in proximity to one another) is 95% or less of the signal detected in the absence of the quencher moiety (when the signal partners are separated). For example, in some cases, the signal detected in the presence of the quencher moiety can be 90% or less, 80% or less, 70% or less, 60% or less, 50% or less, 40% or less, 30% or less, 20% or less, 15% or less, 10% or less, or 5% or less of the signal detected in the absence of the quencher moiety. In some cases, no signal (e.g., above background) is detected in the presence of the quencher moiety.

In some cases, the signal detected in the absence of the quencher moiety (when the signal partners are separated) is at least 1.2 fold greater (e.g., at least 1.3fold, at least 1.5 fold, at least 1.7 fold, at least 2 fold, at least 2.5 fold, at least 3 fold, at least 3.5 fold, at least 4 fold, at least 5 fold, at least 7 fold, at least 10 fold, at least 20 fold, or at least 50 fold greater) than the signal detected in the presence of the quencher moiety (when the signal partners are in proximity to one another).

In some cases, the signal moiety is a fluorescent label. In some such cases, the quencher moiety quenches the signal (the light signal) from the fluorescent label (e.g., by absorbing energy in the emission spectra of the label). Thus, when the quencher moiety is not in proximity with the signal moiety, the emission (the signal) from the fluorescent label is detectable because the signal is not absorbed by the quencher moiety. Any convenient donor acceptor pair (signal moiety/quencher moiety pair) can be used and many suitable pairs are known in the art.

In some cases the quencher moiety absorbs energy from the signal moiety (also referred to herein as a "detectable label") and then emits a signal (e.g., light at a different wavelength). Thus, in some cases, the quencher moiety is itself a signal moiety (e.g., a signal moiety can be 6-carboxyfluorescein while the quencher moiety can be 6-carboxy-tetramethylrhodamine), and in some such cases, the pair could also be a FRET pair. In some cases, a quencher moiety is a dark quencher. A dark quencher can absorb excitation energy and dissipate the energy in a different way (e.g., as heat). Thus, a dark quencher has minimal to no fluorescence of its own (does not emit fluorescence). Examples of dark quenchers are further described in U.S. Pat. Nos. 8,822,673 and 8,586,718; U.S. patent publications 20140378330, 20140349295, and 20140194611; and international patent applications: WO200142505 and WO200186001, all if which are hereby incorporated by reference in their entirety.

Examples of fluorescent labels include, but are not limited to: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, quantum dots, and a tethered fluorescent protein.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, and Pacific Orange.

In some cases, a detectable label is a fluorescent label selected from: an Alexa Fluor® dye, an ATTO dye (e.g., ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, ATTO 740), a DyLight dye, a cyanine dye (e.g., Cy2, Cy3, Cy3.5, Cy3b, Cy5, Cy5.5, Cy7, Cy7.5), a FluoProbes dye, a Sulfo Cy dye, a Seta dye, an IRIS Dye, a SeTau dye, an SRfluor dye, a Square dye, fluorescein (FITC), tetramethylrhodamine (TRITC), Texas Red, Oregon Green, Pacific Blue, Pacific Green, Pacific Orange, a quantum dot, and a tethered fluorescent protein.

Examples of ATTO dyes include, but are not limited to: ATTO 390, ATTO 425, ATTO 465, ATTO 488, ATTO 495, ATTO 514, ATTO 520, ATTO 532, ATTO Rho6G, ATTO 542, ATTO 550, ATTO 565, ATTO Rho3B, ATTO Rho11, ATTO Rho12, ATTO Thio12, ATTO Rho101, ATTO 590, ATTO 594, ATTO Rho13, ATTO 610, ATTO 620, ATTO Rho14, ATTO 633, ATTO 647, ATTO 647N, ATTO 655, ATTO Oxa12, ATTO 665, ATTO 680, ATTO 700, ATTO 725, and ATTO 740.

Examples of AlexaFluor dyes include, but are not limited to: Alexa Fluor® 350, Alexa Fluor® 405, Alexa Fluor® 430, Alexa Fluor® 488, Alexa Fluor® 500, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, Alexa Fluor® 750, Alexa Fluor® 790, and the like.

Examples of quencher moieties include, but are not limited to: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and metal clusters such as gold nanoparticles, and the like.

In some cases, a quencher moiety is selected from: a dark quencher, a Black Hole Quencher® (BHQ®) (e.g., BHQ-0, BHQ-1, BHQ-2, BHQ-3), a Qxl quencher, an ATTO quencher (e.g., ATTO 540Q, ATTO 580Q, and ATTO 612Q), dimethylaminoazobenzenesulfonic acid (Dabsyl), Iowa Black RQ, Iowa Black FQ, IRDye QC-1, a QSY dye (e.g., QSY 7, QSY 9, QSY 21), AbsoluteQuencher, Eclipse, and a metal cluster.

Examples of an ATTO quencher include, but are not limited to: ATTO 540Q, ATTO 580Q, and ATTO 612Q. Examples of a Black Hole Quencher® (BHQ®) include, but are not limited to: BHQ-0 (493 nm), BHQ-1 (534 nm), BHQ-2 (579 nm) and BHQ-3 (672 nm).

For examples of some detectable labels (e.g., fluorescent dyes) and/or quencher moieties, see, e.g., Bao et al., Annu Rev Biomed Eng. 2009; 11:25-47; as well as U.S. Pat. Nos. 8,822,673 and 8,586,718; U.S. patent publications 20140378330, 20140349295, 20140194611, 20130323851, 20130224871, 20110223677, 20110190486, 20110172420, 20060179585 and 20030003486; and international patent applications: WO200142505 and WO200186001, all of which are hereby incorporated by reference in their entirety.

Nucleic Acid Modifications

In some cases, a labeled detector RNA comprises one or more modifications, e.g., a base modification, a backbone modification, a sugar modification, etc., to provide the nucleic acid with a new or enhanced feature (e.g., improved stability). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound; however, linear compounds are generally suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Backbones and Modified Internucleoside Linkages

Examples of suitable modifications include modified nucleic acid backbones and non-natural internucleoside linkages. Nucleic acids (having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some cases, a labeled detector RNA comprises one or more phosphorothioate and/or heteroatom internucleoside linkages, in particular —CH$_2$—NH—O—CH$_2$—, —CH$_2$—N(CH$_3$)—O—CH$_2$-(known as a methylene(methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677. Suitable amide internucleoside linkages are disclosed in t U.S. Pat. No. 5,602,240.

Also suitable are nucleic acids having morpholino backbone structures as described in, e.g., U.S. Pat. No. 5,034,506. For example, in some cases, a labeled detector RNA comprises a 6-membered morpholino ring in place of a ribose ring. In some cases, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Mimetics

A labeled detector RNA can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—$CH_2$—), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (Wahlestedt et al., Proc. Natl. Acad. Sci. U.S.A., 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Modified Sugar Moieties

A labeled detector RNA can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2$ $CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a $O(CH_2)_2O$ $N(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other suitable sugar substituent groups include methoxy (—O—$CH_3$), aminopropoxy (—O $CH_2$ $CH_2$ $CH_2NH_2$), allyl (—$CH_2$—CH=$CH_2$), —O-allyl (—O— $CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A labeled detector RNA may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

3) Kit Comprising Two Different C2c2 Proteins, and Two Different Labeled Detector RNAs In some cases, a subject kit comprises: (a) a first labeled detector RNA that lacks U but comprises at least one A (e.g., at least 2, at least 3, or at least 4 As) and comprises a first FRET pair and/or a first quencher/fluor pair; (b) a second labeled detector RNA that lacks A but comprises at least one U (e.g., at least 2, at least 3, or at least 4 Us) and comprises a second FRET pair and/or a second quencher/fluor pair; (c) a first C2c2 protein, and/or a nucleic acid encoding said first C2c2 protein, wherein the first C2c2 protein cleaves adenine+ RNAs (RNAs that include A) when activated but does not cleave RNAs that lack A (e.g., polyU RNAs) [e.g., the first C2c2 protein can cleave the first labeled detector RNA but not the second labeled detector RNA]; and (d) a second C2c2 protein, and/or a nucleic acid encoding said second C2c2 protein, wherein the second C2c2 protein cleaves uracil+ RNAs (RNAs that include U) when activated but does not cleave RNAs that lack U (e.g., polyA RNAs) (e.g., the second C2c2 protein can cleave the second labeled detector RNA but not the first labeled detector RNA).

In some cases, the first labelled detector RNA lacks U and includes a stretch of from 2 to 15 consecutive As (e.g., from 2 to 12, 2 to 10, 2 to 8, 2 to 6, 2 to 4, 3 to 15, 3 to 12, 3 to 10, 3 to 8, 3 to 6, 3 to 5, 4 to 15, 4 to 12, 4 to 10, 4 to 8, or 4 to 6 consecutive As). In some cases, the first labelled detector RNA lacks U and includes a stretch of at least 2 consecutive As (e.g., at least 3, at least 4, or at least 5 consecutive As). In some cases, the second labelled detector RNA lacks A and includes a stretch of from 2 to 15 consecutive Us (e.g., from 2 to 12, 2 to 10, 2 to 8, 2 to 6, 2 to 4, 3 to 15, 3 to 12, 3 to 10, 3 to 8, 3 to 6, 3 to 5, 4 to 15, 4 to 12, 4 to 10, 4 to 8, or 4 to 6 consecutive Us). In some cases, the second labelled detector RNA lacks A and includes a stretch of at least 2 consecutive Us (e.g., at least 3, at least 4, or at least 5 consecutive Us).

In some cases, such a kit further includes: (e) a first C2c2 guide RNA (and/or a nucleic acid encoding the first C2c2 guide RNA), e.g., a nucleic acid comprising a nucleotide sequence encoding the first C2c2 guide RNA, where the nucleic acid includes a sequence insertion site for the insertion of a guide sequence (e.g., a nucleotide sequence that hybridizes to a target RNA) by a user); and (f) a second C2c2 guide RNA (and/or a nucleic acid encoding the second C2c2 guide RNA), e.g., a nucleic acid comprising a nucleotide sequence encoding the second C2c2 guide RNA, where the nucleic acid includes a sequence insertion site for the insertion of a guide sequence (e.g., a nucleotide sequence that hybridizes to a target RNA) by a user). The first C2c2 guide RNA comprises a first nucleotide sequence that hybridizes with a first single stranded target RNA and a second nucleotide sequence that binds to the first C2c2 protein. The second C2c2 guide RNA comprises a first nucleotide sequence that hybridizes with a second single stranded target RNA and a second nucleotide sequence that binds to the second C2c2 protein. The first C2c2 protein is not activated by the second C2c2 guide RNA, and the first C2c2 protein cleaves ssRNA that includes at least one A (e.g., does not cleave ssRNA that lacks A). The second C2c2 protein is not activated by the first C2c2 guide RNA, and the second C2c2 protein cleaves ssRNA that includes at least one U (e.g., does not cleave ssRNA that lacks U).

The following are non-limiting examples (listed as a) through w), below) of first and second C2c2 proteins suitable for inclusion in a kit of the present disclosure:

a) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Hhe Cas13a amino acid sequence depicted in FIG. 56K;

b) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Rca Cas13a amino acid sequence depicted in FIG. 56G;

c) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Ppr Cas13a amino acid sequence depicted in FIG. 56B;

d) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Lne Cas13a amino acid sequence depicted in FIG. 56I;

e) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Lbu Cas13a amino acid sequence depicted in FIG. 56C;

f) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Lwa Cas13a amino acid sequence depicted in FIG. 56E;

g) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Lsh Cas13a amino acid sequence depicted in FIG. 56D;

h) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Hhe Cas13a amino acid sequence depicted in FIG. 56K;

i) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Rca Cas13a amino acid sequence depicted in FIG. 56G;

j) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Ppr Cas13a amino acid sequence depicted in FIG. 56B;

k) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lne Cas13a amino acid sequence depicted in FIG. 56I;

l) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lbu Cas13a amino acid sequence depicted in FIG. 56C;

m) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lwa Cas13a amino acid sequence depicted in FIG. 56E;

n) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lsh Cas13a amino acid sequence depicted in FIG. 56D;

o) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lse Cas13a amino acid sequence depicted in FIG. 56A;

p) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Hhe Cas13a amino acid sequence depicted in FIG. 56K;

q) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Rca Cas13a amino acid sequence depicted in FIG. 56G;

r) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Ppr Cas13a amino acid sequence depicted in FIG. 56B;

s) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lne Cas13a amino acid sequence depicted in FIG. 56I;

t) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lbu Cas13a amino acid sequence depicted in FIG. 56C;

u) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lwa Cas13a amino acid sequence depicted in FIG. 56E;

v) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lsh Cas13a amino acid sequence depicted in FIG. 56F; or w) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lse Cas13a amino acid sequence depicted in FIG. 56A.

C2c2 Protein

A C2c2 protein suitable for inclusion in a kit of the present disclosure binds to a C2c2 guide RNA, is guided to a single stranded target RNA by the guide RNA (which hybridizes to the target RNA), and is thereby 'activated.' If the HEPN1 and HEPN2 domains of the C2c2 protein are intact, once activated, the C2c2 protein cleaves the target RNA, but also cleaves non-target RNAs.

In some cases, a C2c2 protein suitable for inclusion in a kit of the present disclosure includes an amino acid sequence having 80% or more (e.g., 85% or more, 90% or more, 95% or more, 98% or more, 99% or more, 99.5% or more, or 100%) amino acid sequence identity with the amino acid sequence set forth in any one of SEQ ID NOs: 1-6. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the *Listeria seeligeri* C2c2 amino acid sequence set forth in SEQ ID NO:1. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the *Leptotrichia buccalis* C2c2 amino acid sequence set forth in SEQ ID NO:2. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the *Rhodobacter capsulatus* C2c2 amino acid sequence set forth in SEQ ID NO:4. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the *Carnobacterium gallinarum* C2c2 amino acid sequence set forth in SEQ ID NO:5. In some cases, a C2c2 protein suitable for inclusion in a kit of the present disclosure comprises an amino acid sequence having at least 80%, at least 85%, at least 90%, at least 95%, at least 98%, at least 99%, or 100%, amino acid sequence identity to the Herbinix hemicellulosilytica C2c2 amino acid sequence set forth in SEQ ID NO:6. In some cases, a C2c2 protein suitable for inclusion in a kit of the present disclosure includes an amino acid sequence having 80% or more amino acid sequence identity with the *Leptotrichia buccalis* (Lbu) C2c2 amino acid sequence set forth in SEQ ID NO: 2. In some cases, a C2c2 protein suitable for inclusion in a kit of the present disclosure is a *Leptotrichia buccalis* (Lbu) C2c2 protein (e.g., see SEQ ID NO: 2). In some cases, a C2c2 protein suitable for inclusion in a kit of the present disclosure includes the amino acid sequence set forth in any one of SEQ ID NOs: 1-2 and 4-6.

In some cases, a C2c2 protein included in a kit of the present disclosure is not a *Leptotrichia shahii* (Lsh) C2c2 protein. In some cases, a C2c2 protein included in a kit of the present disclosure is not a C2c2 polypeptide having at least 80%, at least 85%, at least 90%, at least 95%, at least 98%, at least 99%, or 100%, amino acid sequence identity to the Lsh C2c2 polypeptide set forth in SEQ ID NO:3.

In some cases, a C2c2 protein suitable for inclusion in a kit of the present disclosure is more efficient, by a factor of 1.2-fold or more, than a *Leptotrichia shahii* (Lsh) C2c2 protein at cleaving RNA that is not targeted by a C2c2 guide RNA of the method. In some cases, the C2c2 protein is more efficient, by a factor of 1.5-fold or more, than a *Leptotrichia shahii* (Lsh) C2c2 protein at cleaving RNA that is not targeted by a C2c2 guide RNA of the method. In some cases, the C2c2 polypeptide used in a method of the present disclosure, when activated, cleaves non-target RNA at least 1.2-fold, at least 1.5-fold, at least 2-fold, at least 2.5-fold, at least 3-fold, at least 4-fold, at least 5-fold, at least 6-fold, at least 7-fold, at least 8-fold, at least 9-fold, at least 10-fold, at least 15-fold, at least 20-fold, at least 30-fold, or more than 30-fold, more efficiently than Lsh C2c2.

In some cases, a C2c2 protein suitable for inclusion in a kit of the present disclosure exhibits at least a 50% RNA cleavage efficiency within 1 hour of said contacting (e.g., 55% or more, 60% or more, 65% or more, 70% or more, or 75% or more cleavage efficiency). In some cases, a C2c2 protein suitable for inclusion in a kit of the present disclosure exhibits at least a 50% RNA cleavage efficiency within 40 minutes of said contacting (e.g., 55% or more, 60% or more, 65% or more, 70% or more, or 75% or more cleavage efficiency). In some cases, a C2c2 protein suitable for inclusion in a kit of the present disclosure exhibits at least a 50% RNA cleavage efficiency within 30 minutes of said contacting (e.g., 55% or more, 60% or more, 65% or more, 70% or more, or 75% or more cleavage efficiency).

In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 30 seconds to 60 minutes, e.g., from 1 minute to 60 minutes, from 30 seconds to 5 minutes, from 1 minute to 5 minutes, from 1 minute to 10 minutes, from 5 minutes to 10 minutes, from 10 minutes to 15 minutes, from 15 minutes to 20 minutes, from 20 minutes to 25 minutes, from 25 minutes to 30 minutes, from 30 minutes to 35 minutes, from 35 minutes to 40 minutes, from 40 minutes to 45 minutes, from 45 minutes to 50 minutes, from 50 minutes to 55 minutes, or from 55 minutes to 60 minutes. In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 30 seconds to 5 minutes (e.g., from 1 minute to 5 minutes, e.g., in a time period of 1 minute, 2 minutes, 3 minutes, 4 minutes, or 5 minutes). In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 5 minutes to 10 minutes (e.g., in a time period of 5 minutes, 6 minutes, 7 minutes, 8 minutes, 9 minutes, or 10 minutes). In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 10 minutes to 15 minutes (e.g., 10 minutes, 11 minutes, 12 minutes, 13 minutes, 14 minutes, or 15 minutes). In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 15 minutes to 20 minutes. In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 20 minutes to 25 minutes. In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 25 minutes to 30 minutes. In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 30 minutes to 35 minutes. In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 35 minutes to 40 minutes. In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 40 minutes to 45 minutes. In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 45 minutes to 50 minutes. In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 50 minutes to 55 minutes. In some cases, a C2c2 protein suitable for inclusion in a kit of the present disclosure cleaves at least 50%, at least 60%, at least 70%, at least 80%, at least 90%, at least 95%, at least 98%, at least 99%, or more than 99%, of the RNA present in a sample in a time period of from 55 minutes to 60 minutes.

In some cases, the C2c2 protein included in a kit of the present disclosure is not a *Leptotrichia shahii* (Lsh) C2c2 protein. In some cases, the C2c2 protein is more efficient than a *Leptotrichia shahii* (Lsh) C2c2 protein (e.g., at cleaving non-target RNA) by a factor of 1.2-fold or more (e.g., 1.5-fold or more, 1.7-fold or more, or 2-fold or more). As such, in some cases, a C2c2 protein suitable for inclusion in a kit of the present disclosure is more efficient, by a factor of 1.2-fold or more (e.g., 1.5-fold or more, 1.7-fold or more, or 2-fold or more), than a *Leptotrichia shahii* (Lsh) C2c2 protein at cleaving RNA that is not targeted by the C2c2 guide RNA of the method. In some cases, a C2c2 protein suitable for inclusion in a kit of the present disclosure, when activated, cleaves non-target RNA at least 1.2-fold, at least 1.5-fold, at least 2-fold, at least 2.5-fold, at least 3-fold, at least 4-fold, at least 5-fold, at least 6-fold, at least 7-fold, at least 8-fold, at least 9-fold, at least 10-fold, at least 15-fold, at least 20-fold, at least 30-fold, or more than 30-fold, more efficiently than Lsh C2c2.

Positive Controls

A kit of the present disclosure that comprises a labeled detector RNA and a C2c2 polypeptide can also include a positive control target RNA. In some cases, the kit also includes a positive control guide RNA that comprises a nucleotide sequence that hybridizes to the control target RNA. In some cases, the positive control target RNA is provided in various amounts, in separate containers. In some cases, the positive control target RNA is provided in various known concentrations, in separate containers, along with control non-target RNAs.

Nucleic Acid Encoding a C2c2 Guide RNA and/or a Precursor C2c2 Guide RNA Array and/or a C2c2 Protein While the RNAs of the disclosure (e.g., C2c2 guide RNAs and precursor C2c2 guide RNA arrays) can be synthesized using any convenient method (e.g., chemical synthesis, in vitro using an RNA polymerase enzyme, e.g., T7 polymerase, T3 polymerase, SP6 polymerase, etc.), nucleic acids encoding 2c2 guide RNAs and/or precursor C2c2 guide RNA arrays are also envisioned. Additionally, while C2c2 proteins of the disclosure can be provided (e.g., as part of a kit) in protein form, nucleic acids (such as mRNA and/or DNA) encoding the C2c2 protein(s) can also be provided.

For example, in some embodiments, a kit of the present disclosure comprises a nucleic acid (e.g., a DNA, e.g., a recombinant expression vector) that comprises a nucleotide sequence encoding a C2c2 guide RNA. In some cases, the nucleotide sequence encodes a C2c2 guide RNA without a guide sequence. For example, in some cases, the nucleic acid comprises a nucleotide sequence encoding a constant region of a C2c2 guide RNA (a C2c2 guide RNA without a guide sequence), and comprises an insertion site for a nucleic acid encoding a guide sequence. In some embodiments, a kit of the present disclosure comprises a nucleic acid (e.g., an mRNA, a DNA, e.g., a recombinant expression vector) that comprises a nucleotide sequence encoding a C2c2 protein.

In some embodiments, a kit of the present disclosure comprises a nucleic acid (e.g., a DNA, e.g., a recombinant expression vector) that comprises a nucleotide sequence encoding a precursor C2c2 guide RNA array (e.g., in some cases where each guide RNA of the array has a different guide sequence). In some cases, one or more of the encoded guide RNAs of the array does not have a guide sequence, e.g., the nucleic acid can include insertion site(s) for the guide sequence(s) of one or more of the guide RNAs of the array. In some cases, a subject C2c2 guide RNA can include a handle from a precursor crRNA but does not necessarily have to include multiple guide sequences.

In some cases, the C2c2 guide RNA-encoding nucleotide sequence (and/or the precursor C2c2 guide RNA array-encoding nucleotide sequence) is operably linked to a promoter, e.g., a promoter that is functional in a prokaryotic cell, a promoter that is functional in a eukaryotic cell, a promoter that is functional in a mammalian cell, a promoter that is functional in a human cell, and the like. In some cases, a nucleotide sequence encoding a C2c2 protein is operably linked to a promoter, e.g., a promoter that is functional in a prokaryotic cell, a promoter that is functional in a eukaryotic cell, a promoter that is functional in a mammalian cell, a promoter that is functional in a human cell, a cell type-specific promoter, a regulatable promoter, a tissue-specific promoter, and the like.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-90 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Aspect 1. A method of detecting a single stranded target RNA in a sample comprising a plurality of RNAs, the method comprising:
  a) contacting the sample with: (i) a C2c2 guide RNA that hybridizes with the single stranded target RNA; and (ii) a C2c2 protein that cleaves RNAs present in the sample; and
  b) measuring a detectable signal produced by C2c2 protein-mediated RNA cleavage.

Aspect 2. A method of detecting a single stranded target RNA in a sample comprising a plurality of RNAs, the method comprising:
  (a) contacting the sample with: (i) a precursor C2c2 guide RNA array comprising two or more C2c2 guide RNAs each of which has a different guide sequence; and (ii) a C2c2 protein that cleaves the precursor C2c2 guide RNA array into individual C2c2 guide RNAs, and also cleaves RNAs of the sample; and
  (b) measuring a detectable signal produced by C2c2 protein-mediated RNA cleavage.

Aspect 3. The method according to aspect 1 or 2 aspect, wherein the C2c2 protein cleaves at least 50% of the RNAs present in the sample within 1 hour of said contacting.

Aspect 4. The method according to aspect 3, wherein the C2c2 protein cleaves at least 50% of the RNAs present in the sample within 40 minutes of said contacting.

Aspect 5. The method according to aspect 4, wherein the C2c2 protein cleaves at least 50% of the RNAs present in the sample within 5 minutes of said contacting.

Aspect 6. The method according to aspect 5, wherein the C2c2 protein cleaves at least 50% of the RNAs present in the sample within 1 minute of said contacting.

Aspect 7. The method according to aspect 1, wherein the C2c2 protein cleaves from 50% to more than 90% of the RNAs present in the sample within 1 minute of said contacting.

Aspect 8. The method according to any one of aspects 1-7, wherein the minimum concentration at which the single stranded target RNA can be detected is in a range of from 500 fM to 1 nM.

Aspect 9. The method according to any one of aspects 1-7, wherein the single stranded target RNA can be detected at a concentration as low as 800 fM.

Aspect 10. The method according to any of aspects 1-9, wherein the C2c2 protein is not a *Leptotrichia shahii* (Lsh) C2c2 protein comprising an amino acid sequence having at least 80%, at least 85%, at least 90%, at least 95%, at least 98%, at least 99%, or 100%, amino acid sequence identity to the amino acid sequence set forth in SEQ ID NO:3.

Aspect 11. The method according to aspect 10, wherein the C2c2 protein cleaves non-target RNA at least 1.2-fold efficiently than a *Leptotrichia shahii* (Lsh) C2c2 protein comprising at least 80%, at least 85%, at least 90%, at least 95%, at least 98%, at least 99%, or 100%, amino acid sequence identity to the amino acid sequence set forth in SEQ ID NO:3.

Aspect 12. The method according to aspect 11, wherein the C2c2 protein cleaves non-target RNA at least 1.5-fold efficiently than a *Leptotrichia shahii* (Lsh) C2c2 protein comprising the amino acid sequence set forth in SEQ ID NO:3.

Aspect 13. The method according to any of aspects 1-9, wherein the C2c2 protein comprises an amino acid sequence having 80% or more amino acid sequence identity with the amino acid sequence set forth in any one of SEQ ID NOs:1, 2, or 4-6.

Aspect 14. The method according to any of aspects 1-9, wherein the C2c2 protein comprises an amino acid sequence having 80% or more amino acid sequence identity with the *Leptotrichia buccalis* (Lbu) C2c2 amino acid sequence set forth in SEQ ID NO: 2.

Aspect 15. The method according to any of aspects 1-9, wherein the C2c2 protein comprises an amino acid sequence having 80% or more amino acid sequence identity with the *Listeria seeligeri* C2c2 amino acid sequence set forth in SEQ ID NO: 1.

Aspect 16. The method according to any of aspects 1-9, wherein the C2c2 protein comprises the amino acid sequence set forth in any one of SEQ ID NOs: 1-2 and 4-6.

Aspect 17. The method according to aspect 1, wherein the C2c2 protein comprises an amino acid sequence having at least 80% amino acid sequence identity to the C2c2 amino acid sequence set forth in SEQ ID NO:2, and comprises a substitution of one or more of R472, H477, R1048, and H1053.

Aspect 18. The method according to aspect 1, wherein the C2c2 protein comprises an amino acid sequence having at least 80% amino acid sequence identity to the C2c2 amino acid sequence set forth in SEQ ID NO:2, and comprises a substitution of amino acids R472 and H477.

Aspect 19. The method according to aspect 1, wherein the C2c2 protein comprises an amino acid sequence having at least 80% amino acid sequence identity to the C2c2 amino acid sequence set forth in SEQ ID NO:2, and comprises a substitution of amino acids R1048 and H1053.

Aspect 20. The method according to aspect 1, wherein the C2c2 protein comprises an amino acid sequence having at least 80% amino acid sequence identity to the C2c2 amino acid sequence set forth in SEQ ID NO:2, and comprises a substitution of amino acids R472, H477, R1048, and H1053.

Aspect 21. The method according to any one of aspects 1-20, wherein the sample is contacted for 2 hours or less prior to said measuring.

Aspect 22. The method according to aspect 21, wherein the sample is contacted for 60 minutes or less prior to said measuring.

Aspect 23. The method according to aspect 22, wherein the sample is contacted for 30 minutes or less prior to said measuring.

Aspect 24. The method according to aspect 23, wherein the sample is contacted for 10 minutes or less prior to said measuring.

Aspect 25. The method according to aspect 24, wherein the sample is contacted for 1 minute or less prior to said measuring.

Aspect 26. The method according to any one of aspects 1-25, comprising determining an amount of target RNA present in the sample.

Aspect 27. The method according to aspect 26, wherein said determining comprises:
measuring the detectable signal to generate a test measurement;
measuring a detectable signal produced by a reference sample to generate a reference measurement; and
comparing the test measurement to the reference measurement to determine an amount of target RNA present in the sample.

Aspect 28. The method according to aspect 26, comprising:
measuring the detectable signal to generate a test measurement,
measuring a detectable signal produced by each of two or more reference samples, wherein the two or more reference samples each include a different amount of a positive control RNA, to generate two or more reference measurements, and
comparing the test measurement to the two or more reference measurements to determine an amount of target RNA present in the sample.

Aspect 29. The method according to any one of aspects 1-28, wherein the sample comprises from 5 to $10^7$ RNAs that differ from one another in sequence.

Aspect 30. The method according to any one of aspects 1-28, wherein the sample comprises from 10 to $10^6$ RNAs that differ from one another in sequence.

Aspect 31. The method according to any one of aspects 1-30, wherein the sample comprises RNAs from a cell lysate.

Aspect 32. The method according to any one of aspects 1-31, wherein measuring a detectable signal comprises one or more of: gold nanoparticle based detection, fluorescence polarization, colloid phase transition/dispersion, electrochemical detection, and semiconductor-based sensing.

Aspect 33. The method according to any one of aspects 1-32, wherein (i) the method comprises contacting the sample with a labeled detector RNA comprising a fluorescence-emitting dye pair (i.e., a fluorescence resonance energy transfer (FRET) pair and/or a quencher/fluor pair), (ii) the C2c2 protein cleaves the labeled detector RNA, and (iii) the detectable signal is produced by the FRET pair and/or the quencher/fluor pair.

Aspect 34. The method according to aspect 33, wherein the labeled detector RNA produces an amount of detectable signal prior to being cleaved, and the amount of detectable signal is reduced when the labeled detector RNA is cleaved.

Aspect 35. The method according to aspect 33, wherein the labeled detector RNA produces a first detectable signal prior to being cleaved and a second detectable signal when the labeled detector RNA is cleaved.

Aspect 36. The method according to aspect 35, wherein the labeled detector RNA comprises a FRET pair and a quencher/fluor pair.

Aspect 37. The method according to any one of aspects 33-36, wherein the labeled detector RNA comprises a FRET pair.

Aspect 38. The method according to aspect 33, wherein a detectable signal is produced when the labeled detector RNA is cleaved.

Aspect 39. The method according to aspect 33, wherein an amount of detectable signal increases when the labeled detector RNA is cleaved.

Aspect 40. The method according to aspect 38 or 3 aspect 9, wherein the labeled detector RNA comprises a quencher/fluor pair.

Aspect 41. The method according to any of aspects 33-40, wherein the labeled detector RNA comprises a modified nucleobase, a modified sugar moiety, and/or a modified nucleic acid linkage.

Aspect 42. The method according to any one of aspects 1-41, wherein said contacting is carried out in an acellular sample.

Aspect 43. The method according to any one of aspects 1-41, wherein said contacting is carried out in a cell in vitro, ex vivo, or in vitro.

Aspect 44. A method of cleaving a precursor C2c2 guide RNA array into two or more C2c2 guide RNAs, the method comprising:
contacting a precursor C2c2 guide RNA array comprising two or more C2c2 guide RNAs each of which has a different guide sequence, with a C2c2 protein, wherein the C2c2 protein cleaves the precursor C2c2 guide RNA array into individual C2c2 guide RNAs.

Aspect 45. The method according to aspect 44, wherein the C2c2 protein lacks a catalytically active HEPN1 domain and/or lacks a catalytically active HEPN2 domain.

Aspect 46. The method according to aspect 44 or aspect 45, wherein the precursor C2c2 guide RNA array comprises two or more C2c2 guide RNAs that target different target sequences within the same target RNA molecule.

Aspect 47. The method according to any one of aspects 44-46, wherein the precursor C2c2 guide RNA array comprises two or more C2c2 guide RNAs that target different target RNA molecules.

Aspect 48. The method according to any one of aspects 44-47, wherein said contacting does not take place inside of a cell.

Aspect 49. The method according to any one of aspects 44-48, wherein at least one of the guide RNAs and/or the precursor C2c2 guide RNA array is detectably labeled.

Aspect 50. A kit for detecting a target RNA in a sample comprising a plurality of RNAs, the kit comprising:
  (a) a precursor C2c2 guide RNA array, and/or a nucleic acid encoding said precursor C2c2 guide RNA array, wherein the precursor C2c2 guide RNA array comprises two or more C2c2 guide RNAs each of which has a different guide sequence and/or an insertion site for a guide sequence of choice; and
  (b) a C2c2 protein.

Aspect 51. The kit of aspect 50, wherein the C2c2 protein lacks a catalytically active HEPN1 domain and/or lacks a catalytically active HEPN2 domain.

Aspect 52. The kit of aspect 50 or aspect 51, wherein the precursor C2c2 guide RNA array comprises two or more C2c2 guide RNAs that target different target sequences within the same target RNA molecule.

Aspect 53. The kit of any one of aspects 50-52, wherein the precursor C2c2 guide RNA array comprises two or more C2c2 guide RNAs that target different target RNA molecules.

Aspect 54. The kit of any one of 5 aspects 0-53, wherein at least one of the guide RNAs and/or the precursor C2c2 guide RNA array is detectably labeled.

Aspect 55. The kit of any one of aspects 50-54, further comprising a labeled detector RNA comprising a fluorescence-emitting dye pair (i.e., a FRET pair and/or a quencher/fluor pair).

Aspect 56. A kit for detecting a target RNA in a sample comprising a plurality of RNAs, the kit comprising:
  (a) a labeled detector RNA comprising a fluorescence-emitting dye pair (i.e., a FRET pair and/or a quencher/fluor pair); and
  (b) a C2c2 protein.

Aspect 57. The kit of aspect 56, comprising a positive control target RNA.

Aspect 58. The kit of aspect 57, where in the positive control target RNA is present in different amounts in each of two or more containers.

Aspect 59. The kit of any one of aspects 56-58, comprising at least one of:
  (c) a C2c2 guide RNA and/or a nucleic acid encoding said C2c2 guide RNA;
  (d) a precursor C2c2 guide RNA and/or a nucleic acid encoding said precursor C2c2 guide RNA; and
  (e) a precursor C2c2 guide RNA array, and/or a nucleic acid encoding said precursor C2c2 guide RNA array, wherein the precursor C2c2 guide RNA array comprises two or more C2c2 guide RNAs each of which has a different guide sequence and/or an insertion site for a guide sequence of choice.

Aspect 60. The kit of any one of aspects 56-59, comprising a DNA comprising a nucleotide sequence that encodes a C2c2 guide RNA with or without a guide sequence.

Aspect 61. The kit of aspect 60, wherein the DNA comprises an insertion sequence for the insertion of a guide sequence.

Aspect 62. The kit of aspect 60 or aspect 61, wherein the DNA is an expression vector and the C2c2 guide RNA is operably linked to a promoter.

Aspect 63. The kit of aspect 62, wherein the promoter is a T7 promoter.

Aspect 64. The kit of any one of aspects 56-63, comprising a C2c2 endoribonuclease variant that lacks nuclease activity.

Aspect 65. The kit of any one of aspects 56-64, wherein the labeled detector RNA comprises a FRET pair.

Aspect 66. The kit of any one of aspects 56-65, wherein the labeled detector RNA comprises a quencher/fluor pair.

Aspect 67. The kit of any one of aspects 56-66, wherein the labeled detector RNA comprises a FRET pair that produces a first detectable signal and a quencher/fluor pair that produces a second detectable signal.

Aspect 68. A variant C2c2 polypeptide comprising:
  a) an amino acid sequence having at least 80%, at least 85%, at least 90%, at least 95%, at least 98%, or at least 99%, amino acid sequence identity to the amino acid sequence set forth in SEQ ID NO:2, and comprises substitution of: i) amino acids R472 and H477; ii) amino acids R1048 and H1053; or iii) amino acids R472, H477, R1048, and H1053;
  b) an amino acid sequence having at least 80%, at least 85%, at least 90%, at least 95%, at least 98%, or at least 99%, amino acid sequence identity to the amino acid sequence set forth in SEQ ID NO:1, and comprises substitution of: i) amino acids R445 and H450; ii) amino acids R1016 and H1021; or iii) amino acids R445, H450, R1016, and H1021;
  c) an amino acid sequence having at least 80%, at least 85%, at least 90%, at least 95%, at least 98%, or at least 99%, amino acid sequence identity to the amino acid sequence set forth in SEQ ID NO:4, and comprises substitution of: i) amino acids R464 and H469; ii) amino acids R1052, and H1057; or iii) amino acids R464, H469, R1052, and H1057;
  d) an amino acid sequence having at least 80%, at least 85%, at least 90%, at least 95%, at least 98%, or at least 99%, amino acid sequence identity to the amino acid sequence set forth in SEQ ID NO:5, and comprises substitution of: i) amino acids R467 and H472; ii) amino acids R1069, and H1074; or iii) amino acids R467, H472, R1069, and H1074; or
  e) an amino acid sequence having at least 80%, at least 85%, at least 90%, at least 95%, at least 98%, or at least 99%, amino acid sequence identity to the amino acid sequence set forth in SEQ ID NO:6, and comprises substitution of: i) amino acids R472 and H477; ii) amino acids R1044 and H1049; iii) or amino acids R472, H477, R1044, and H1049.

Aspect 69. A variant C2c2 polypeptide of 68, wherein the variant C2c2 polypeptide has reduced or undetectable cleavage of ss RNA (e.g., RNA-guided cleavage activity), but retains the ability to bind C2c2 guide RNA and ssRNA, and retains the ability to cleave precursor C2c2 guide RNA.

Aspect 70. A nucleic acid comprising a nucleotide sequence encoding a variant C2c2 polypeptide of aspect 68 or aspect 69.

Aspect 71. The nucleic acid of aspect 70, wherein the nucleotide sequence is operably linked to a constitutive promoter or a regulatable promoter.

Aspect 72. A recombinant expression vector comprising the nucleic acid of aspect 70 or aspect 71.

Aspect 73. A host cell genetically modified with the nucleic acid of aspect 70 or aspect 71, or with the recombinant expression vector of aspect 72.

Aspect 74. The host cell of aspect 73, wherein the host cell is a eukaryotic cell.

Aspect 75. The host cell of aspect 73, wherein the host cell is a prokaryotic cell.

Aspect 76. The host cell of any one of aspects 73-75, wherein the host cell is in vitro, ex vivo, or in vivo.

Aspect 77. A method of detecting at least two different single stranded target RNAs in a sample comprising a plurality of RNAs, the method comprising:
  a) contacting the sample with:
    (i) a first C2c2 protein that cleaves single stranded RNAs (ssRNAs) that include at least one A;
    (ii) a second C2c2 protein that cleaves ssRNAs that include at least one U;
    (iii) a first C2c2 guide RNA that comprises a first nucleotide sequence that hybridizes with the first single stranded target RNA and a second nucleotide sequence that binds to the first C2c2 protein; and
    (iv) a second C2c2 guide RNA that comprises a first nucleotide sequence that hybridizes with the second single stranded target RNA and a second nucleotide sequence that binds to the second C2c2 protein;
    wherein the first C2c2 protein is not activated by the second C2c2 guide RNA, and wherein the first C2c2 protein cleaves ssRNA that includes at least one A, and wherein the second C2c2 protein is not activated by the first C2c2 guide RNA, and wherein the second C2c2 protein cleaves ssRNA that includes at least one U; and
  b) measuring a detectable signal produced by RNA cleavage mediated by the first and the second C2c2 proteins, wherein a first detectable signal is produced upon activation of the first C2c2 protein and a second detectable signal is produced upon activation of the second C2c2 protein, wherein detection of the first signal indicates the presence in the sample of the first target ssRNA, and wherein detection of the second signal indicates the presence in the sample of the second target ssRNA.

Aspect 78. The method of aspect 77, wherein:
  a) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Hhe Cas13a amino acid sequence depicted in FIG. 56K;
  b) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Rca Cas13a amino acid sequence depicted in FIG. 56G;
  c) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Ppr Cas13a amino acid sequence depicted in FIG. 56B;
  d) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Lne Cas13a amino acid sequence depicted in FIG. 56I;
  e) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Lbu Cas13a amino acid sequence depicted in FIG. 56C;
  f) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Lwa Cas13a amino acid sequence depicted in FIG. 56E;
  g) the first C2c2 protein comprises an amino acid sequence having at least 75%, at least 80%, at least 85%, at least 90%, at least 95%, at least 98%, at least 99%, or 100%, amino acid sequence identity to the Lba Cas13a amino acid sequence depicted in FIG. 56F; and the second C2c2 protein comprises an amino acid sequence having at least 75%, at least 80%, at least 85%, at least 90%, at least 95%, at least 98%, at least 99%, or 100%, amino acid sequence identity to the Lsh Cas13a amino acid sequence depicted in FIG. 56D;
  h) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Hhe Cas13a amino acid sequence depicted in FIG. 56K;
  i) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Rca Cas13a amino acid sequence depicted in FIG. 56G;
  j) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Ppr Cas13a amino acid sequence depicted in FIG. 56B;

k) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lne Cas13a amino acid sequence depicted in FIG. 56I;

l) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lbu Cas13a amino acid sequence depicted in FIG. 56C;

m) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lwa Cas13a amino acid sequence depicted in FIG. 56E;

n) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lsh Cas13a amino acid sequence depicted in FIG. 56D;

o) the first C2c2 protein comprises an amino acid sequence having at least 75%, at least 80%, at least 85%, at least 90%, at least 95%, at least 98%, at least 99%, or 100%, amino acid sequence identity to the Ere Cas13a amino acid sequence depicted in FIG. 56J; and the second C2c2 protein comprises an amino acid sequence having at least 75%, at least 80%, at least 85%, at least 90%, at least 95%, at least 98%, at least 99%, or 100%, amino acid sequence identity to the Lse Cas13a amino acid sequence depicted in FIG. 56A;

p) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Hhe Cas13a amino acid sequence depicted in FIG. 56K;

q) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Rca Cas13a amino acid sequence depicted in FIG. 56G;

r) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Ppr Cas13a amino acid sequence depicted in FIG. 56B;

s) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lne Cas13a amino acid sequence depicted in FIG. 56I;

t) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lbu Cas13a amino acid sequence depicted in FIG. 56C;

u) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lwa Cas13a amino acid sequence depicted in FIG. 56E;

v) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lsh Cas13a amino acid sequence depicted in FIG. 56F; or w) the first C2c2 protein comprises an amino acid sequence having at least 75%, at least 80%, at least 85%, at least 90%, at least 95%, at least 98%, at least 99%, or 100%, amino acid sequence identity to the Cam Cas13a amino acid sequence depicted in FIG. 56H; and the second C2c2 protein comprises an amino acid sequence having at least 75%, at least 80%, at least 85%, at least 90%, at least 95%, at least 98%, at least 99%, or 100%, amino acid sequence identity to the Lse Cas13a amino acid sequence depicted in FIG. 56A.

Aspect 79. The method according to aspect 77 or aspect 78, wherein the method comprises contacting the sample with:
  i) a first labeled detector RNA comprising a first fluorescence resonance energy transfer (FRET) pair and/or first a quencher/fluor pair, where the first labeled detector RNA comprises at least one A and does not comprise U; and
  ii) a second labeled detector RNA comprising a second FRET pair and/or a second quencher/fluor pair, where the second labeled detector RNA comprises at least one U and does not comprise A,
    wherein the first C2c2 protein cleaves the first labelled detector RNA, and the first detectable signal is produced by the first FRET pair and/or the first quencher/fluor pair, and
    wherein the first C2c2 protein cleaves the second labelled detector RNA, and the second detectable signal is produced by the second FRET pair and/or the second quencher/fluor pair.

Aspect 80. The method according to 7 aspect 9, wherein the first labeled detector RNA comprises a stretch of from 2 to 15 consecutive As and/or the second labeled detector RNA comprises a stretch of from 2 to 15 consecutive Us.

Aspect 81. The method according to aspect 79, wherein the first labeled detector RNA comprises a stretch of from 4 to 15 consecutive As and/or the second labeled detector RNA comprises a stretch of from 4 to 15 consecutive Us.

Aspect 82. The method according to aspect 79, wherein the first labeled detector RNA comprises a stretch of at least 3 consecutive As and/or the second labeled detector RNA comprises a stretch of at least 3 consecutive Us.

Aspect 83. The method according to aspect 79, wherein the first labeled detector RNA comprises a stretch of at least 4 consecutive As and/or the second labeled detector RNA comprises a stretch of at least 4 consecutive Us.

Aspect 84. A kit comprising:
  (a) a first labeled detector RNA that lacks U and comprises at least one A and comprises a first fluorescence-emitting dye pair;
  (b) a second labeled detector RNA that lacks A and comprises at least one U and comprises a second fluorescence-emitting dye pair;
  (c) a first C2c2 protein, and/or a nucleic acid encoding said first C2c2 protein, wherein the first C2c2 protein can cleave the first labeled detector RNA but not the second labeled detector RNA (e.g., the first C2c2 protein cleaves adenine+ RNAs when activated and does not cleave RNAs that lack A); and
  (d) a second C2c2 protein, and/or a nucleic acid encoding said second C2c2 protein, wherein the second C2c2 protein can cleave the second labeled detector RNA but not the first labeled detector RNA (e.g., the second C2c2 protein cleaves uracil+ RNAs when activated but does not cleave RNAs that lack U).

Aspect 85. The kit of aspect 84, comprising at least one of:
  (e) a first C2c2 guide RNA and/or a nucleic acid encoding said first C2c2 guide RNA, wherein the first C2c2 guide RNA comprises a constant region sequence that binds to the first C2c2 protein;
  (f) a second C2c2 guide RNA and/or a nucleic acid encoding said second C2c2 guide RNA, wherein the second C2c2 guide RNA comprises a constant region sequence that binds to the second C2c2 protein;
  (g) a nucleic acid comprising a nucleotide sequence encoding a constant region sequence that binds to the first C2c2 protein and an insertion site for a guide sequence of choice;
  (h) a nucleic acid comprising a nucleotide sequence encoding a constant region sequence that binds to the second C2c2 protein and an insertion site for a guide sequence of choice.

Aspect 86. The kit of aspect 84, comprising a nucleic acid comprising a nucleotide sequence encoding a first C2c2 guide RNA, wherein the first C2c2 guide RNA comprises a constant region sequence that binds to the first C2c2 protein.

Aspect 87. The kit of aspect 84, comprising a nucleic acid comprising a nucleotide sequence encoding a second C2c2 guide RNA, wherein the second C2c2 guide RNA comprises a constant region sequence that binds to the second C2c2 protein.

Aspect 88. The kit of aspect 84, comprising a nucleic acid comprising a nucleotide sequence encoding a constant region sequence that binds to the first C2c2 protein and an insertion site for a guide sequence of choice.

Aspect 89. The kit of aspect 84, comprising a nucleic acid comprising a nucleotide sequence encoding a constant region sequence that binds to the second C2c2 protein and an insertion site for a guide sequence of choice.

Aspect 90. The kit of any one of aspects 86-89, wherein the nucleic acid is an expression vector and the nucleotide sequence is operably linked to a promoter.

Examples

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

The data described herein show that C2c2 possesses two distinct ribonuclease activities responsible for CRISPR RNA processing and ssRNA degradation. Maturation of precursor CRISPR RNAs (pre-crRNAs) is a relatively slow, highly specific catalytic event. In contrast, upon binding to target RNAs bearing sequence complementarity to the guide segment of the crRNA, C2c2 is activated as a robust general RNase that cleaves RNA in cis and in trans by initiating strand scission at uracil nucleotides. The data show that this trans cleavage activity can be harnessed for ultra-sensitive RNA detection within complex mixtures.

Example 1: C2c2 Recombinant Protein Purification

Figure 1B:
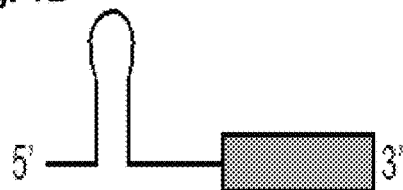
Figure 1C:
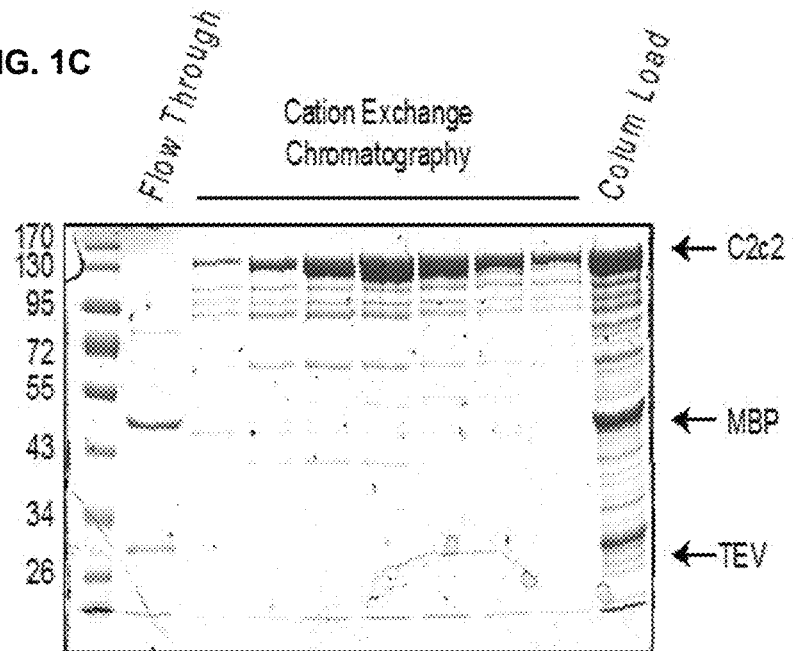
Figure 1D:
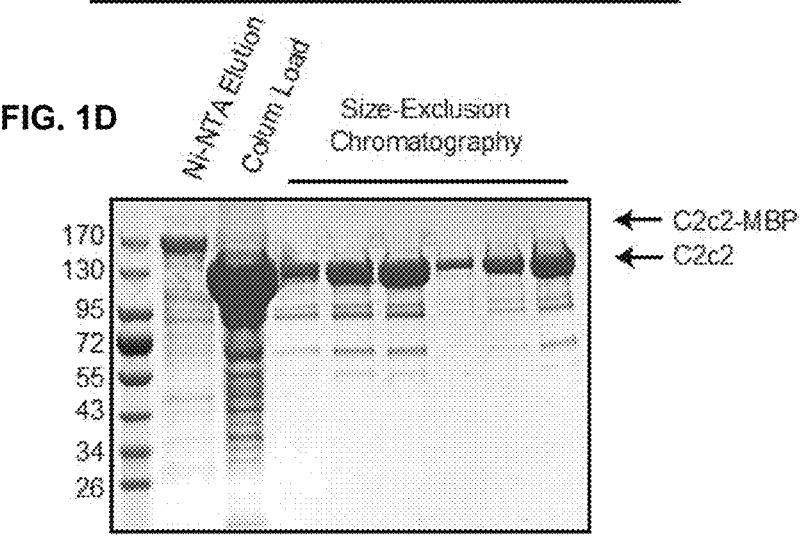
Figure 1E:
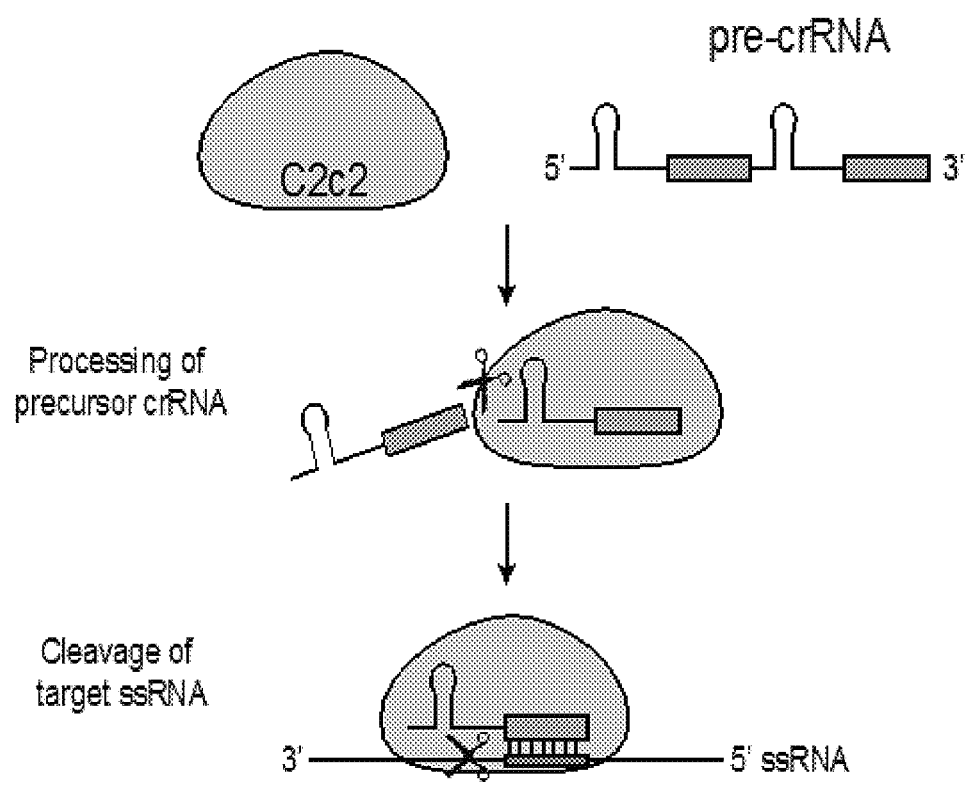

FIG. 1A-1E. Summary of endogenous C2c2 locus and heterologous expression and purification of recombinant C2c2 protein. FIG. 1A. Schematic diagram of *Leptotrichia buccalis* C2c2 locus. Predicted HEPN active sites indicated in yellow with active site residues noted. FIG. 1B. Schematic diagram of mature crRNA from this Type VI CRISPR system. FIG. 1C. Sodium dodecyl sulfate-polyacrylamide gel electrophoresis (SDS-PAGE) analysis of cation exchange chromatography fractions. *E. coli* cells expressing His-maltose binding protein (MBP)-C2c2 were harvested and lysed by sonication. Lysates were cleared by centrifugation and then the His-MBP-C2c2 was isolated over metal ion affinity chromatography. Protein eluates were incubated with TEV protease to cleave off the His-MBP tag. Cleaved protein was loaded onto HiTrap heparin column and eluted over a linear KCl gradient. Elution fractions were loaded onto a 10% SDS-PAGE gel for analysis. FIG. 1D. Cation exchange chromatography fractions were pooled, concentrated and then loaded onto S200 size-exclusion chromatography column. Fractions from size exchange chromatography were analyzed via SDS-PAGE. FIG. 1E. Working model for C2c2 enzymatic activity.

Example 2: C2c2 is a Programmable Endoribonuclease

Figure 2:
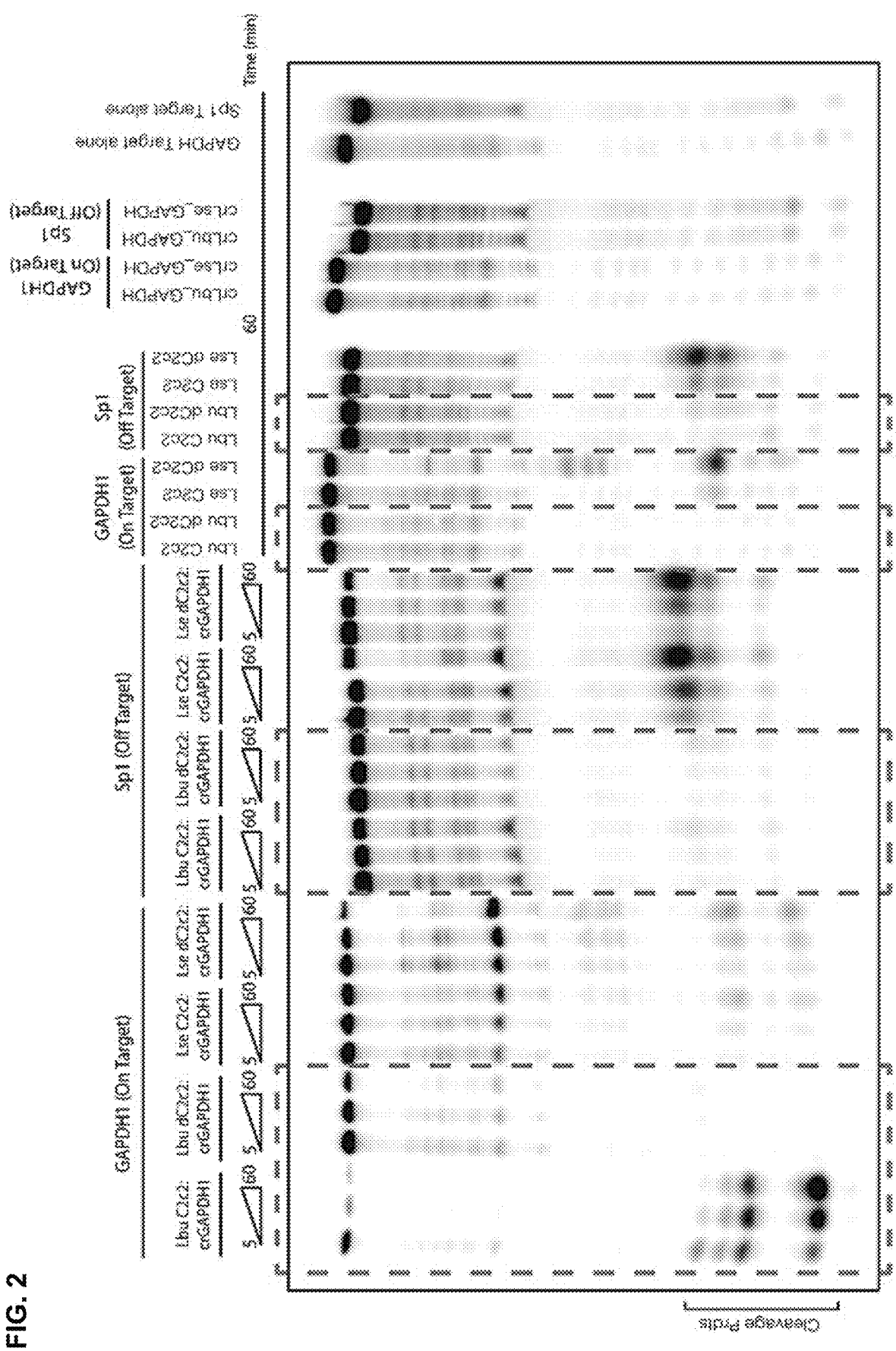
FIG. 2 depicts results from cleavage assays that were performed using C2c2 protein.

Purified C2c2 cleaved single-stranded RNA (ssRNA) in a crRNA-directed manner that was dependent on the presence of catalytically-active HEPN domains (FIG. 2)

FIG. 2. Cleavage assays were performed in 20 mM Tris-HCl pH 6.8, 50 mM KCl, 5 mM $MgCl_2$, 5% glycerol. 100 nM C2c2 protein was preincubated with crRNA at a ratio of 2:1 for 10 mins at 37° C. to promote complex assembly. Addition of ~1 nM 5' $^{32}P$ labeled ssRNA initiated the reaction and time-points were taken by quenching with formamide loading buffer. Cleavage product formation was resolved by 15% denaturing urea-PAGE and visualized using a phoshorimager. Inactivated protein (indicated by dC2c2 notation) is a quadruple point mutant (R472A, H477A, R1048A, H1053A) which eliminates both the arginine and histidine from the $R-X_{4-6}-H$ HEPN motif in both predicted active sites. In this gel, lanes of interest are highlighted by the red boxes. No cleavage activity is detected with off-target ssRNA or when the HEPN domains are inactivated.

Example 3: C2c2 Cleavage Activity is Specific to Single Stranded RNA

Figure 3:
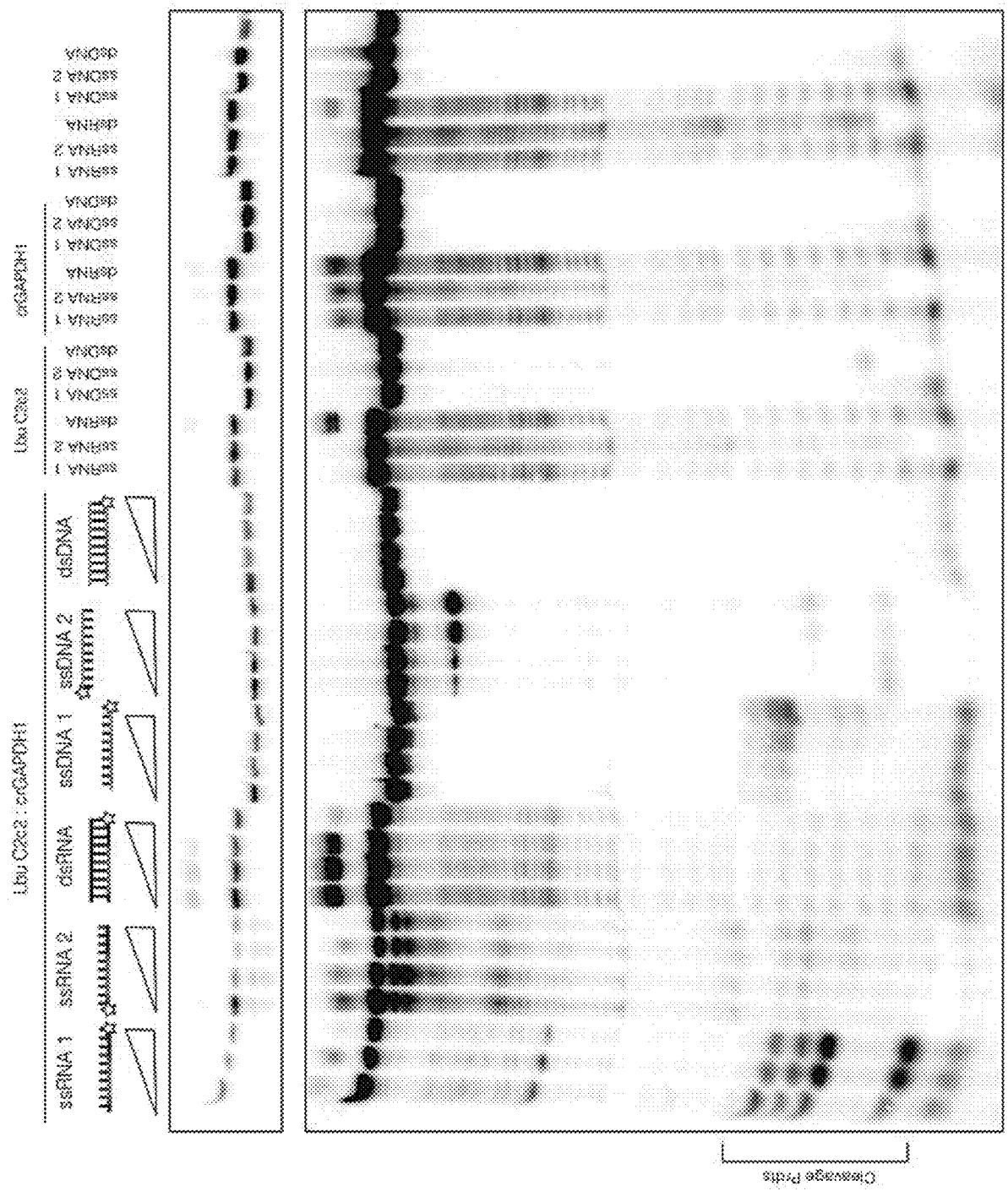
FIG. 3 depicts results showing that C2c2 robustly cleaved single stranded RNA.

C2c2 exhibited no cleavage of double-stranded RNA or DNA, with limited cleavage of single-stranded DNA at a much reduced rate as compared to ssRNA (FIG. 3).

FIG. 3. C2c2 robustly cleaved single stranded RNA and did not cleave double stranded substrates. Cleavage assay conditions as per FIG. 2. Cleavage products were resolved on a 15% denaturing urea-PAGE gel. Samples were taken at 5, 10, 30, 75 mins, with all controls lanes incubated in parallel for 75 mins. Cleavage products of the expected size range can be detected only in the ssRNA reactions and to a lesser extent in the single stranded DNA conditions. 3' end labeling of the single stranded RNA target demonstrates that cleavage is occurring outside of the target-spacer hybridization region. Labels to top of figure indicate whether protein ("Lbu C2c2") or C2c2 guide RNA ("crGAPDH1") were added. Controls included (i) protein but no guide RNA, (ii) guide RNA but no protein, and (iii) no protein and no guide RNA.

Example 4: C2c2 Processes Precursor crRNAs into Mature crRNAs

C2c2 processed precursor crRNAs to mature crRNAs in a HEPN-domain independent manner (FIG. 4A-4B), indicating the presence of an additional endonuclease domain.

Figure 4A:
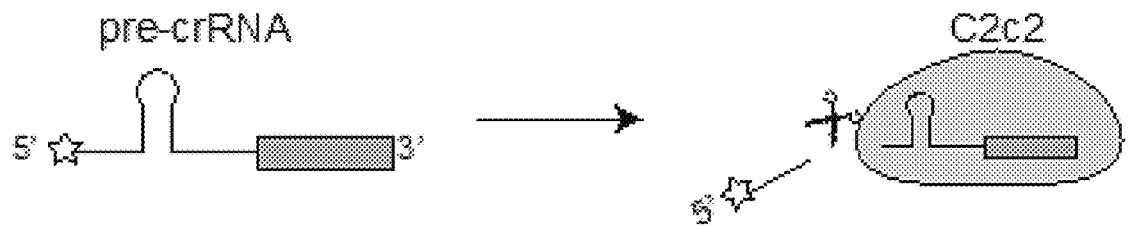
FIG. 4A-4B present a diagram and results from various cleavage assays using C2c2 protein.
Figure 4B:
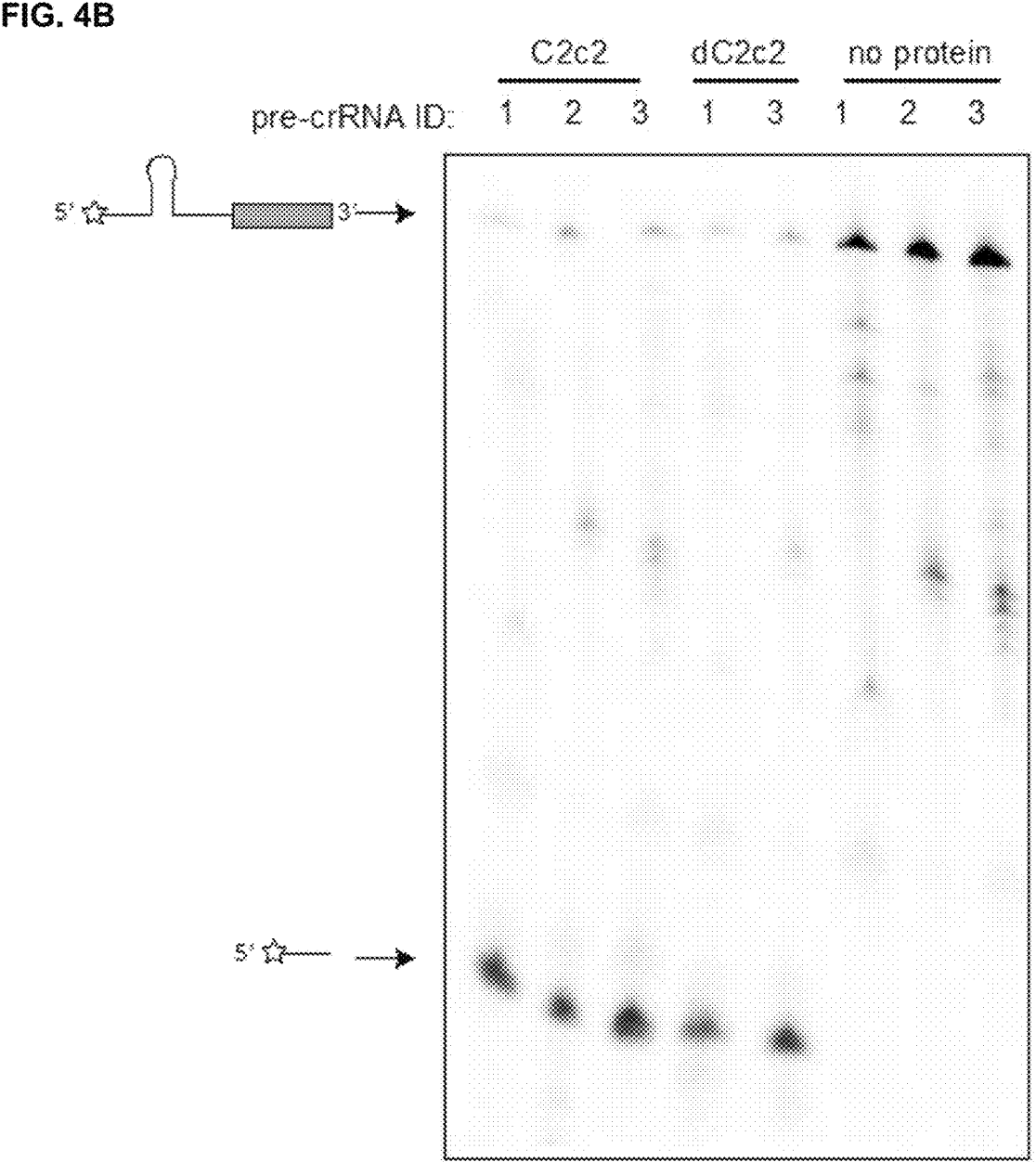

FIG. 4A. Diagram of pre-crRNA processing reaction catalyzed by C2c2. FIG. 4B. 100 nM Lbu C2c2 was incubated in 20 mM HEPES pH 6.8, 50 mM KCl, 5 mM $MgCl_2$, 5% glycerol with ~5 nM 5' $^{32}P$ labeled ssRNA for 60 min prior to quenching with formamide loading buffer. Reaction products were resolved on 15% denaturing urea-PAGE gel and visualized with a phosphoimager. Inactivated protein (indicated by dC2c2 notation) is a quadruple point mutant (R472A, H477A, R1048A, H1053A) which eliminates both the arginine and histidine from the $R-X_{4-6}-H$ HEPN motif in both predicted active sites. Three different pre-crRNA with variable spacer sequences were tested for C2c2 processing capacity.

Example 5: Sensitive Detection of Transcripts in Complex Mixtures

Figure 5:
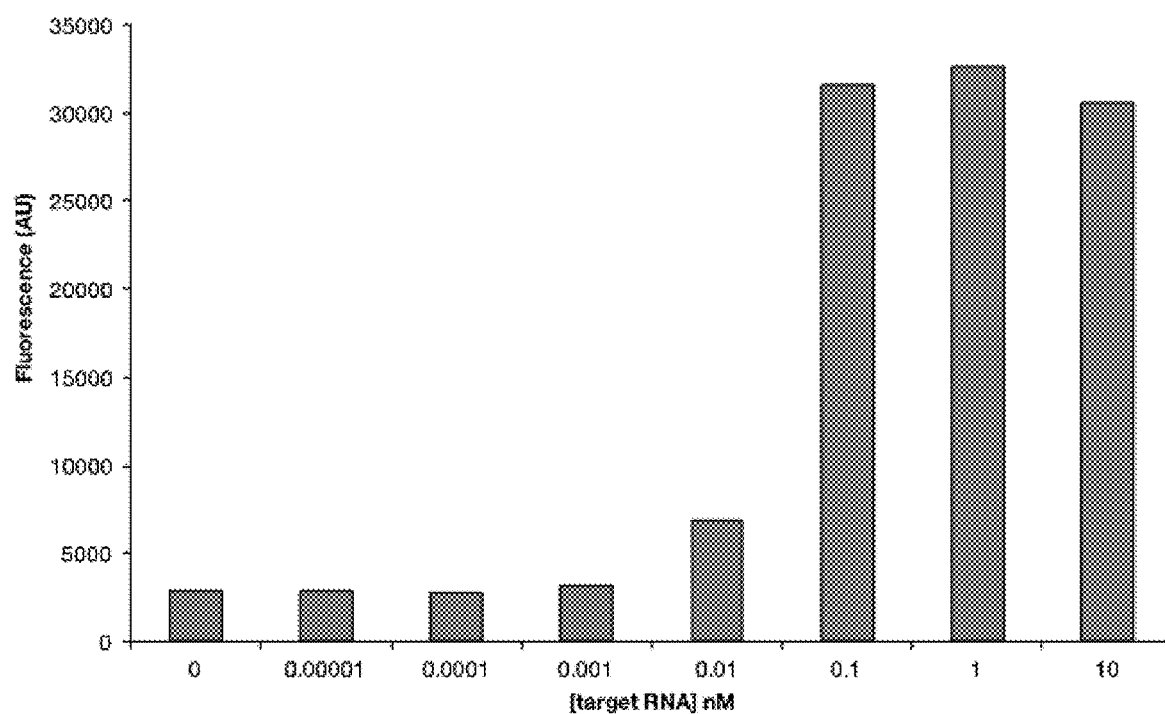
FIG. 5 depicts results from experiments performed using a labeled detector RNA (using a quencher/fluor pair) to detect RNA cleave by C2c2 protein.

C2c2 was used to detect target transcripts in complex mixtures (FIG. 5).

FIG. 5. 50 nM C2c2:crRNA targeting lambda2 ssRNA was incubated with 185 nM of RNAase-Alert substrate (A small Fluorescence-Quencher RNA oligonucleotide—a labeled detector RNA labeled with a quencher/fluor pair) and 100 ng of HEK293T total RNA in the presence of increasing amounts of lambda2 ssRNA (0-10 nM) for 30 minutes at 37C. An increase in fluorescence was observed when 'activated' C2c2 (C2c2:crRNA:lamda2 ssRNA) cleaved the RNAse-Alert substrate releasing the fluor from the quencher moiety.

Example 6: Precursor crRNA (Pre-crRNA) Processing by C2c2 Protein

Figure 6:
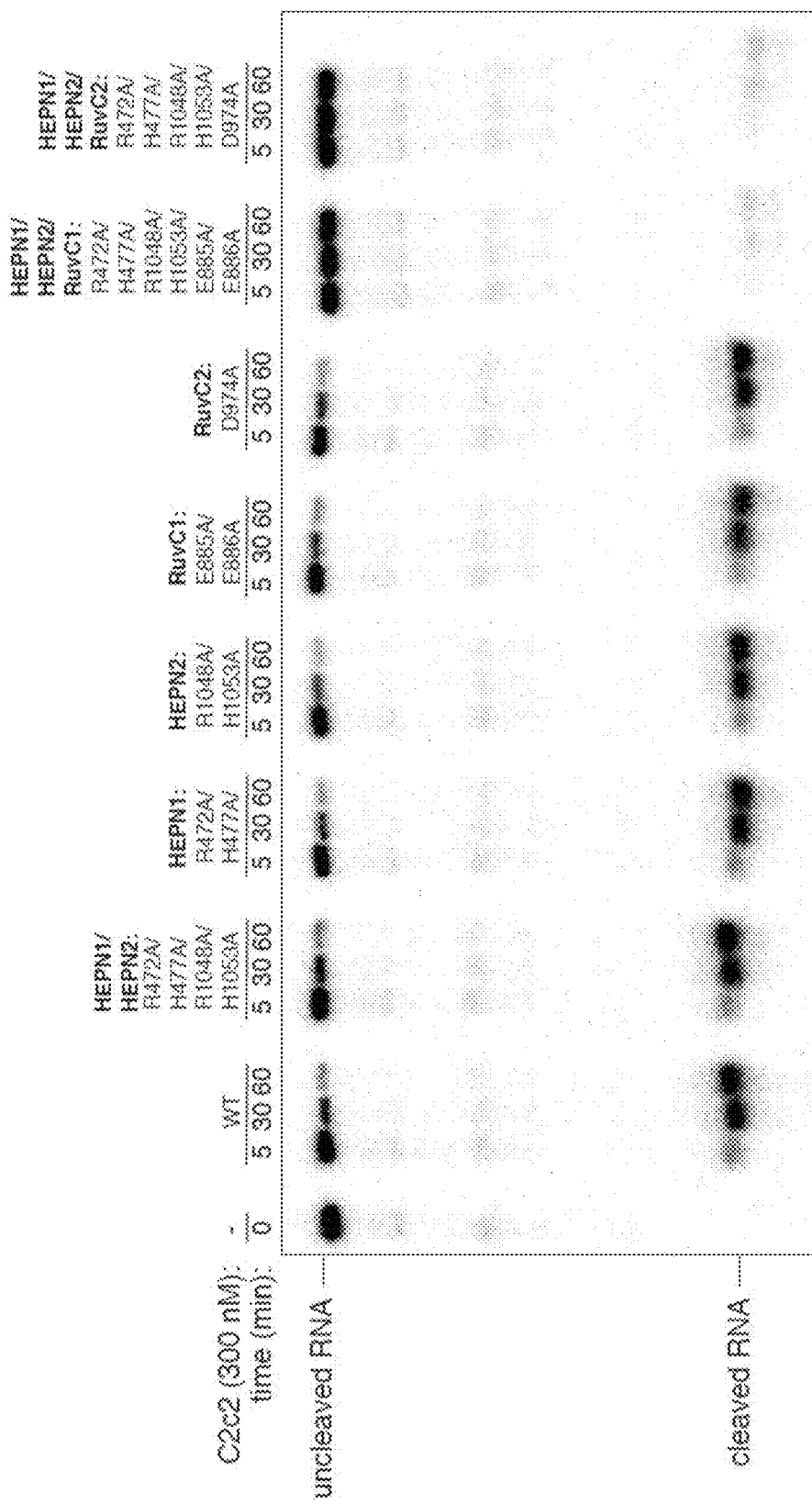
FIG. 6 depicts results from experiments that demonstrate pre-crRNA processing by C2c2 protein.

C2c2 cleaved (Processed) precursor crRNA (pre-crRNA), and this cleavage was independent of a HEPN-domain (FIG. 6).

FIG. 6. 300 nM of C2c2 was incubated with 1 nM 5'-$^{32}$P-labelled pre-crRNA for 0-60 minutes at 37C. RNA products were separated on 15% urea-PAGE and imaged using a phosphorimager. Successful processing of the pre-crRNA is determined by the presence of smaller 'cleaved RNA' product.

Example 7

Materials and Methods

The following materials and methods were used, and are applicable to Examples 8-12.

C2c2 phylogenic and candidate selection. C2c2 maximum-likelihood phylogenies were computed using RAxML with the PROTGAMMALG evolutionary model and 100 bootstrap samplings. Sequences were aligned by MAFFT with the 'einsi' method. Niewoehner, O. & Jinek, M. Structural basis for the endoribonuclease activity of the type III-A CRISPR-associated protein Csm6. RNA 22, 318-329 (2016). Candidate homologs were selected to sample main branches of the protein family.

C2c2 Protein production and purification. Expression vectors for protein purification were assembled using synthetic gBlocks ordered from Integrated DNA Technologies. The codon-optimized C2c2 genomic sequence was N-terminally tagged with a $His_6$-MBP-TEV cleavage site, with expression driven by a T7 promoter (map available upon request). Mutant proteins were cloned via round-the-horn, site-directed mutagenesis of wild-type C2c2 constructs. Expression vectors were transformed into Rosetta2 *E. coli* cells grown in 2×YT broth at 37° C. *E. coli* cells were induced during log phase with 0.5 M isopropyl β-D-1-thiogalactopyranoside (ITPG), and the temperature was reduced to 16° C. for overnight expression of His-MBP-C2c2. Cells were subsequently harvested, resuspended in lysis buffer (50 mM Tris-HCl pH 7.0, 500 mM NaCl, 5% glycerol, 1 mM tris(2-carboxyethyl)phosphine (TCEP), 0.5 mM phenylmethane sulfonyl fluoride (PMSF), and ethylenediaminetetraacetic acid (EDTA)-free protease inhibitor (Roche) and lysed by sonication, and the lysates were clarified by centrifugation. Soluble His-MBP-C2c2 was isolated over metal ion affinity chromatography, and protein-containing eluate was incubated with tobacco etch virus (TEV) protease at 4° C. overnight while dialyzing into ion exchange buffer (50 mM Tris-HCl pH 7.0, 250 mM KCl, 5% glycerol, 1 mM TCEP) in order to cleave off the $His_6$-MBP tag. Cleaved protein was loaded onto a HiTrap SP column and eluted over a linear KCl (0.25-1.5 M) gradient. Cation exchange chromatography fractions were pooled and concentrated with 30 kD cutoff concentrators (Thermo Fisher). The C2c2 protein was further purified via size-exclusion chromatography on an 5200 column and stored in gel filtration buffer (20 mM Tris-HCl pH 7.0, 200 mM KCl, 5% glycerol, 1 mM TCEP) for subsequent enzymatic assays.

Generation of ssRNA. All RNAs used in this study were transcribed in vitro except for crRNA AES461 which was ordered synthetically (Integrated DNA Technologies) [see FIG. 15 and FIG. 19]. In vitro transcription reactions were performed as previously described with the following modifications: the T7 polymerase concentration was reduced to 10 µg/mL, and the UTP concentration was reduced to 2.5 mM. Transcriptions were incubated at 37° C. for 1-2 hrs to reduce non-template addition of nucleotides. All transcription reactions were purified using 15% denaturing PAGE gels. All RNAs were resuspended in cleavage buffer (20 mM HEPES pH 6.8, 50 mM KCl, 5 mM $MgCl_2$, and 5% glycerol). For radioactive experiments, 5' triphosphates were removed by calf intestinal phosphate (New England Biolabs) prior to radiolabeling and ssRNA substrates were then 5'-end labeled using T4 polynucleotide kinase (New England Biolabs) and $[\gamma-^{32}P]$-ATP (Perkin Elmer) as described previously. Sternberg, S. H., Haurwitz, R. E. & Doudna, J. A. Mechanism of substrate selection by a highly specific CRISPR endoribonuclease. RNA 18, 661-672 (2012).

DNA substrates used in this study are presented in Table 2, FIG. 14.

RNA substrates used in this study are presented in Table 3, FIG. 15.

Pre-crRNA processing assays. Pre-crRNA cleavage assays were performed at 37° C. in processing buffer (20 mM HEPES pH 6.8, 50 mM KCl, 5 mM $MgCl_2$, 10 µg/mL bovine serum albumin (BSA), 10 µg/mL tRNA, 0.05% Igepal CA-630 and 5% glycerol) with a 100-fold molar excess of C2c2 relative to 5'-labeled pre-crRNA (final concentrations of 100 nM and >1 nM, respectively). Unless otherwise indicated, reaction was quenched after 60 mins with 1.5×RNA loading dye (100% formamide, 0.025 w/v % bromophenol blue, and 200 µg $mL^{-1}$ heparin). After quenching, reactions were denatured at 95° C. for 5 min prior to resolving by 12% or 15% denaturing PAGE(0.5× TBE buffer). Metal dependence of the reaction was tested by addition of EDTA or EGTA to reaction buffer at concentrations varying from 10-100 mM. Bands were visualized by phosphorimaging and quantified with ImageQuant (GE Healthcare). The percent cleavage was determined as the ratio of the product band intensity to the total intensity of both the product and uncleaved pre-crRNA bands and normalized for background within each measured substrate using ImageQuant TL Software (GE Healthcare) and fit to a one phase exponential association using Prism (GraphPad).

Product Size Mapping. Cleavage product length was determined biochemically by comparing gel migration of product bands to alkaline hydrolysis and RNase T1 digestion ladders using the RNase T1 Kit from Ambion. For hydrolysis ladder, 15 nM full length RNA substrates were incubated at 95° C. in 1× alkaline hydrolysis buffer (Ambion) for 5 mins. Reactions were quenched with 1.5×RNA loading buffer, and cooled to −20° C. to immediately stop hydrolysis. For RNase T1 ladder, 15 nM full length RNA substrates were unfolded in 1× RNA sequencing buffer (Ambion) at 65° C. Reactions were cooled to ambient temperature, and then 1 µl of RNase T1 was added to reaction. After 15 mins, reactions were stopped by phenol-chloroform extraction and 1.5× RNA loading buffer was added for storage. Hydrolysis bands were resolved in parallel to cleavage samples on 15% denaturing PAGE and visualized by phosphorimaging.

Target cleavage assays. Target cleavages assays were performed at 25° C. and 37° C. in cleavage buffer (20 mM HEPES pH 6.8, 50 mM KCl, 5 mM $MgCl_2$, and 5% glycerol). crRNA guides were pre-folded by heating to 65° C. for 5 min and then slowly cooling to ambient temperature in cleavage buffer. RNP complex formation was performed in cleavage buffer, generally at a molar ratio of 2:1 protein to crRNA at 37° C. for 10 min, prior to adding 5'-end labeled target and/or other non-radiolabeled RNA target substrates. Unless otherwise indicated, final concentrations of protein, guide, and targets were 100 nM, 50 nM, and >1 nM respectively for all reactions. Reactions were quenched with 1.5× RNA loading dye and resolved by 15% denaturing PAGE(0.5× TBE buffer). Bands were visualized by phosphorimaging and quantified with ImageQuant (GE Healthcare). The percent cleavage was determined as the ratio of total banding intensity for all shorter products relative to the uncleaved band and normalized for background within each measured substrate using ImageQuant TL Software (GE Healthcare) and fit to a one phase exponential association using Prism (GraphPad).

crRNA filter-binding assays. Filter binding assays was carried out in RNA processing buffer (20 mM HEPES pH 6.8, 50 mM KCl, 5 mM $MgCl_2$, 10 µg/mL BSA, 10 µg/mL yeast tRNA, 0.01% Igepal CA-630 and 5% glycerol). LbuC2c2 was incubated with radiolabeled crRNA (<0.1 nM) for 1 hr at 37° C. Tufryn, Protran and Hybond-N+ were assembled onto a dot-blot apparatus in the order listed above. The membranes were washed twice with 50 µL Equilibration Buffer (20 mM HEPES pH 6.8, 50 mM KCl, 5 mM $MgCl_2$ and 5% glycerol) before the sample was applied to the membranes. Membranes were again washed with 50 µL Equilibration Buffer, dried and visualized by phosphorimaging. Data were quantified with ImageQuant TL Software (GE Healthcare) and fit to a binding isotherm using Prism (GraphPad Software). All experiments were carried out in triplicate. Dissociation constants and associated errors are reported in the figure legends.

Electrophoretic mobility-shift assays. In order to avoid the dissociation of the LbuC2c2-dHEPN1/dHEPN2: crRNA complex at low concentrations during ssRNA-binding experiments, binding reactions contained a constant excess of LbuC22c2-dHEPN1/dHEPN2 (200 nM), and increasing concentrations of crRNA-A and <0.1 nM target ssRNA. Assays were carried out in C2c2 electrophoretic mobility shift assay (EMSA) buffer (20 mM HEPES pH 6.8, 50 mM KCl, 10 µg/mL BSA, 100 µg/mL yeast tRNA, 0.01% Igepal CA-630 and 5% glycerol). LbuC2c2-crRNA-A complexes were pre-formed as described above for 10 min at 37° C.

before the addition of 5'-radiolabelled ssRNA substrate and a further incubation for 45 mins at 37° C. Samples were then resolved by 8% native PAGE at 4° C. (0.5× TBE buffer). Gels were imaged by phosphorimaging, quantified using ImageQuant TL Software (GE Healthcare) and fit to a binding isotherm using Prism (GraphPad Software). All experiments were carried out in triplicate. Dissociation constants and associated errors are reported in the figure legends.

Fluorescent RNA detection assay. LbuC2c2:crRNA complexes were preassembled by incubating 1 µM of Lbu-C2c2: C2c2 with 500 nM of crRNA for 10 min at 37° C.. These complexes were then diluted to 100 nM LbuC2c2: 50 nM crRNA-λ2 in RNA processing buffer (20 mM HEPES pH 6.8, 50 mM KCl, 5 mM $MgCl_2$, 10 µg/mL BSA, 10 µg/mL yeast tRNA, 0.01% Igepal CA-630 and 5% glycerol) in the presence of 185 nM of RNAase-Alert substrate (Thermo-Fisher), 100 ng of HeLa total RNA and increasing amounts of ssRNA (0-1 nM). These reactions were incubated in a fluorescence plate reader for up to 120 minutes at 37° C. with fluorescence measurements taken every 5 minutes ($\lambda_{ex}$: 485 nm; $\lambda_{em}$: 535 nm). Background-corrected fluorescence values were obtained by subtracting fluorescence values obtained from reactions carried out in the absence of target ssRNA. Maximal fluorescence was measured by incubating 50 nM RNaseA with 185 nM of RNAase-Alert substrate. For coupled pre-crRNA processing and RNA detection assays, LbuCas9-sgRNA complexes were preassembled by incubating 1 µM of Lbu-C2c2:C2c2 with 500 nM of pre-crRNA-A-λ2 for 20 min at 37° C. and reactions carried out as described above in the presence of increasing amounts of ssRNA A and ssRNA λ2 (0-1 nM each). In each case, error bars represent the standard deviation from three independent experiments.

Example 8: C2c2 Family Processes Precursor crRNA Transcripts to Generate Mature crRNAs Type VI CRISPR loci lack an obvious Cas6 or Cas5d-like endonuclease or tracrRNA. The question was asked whether C2c2 itself might possess pre-crRNA processing activity. To test this, recombinant C2c2 homologs from *Leptotrichia buccalis* (Lbu), *Leptotrichia shahii* (Lsh), and *Listeria seeligeri*(Lse), which originate from three distinct branches of the C2c2 protein family, were expressed in *Escherichia coli* and purified. FIG. 9A-9B.

All three proteins cleaved 5'-end radiolabeled pre-crRNA substrates consisting of a full-length consensus repeat sequence and a 20 nucleotide (nt) spacer sequence in 60 minutes. FIG. 9C. The cleavage site for all pre-crRNA homologs was mapped using T1 RNase and hydroxide hydrolysis ladders; it was shown that processing occurs at positions two or five nts upstream of the predicted hairpin structure depending on the homolog. FIG. 9C.

It is possible that cellular factors can further process the crRNA, as sequencing data from heterologous expression of LseC2c2 and LshC2c2 operons in *E. coli* found similar but not identical processing events. Cleavage assays with LbuC2c2 and a pre-crRNA containing a tandem hairpin-repeat array resulted in two products corresponding to two successive cleavage events (FIG. 16A-16F), consistent with a role for C2c2 in processing primary crRNA transcripts. These results demonstrate that within Type VI CRISPR systems C2c2 homologs catalyze maturation of their associated crRNAs.

FIG. 9A-9C. C2c2 family processes precursor crRNA transcripts to generate mature crRNAs. FIG. 9A, Maximum-likelihood phylogenetic tree of C2c2 proteins. Full details including accessions, organism names, and bootstrap values are provided in FIG. 22A. Homologs used in this study are highlighted in yellow. FIG. 9B, Diagram of the three different Type VI CRISPR loci. Black rectangles denote repeat elements, whereas yellow diamonds denote spacer sequences. Cas1 and Cas2 are only found in the genomic vicinity of Lsh C2c2. FIG. 9C, CC2c2-mediated cleavage of pre-crRNA derived from the LbuC2c2, LseC2c2 and LshC2c2. OH: alkaline hydrolysis ladder; T1: T1 RNase hydrolysis ladder; Processing cleavage reactions were performed with 100 nM C2c2 and >1 nM pre-crRNA. A schematic of cleavage is depicted on right, and the predicted pre-crRNA secondary structure is diagramed below, with arrows indicating the mapped C2c2 cleavage site.

Figures 22A, 22B:
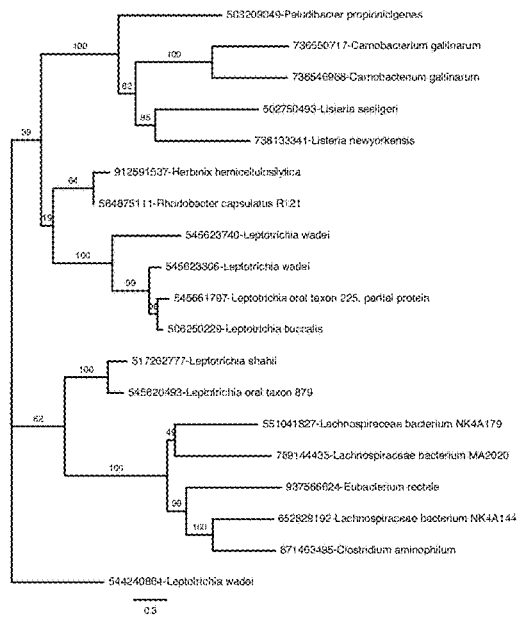
FIG. 22A-22B depict a phylogenetic tree of C2c2 family and C2c2 alignment. *Leptotrichia_buccalis* (SEQ ID NO: 2); *Listeria_seeligeri* (SEQ ID NO: 1); *Leptotrichia_shahii* (SEQ ID NO: 3).

FIG. 22A-22B. Complete phylogenetic tree of C2c2 family and C2c2 alignment. FIG. 22A, Maximum-likelihood phylogenetic reconstruction of C2c2 proteins. Leaves include GI protein numbers and organism of origin; bootstrap support values, out of 100 resamplings, are presented for inner split. Scale is in substitutions per site. FIG. 22B, multiple sequence alignment of the three analyzed homologs of C2c2, coordinates are based on LbuC2c2.

Figure 23A:
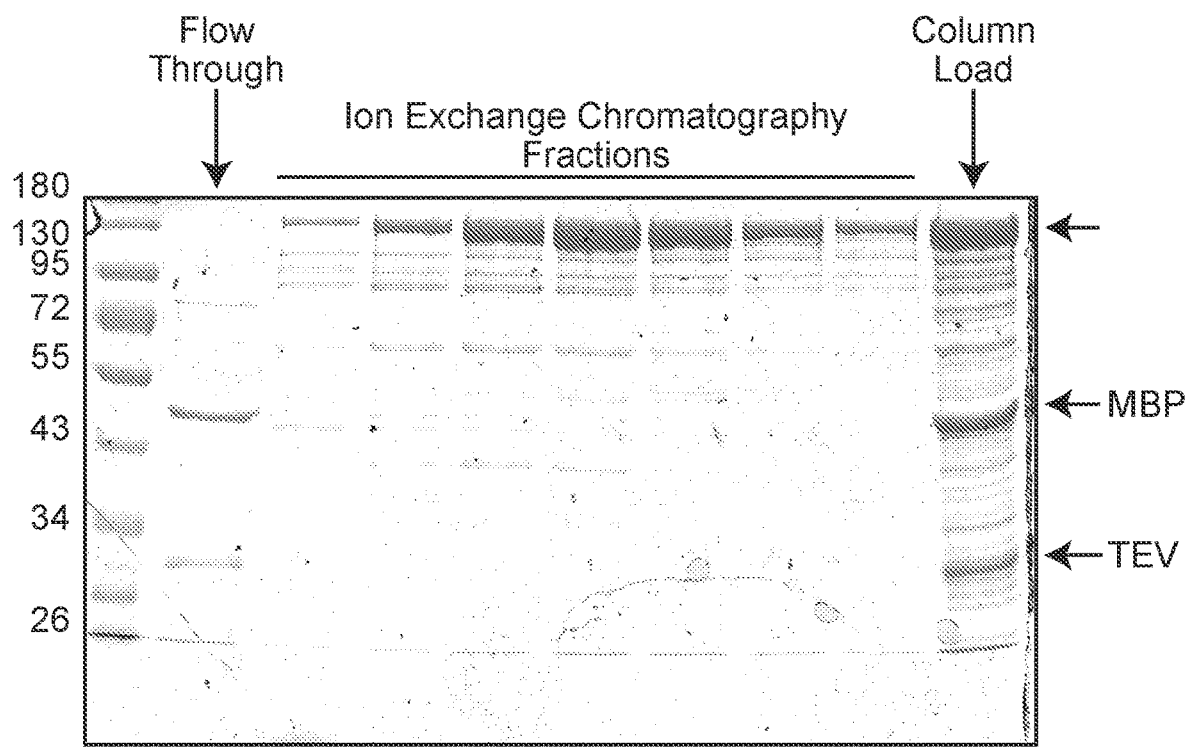
Figure 23B:
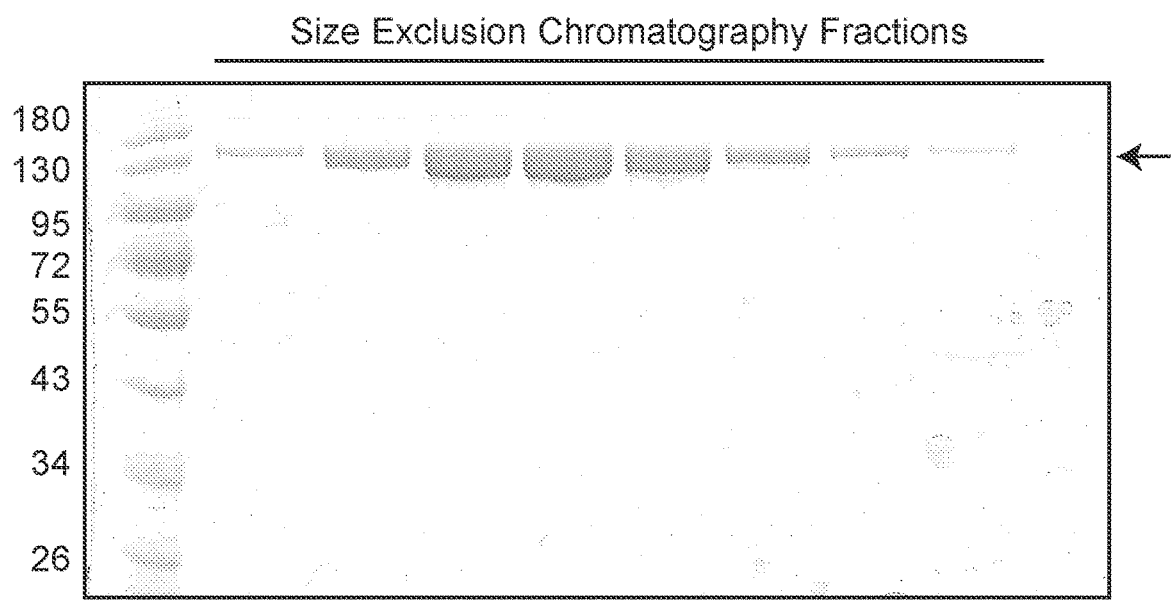

FIG. 23A-23D. Purification and Production of C2c2. All C2c2 homologs were expressed in *E. coli* as His-MBP fusions and purified by a combination of affinity, ion exchange and size exclusion chromatography. $Ni^+$ affinity tag was removed by incubation with TEV protease. Representative SDS-PAGE gels of chromatography fractions are shown above in (FIG. 23A-23B). FIG. 23C, The chromatograph from Superdex 200 (16/60) column demonstrating that C2c2 elutes off as a single peak, devoid of nucleic acid. FIG. 23D, SDS PAGE analysis of all purified proteins used in this manuscript.

Figure 16A:
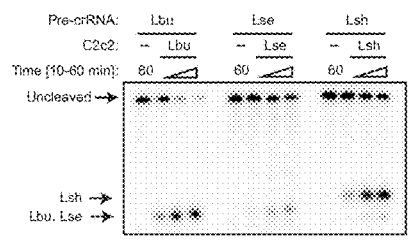
FIG. 16A-16F depict data showing that pre-crRNA processing by C2c2 is spacer sequence independent, can occur on tandem crRNA arrays, is affected by mutations in the 5' and/or 3' flanking region of the pre-cRNA, and is metal independent.
Figure 16B:
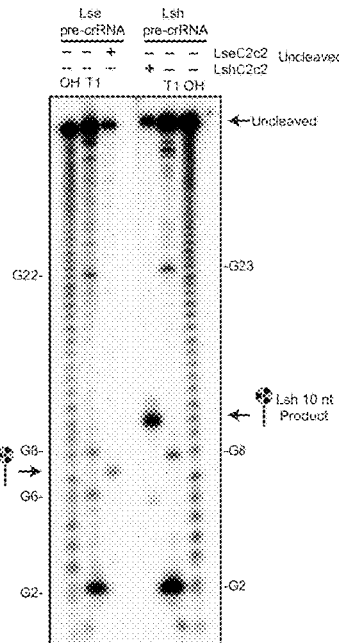
Figure 16C:
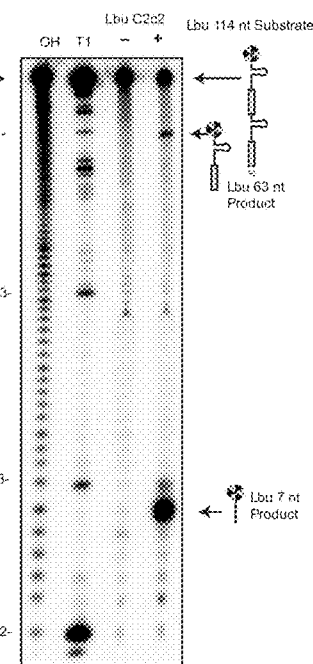
Figure 16D:
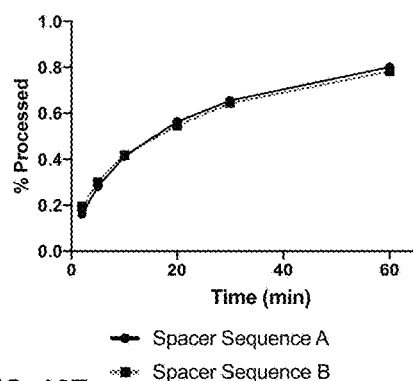
Figure 16E:
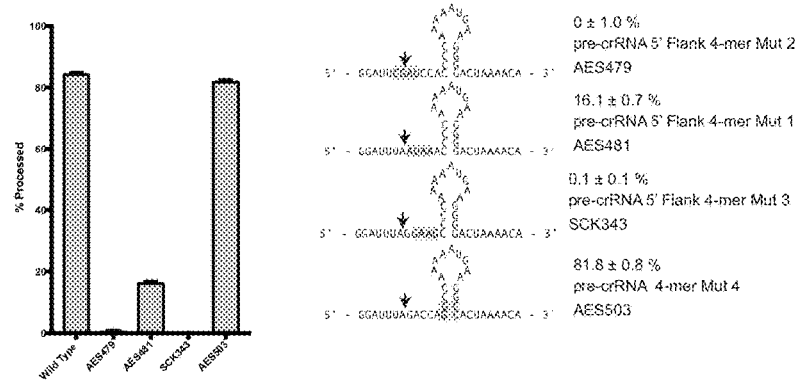
Figure 16F:
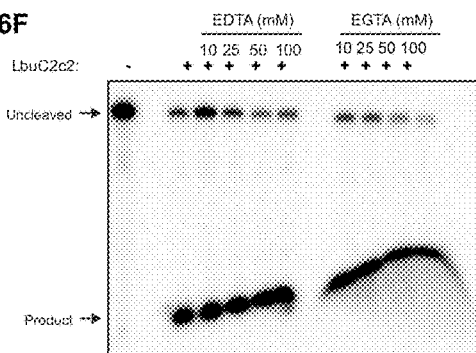

FIG. 16A-16F. pre-crRNA processing by C2c2 is spacer sequence independent, can occur on tandem crRNA arrays, affected by mutations in the 5'flanking region of the pre-cRNA and is metal independent. a, Representative time-course pre-crRNA cleavage assay demonstrating the similar rates of LbuC2c2, LshC2c2, and LseC2c2 pre-crRNA processing. b, Cleavage site mapping of LseC2c2 and LshCC2c2 cleavage of a single cognate pre-crRNA array. OH: alkaline hydrolysis ladder; T1: T1 RNase hydrolysis ladder. Cleavage reactions were performed with 100 nM Lbu C2c2 and <1 nM pre-crRNA. A schematic of cleavage products is depicted, with arrows indicating the mapped C2c2 cleavage products. c, Cleavage site mapping of LbuCC2c2 cleavage of a tandem pre-crRNA array. OH: alkaline hydrolysis ladder; T1: T1 RNase hydrolysis ladder. Cleavage reactions were performed with 100 nM Lbu C2c2 and <1 nM pre-crRNA. A schematic of cleavage products is depicted on right, with arrows indicating the mapped C2c2 cleavage products. d, Representative LbuC2c2 pre-crRNA cleavage time-course demonstrating that similar rates of pre-crRNA processing occur independent of crRNA spacer sequence. e, LbuC2c2 4-mer mutant pre-crRNA processing data demonstrating the importance of the 5' single-stranded flanking region for efficient pre-crRNA processing. Percentage of pre-crRNA processing was measured after 60 mins (mean±s.d., n=3). f, Denaturing gel illustrating processing activity at a range of different EDTA and EGTA concentrations. High concentrations of chelators change the expected migration pattern of products Example 9: LbuC2c2 Mediated crRNA Biogenesis Depends on Both Structure and Sequence of CRISPR Repeats Other pre-crRNA processing enzymes, such as Cas6 and Cas5d, recognize the hairpin of their respective CRISPR repeat sequence in a highly specific manner. The sequence and structural requirements for LbuC2c2 guide RNA processing were determined. Cleavage assays were performed with pre-crRNAs harboring mutations in either the stem loop or the single-stranded flanking regions of the consensus repeat sequence (FIG. 10A-10C). Pre-crRNA cleavage activity was significantly attenuated upon altering the length of the stem in the repeat region; while the repeat consensus 4-base pair (bp) stem resulted in 85±0.7% cleavage at after 60 min, −1 bp and +1 bp stems resulted in only 54±1.3% and 6±3.8% cleavage, respectively (FIG. 10a). Similarly, inversion of the stem loop or reduction of the loop length reduced processing activity. Initial studies with contiguous 4-nt mutations including or near the scissile bond completely abolished LbuC2c2's capacity to process the pre-crRNAs (FIG. 16D). A more extensive mutational analysis of the full crRNA repeat sequence revealed two distinct regions on either side of the hairpin with marked sensitivity to base changes (FIG. 10B; FIG. 17). Processing activity was completely unaffected by the presence of divalent metal ion chelators EDTA or EGTA (FIG. 10C; FIG. 16E). Collectively, these data indicate that C2c2 pre-crRNA cleavage is a divalent metal ion-independent process governed by a combination of structural- and sequence-specific recognition of repeat-derived hairpins within the precursor CRISPR transcript.

FIG. 10A-10C. LbuC2c2 mediated crRNA biogenesis depends on both structure and sequence of CRISPR repeats. FIG. 10A, Representative gel of LbuC2c2 processing of pre-crRNAs containing structural mutations within the stem and loop regions of hairpin. Processed percentages listed below are quantified at 60 min for each condition (mean±s.d., n=3). FIG. 10B, Graphical map showing the dependence of pre-crRNA processing on the CRISPR repeat sequence. The wild-type repeat sequence is shown below with individual bars representing 2 nucleotide mutations as noted in red above. The cleavage site is indicated by cartoon scissors. Percentage processed was measured after 60 mins (mean±s.d., n=3). Diagramed hairpins of tested mutants can be found in FIGS. 16A-16F and FIG. 17. FIG. 2C, Diavalent metal dependence of processing reaction was challenged by addition of 10-100 mM EDTA to standard processing reaction conditions. Reaction end point at 60 min is shown.

FIG. 17. Detailed summary of the effect of pre-crRNA double mutations on pre-crRNA processing activity. Percentage of pre-crRNA processing was measured after 60 mins (mean±s.d., n=3), as per Methods. Mutated nucleotides are highlighted in yellow. See FIG. 10B for graphical representation.

Example 10: LbuC2c2 Catalyzes Guide-Dependent ssRNA Degradation on Cis and Trans Targets Following maturation, crRNAs typically bind with high affinity to Cas effector protein(s) to create RNA-guided surveillance complexes capable of sequence-specific nucleic acid recognition. To test the functionality of the C2c2-processed crRNA, the LbuC2c2 protein, which demonstrated the most robust activity in initial cleavage experiments, was used. For multiple ssRNA substrates, it was observed that LbuC2c2 efficiently cleaved only when bound to the complementary crRNA, indicating that LbuC2c2:crRNA cleaves ssRNA in an RNA-guided fashion (FIG. 11b). This activity is hereafter referred to as on-target or cis-target cleavage (FIG. 11a). LbuC2c2-mediated cis cleavage resulted in a laddering of multiple products, with cleavage preferentially occurring before uracil residues, analo-gous to LshC2c2 (FIG. 18A-18B)[9], This activity is distinct from other class II CRISPR effectors (such as Cas9 and Cpf1) that catalyze target nucleic acid cleavage only within a defined region specified by base pairing to the crRNA. The ability of LbuC2c2 to act as a crRNA-activated non-specific RNA endonuclease in trans (i.e. C2c2-catalyzed cleavage of RNA molecules that are not targeted by the crRNA) was tested (FIG. 11A). This ability was investigated by repeating non-target cleavage reactions in the presence of unlabeled, on-target (crRNA-complementary) ssRNA. Rapid degradation of 5'-labeled non-target RNA under these trans cleavage conditions was observed (FIG. 11B). This result suggests that recognition of a target ssRNA complementary to the spacer segment of the crRNA activates C2c2 for rapid and non-specific degradation of RNA in trans. The similar RNA cleavage rates and near identical cleavage products observed for both cis on-target cleavage and trans non-target cleavage implicate the same nuclease center in both activities. Furthermore, these results suggest that what is observed as "cis" activity is simply trans activity that occurs when only one substrate is available (FIG. 18A-18B).

FIG. 11A-11C. LbuC2c2 catalyzes guide-dependent ssRNA degradation on cis and trans targets. FIG. 11A, Schematic of the two modes of C2c2, guide dependent ssRNA degradation. FIG. 11B, Cleavage of two distinct radiolabeled ssRNA substrates, A and B, by LbuC2c2. Complexes of 100 nM C2c2 and 50 nM crRNA were pre-formed at 37° C. and reaction was initiated upon addition of >1 nM 5'-labeled target RNA at 25° C. Trans cleavage reactions contained equal molar (>1 nM) concentrations of radiolabeled non-guide-complementary substrate, and unlabeled on target ssRNA. FIG. 11C, LbuC2c2 loaded with crRNA with spacer A was challenged for cleavage activity under both cis (target A labeled) and trans (target B labeled in the presence of unlabeled target A) cleavage conditions in the presence of EDTA.

Figure 18A:
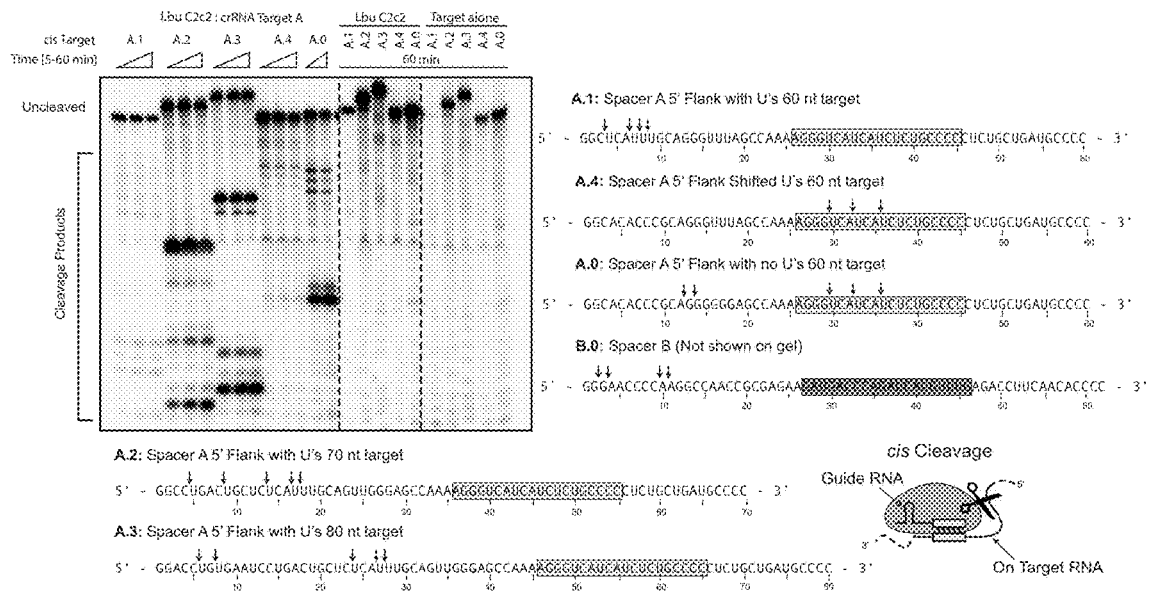
FIG. 18A-18B depict LbuC2c2 ssRNA target cleavage site mapping.
Figure 18B:
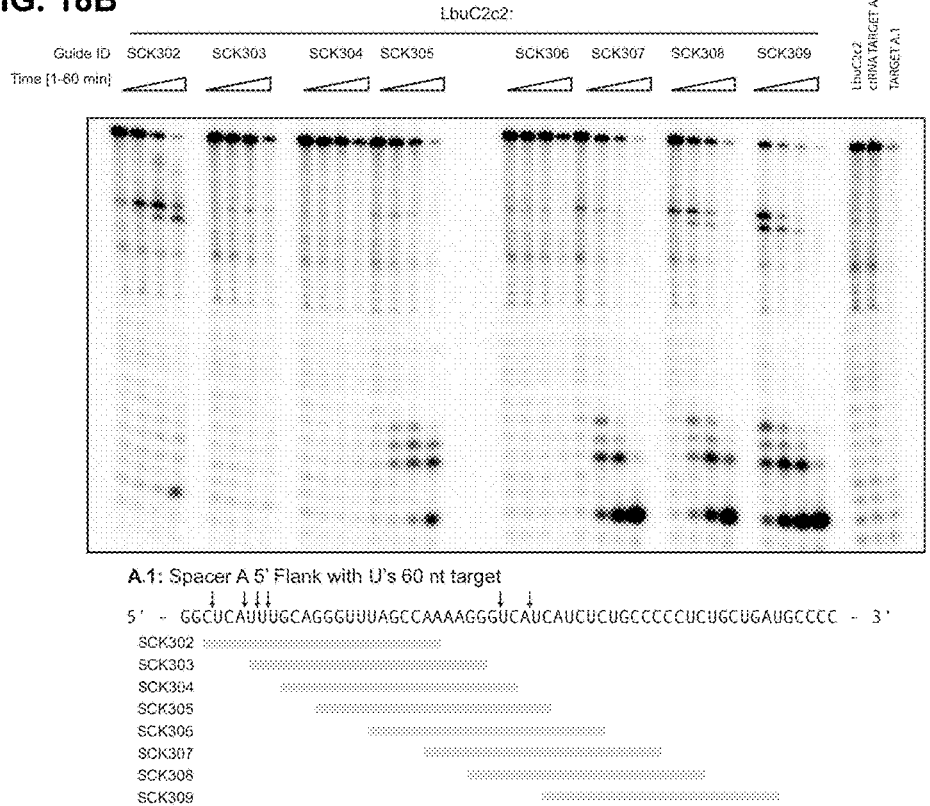

FIG. 18A-18B. LbuC2c2 ssRNA target cleavage site mapping a, ssRNA target cleavage assay carried as per Methods demonstrating LbuC2c2-mediated 'cis'-cleavage of several radiolabeled ssRNA substrates with identical spacer-complementary sequences but distinct 5' flanking sequences of variable length and nucleotide composition. Sequences of ssRNA substrates are shown to the right and bottom of the gel with spacer complementary sequences for crRNA-A and crRNA-B are highlighted in yellow and red, respectively. Arrows indicate predicted cleavage sites. Gel was cropped for clarity. It should be noted that the pattern of cleavage products produced on different substrates (e.g. A.1 vs. A.2 vs. A.3) indicates that the cleavage site choice is primarily driven by a uracil preference and exhibits an apparent lack of a 'crRNA-ruler-based' cleavage mechanism, which is in contrast to what is observed for other Class II CRISPR single effector complexes such as Cas9 and Cpf1 <ref?>. Interestingly, the cleavage pattern observed for substrate A.0 hints at a secondary preference for polyG sequences, that might conceivably form G-quadraplexes or similar secondary structures. b, LbuC2c2 ssRNA target cleavage assay as per Methods, using a range of crRNAs that tile the length of the ssRNA target. The sequence of the ssRNA substrates used in this experiment is shown below the gel with spacer complementary sequences for each crRNA highlighted in yellow. Arrows indicate predicted cleavage sites. Likewise, it should be noted that for every crRNA the cleavage product length distribution is very similar, again indicating an apparent lack of a 'crRNA-ruler-based' cleavage mechanism. The absence of a several cleavage products in a subset of the reactions might be explained by the presence of bound C2c2:crRNA on the ssRNA target sterically occluding access to uracils by any cis (intramolecular) or trans (intermolecular) LbuC2c2 active sites. While proper analysis for PFS preference for LbuC2c2 is beyond the scope of this study, minimal impact of 3' flanking sequence was observed. Expected PFS base is noted in diagram next to each guide tested in red.

Example 11: LbuC2c2 Contains Two Distinct Ribonuclease Activities

Figure 20A:
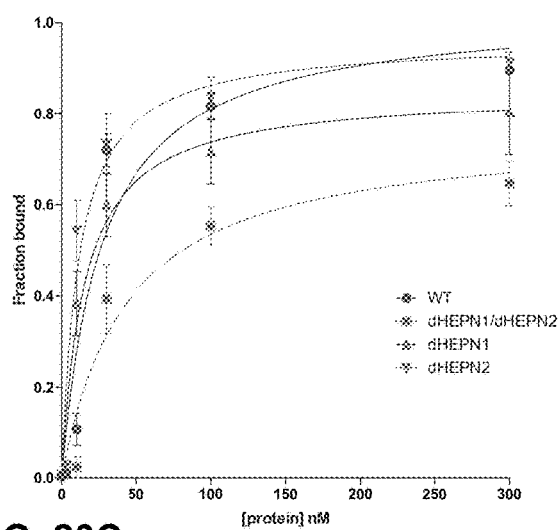
FIG. 20A-20C depict binding data for LbuC2c2 to mature crRNA and target ssRNA.
Figure 20B:
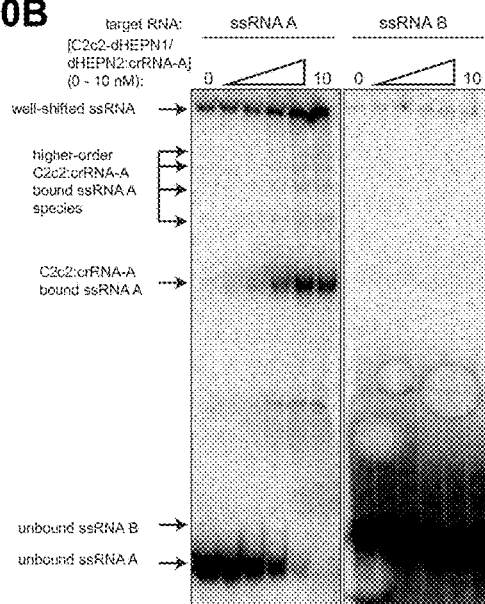
Figure 20C:
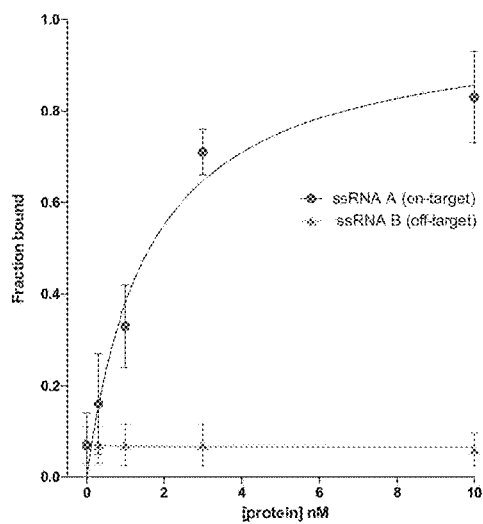

Pre-crRNA processing activity occurred at an apparent rate 80-fold slower than crRNA-mediated cleavage of either target RNA or a non-complementary trans-ssRNA (FIG. 12a). Under saturating enzyme conditions, pre-crRNA processing reached only ~85% after 1 h, while the rate of RNA-guided cleavage of trans substrates was nearly unmeasurable due to reaction completion within 1 min at 37° C. (FIG. 19A-19C). It was also found that in contrast to pre-crRNA processing, RNA-guided cleavage was completely abolished in the presence of EDTA, indicating that this activity is divalent metal ion-dependent (FIG. 11c). Given the clear differences in kinetics and metal ion dependence between pre-crRNA processing and RNA-guided cleavage, it was reasoned that C2c2 might represent a novel class of CRISPR effector proteins possessing two orthogonal RNA cleavage activities: one for crRNA maturation, and the other for crRNA-directed, non-specific RNA degradation. To test this hypothesis, several residues within the conserved HEPN domains of the LbuC2c2, which are predicted to contain RNA cleavage active sites, were systematically mutated; and pre-crRNA processing and RNA-guided RNase activity of the mutants was assessed (FIG. 12b). Double and quadruple mutants of conserved HEPN residues (R472A, R477A, R1048A and R1053) retained robust pre-crRNA cleavage activity (FIG. 12c). By contrast, all HEPN mutants abolished RNA-guided cleavage activity while not affecting crRNA or ssRNA-binding ability (FIG. 20A-20C). The discrepancies in cleavage rates and differential sensitivity to point mutations and EDTA show that pre-crRNA processing and RNA-directed RNA cleavage are mediated by distinct catalytic centers within the C2c2 protein, the former metal-independent and the latter requiring divalent metal-dependent HEPN domains.

FIG. 12A-12D. LbuC2c2 contains two distinct ribonuclease activities. FIG. 4A, Quantified time course data of cis ssRNA target (black) and pre-crRNA (teal) cleavage by LbuC2c2 performed at 37° C. Exponential fits are shown as solid lines (n=3) and calculated first order rate constants ($k_{obs}$) are 9.74±1.15 and 0.12±0.02 for cis target and pre-crRNA cleavage respectively. FIG. 12B, Domain architecture of LbuC2c2 depicting the location of HEPN mutations FIGS. 12C and 12D, Ribonuclease activity of double and quadruple HEPN domain mutants for pre-crRNA processing in FIG. 12C and ssRNA targeting in FIG. 12D. cis and trans cleavage reactions performed as in FIG. 11c, utilizing crRNA targeting spacer A for both activities.

FIG. 19A-19C Dependence of crRNA spacer length, reaction temperature, 5'-end sequence of crRNA on target RNA cleavage efficiency. FIG. 19A, LbuC2c2 ssRNA target cleavage assay carried out, as per Methods with crRNAs possessing 16-nt, 20-nt or 24-nt spacers. FIG. 19B, LbuC2c2 ssRNA target cleavage time-course carried out at either 25° C. or 37° C., as per Methods. FIG. 19C, LbuC2c2 ssRNA target cleavage time-course carried out as per Methods with crRNAs possessing different 5'-flanking nucleotide mutations. Mutations are highlighted in red. 1-2 nucleotide 5' extensions negligibly impacted cleavage efficiencies. In contrast shortening the flanking region to 3 nts slowed cleavage efficiencies. Exponential fits are shown as solid lines for representative replicates.

FIG. 20A-20C. Binding data for LbuC2c2 to mature crRNA and target ssRNA. FIG. 20A, Filter binding assays were conducted as described in the Methods to determine the binding affinity of mature crRNA-A to LbuC2c2-WT, LbuC2c2-dHEPN1, LbuC2c2-dHEPN2, or LbuC2c2-dHEPN1/dHEPN2. The quantified data were fitted to standard binding isoforms. Error bars represent the standard deviation from three independent experiments. Measured dissociation constants from three independent experiments (mean±sd) were 27.1±7.5 nM (LbuC2c2-WT), 15.2±3.2 nM (LbuC2c2-dHEPN1), 11.5±2.5 nM (LbuC2c2-dHEPN2), and 43.3±11.5 nM (LbuC2c2-dHEPN1/dHEPN2). FIG. 20B, Representative electrophoretic mobility shift assay for binding reactions between LbuC2c2-dHEPN1/dHEPN2: crRNA-A and either 'on-target' A ssRNA or 'off-target' B ssRNA, as indicated. Three independent experiments were conducted as described in the Methods. The gel was cropped for clarity. FIG. 20C, Quantified binding data from (b) were fitted to standard binding isoforms. Error bars represent the standard deviation from three independent experiments. Measured dissociation constants from three independent experiments (mean±sd) were 1.62±0.43 nM for ssRNA A and N.D (>>10 nM) for ssRNA B.

Figure 13A:
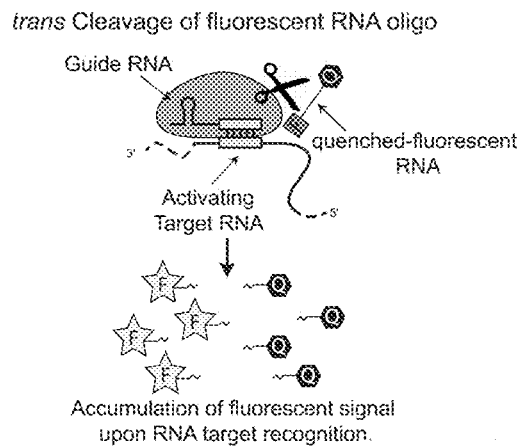
FIG. 13A-13D depict C2c2-mediated sensitive visual detection of transcripts in complex mixtures.
Figure 13B:
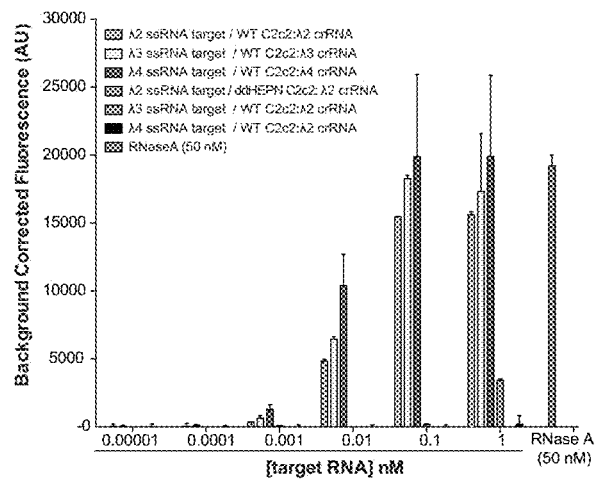
Figure 21:
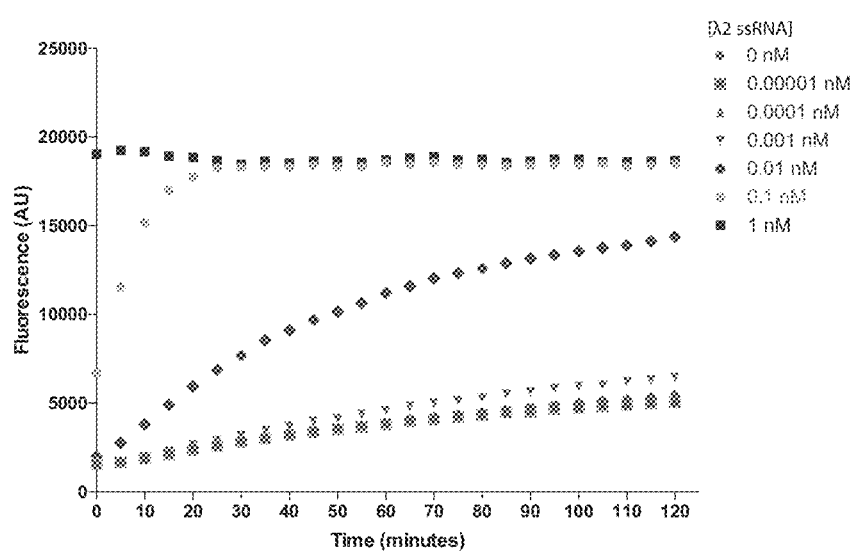
FIG. 21 depicts an RNase detection assay λ2-ssRNA time course.

Example 12: C2c2 Provides Sensitive Visual Detection of Transcripts in Complex Mixtures C2c2's robust RNA-stimulated cleavage of trans substrates can be employed as a means of detecting specific RNAs within a pool of transcripts. To date, the most sensitive RNA-detection strategies require multiple rounds of polymerase- and/or reverse-transcriptase-based amplification As an alternative, it was tested whether C2c2's RNA-guided trans endonuclease activity could be harnessed to cleave a fluorophore-quencher-labeled reporter RNA substrate, thereby resulting in an increase in fluorescence upon target RNA-triggered RNase activation (FIG. 13a). Briefly, LbuC2c2 was loaded with bacteriophage λ-targeting crRNAs and tested for its ability to detect the corresponding λ ssRNA targets spiked into HeLa cell total RNA. If LbuC2c2 were to successfully detect the complementary target, the trans cleavage activity would be activated to cleave the reporter, liberating the fluorophore from the quencher. Upon addition of as little as 1-10 pM of complementary λ target-RNA, a substantial crRNA-specific increase in fluorescence was observed after 30 minutes (FIG. 13b and FIG. 21). Control experiments with either C2c2:crRNA complex alone or in the presence of crRNA and a non-complementary target RNA resulted in negligible increases in fluorescence relative to an RNase A positive control (FIG. 13b and FIG. 21). At the 10 pM concentration of a λ target RNA, only ~0.02% of the C2c2:crRNA complex is predicted to be in the active state, yet the observed fluorescent signal reflected ~25-50% cleavage of the reporter RNA substrate, depending on the RNA target, suggesting robust multi-turnover enzymatic activity by LbuC2c2. Thus, crRNA-directed trans cleavage is potent and detectable even at extremely low levels of active protein.

Given that C2c2 processes its own pre-crRNA, it was tested whether pre-crRNA processing and RNA detection could be combined in a single reaction. To test this idea, tandem crRNA-repeat containing spacers complementary to target RNAs A and λ2 were designed, and their ability to detect decreasing amounts of A and 22 RNA spiked into HeLa total RNA was tested. A significant increase in fluorescence, similar in magnitude and sensitivity to experiments using mature crRNAs, was observed (FIG. 13b, 13c), suggesting that a tandem pre-crRNA can be successfully processed and utilized by C2c2 for RNA targeting. These data highlight the potential for multiplexed RNA detection of single and/or multiple RNA molecules in one assay using a single tandem pre-crRNA transcript.

Figure 13C:
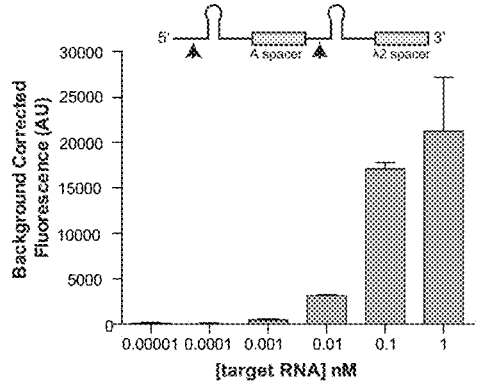
Figure 13D:
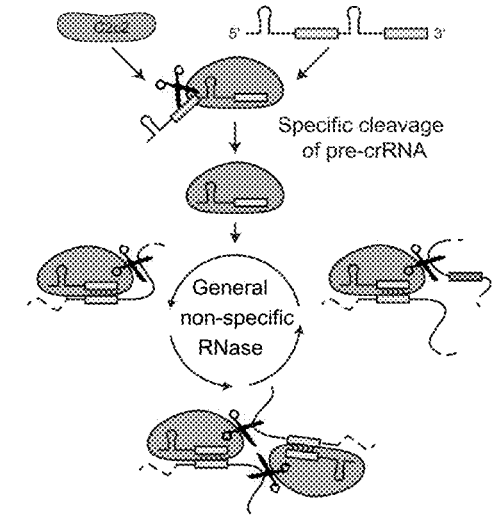

Without being bound to theory, it is proposed that when invasive transcripts are detected within the host cell via base pairing with crRNAs, C2c2 is activated for promiscuous cleavage of RNA in trans (FIG. 13d).

FIG. 13A-13D. C2c2 provides sensitive visual detection of transcripts in complex mixtures. FIG. 13A, Illustration of RNA detection approach by C2c2 using a quenched fluorescent RNA reporter. Upon complementary target RNA binding, C2c2 catalyzes the degradation of the reporter RNA resulting in accumulation of fluorescent signal. FIG. 13B, Quantification of fluorescence signal after 30 minutes for varying concentrations of target RNA by C2c2 in the presence of 100 ng total RNA. RNaseA shown as positive RNA degradation control. Data shown as mean±s.d. for n=3 independent experiments. FIG. 13C, Tandem pre-crRNA processing also enables RNA detection. Data shown as mean±s.d. for n=3 independent experiments. FIG. 13D, Model of the Type VI CRISPR pathway highlighting both of C2c2's ribonuclease activities.

FIG. 21. RNase detection assay λ2-ssRNA time course. LbuC2c2:crRNA-λ2 was incubated with RNAase-Alert substrate (Thermo-Fisher)) and 100 ng HeLa total RNA in the presence of increasing amounts of λ2 ssRNA (0-1 nM) for 120 minutes at 37° C. Fluorescence measurements were taken every 5 minutes. The 1 nM λ2 ssRNA reaction reached saturation before the first time point could be measured. Error bars represent the standard deviation from three independent experiments.

Example 13

Materials and Methods

MEC2c2 phylogenic and candidate selection. C2c2 maximum-likelihood phylogenies were computed using RAxML with the PROTGAMMALG evolutionary model and 100 bootstrap samplings. Sequences were aligned by MAFFT with the 'einsi' method.

C2c2 protein production and purification. Expression vectors for protein purification were assembled using synthetic gBlocks ordered from Integrated DNA Technologies. The codon-optimized C2c2 genomic sequence was N-terminally tagged with a $His_6$-MBP-TEV cleavage site, with expression driven by a T7 promoter. Mutant proteins were cloned via site-directed mutagenesis of wild-type C2c2 constructs. Expression vectors were transformed into Rosetta2 *E. coli* cells grown in 2×YT broth at 37° C. *E. coli* cells were induced during log phase with 0.5 M ITPG, and the temperature was reduced to 16° C. for overnight expression of His-MBP-C2c2. Cells were subsequently harvested, resuspended in lysis buffer (50 mM Tris-HCl pH 7.0, 500 mM NaCl, 5% glycerol, 1 mM TCEP, 0.5 mM PMSF, and EDTA-free protease inhibitor (Roche)) and lysed by sonication, and the lysates were clarified by centrifugation. Soluble His-MBP-C2c2 was isolated over metal ion affinity chromatography, and protein-containing eluate was incubated with TEV protease at 4° C. overnight while dialyzing into ion exchange buffer (50 mM Tris-HCl pH 7.0, 250 mM KCl, 5% glycerol, 1 mM TCEP) in order to cleave off the $His_6$-MBP tag. Cleaved protein was loaded onto a HiTrap SP column and eluted over a linear KCl (0.25-1.5 M) gradient. Cation exchange chromatography fractions were pooled and concentrated with 30 kD cutoff concentrators (Thermo Fisher). The C2c2 protein was further purified via size-exclusion chromatography on an S200 column and stored in gel filtration buffer (20 mM Tris-HCl pH 7.0, 200 mM KCl, 5% glycerol, 1 mM TCEP) for subsequent enzymatic assays. Expression plasmids are deposited with Addgene.

Generation of RNA. All RNAs used in this study were transcribed in vitro except for crRNA AES461 which was ordered synthetically (Integrated DNA Technologies) [see FIG. 33]. In vitro transcription reactions were performed as previously described with the following modifications: the T7 polymerase concentration was reduced to 10 µg/mL, and the UTP concentration was reduced to 2.5 mM. Transcriptions were incubated at 37° C. for 1-2 hr to reduce non-template addition of nucleotides and quenched via treatment with DNase I at 37° C. for 0.5-1 hr. Transcription reactions were purified by 15% denaturing polyacrylamide gel electrophoresis (PAGE), and all RNAs were resuspended in cleavage buffer (20 mM HEPES pH 6.8, 50 mM KCl, 5 mM $MgCl_2$, and 5% glycerol). For radioactive experiments, 5' triphosphates were removed by calf intestinal phosphate (New England Biolabs) prior to radiolabeling and ssRNA substrates were then 5'-end labeled using T4 polynucleotide kinase (New England Biolabs) and $[\gamma-^{32}P]$-ATP (Perkin Elmer) as described previously.

Pre-crRNA processing assays. Pre-crRNA cleavage assays were performed at 37° C. in RNA processing buffer (20 mM HEPES pH 6.8, 50 mM KCl, 5 mM $MgCl_2$, 10 µg/mL BSA, 10 µg/mL tRNA, 0.05% Igepal CA-630 and 5% glycerol) with a 100-fold molar excess of C2c2 relative to 5'-labeled pre-crRNA (final concentrations of 100 nM and <1 nM, respectively). Unless otherwise indicated, reaction was quenched after 60 min with 1.5× RNA loading dye (100% formamide, 0.025 w/v % bromophenol blue, and 200 µg $mL^{-1}$ heparin). After quenching, reactions were denatured at 95° C. for 5 min prior to resolving by 12% or 15% denaturing PAGE (0.5× TBE buffer). Metal dependence of the reaction was tested by addition of EDTA or EGTA to reaction buffer at concentrations varying from 10-100 mM. Bands were visualized by phosphorimaging and quantified with ImageQuant (GE Healthcare). The percent cleavage was determined as the ratio of the product band intensity to the total intensity of both the product and uncleaved pre-crRNA bands and normalized for background within each measured substrate using ImageQuant TL Software (GE Healthcare) and fit to a one phase exponential association using Prism (GraphPad).

Product Size Mapping and 3' end moiety identification. Cleavage product length was determined biochemically by comparing gel migration of product bands to alkaline hydrolysis and RNase T1 digestion ladders using the RNase T1 Kit from Ambion. For hydrolysis ladder, 15 nM full-length RNA substrates were incubated at 95° C. in 1× alkaline hydrolysis buffer (Ambion) for 5 min. Reactions were quenched with 1.5× RNA loading buffer, and cooled to −20° C. to immediately stop hydrolysis. For RNase T1 ladder, 15 nM full length RNA substrates were unfolded in 1× RNA sequencing buffer (Ambion) at 65° C. Reactions were cooled to ambient temperature, and then 1 U of RNase T1 (Ambion) was added to reaction. After 15 min, reactions were stopped by phenol-chloroform extraction and 1.5× RNA loading buffer was added for storage. Hydrolysis bands were resolved in parallel to cleavage samples on 15% denaturing PAGE and visualized by phosphorimaging. For 3' end moiety identification, products from the processing reaction were incubated with 10 U of T4 polynucleotide kinase (New England Biolabs) for 1 hr at 37° C. in processing buffer. Reactions were quenched with 1.5× RNA loading buffer, resolved on 20% denaturing PAGE and visualized by phosphorimaging.

Small RNA sequencing analysis. RNA reads from Smakov et al. were downloaded from SRA runs SRR3713697, SRR3713948, and SRR3713950. The paired-end reads were locally mapped to the reference sequences using Bowtie2 with the following options: "--reorder--very-fast-local--local". The mapping was then filtered to retain only alignments that contained no mismatch using mapped.py with the "-m 0-p both" options. BAM file of the resulting mapping available. Read coverage was visualized using Geneious and plotted using Prism (GraphPad).

Target cleavage assays. Target cleavages assays were performed at 25° C. or 37° C. in cleavage buffer (20 mM HEPES pH 6.8, 50 mM KCl, 5 mM $MgCl_2$, and 5% glycerol). crRNA guides were pre-folded by heating to 65° C. for 5 min and then slowly cooling to ambient temperature in cleavage buffer. C2c2:crRNA complex formation was performed in cleavage buffer, generally at a molar ratio of 2:1 protein to crRNA at 37° C. for 10 min, prior to adding 5'-end labeled target and/or other non-radiolabeled RNA target substrates. Unless otherwise indicated, final concentrations of protein, guide, and targets were 100 nM, 50 nM, and <1 nM respectively for all reactions. Reactions were quenched with 1.5× RNA loading dye and resolved by 15% denaturing PAGE (0.5× TBE buffer). Bands were visualized by phosphorimaging and quantified with ImageQuant (GE Healthcare). The percent cleavage was determined as the ratio of total banding intensity for all shorter products relative to the uncleaved band and normalized for background within each measured substrate using ImageQuant TL Software (GE Healthcare) and fit to a one phase exponential association using Prism (GraphPad).

crRNA filter-binding assays. Filter binding assays was carried out in RNA processing buffer (20 mM HEPES pH 6.8, 50 mM KCl, 5 mM $MgCl_2$, 10 μg/mL BSA, 10 μg/mL yeast tRNA, 0.01% Igepal CA-630 and 5% glycerol). LbuC2c2 was incubated with radiolabeled crRNA (<0.1 nM) for 1 hr at 37° C. Tufryn, Protran and Hybond-N+ were assembled onto a dot-blot apparatus in the order listed above. The membranes were washed twice with 50 μL Equilibration Buffer (20 mM HEPES pH 6.8, 50 mM KCl, 5 mM $MgCl_2$ and 5% glycerol) before the sample was applied to the membranes. Membranes were again washed with 50 μL Equilibration Buffer, dried and visualized by phosphorimaging. Data were quantified with ImageQuant TL Software (GE Healthcare) and fit to a binding isotherm using Prism (GraphPad Software). All experiments were carried out in triplicate. Dissociation constants and associated errors are reported in the figure legends.

Electrophoretic mobility-shift assays. In order to avoid the dissociation of the LbuC2c2-dHEPN1/dHEPN2: crRNA complex at low concentrations during ssRNA-binding experiments, binding reactions contained a constant excess of LbuC22c2-dHEPN1/dHEPN2 (200 nM), and increasing concentrations of crRNA-A and <0.1 nM target ssRNA. Assays were carried out in C2c2 EMSA buffer (20 mM HEPES pH 6.8, 50 mM KCl, 10 μg/mL BSA, 100 μg/mL yeast tRNA, 0.01% Igepal CA-630 and 5% glycerol). LbuC2c2-crRNA-A complexes were pre-formed as described above for 10 min at 37° C. before the addition of 5'-radiolabelled ssRNA substrate and a further incubation for 45 min at 37° C. Samples were then resolved by 8% native PAGE at 4° C. (0.5× TBE buffer). Gels were imaged by phosphorimaging, quantified using ImageQuant TL Software (GE Healthcare) and fit to a binding isotherm using Prism (GraphPad Software). All experiments were carried out in triplicate. Dissociation constants and associated errors are reported in the figure legends.

Fluorescent RNA detection assay. LbuC2c2:crRNA complexes were preassembled by incubating 1 μM of Lbu-C2c2: C2c2 with 500 nM of crRNA for 10 min at 37° C.. These complexes were then diluted to 100 nM LbuC2c2: 50 nM crRNA-λ2 in RNA processing buffer (20 mM HEPES pH 6.8, 50 mM KCl, 5 mM $MgCl_2$, 10 μg/mL BSA, 10 μg/mL yeast tRNA, 0.01% Igepal CA-630 and 5% glycerol) in the presence of 185 nM of RNAase-Alert substrate (ThermoFisher), 100 ng of HeLa total RNA and increasing amounts of target 60 nt ssRNA (0-1 nM). These reactions were incubated in a fluorescence plate reader for up to 120 min at 37° C. with fluorescence measurements taken every 5 min ($\lambda_{ex}$: 485 nm; $\lambda_{em}$: 535 nm). Background-corrected fluorescence values were obtained by subtracting fluorescence values obtained from reactions carried out in the absence of target ssRNA. Maximal fluorescence was measured by incubating 50 nM RNaseA with 185 nM of RNAase-Alert substrate. For measurement of crRNA-ACTB mediated LbuC2c2 activation by beta-actin mRNA in human total RNA, LbuCas9:crRNA complexes were preassembled by incubating 1 μM of LbuC2c2 with 500 nM of crRNA-ACTB for 10 min at 37° C. and reactions were carried out in the conditions above in the presence of increasing amounts (0-1 μg) of either HeLa cell total RNA or *E. Coli* total RNA (as a negative control). These reactions were incubated in a fluorescence plate reader for up to 180 min at 37° C. with fluorescence measurements taken every 5 min ($\lambda_{ex}$: 485 nm; $\lambda_{em}$: 535 nm). Background-corrected fluorescence values were obtained by subtracting fluorescence values obtained from reactions carried out in the absence of target ssRNA. For coupled pre-crRNA processing and RNA detection assays, LbuCas9-crRNA complexes were preassembled by incubating 1 μM of LbuC2c2 with 500 nM of pre-crRNA-A-λ2 for 20 min at 37° C. and reactions carried out as described above in the presence of increasing amounts of ssRNA A and ssRNA λ2 (0-1 nM each). In each case, error bars represent the standard deviation from three independent experiments.

Background cleavage in total RNA. LbuC2c2:crRNAλ4 complexes were assembled as previously described for fluorescence RNA detection assay. Complexes were incubated in RNA processing buffer in the presence of 3 ug total RNA with and without 10 nM λ4 ssRNA target. After 2 hr, RNA was isolated by trizol extraction and ethanol precipitation. The RNA fragment size distribution of resuspended samples was resolved using Small RNA Analysis Kit (Agilent) on a Bioanalyzer 2100 (Agilent) using the manufacturer's protocol. Fluorescent intensity curves were normalized in Prism for curve overlay (GraphPad Software).

Results

Figure 30A:
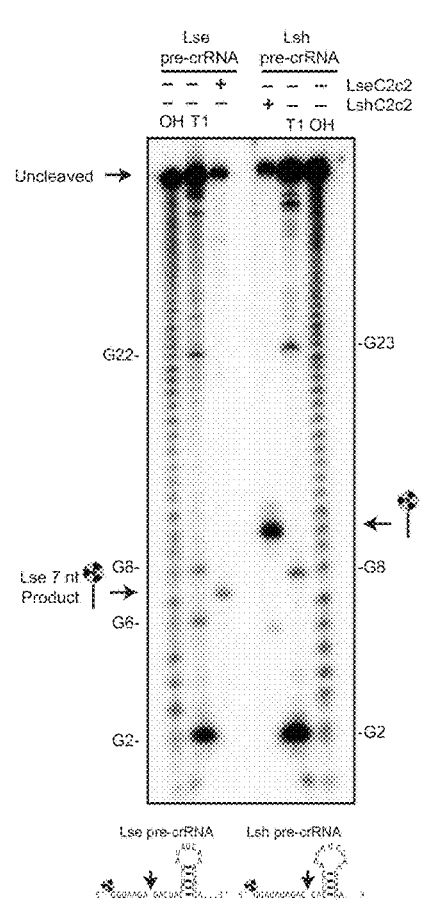
FIG. 30A-30I depict mapping of pre-crRNA processing by C2c2 in vitro and in vivo. a, Cleavage site mapping of LseC2c2 and LshCc2c2 cleavage of a single cognate pre-crRNA array. OH: alkaline hydrolysis ladder; T1: T1 RNase hydrolysis ladder. Cleavage reactions were performed with 100 nM C2c2 and <1 nM pre-crRNA. left (SEQ ID NO: 137); right (SEQ ID NO: 138) b-i, Re-analysis of LshC2c2 (b-f) and LseC2c2 (g-i) CRISPR array RNA sequencing experiments from Shmakov et al. 10 (FIG. S7 and FIG. 5, respectively). All reads (b,g) and filtered reads (55 nt or less; as per original Shmakov et al. analysis; c,h) were stringently aligned to each CRISPR array using Bowtie2 (see Methods). Detailed views of individual CRISPR repeat-spacers are shown for Lsh (d-f) and Lse (i). Differences in 5' end pre-crRNA processing are indicated by arrows below each sequence. BAM alignment files of the analysis are available. This mapping clearly indicates that the 5' ends of small RNA sequencing reads generated from Lsh pre-crRNAs map to a position 2 nts from the base of the predicted hairpin, in agreement with the in vitro processing data (a). This pattern holds for all mature crRNAs detected from both native expression in *L. shahii* and heterologous expression in *E. coli*. Unfortunately, the LseC2c2 crRNA sequencing data (used in g-i) is less informative due to low read depth, and each aligned crRNA exhibits a slightly different 5' end with little obvious uniformity. The mapping for one of the processed repeats (repeat-spacer 2; i) is in agreement with the data but only with low confidence due to the insufficient read depth. d: SEQ ID NO: 139; e: SEQ ID NO: 140; f: SEQ ID NO: 141 and i: SEQ ID NO: 142.
Figure 30B:
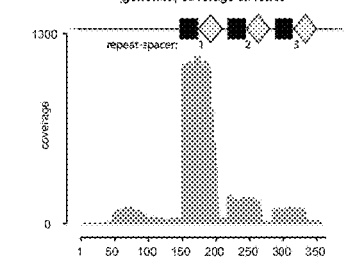
Figure 30C:
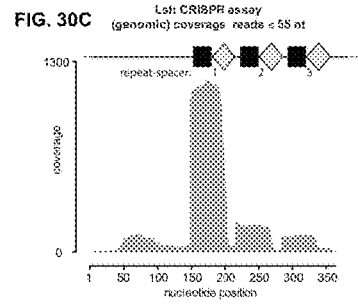
Figure 30D:
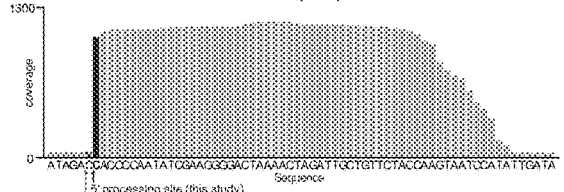
Figure 30E:
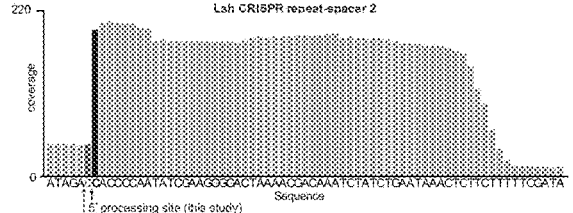
Figure 30F:
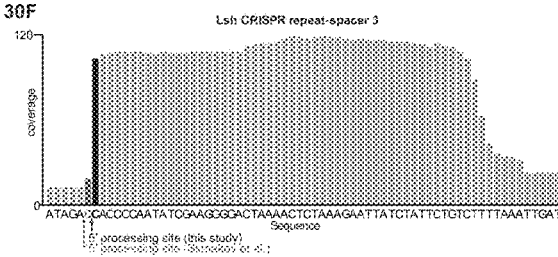
Figure 30G:
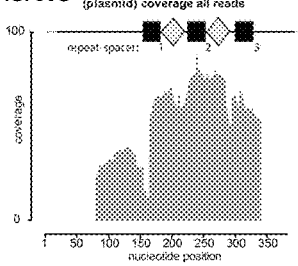
Figure 30H:
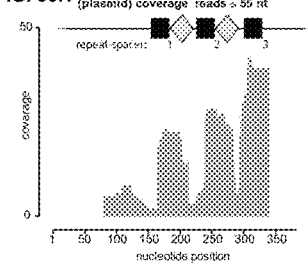
Figure 30I:
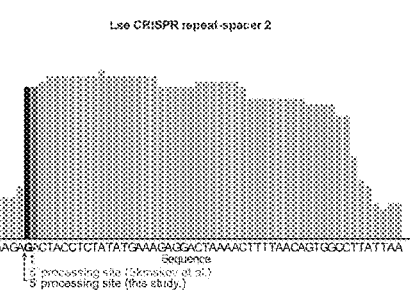
Figure 31A:
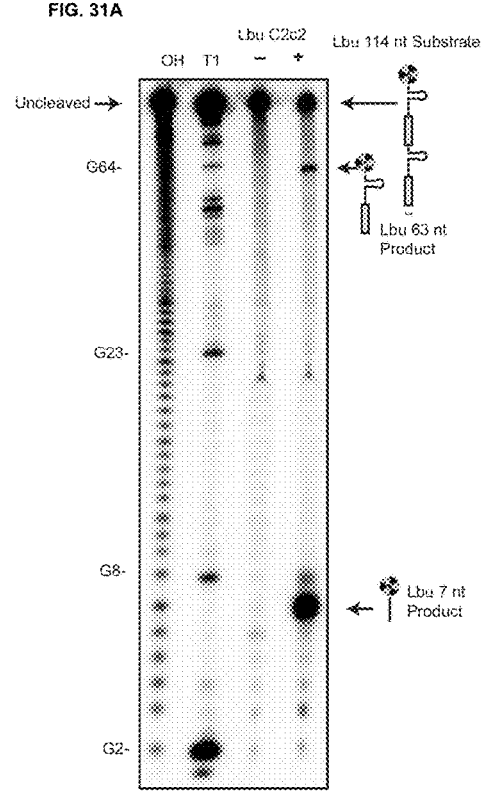
FIG. 31A-31D depict that pre-crRNA processing by C2c2 is spacer-sequence independent, can occur on tandem crRNA arrays, is affected by mutations in the 5' flanking region of the pre-cRNA and produces a 3' phosphate product. a, Cleavage site mapping of LbuCc2 cleavage of a tandem pre-crRNA array. OH: alkaline hydrolysis ladder; T1: T1 RNase hydrolysis ladder. Cleavage reactions were performed with 100 nM LbuC2c2 and <1 nM pre-crRNA. A schematic of cleavage products is depicted on right, with arrows indicating the mapped C2c2 cleavage products. b, LbuC2c2 4-mer mutant pre-crRNA processing data demonstrating the importance of the 5' single-stranded flanking region for efficient pre-crRNA processing. Percentage of pre-crRNA processing was measured after 60 min (mean±s.d., n=3). top to bottom (SEQ ID NOs: 143-146). c, Representative LbuC2c2 pre-crRNA cleavage time-course demonstrating that similar rates of pre-crRNA processing occur independent of crRNA spacer sequence pseudo-first-order rate constants (kobs) (mean±s.d.) are 0.07±0.04 min-1 and 0.08±0.04 min-1 for spacer A and spacer □2, respectively. d, End group analysis of cleaved RNA by T4 polynucleotide kinase (PNK) treatment. Standard processing assay conditions were used to generate cleavage product, which was then incubated with PNK for 1 hr to remove any 2', 3'-cyclic phosphates/3' monophosphates. Retarded migration of band indicates removal of the charged, monophosphate from the 3' end of radiolabeled 5' product.

Type VI CRISPR loci lack an obvious Cas6 or Cas5d-like endonuclease or tracrRNA. Using purified recombinant C2c2 protein homologs from three distinct branches of the C2c2 protein family (FIG. 24a-24b and FIG. 28 and FIG. 29), that data presented here show that all three C2c2 enzymes cleave 5'-end radiolabeled pre-crRNA substrates consisting of a full-length consensus repeat sequence and a 20 nucleotide (nt) spacer sequence (FIG. 24c). The cleavage site for each pre-crRNA:C2c2 homolog pair was mapped, revealing that processing occurs at a position either two or five nucleotides upstream of the predicted repeat-sequence hairpin structure, depending on the C2c2 homolog (FIG. 24c, FIG. 30A). Surprisingly, the biochemically mapped 5'-cleavage sites did not agree with previously reported cleavage sites for *Leptotrichia shahii* (LshC2c2) or *Listeria seeligeri* (LseC2c2) pre-crRNAs. Re-analysis of Shmakov et al.'s RNA sequencing data set indicated agreement of the in vivo cleavage site with the in vitro site reported here (FIG. 30b-i). Furthermore, cleavage assays using C2c2 from *Leptotricia buccalis* (LbuC2c2) and a larger pre-crRNA comprising a tandem hairpin-repeat array resulted in two products resulting from two separate cleavage events (FIG. 31a), consistent with a role for C2c2 in processing precursor crRNA transcripts generated from Type VI CRISPR loci.

Figure 25A:
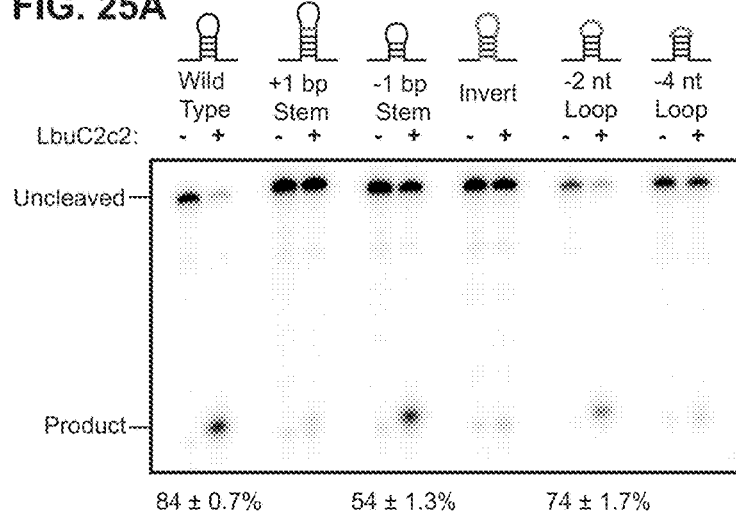
FIG. 25A-25C depict data showing that LbuC2c2 mediated crRNA biogenesis depends on both structure and sequence of CRISPR repeats. a, Representative cleavage assay by LbuC2c2 on pre-crRNAs containing structural mutations within the stem and loop regions of hairpin. Processed percentages listed below are quantified at 60 min (mean±s.d., n=3). b, Bar graph showing the dependence of pre-crRNA processing on the CRISPR repeat sequence. The wild-type repeat sequence is shown below (SEQ ID NO: 38) with individual bars representing tandem nucleotide mutations as noted in red. The cleavage site is indicated by cartoon scissors. Percentage processed was measured after 60 min (mean±s.d., n=3). Diagrammed hairpins of tested mutants can be found in Extended Data FIGS. 3-4 c, Divalent metal ion dependence of the crRNA processing reaction was tested by addition of 10-50 mM EDTA and EGTA to standard reaction conditions.
Figure 25C:
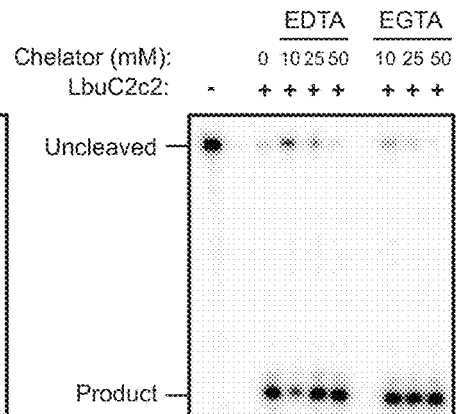
Figure 25B:
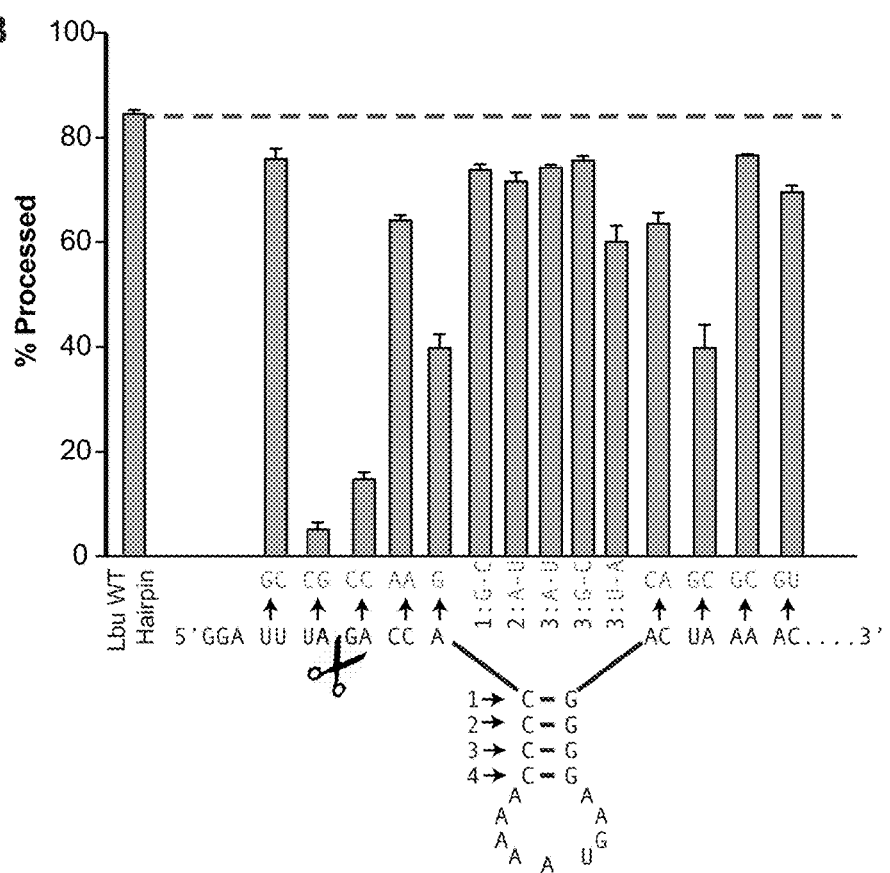
Figure 31B:
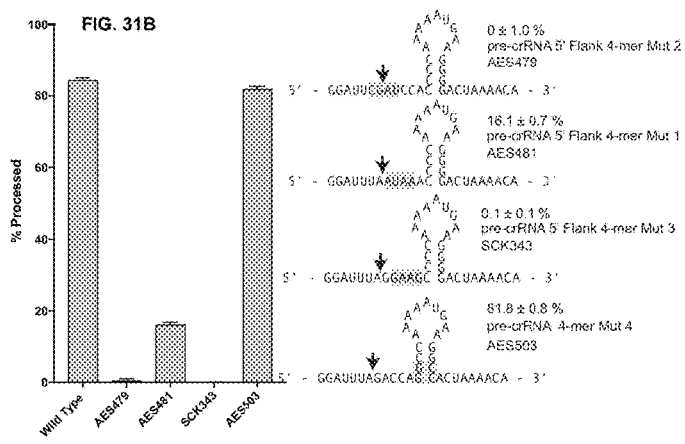
Figure 31C:
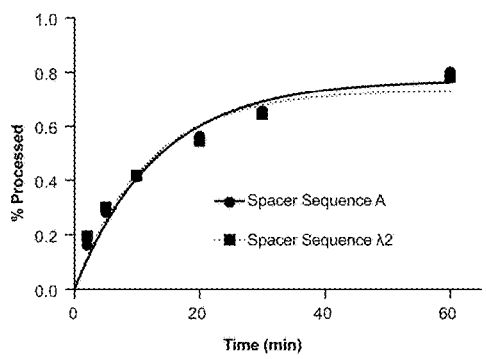

To understand the substrate requirements and mechanism of C2c2 guide RNA processing, pre-crRNAs harboring mutations in either the stem loop or the single-stranded flanking regions of the consensus repeat sequence were generated and their ability to be processed by LbuC2c2 was tested (FIG. 25). The data showed that C2c2-catalyzed cleavage was attenuated upon altering the length of the stem in the repeat region (FIG. 25a). Inversion of the stem loop or reduction of the loop length also reduced C2c2's processing activity, while contiguous 4-nt mutations including or near the scissile bond completely abolished it (FIG. 31b). A more extensive mutational analysis of the full crRNA repeat sequence revealed two distinct regions on either side of the hairpin with marked sensitivity to base changes (FIG. 25b). By contrast, there was no dependence on the spacer sequence for kinetics of processing (FIG. 31c). This sensitivity to both flanking regions of the hairpin is reminiscent of the sequence and structural motifs required by many Cas6 and Cas5d enzymes. In contrast, Cpf1 does not have any dependence on the 3' hairpin flanking region, as the variable spacer region abuts the hairpin stem.

Figure 31D:
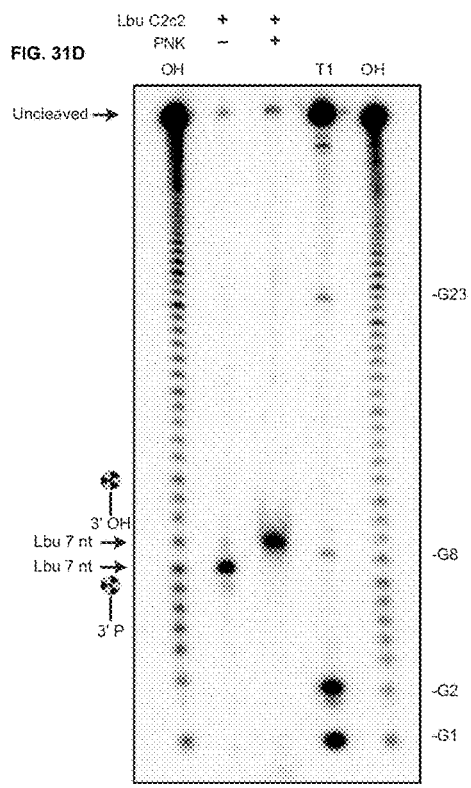
Figure 34A:
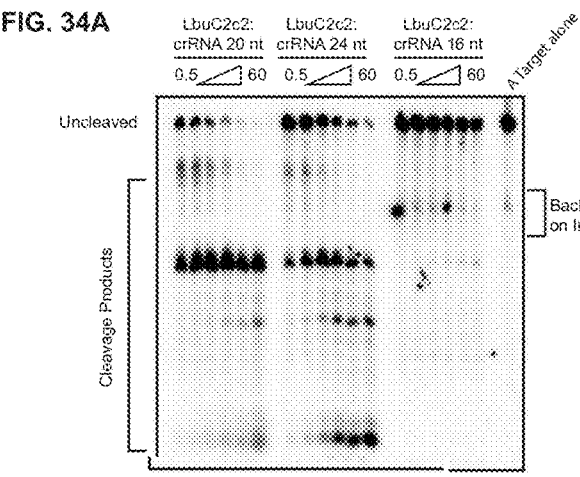
FIG. 34A-34D depict dependence of RNA targeting on crRNA variants, temperature and point mutations. a, LbuC2c2 ssRNA target cleavage assay carried out, as per Methods with crRNAs possessing 16-nt, 20-nt or 24-nt spacers. b, LbuC2c2 ssRNA target cleavage time-course carried out at either 25 □C and 37 □C as per methods. c, LbuC2c2 ssRNA target cleavage timecourse carried out as per Methods with crRNAs possessing different 5'-flanking nucleotide mutations. Mutations are highlighted in red. 1-2 nucleotide 5' extensions negligibly impacted cleavage efficiencies. In contrast, shortening the flanking region to 3 nts slowed cleavage rates. Triangle (SEQ ID NO: 9); Diamond (SEQ ID NO: 147); Circle (SEQ ID NO: 148); Square (SEQ ID NO: 149); d Impact of point mutations on ribonuclease activity of C2c2 in conserved residue mutants within HEPN motifs for ssRNA targeting.
Figure 34B:
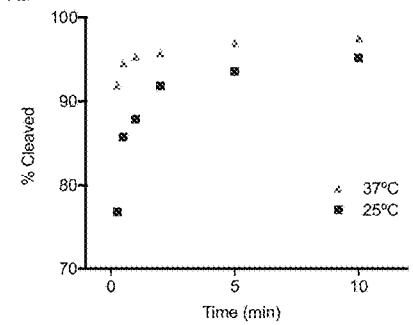
Figure 34C:
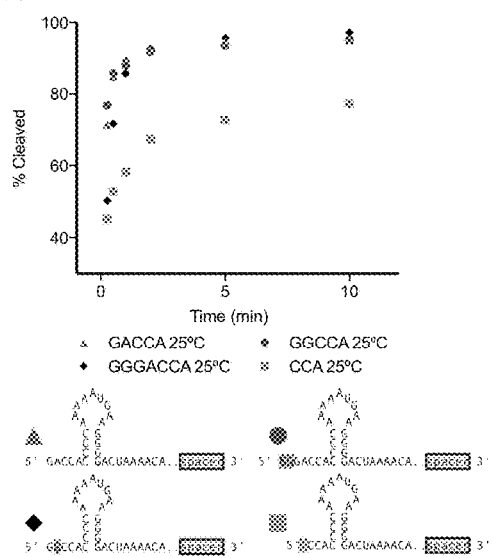
Figure 34D:
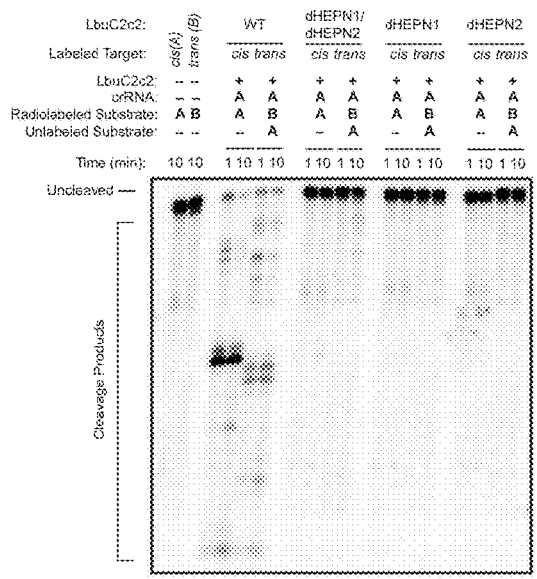

Mechanistic studies of LbuC2c2 revealed that processing activity was unaffected by the presence of divalent metal ion chelators EDTA or EGTA (FIG. 25c), indicative of a metal ion-independent RNA hydrolytic mechanism. Metal ion-independent RNA hydrolysis is typified by the formation of a 2', 3'-cyclic phosphate and 5'-hydroxide on the 5' and 3' halves of the crRNA cleavage products, respectively. To determine the end-group chemical identity of C2c2-processed substrates, the 5' flanking products were further incubated with T4 polynucleotide kinase, which removes 2',3'-cyclic phosphates to leave a 3-hydroxyl. Altered denaturing-gel migration of the 5' flanking product was observed after kinase treatment, consistent with the removal of a Y phosphate group (FIG. 31d). The divalent metal ion independence of C2c2's pre-crRNA processing activity is in stark contrast with the divalent metal ion dependency of Cpf1, the only other single-protein CRISPR effector shown to perform guide processing. Collectively, these data indicate that C2c2-catalyzed pre-crRNA cleavage is a divalent metal ion-independent process that likely uses a general acid-base catalysis mechanism.

Following maturation, crRNAs typically bind with high affinity to Cas effector protein(s) to create RNA-guided surveillance complexes capable of sequence-specific nucleic acid recognition. In agreement with previous work using LshC2c2, LbuC2c2 catalyzed efficient target RNA cleavage only when such substrates could base pair with a complementary sequence in the crRNA (FIGS. 32-34). Given the promiscuous pattern of cleavage observed for C2c2 (FIG. 33), the ability of LbuC2c2 to act as a crRNA-activated non-specific RNA endonuclease in trans was tested (FIG. 32b). In striking contrast to non-target cleavage experiments performed in cis and consistent with previous observations for LshC2c2, rapid degradation of non-target RNA in trans was observed (FIG. 32b). This result shows that target recognition activates C2c2 for general non-specific degradation of RNA. Importantly, the similar RNA cleavage rates and near-identical cleavage products observed for both cis on-target cleavage and trans non-target cleavage of the same RNA substrate implicate the same nuclease center in both activities (FIG. 32b).

Notably, crRNA-mediated cleavage of target ssRNA occurred at an ~80-fold faster rate than pre-crRNA processing (FIG. 26a), and in contrast to pre-crRNA processing, RNA-guided target cleavage was severely reduced in the presence of EDTA, indicating that this activity is divalent metal ion-dependent (FIG. 26a, (FIG. 32c, FIG. 34). Given these clear differences, it was reasoned that C2c2 might possess two orthogonal RNA cleavage activities: one for crRNA maturation, and the other for crRNA-directed, non-specific RNA degradation. To test this hypothesis, several residues within the conserved HEPN motifs of LbuC2c2 were systematically mutated, and pre-crRNA processing and RNA-guided RNase activity of the mutants was assessed (FIG. 26, FIG. 34d). Double and quadruple mutants of conserved HEPN residues (R472A, R477A, R1048A and R1053) retained robust pre-crRNA cleavage activity (FIG. 26c). By contrast, all HEPN mutations abolished RNA-guided cleavage activity while not affecting crRNA or ssRNA-binding ability (FIGS. 34d, 35).

Figure 35A:
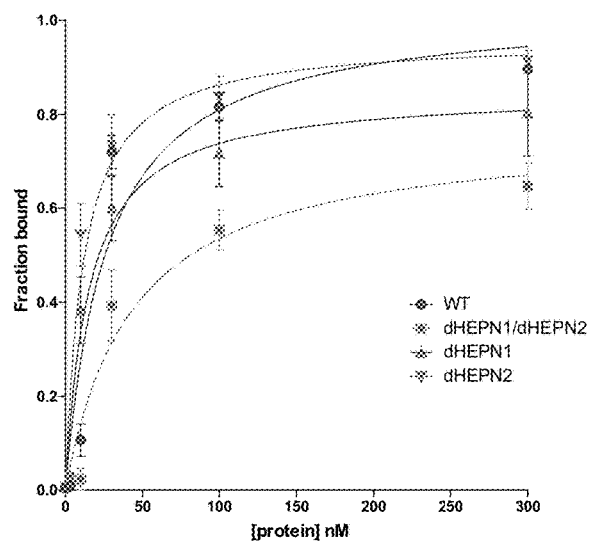
FIG. 35A-35D depict binding data for LbuC2c2 to mature crRNA and target ssRNA. a, Filter binding assays were conducted as described in the Methods to determine the binding affinity of mature crRNA-A_GG to LbuC2c2-WT, LbuC2c2-dHEPN1, LbuC2c2-dHEPN2, or LbuC2c2-dHEPN1/dHEPN2. The quantified data were fit to standard binding isotherms. Error bars represent the standard deviation from three independent experiments. Measured dissociation constants from three independent experiments (mean±sd) were 27.1±7.5 nM (LbuC2c2-WT), 15.2±3.2 nM (LbuC2c2-dHEPN1), 11.5±2.5 nM (LbuC2c2-dHEPN2), and 43.3±11.5 nM (LbuC2c2-dHEPN1/dHEPN2). b, Representative electrophoretic mobility shift assay for binding reactions between LbuC2c2-dHEPN1/dHEPN2: crRNA-A_GG and either 'on-target' A ssRNA or 'off-target' B ssRNA, as indicated. Three independent experiments were conducted as described in the Methods. The gel was cropped for clarity. c, Quantified binding data from (b) were fitted to standard binding isoforms. Error bars represent the standard deviation from three independent experiments. Measured dissociation constants from three independent experiments (mean±sd) were 1.62±0.43 nM for ssRNA A and N.D ($>>10$ nM) for ssRNA B. d, Filter binding assays were conducted as described in the Methods to determine the binding affinity of mature crRNA-A_GA to LbuC2c2-WT and LbuC2c2-R1079A. The quantified data were fit to standard binding isotherms. Error bars represent the standard deviation from three independent experiments. Measured dissociation constants from three independent experiments (mean±sd) were 4.65±0.6 nM (LbuC2c2-WT) and 2.52±0.5 nM (LbuC2c2-R1079A). It is of note that these binding affinities differ from panel a. This difference is accounted for in a slight difference in the 5' sequence of the guide with panel a guides beginning with a 5'-GGCCA . . . and panel d 5'-GACCA. While the native sequence guide (5'-GACCA) binds tighter to LbuC2c2, no difference is seen in the RNA targeting efficiencies of these guide variants (Extended Data FIG. 6c).
Figure 35B:
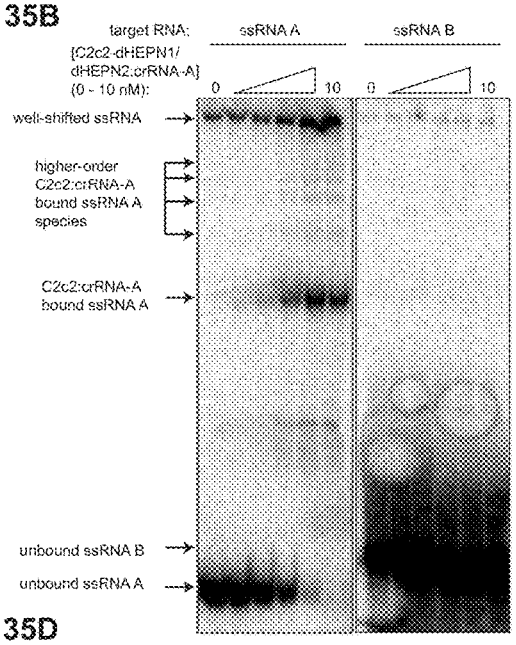
Figure 35C:
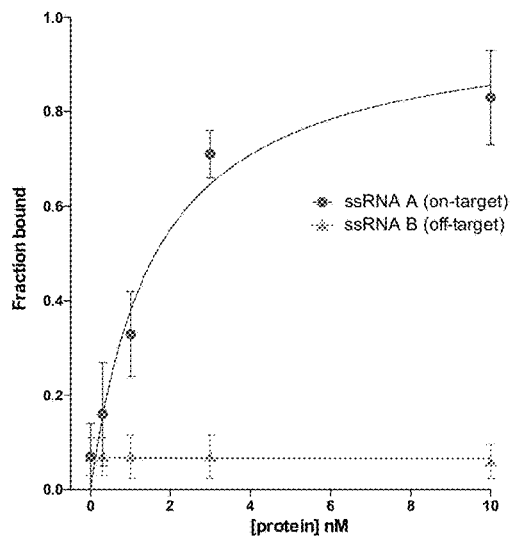
Figure 35D:
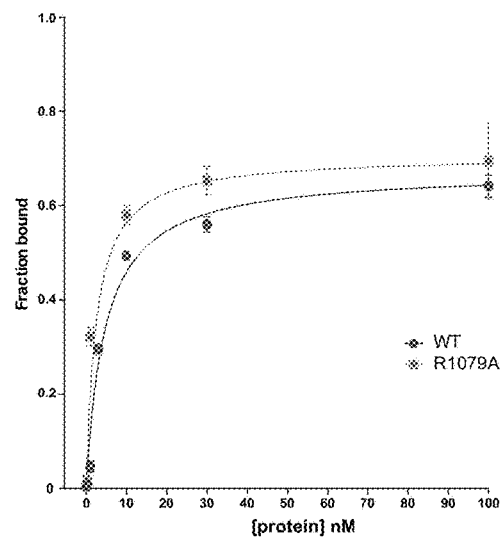

Next, mutations were sought that would abrogate pre-crRNA processing activity without disrupting target RNA cleavage. Given that we were unable to predict any other potential RNase motifs beyond the HEPN motifs, and that C2c2 proteins bear no homology to Cpf1, the charged residues throughout LbuC2c2 were systematically mutated. An arginine residue (R1079A) was identified that upon mutation resulted in severely attenuated pre-crRNA processing activity (FIG. 26c). This C2c2 mutant enzyme retained crRNA-binding ability as well as RNA target cleavage activity (FIG. 35d, FIG. 26d,). Taken together, the results show that distinct active sites within the C2c2 protein catalyze pre-crRNA processing and RNA-directed RNA cleavage.

Figure 27A:
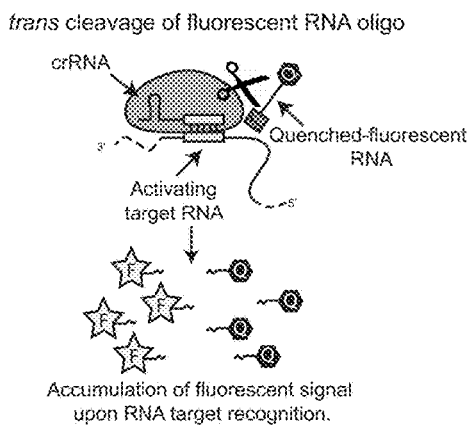
FIG. 27A-27E shows that C2c2 provides sensitive detection of transcripts in complex mixtures. a, Illustration of LbuC2c2 RNA detection approach using a quenched fluorescent RNA reporter. b, Quantification of fluorescence signal generated by LbuC2c2 after 30 min for varying concentrations of target RNA in the presence of human total RNA. RNase A shown as positive RNA degradation control. (mean±s.d., n=3) c,. Quantification of fluorescence signal generated by LbuC2c2 loaded with a β-actin targeting crRNA after 3 h for varying amounts of human total RNA or bacterial total RNA (as a β-actin null negative control). (mean±s.d., n=3) d, Tandem pre-crRNA processing also enables RNA detection. (mean±s.d., n=3) e, Model of the Type VI CRISPR pathway highlighting both of C2c2's ribonuclease activities.
Figure 27B:
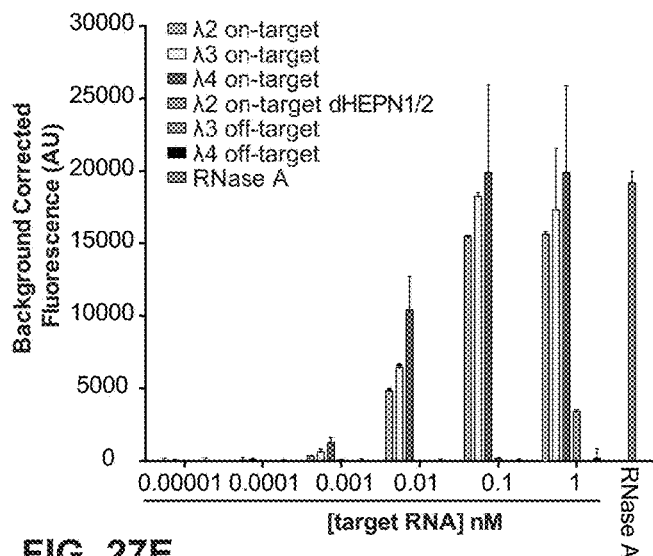
Figure 36A:
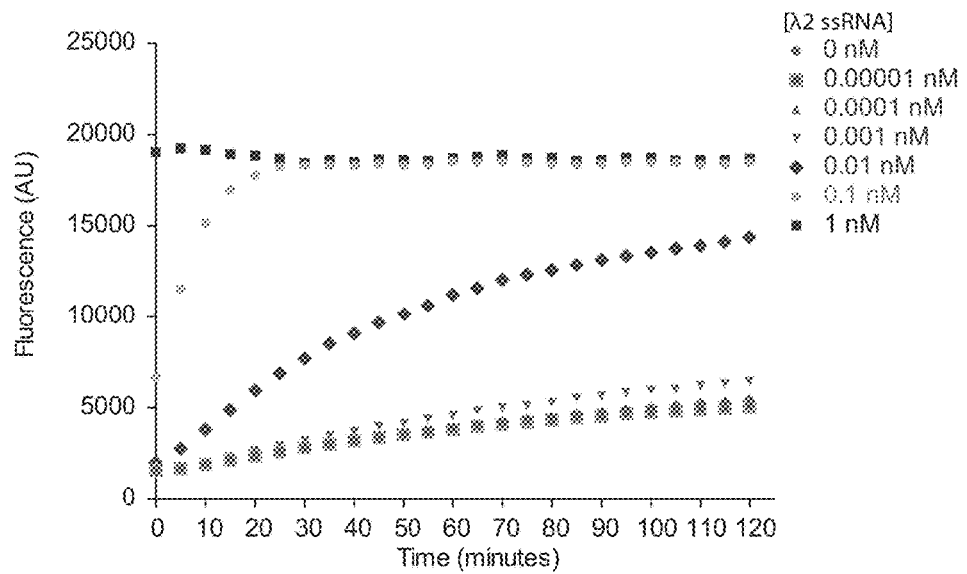
FIG. 36A-36B depict an RNase detection assay λ2-ssRNA time-course. a, LbuC2c2:crRNA-X2 was incubated with RNAase-Alert substrate (Thermo-Fisher) and 100 ng HeLa total RNA in the presence of increasing amounts of λ2 ssRNA (0-1 nM) for 120 min at 37° C. Fluorescence measurements were taken every 5 min. The 1 nM λ2 ssRNA reaction reached saturation before the first time point could be measured. Error bars represent the standard deviation from three independent experiments. b, LbuC2c2:crRNA-λ4 or apo LbuC2c2 was incubated in HeLa total RNA for 2 hours in the presence or absence of on-target activating λ4 ssRNA. Degradation of background small RNA was resolved on a small RNA chip in a Bioanalyzer 2100 as per Methods. Small differences are seen in the fragment profile of between apo LbuC2c2 and LbuC2c2: crRNA-λ4. In contrast, upon addition of the on-target ssRNA to the reaction, a drastic broadening and shifting of the tRNA peak reveals extensive degradation of other structured and nonstructured RNA's present in the reaction upon activation of LbuC2c2 trans activity.
Figure 36B:
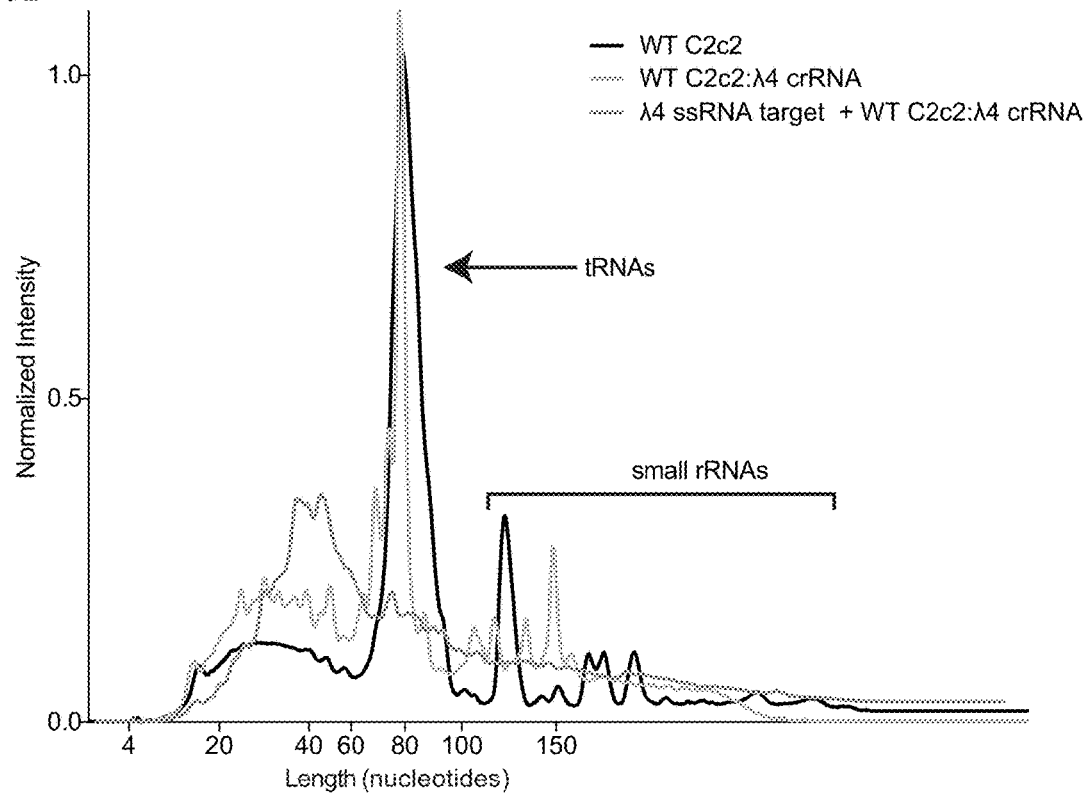

It was next tested whether C2c2's robust RNA-stimulated cleavage of trans substrates can be employed as a means of detecting specific RNAs within a pool of transcripts. While many polymerase-based methods have been developed for RNA amplification and subsequent detection, few approaches are able to directly detect the target RNA without significant engineering or stringent design constraints for each new RNA target. As a readily-programmable alternative, it was tested whether C2c2's RNA-guided trans endonuclease activity could be harnessed to cleave a fluorophore-quencher-labeled reporter RNA substrate, thereby resulting in increased fluorescence upon target RNA-triggered RNase activation (FIG. 27a). LbuC2c2 was loaded with bacteriophage λ-targeting crRNAs and tested for its ability to detect the corresponding λ ssRNA targets spiked into HeLa cell total RNA. Upon addition of as little as 1-10 pM complementary λ target-RNA, a substantial crRNA-specific increase in fluorescence occurred within 30 min (FIG. 27b and FIG. 36a). Control experiments with either C2c2: crRNA complex alone or in the presence of crRNA and a non-complementary target RNA resulted in negligible increases in fluorescence relative to an RNase A positive control (FIG. 27b and FIG. 36a). It was noted that at the 10 pM concentration of a λtarget RNA, only ~0.02% of the C2c2:crRNA complex was predicted to be in the active state, yet the observed fluorescent signal reflected ~25-50% cleavage of the reporter RNA substrate, depending on the RNA target. Fragment size resolution of the background RNA in these reactions revealed significant degradation, even on highly structured tRNAs (FIG. 36b). Since reporter RNA cleavage occurred in the presence of a vast excess of unlabeled RNA, we conclude that LbuC2c2 is a robust multiple-turnover enzyme capable of at least $10^4$ turnovers per target RNA recognized. Thus, in contrast to previous observations, crRNA-directed trans cleavage is potent and detectable even at extremely low levels of activated protein.

Figure 27C:
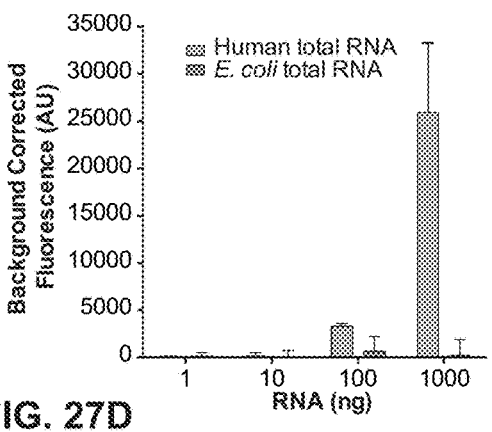
Figure 27D:
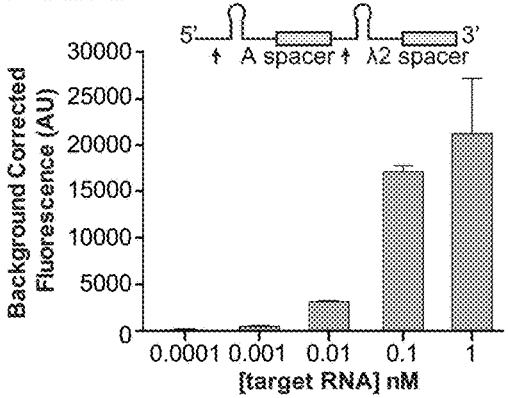
Figure 27E:
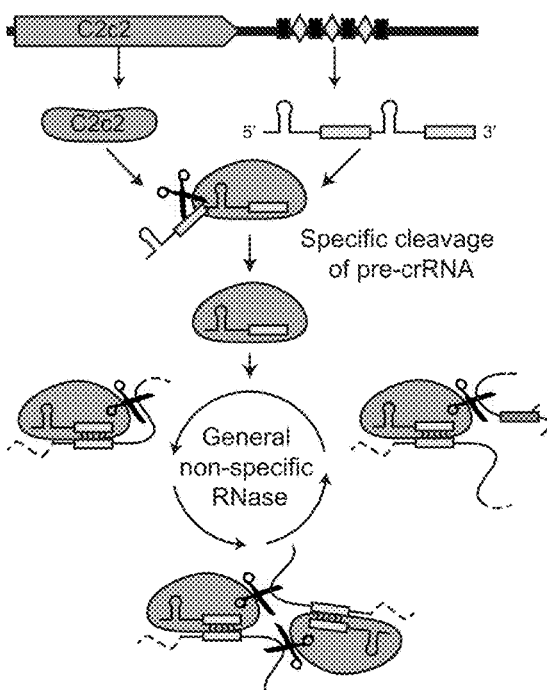
Figures 28A, 28B:
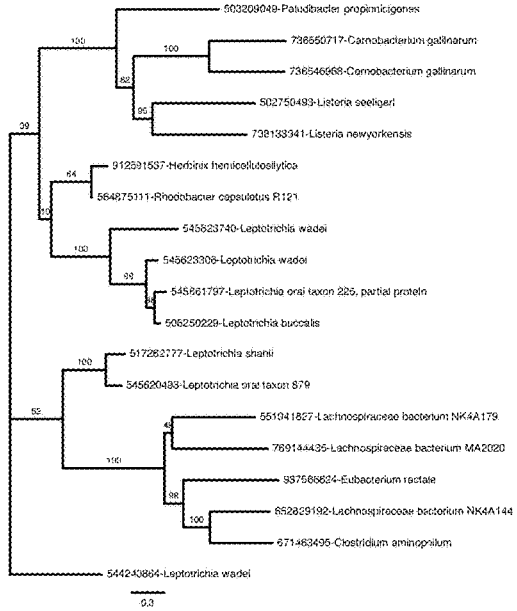
FIG. 28A-28B depict a complete phylogenetic tree of C2c2 family and C2c2 alignment. a, Maximum-likelihood phylogenetic reconstruction of C2c2 proteins. Leaves include GI protein numbers and organism of origin; bootstrap support values, out of 100 resamplings, are presented for inner split. Scale is in substitutions per site. b, Multiple sequence alignment of the three analyzed homologs of C2c2; coordinates are based on LbuC2c2.*Leptotrichia_buccalis* (SEQ ID NO: 2); *Listeria_seeligeri* (SEQ ID NO: 1); *Leptotrichia_shahii* (SEQ ID NO: 3).
Figure 29A:
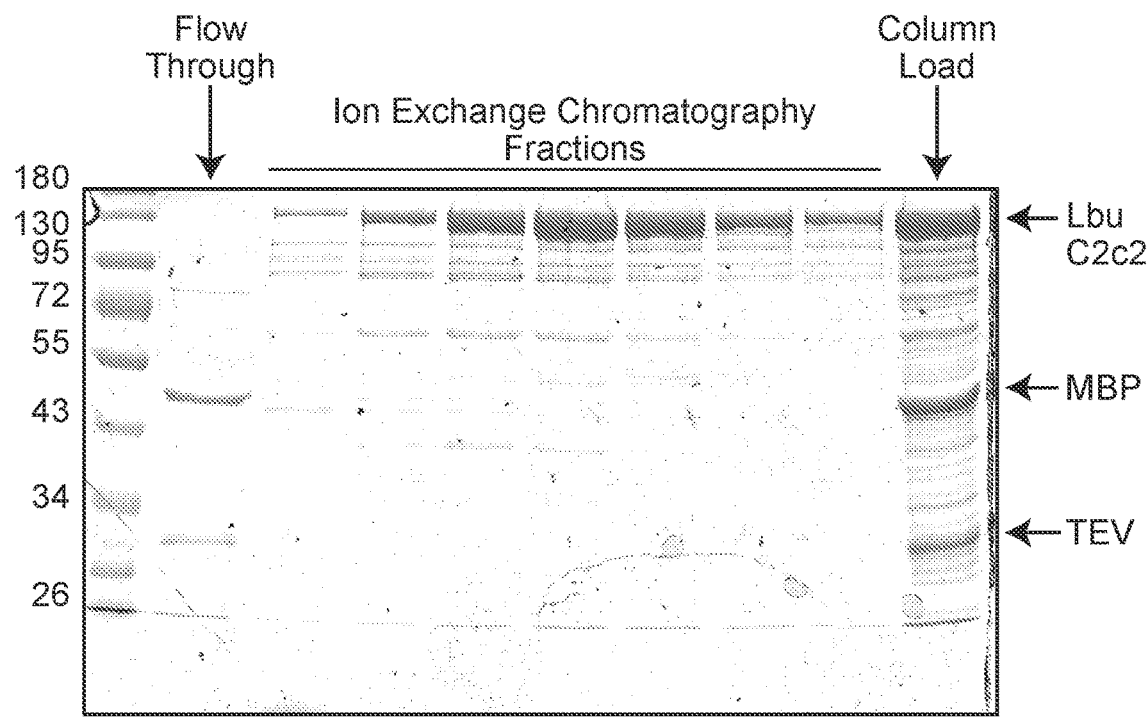
Figure 29B:
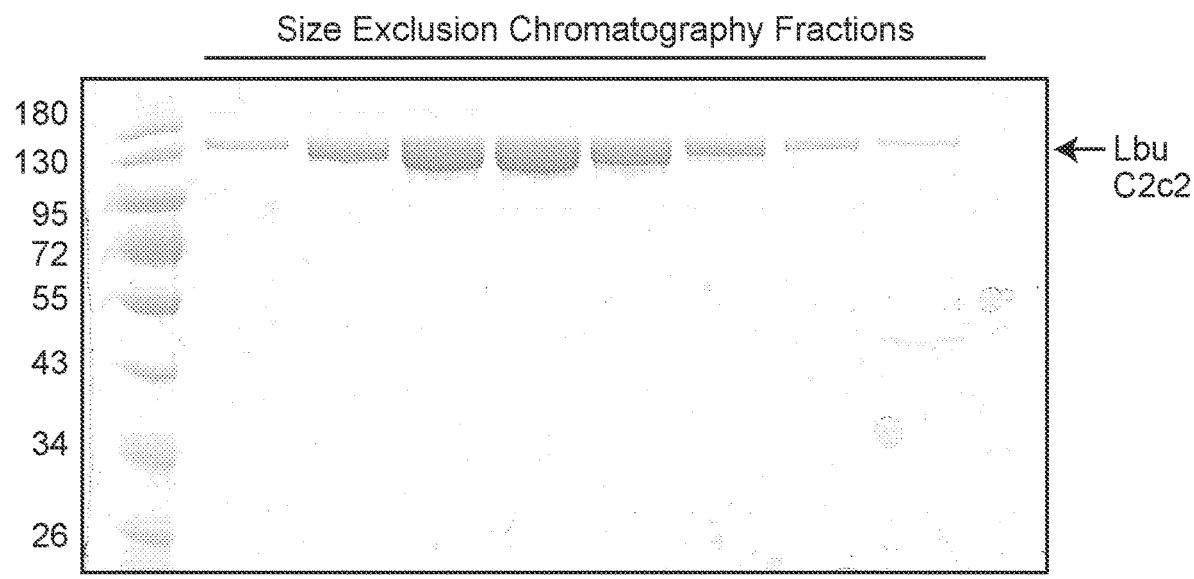

To extend this LbuC2c2 RNA detection system, a crRNA was designed to target endogenous beta-actin mRNA. A measurable increase in fluorescence was observed in the presence of human total RNA relative to E. coli total RNA, demonstrating the specificity of this method (FIG. 27c). Furthermore, given that C2c2 processes its own guide, pre-crRNA processing and RNA detection was combined in a single reaction by designing tandem crRNA-repeat containing spacers complementary to target RNAs A and λ2. LbuC2c2 incubated with this unprocessed tandem guide RNA in the detection assay generated a significant increase in fluorescence similar in magnitude and sensitivity to experiments using mature crRNAs (FIG. 27b, 27d). Taken together, these data highlight the exciting opportunity to take advantage of C2c2's two distinct RNase activities for a range of biotechnological applications (FIG. 27e).

In bacteria, C2c2 likely operates as a sentinel for viral RNAs. Without being bound by theory, we propose that when invasive transcripts are detected within the host cell via base pairing with crRNAs, C2c2 is activated for promiscuous cleavage of RNA in trans (FIG. 27e). As a defense mechanism, this bears striking similarity to RNase L and caspase systems in eukaryotes, whereby a cellular signal triggers promiscuous ribonucleolytic or proteolytic degradation within the host cell, respectively, leading to apoptosis. While the RNA targeting mechanisms of Type III CRISPR systems generally result in RNA cleavage within the protospacer-guide duplex, recent examples of associated nucleases Csx1 and Csm6 provide compelling parallels between the Type VI systems and the multi-component Type III inference complexes.

The data described herein show that CRISPR-C2c2 proteins represent a new class of enzyme capable of two separate RNA recognition and cleavage activities. Efficient pre-crRNA processing requires sequence and structural motifs within the CRISPR repeat which prevent non-endogenous crRNA loading and helps to reduce the potential toxicity of this potent RNase. The entirely different pre-crRNA processing mechanisms of C2c2 and the Type V CRISPR effector protein Cpf1 indicate that each protein family has converged upon independent activities encompassing both the processing and interference functions of their respective CRISPR pathways. Furthermore, the two distinct catalytic capabilities of C2c2 can be harnessed in concert for RNA detection, as the activation of C2c2 to cleave thousands of trans-RNAs for every target RNA detected enables potent signal amplification. The capacity of C2c2 to process its own guide RNAs from arrays allows the use of tissue-specific Pol II promoters for guide expression, in addition to target multiplexing for a wide range of applications. The C2c2 enzyme is unique within bacterial adaptive immunity for its dual RNase activities, and highlights the utility of harnessing CRISPR proteins for precise nucleic acid manipulation in cells and cell-free systems.

Example 14

Figure 37:
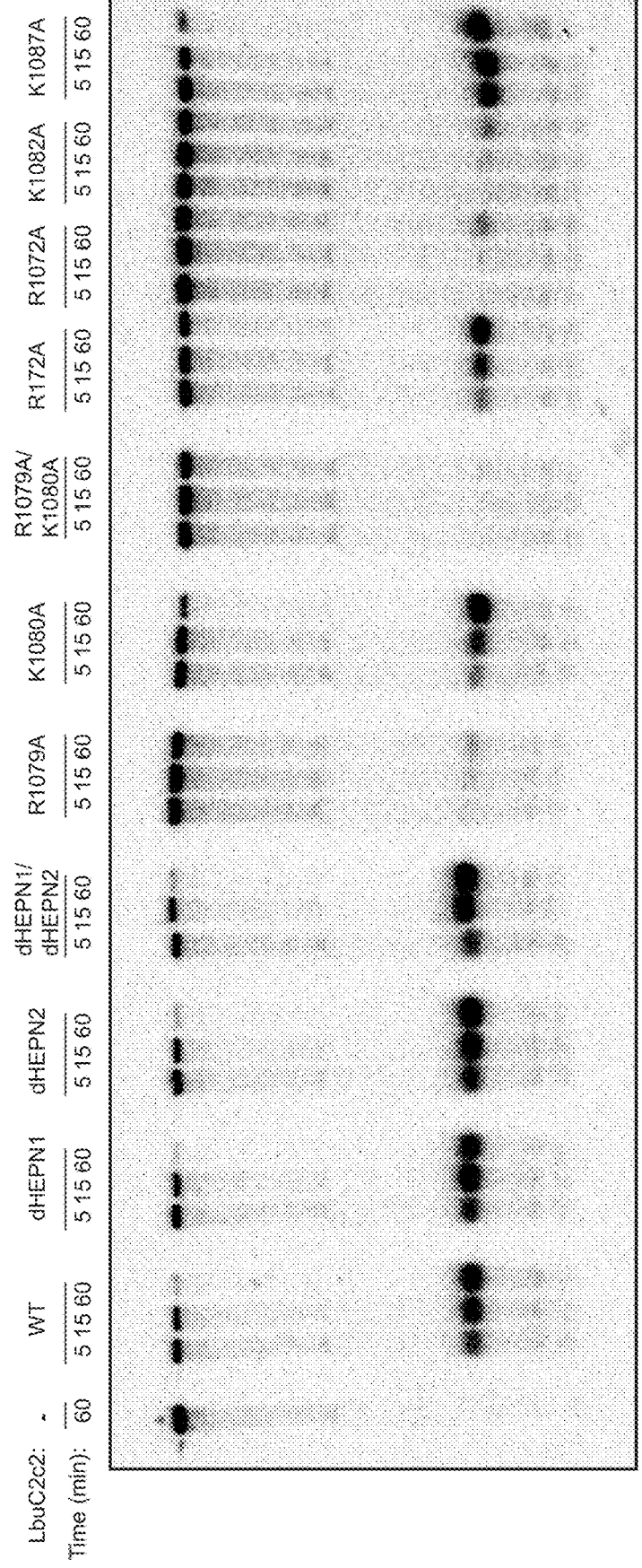
FIG. 37 depicts cleavage experiments demonstrating severely reduced cleavage of precursor guide RNA (guide RNA processing) by LbuC2c2 when the protein includes a mutation at any amino acid position selected from R1079 (e.g., R1079A), R1072 (e.g., R1072A), and K1082 (e.g., K1082A).

Additional amino acid positions were identified in LbuC2c2 that when mutated result in severely attenuated pre-crRNA processing activity (FIG. 37). The amino acid positions included R1079 (e.g., R1079A), R1072 (e.g., R1072A), and K1082 (e.g., K1082A).

Example 15

Cas13a enzymes comprise two distinct functional groups that recognize orthogonal sets of crRNAs and possess different ssRNA cleavage specificities. Cas13a pre-crRNA processing is not essential for ssRNA cleavage, although it enhances ssRNA targeting for crRNAs encoded internally within the CRISPR array. Two Cas13a protein subfamilies were defined, which subfamilies can operate in parallel for RNA detection and destruction both in bacteria and for diagnostic applications.

Materials and Methods

Cas13a phylogenic and repeat conservation analysis. Cas13a maximum-likelihood phylogenies were computed using RAxML (Stamatakis, Bioinformatics. 2014 May 1;30 (9):1312-3) with the PROTGAMMALG evolutionary model and 100 bootstraps. Protein clades alpha and beta were defined as branch points with bootstrap values greater than 90, suggesting high confidence in having a common ancestor. The remaining proteins were labeled as ambiguous ancestry, as the phylogenetic relationships between them were low confidence, reflected in bootstrap values less than 90. Sequences were aligned by MAFFT with the 'einsi' method (Katoh and Standley, Mol Biol Evol. 2013 April; 30(4):772-80). Candidates were selected to represent each of the major branches of the Cas13a protein tree. Alignments were performed for all non-redundant homologs (FIG. 41) and candidate proteins. Comparison of the CRISPR-RNA (crRNA) repeats was carried out by calculating pairwise similarity scores using the Needleman-Wunsch algorithm through the Needle tool on EMBL-EBI (McWilliam et al., Nucleic Acids Res. 2013 July;41(Web Server issue):W597-600). Hierarchical clustering of CRISPR crRNA was performed in R using the similarity score matrix.

Cas13a protein expression and purification. Expression vectors for protein purification were assembled using synthetic gBlocks ordered from Integrated DNA Technologies (IDT). The codon-optimized Cas13a genomic sequences were N-terminally tagged with a $His_6$-MBP-TEV cleavage site sequence, with expression driven by a T7 promoter. Mutant proteins were cloned via site-directed mutagenesis of wild-type Cas13a constructs. Purification of all homologs was carried out as described in Examples 7 and 13, above. Briefly, expression vectors were transformed into Rosetta2 DE3 or BL21 E. coli cells grown in 2×YT broth at 37° C., induced at mid-log phase with 0.5 mM IPTG, and then transferred to 16° C. for overnight expression. Cell pellets were resuspended in lysis buffer (50 mM Tris-Cl pH 7.0, 500 mM NaCl, 5% glycerol, 1 mM TCEP, 0.5 mM PMSF, and EDTA-free protease inhibitor (Roche)), lysed by sonication, and clarified by centrifugation at 15,000 g. Soluble $His_6$-MBP-TEV-Cas13a was isolated over metal ion affinity chromatography, and in order to cleave off the $His_6$-MBP tag, the protein-containing eluate was incubated with TEV protease at 4° C. overnight while dialyzing into ion exchange buffer (50 mM Tris-Cl pH 7.0, 250 mM KCl, 5% glycerol, 1 mM TCEP). Cleaved protein was loaded onto a HiTrap SP column (GE Healthcare) and eluted over a linear KCl (0.25-1.5 M) gradient. Cas13a containing fractions were pooled, concentrated, and further purified via size-exclusion chromatography on a S200 column (GE Healthcare) in gel filtration buffer (20 mM Tris-Cl pH 7.0, 200 mM KCl, 5% glycerol, 1 mM TCEP) and were subsequently stored at −80°

C. All homologs were purified using this protocol except LwaCas13a which was bound to a HiTrap Heparin column instead of a SP column, and the size-exclusion chromatography step was omitted due to sufficient purity of the sample post ion-exchange. All expression plasmids are deposited with Addgene.

In-vitro RNA transcription. All pre-crRNAs, mature crRNAs, and targets were transcribed in vitro using previously described methods (Sternberg et al., RNA. 2012 Apr;18(4): 661-72) and as described in the above Examples. Briefly, all substrates were transcribed off a single-stranded DNA oligonucleotide template (IDT), except for mature crRNAs requiring a non-GR 5' terminus. For these mature crRNAs, T7 polymerase templates containing a Hammerhead Ribozyme sequence immediately upstream of the mature crRNA sequence were generated using overlap PCR, and then purified for use as the template for T7 transcription (see FIG. 50 (Table 5) for sequences). Lbu six-mer CRISPR array in vitro transcription template was synthesized by GeneArt (Thermofisher) as a plasmid. The T7 promoter-CRISPR array region was PCR amplified and purified prior to use as the template for T7 transcription. All transcribed RNAs were purified using 15% Urea-PAGE, except for the array which was purified using 6% Urea-PAGE. All RNAs were subsequently treated with calf alkaline phosphatase to remove 5' phosphates. Radiolabeling was performed as previously described (Sternberg et al., RNA. 2012 April; 18(4):661-72), and as described in the above Examples. A, C, G and U homopolymers, and fluorescently-labeled RNA reporters for trans-ssRNA cleavage were synthesized by IDT. Homopolymers were purified using 25% Urea-PAGE after radiolabeling to reduce substrate heterogeneity.

Radiolabeled ssRNA nuclease assays. pre-crRNA processing assays were performed at 37° C. in RNA processing buffer (20 mM HEPES-Na pH 6.8, 50 mM KCl, 5 mM $MgCl_2$, 10 µg/mL BSA, 10 µg/mL tRNA, 0.05% Igepal CA-630 and 5% glycerol) with a 100-fold molar excess of Cas13a relative to 5'-labeled pre-crRNA (final concentrations of 100 nM and <1 nM, respectively). Unless otherwise indicated, reactions were quenched after 60 min with 1.5× RNA loading dye (100% formamide, 0.025% bromophenol blue, and 200 µg $mL^{-1}$ heparin). After quenching, reactions were denatured at 95° C. for 5 min prior to resolving by 15% denaturing PAGE (0.5×TBE buffer). Target cleavages assays were performed at 37° C. in cleavage buffer (20 mM HEPES-Na pH 6.8, 50 mM KCl, 5 mM $MgCl_2$, and 5% glycerol). Generally, Cas13a:crRNA complex formation was performed in cleavage buffer, at a molar ratio of 2:1 protein to crRNA at 37° C. for 60 min, prior to adding 5'-labeled target and/or other non-radiolabeled RNA target substrates. Unless otherwise indicated, final concentrations were 100 nM Cas13a, 50 nM crRNA or pre-crRNA, 50 nM crRNA-complementary target ssRNA (henceforth referred to as 'activator') and <1 nM trans-ssRNA target. All bands were visualized by phosphorimaging (Typhoon, GE Healthcare) and quantified with ImageQuant (GE Healthcare). For pre-crRNA processing, the percent cleavage was determined as the ratio of the product band intensity to the total intensity of both the product and uncleaved pre-crRNA bands and normalized for background within each measured substrate. For trans-ssRNA cleavage reactions, the percentage cleavage was determined as the ratio of all fragments smaller than the target to the total intensity within the lane and normalized for background within each substrate. These data were subsequently fit to a single-exponential decay using Prism7 (GraphPad) and cleavage rates are reported in figure legends.

Fluorescent ssRNA nuclease assays. Cas13a:crRNA complexes were assembled in cleavage buffer, as described above. 150 nM of RNase Alert reporter (IDT) and various final concentrations (0-1 µM) of ssRNA-activator were added to initiate the reaction. Notably these reactions are in the absence of competitor tRNA or total RNA, to more accurately measure trans-cleavage activity. These reactions were incubated in a fluorescence plate reader (Tecan Infinite Pro F2000) for up to 120 min at 37° C. with fluorescence measurements taken every 5 min ($\lambda_{ex}$: 485 nm; $\lambda_{em}$: 535 nm). Background-corrected fluorescence values were obtained by subtracting fluorescence values obtained from reactions carried out in the absence of target ssRNA activator. For determining homolog sensitivities and array processing effects, background corrected values were fit to a single-exponential decay using Prism7 (GraphPad) and the calculated rates were plotted with their associated standard deviations from n=3. For comparing non-cognate crRNA directed trans-ssRNA cleavage, initial reaction rates were instead calculated due to discrepancies in fluorescence plateau values across the dataset. Rates were then scaled relative to the cognate crRNA to normalize rates across the homologs. See FIG. 52, FIG. 53, and FIG. 54, presenting Tables 7, 8, and 9, respectively, for normalized values. For fluorescent homopolymer ssRNA reporter studies, Cas13a:crRNA complexes were pre-incubated at 37° C. for 60 mins using standard conditions. Activator ssRNA and 200 nM fluorescent ssRNA reporter were added to initiate the reaction immediately before placing reaction in plate reader. For Lbu- and Lba-Cas13a containing samples with fluorescent homopolymer ssRNA reporters, 10 pM and 1 nM activator was used, respectively. For pre-crRNA array experiments, 300 nM Cas13a was first incubated with 50 nM pre-crRNA array for 1 hr in cleavage buffer to enable binding and processing of the array. 100 pM of each ssRNA activator was added along with 150 nM of RNase Alert reporter (IDT) to initiate the reaction, in biological triplicate for each spacer sequence. Apparent rates were calculated using one single-exponential decay using Prism7 (GraphPad) and calculated rates are plotted with their associated standard deviations.

crRNA filter-binding assays. Filter binding assays was carried out as described in the Examples above. Briefly, Cas13a and radiolabeled crRNA were incubated for 1 hr at 37° C. in RNA processing buffer (20 mM HEPES-Na pH 6.8, 50 mM KCl, 5 mM $MgCl_2$, 10 µg/mL BSA, 10 µg/mL yeast tRNA, 0.01% Igepal CA-630 and 5% glycerol). Tufryn, Protran and Hybond-N+ were assembled onto a dot-blot apparatus in the order listed above. The membranes were washed twice with 50 µL Equilibration Buffer (20 mM HEPES-Na pH 6.8, 50 mM KCl, 5 mM $MgCl_2$ and 5% glycerol) before the sample was applied to the membranes. Membranes were again washed with 50 µL Equilibration Buffer, dried and visualized by phosphorimaging. Data were quantified with ImageQuant TL Software (GE Healthcare) and fit to a binding isotherm using Prism (GraphPad Software). All experiments were carried out in triplicate. Dissociation constants and associated errors are reported in the Figure legends.

Results

Most Cas13a Homologs Possess Pre-crRNA Processing Activity

To explore the functional diversity of Cas13a proteins, the pre-crRNA processing activities of ten homologs from across the protein family tree were compared for their capacity to produce mature crRNAs from cognate pre-crRNAs (FIG. 38A; FIG. 39). Similar to the three homologs discussed above, seven additional Cas13a enzymes possess crRNA maturation activity (FIGS. 38B and 38C). Only one of the eleven Cas13a proteins tested to date exhibited no detectable cleavage of its cognate pre-crRNA across a wide range of assay conditions (HheCas13a) (FIG. 38; FIG. 39A). Of the homologs that processed their native crRNAs, all but LshCas13a cleaved at the phosphodiester bond four nucleotides upstream of the conserved crRNA-repeat hairpin (FIGS. 38B and 38C). These results show strong conservation of Cas13a-mediated crRNA biogenesis activity within Type VI-A CRISPR systems.

A Conserved crRNA Maturation Center within Most Cas13a Enzymes

Previous studies have implicated two distinct regions of Cas13a as responsible for pre-crRNA processing. The general Cas13a protein architecture established by the LshCas13a crystal structure consists of an N-terminal domain and two HEPN (higher eukaryotes and prokaryotes nucleotide-binding) domains separated by two helical domains (FIG. 40A) (Liu et al., Cell 2017 Jan. 12;168(1-2):121-134.e12). For LbuCas13a, mutation of a single residue (R1079) within the HEPN2 domain was sufficient to substantially reduce pre-crRNA processing activity. By contrast, mutations at two positions located in the helical 1 domain, R438 and K441, were shown to diminish pre-crRNA cleavage by LshCas13a (Liu et al., Cell 2017 Jan. 12;168(1-2):121-134.e12). While both of these regions may be involved in pre-crRNA processing, it is unclear whether processing by LbuCas13a is inhibited by helical 1 domain mutations, and which domain is primarily responsible for crRNA maturation across the Cas13a protein family.

Conservation of both the helical 1 and HEPN2 domains across 19 Cas13a homologs was examined. Previously reported alignments (Liu et al., Cell 2017 Jan. 12;168(1-2): 121-134.e12; Shmakov et al., Mol Cell. 2015 Nov. 5; 60(3):385-97) conflict in the helical 1 domain region, suggesting high ambiguity in the relationship between homologs in this domain. Minimal conservation within the alignment of the helical 1 domain implicated in pre-crRNA processing was observed; in contrast, consistent conservation is present within the HEPN2 domain (FIG. 40B-40C; FIG. 41). The only pre-crRNA processing-defective homolog, HheCas13a, maintains a majority of the conserved charged residues throughout both domains, suggesting that other parts of the protein or the repeat sequence may be preventing pre-crRNA cleavage. Among the homologs used in this study, LshCas13a is the most divergent across the HEPN2 domain, potentially explaining the alternative catalytic domain and atypical cleavage site selection by this homolog.

The effect of the helical 1 domain residues critical for LshCas13a pre-crRNA processing on LbuCas13a's pre-crRNA processing activity was tested. Four residues (E299, K310, R311 and N314) were tested for their role in pre-crRNA cleavage (FIGS. 40B and 40C) (Liu et al., Cell 2017 Jan. 12;168(1-2):121-134.e12; Shmakov et al., Mol Cell. 2015 Nov. 5; 60(3):385-97). Mutation of these residues to alanine revealed a range of impacts on pre-crRNA processing efficiencies: N314A significantly reduced the cleavage rate, R311A minimally impaired activity, and E299A and K310 had no effect on pre-crRNA processing (FIG. 40D). In parallel, mutagenesis within the HEPN2 domain of LbuCas13a was performed. Alanine substitutions at R1072 and K1082 significantly reduced pre-crRNA cleavage, while other mutations in the same region (D1078A, K1080A and K1087A) had minimal impacts on pre-crRNA processing (FIG. 40E). These results suggest that the HEPN2 and to a lesser extent the helical 1 domains play significant roles in crRNA biogenesis for LbuCas13a, although the residues directly responsible for catalyzing hydrolysis remain unknown. The difference between the regions implicated in pre-crRNA processing across LbuCas13a and LshCas13a (Liu et al., Cell 2017 Jan. 12;168(1-2):121-134.e12) do not necessarily contradict each other, as the 5' terminus of the crRNA is held between HEPN2 and helical 1 domains in the LshCas13a structure (Liu et al., Cell 2017 Jan. 12;168(1-2):121-134.e12). Residues from both domains might play pivotal roles in pre-crRNA processing by either stabilizing substrate binding, promoting proper substrate orientation and/or catalyzing hydrolysis.

The lack of conservation within the HEPN2 domain of LshCas13a, its putative pre-crRNA processing active site, and this enzyme's atypical pre-crRNA cleavage site led us to hypothesize that LshCas13a may utilize a different region within the helical 1 domain to catalyze pre-crRNA processing. In the absence of a three-dimensional structure of a pre-crRNA-bound Cas13a homolog, this hypothesis was tested by mapping the LshCas13a cleavage sites on non-cognate pre-crRNAs (FIG. 40F). LshCas13a was able to process pre-crRNAs from LwaCas13a and LbuCas13a, generating a shifted cleavage site one nucleotide from the predicted hairpin base. In concordance with this observation, processing of the Lsh pre-crRNA by LwaCas13a and LbuCas13a occurs at the standard four-nucleotide interval from the repeat stem, differing from the cognate LshCas13a site. This supports the observations that the distinct LshCas13a processing site depends on the protein architecture, not the pre-crRNA sequence, and that LshCas13a is an outlier within the Cas13a tree with regard to pre-crRNA processing.

Cas13a Enzymes Initiate ssRNA Cleavage at Either Uridines or Adenosines

Previous studies established that Cas13a:crRNA complexes recognize and bind complementary ssRNA targets, hereby referred to as ssRNA activators, to trigger general RNase activity at exposed uridine residues (FIG. 42A). Whether the panel of homologs retained the non-specific degradation activity demonstrated by LbuCas13a and LshCas13a was tested. It was also tested whether the uridine preference within the HEPN active site is universal within the family. To systematically test general RNase activity, the ability of a ternary complex comprising Cas13a:crRNA with a bound ssRNA activator to degrade a trans-ssRNA target was monitored (FIG. 42A). Trans-ssRNA cleavage activity was detected for eight of the ten homologs over the course of one hour (FIG. 42B; FIG. 43A). Most notable of the Cas13a homologs active for trans-ssRNA cleavage is HheCas13a, which possesses no detectable pre-crRNA processing activity, yet catalyzed complete degradation of substrates guided by its cognate full-length pre-crRNA. While the previously characterized homologs LshCas13a (Abudayyeh et al., Science. 2016 Aug. 5; 353(6299):aaf5573) and LbuCas13a both exhibit a preference for uridine 5' to the scissile bond, products of different lengths generated by the other homologs suggests that different active site nucleotide preferences may exist within this protein family (FIG. 43B).

To further probe the trans-ssRNA cleavage nucleotide preferences of the Cas13a homologs, the trans-cleavage capacity of these enzymes was measured using 5-mer homopolymers of A, C, G, and U as substrates. Six homologs were able to cleave these short substrates (FIG. 42C; FIG. 43C; FIG. 50 (Table 5)). Four of the homologs, LbuCas13a, LwaCas13a, HheCas13a, and PprCas13a, exhibited preferred cleavage of the homouridine substrate, although secondary preferences were observed for the homologs with the highest activities (FIG. 42C; FIG. 43D). In contrast, LbaCas13a and EreCas13a preferred homoadenosine, in agreement with biochemically mapped cleavage sites on longer targets (FIG. 43B). Identical product generation from these long substrates by CamCas13a is consistent with adenosine preference by this clade of the Cas13a family tree (FIG. 42, FIG. 39; FIG. 43).

One notable difference between these enzymes was the rate at which trans-ssRNA cleavage reaches saturation under the tested conditions of equimolar ssRNA activator and Cas13a:crRNA interference complex. These enzymatic differences could have dramatic effects on Cas13a's biological role. The variance in trans-ssRNA cleavage within the Cas13a homolog family was quantified. A high-throughput screen utilizing a short fluorescent ssRNA reporter for RNA cleavage to account for both ssRNA activator binding and trans-ssRNA cleavage, the two core properties of Cas13a enzymes that contribute to total enzymatic output, was developed. To interrogate the sensitivity of each Cas13a homolog, decreasing amounts of complementary ssRNA activator were added to initiate the reaction, and the apparent rate of fluorescent ssRNA reporter cleavage was calculated from each of the resulting timecourses. While the calculated rates are a convolution of the ssRNA activator binding affinity and the catalytic turnover rate for each of the enzymes, they give a relative measure of cleavage activity that is comparable across homologs.

Five homologs (LbuCas13a, LwaCas13a, LbaCas13a, HheCas13a and PprCas13a) demonstrated sufficiently detectable cleavage activity within this assay for reproducible analysis. Of these five homologs, LbuCas13a exhibited the most sensitivity, with detectable reporter cleavage in the presence of only 10 fM complementary activator (FIG. 42D). Only two homologs, LwaCas13a and PprCas13a, displayed enough activity to detect the activator in the picomolar range with sensitivities of 10 pM and 100 pM, respectively. LbaCas13a and HheCas13a were much less sensitive, only becoming active at nanomolar levels of reporter, which is close to equimolar relative to the Cas13a complex. Since this assay relies on a substantial number of trans-cleavage events to produce detectable fluorescence, it can be assumed that the three homologs unable to produce detectable signal above background despite similar cleavage site preferences (EreCas13a, CamCas13a, and LshCas13a) possess even less sensitive complementary target sensitivities. The remarkably broad range in sensitivities ($\sim 10^7$-fold) suggests a diverse capacity of Cas13a enzymes to protect a host organism from foreign RNA.

CRISPR Repeat Sequence Determines Non-Cognate Pre-crRNA Processing

The dual activities of Cas13a provide an opportunity to study the interdependence of pre-crRNA processing and targeting between distinct Type VI-A CRISPR operons. To determine the substrate requirements for both activities, the extent to which different homologs can recognize non-cognate crRNAs for guide processing and targeting was tested. Initially, it was attempted to predict bioinformatically the likely crRNA exchangeability through phylogenetic analysis of the Cas13a family and crRNA similarities. This analysis suggested that two distinct clades of homologs exist, termed alpha and beta for clarity (Stamatakis, Bioinformatics. 2014 May 1;30(9):1312-3) (FIG. 44A). Five of the purified homologs exist outside of these clades with ambiguous ancestral relationships; it was questioned if the pre-crRNA (CRISPR repeat) sequence might dictate functional orthogonality. Due to the short and structured content of the CRISPR repeats, a pairwise sequence alignment score matrix was used to build a hierarchical clustering relationship between the CRISPR repeats to score the variation across the family (Burstein et al., Nat Commun. 2016 Feb. 3; 7:10613). Surprisingly, this analysis pointed to the existence of two crRNA clusters, overlapping but distinct from the protein clades determined by the amino acid sequences (FIGS. 44B and 44C). While cluster 1 crRNAs correlate well with a subset of the alpha-clade proteins and all the beta-clade associated crRNAs are within cluster 2, the homologs with ambiguous phylogenetic relationships are split across the two clusters (FIG. 44C).

Figure 44F:
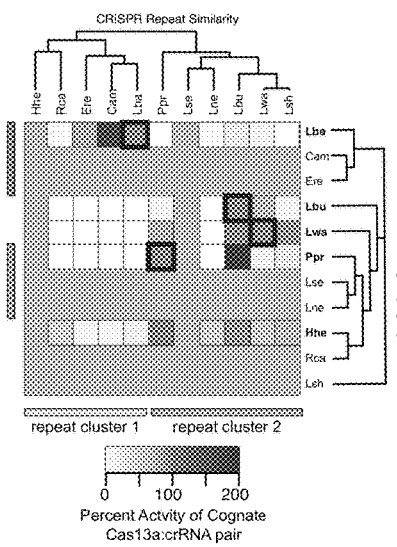

Unable to easily predict Cas13a:crRNA orthogonality using bioinformatic analysis alone, the extent of functional exchangeability between non-cognate crRNAs for both processing and trans-ssRNA target cleavage by each of the Cas13a homologs was tested (FIGS. 44D and 44F). For pre-crRNA processing, it was found that the crRNA clusters defined by the pairwise sequence comparisons predicted their ability to be processed by their associated Cas13a proteins (FIG. 44D). For example, pre-crRNAs from cluster 1 are only processed by the proteins of clade alpha and vice versa for cluster 2 and clade beta. In contrast, the protein classification is less predictive, as most of the ambiguously classified proteins could process sequences from repeat cluster 2, independent of where their repeat sequences were clustered.

Three homologs (PprCas13a, HheCas13a, and Rca13a) were pre-crRNA processing outliers with respect to their position within the crRNA clusters. HheCas13a was unable to cleave any non-cognate pre-crRNAs, and conversely, no homolog, including HheCas13a, processed the Hhe pre-crRNA. This suggests that the inability of HheCas13a to process its cognate pre-crRNA reflects not just the divergent repeat sequence (FIG. 38; FIG. 39), but also the loss of pre-crRNA processing activity within the protein. In contrast, the deviating activity of PprCas13a and RcaCas13a is explained by crRNA repeat sequence divergence. PprCas13a and RcaCas13a process their own crRNAs, yet both also process the crRNA repeat cluster 2 non-cognate sequences. The PprCas13a crRNA repeat sequence differs from the other cluster 2 crRNA repeats across the 5' flanking region cleavage site, suggesting greater substrate flexibility for pre-crRNA processing by PprCas13a. Similarly, a distinguishing sequence feature of the RcaCas13a crRNA is an extended six-base pair stem-loop relative to the standard five-base pair stem-loop present in crRNAs of the rest of the family. It is worth noting that the positional substitution tolerance within each crRNA repeat for Cas13a pre-crRNA processing is consistent with mutation studies of the LbuCas13a:crRNA complex, discussed above, and recent structural insights obtained of the LshCas13a:crRNA complex (Liu et al., Cell 2017 Jan. 12;168(1-2):121-134.e12). Overall, these results suggest that the sequence of a Type VI-A CRISPR repeat dictates its capacity for pre-crRNA processing by the Cas13a family. However, homologs that evolved in the presence of divergent repeats (PprCas13a and RcaCas13a) retain the capacity to process other cluster 2 sequences.

Two Subfamilies of Functionally Orthogonal Cas13a Enzymes

Whether the pre-crRNA processing exchangeability clusters defined in FIG. 44D were competent for directing trans-ssRNA cleavage by non-cognate Cas13a homologs was investigated. To study Cas13a-mediated trans-ssRNA cleavage directed by non-cognate pre-crRNAs and mature crRNAs, the described fluorescence assay described in the above Examples was modified, and the analysis was limited to the five homologs that exhibited significant cleavage activity in the ssRNA-cleavage experiments (see FIG. 42C). Broadly, these results mirrored the pre-crRNA processing results, with the crRNA repeat cluster identity determining functional groups, but with some striking contrasts consistent with processing and targeting being independent enzymatic activities (FIGS. 44E and 44F). For instance, the Ppr pre- and mature crRNA can direct ssRNA cleavage by non-cognate proteins LwaCas13a and LbuCas13a, despite their inability to process these pre-crRNAs. Another surprise is the promiscuity of HheCas13a, which is directed by all cluster 2 pre- and mature crRNAs for trans-ssRNA cleavage, despite lacking pre-crRNA processing activity with any of these guides. This suggests that crRNA maturation is not required for trans-ssRNA cleavage, an observation in agreement with findings that LbuCas13a pre-crRNA processing-deficient mutants possess unaffected trans-ssRNA cleavage capacity.

Figure 45A:
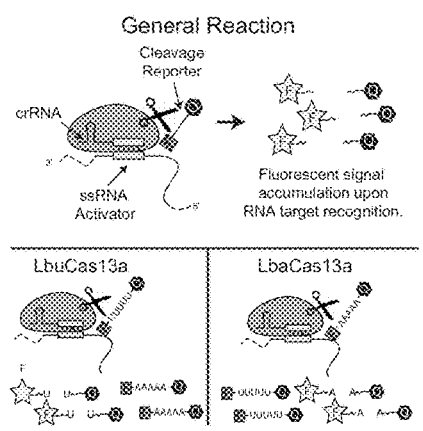
FIG. 45A-45C depict functional validation of orthogonal Cas13a subfamilies for RNA detection.
Figure 45B:
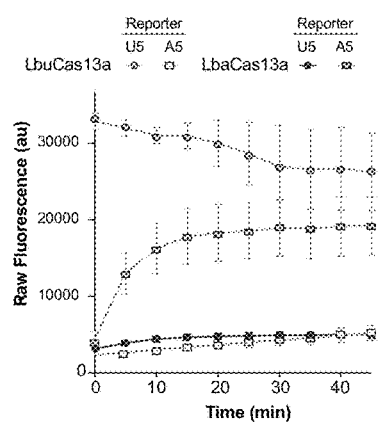
Figure 45C:
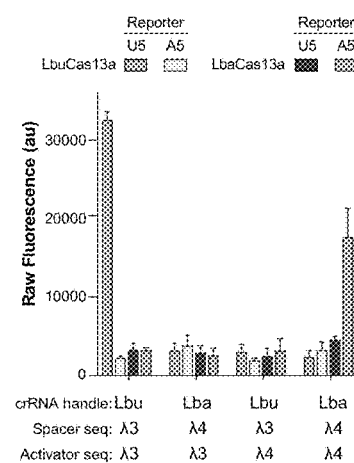

Comparison of crRNA exchangeability for both pre-crRNA processing and trans-ssRNA cleavage defines two functionally orthogonal subfamilies within the Cas13a protein family. The first group (e.g., LbuCas13a) has wide promiscuity for both pre-crRNA processing and trans-ssRNA cleavage directed by crRNAs from across the protein family. This polyphyletic group also shows a preference for uridine within the trans-ssRNA cleavage active site. The second group (e.g., LbaCas13a), defined both by crRNA and protein sequences, has a distinct crRNA exchangeability profile and preferentially cleaves at adenosines during trans-ssRNA target cleavage. To test orthogonal reactivities of these Cas13a subfamilies, it was verified that LbuCas13a and LbaCas13a cleaved homo-A or homo-U ssRNA reporters, respectively (FIGS. 45A and 45B). While the different probes generated similar amounts of fluorescent signal, it should be noted that substantially different quantities of ssRNA activator were added due the differential sensitivities of the homologs (10 pM vs 1 nM for LbuCas13a and LbaCas13a, respectively). To verify orthogonality, a panel of control reactions with all possible non-cognate combinations between crRNA, activator and reporter were tested, with no substantial signal detected except for the cognate combinations (FIG. 45C). Taken together, these results define distinct Cas13a homologs that can function in parallel within the same system.

Pre-crRNA Processing Enhances Targeting Efficiencies within the Context of a CRISPR Array One puzzling finding of this study is the lack of a stringent requirement for mature crRNA to trigger the subsequent trans-ssRNA target cleavage reaction by Cas13a. Additionally, processing deficient mutants of LbuCas13a maintain similar efficiencies of trans-ssRNA cleavage, even when directed by a pre-crRNA instead of a mature crRNA (FIG. 46; FIG. 47). This led to the hypothesis that the role of pre-crRNA processing within Type VI CRISPR loci is not necessarily for efficient ssRNA targeting but instead serves to liberate each crRNA from the confines of a long CRISPR array transcript. It was questioned whether pre-crRNA processing might relieve RNA folding constraints and potential steric hindrance of neighboring Cas13a:crRNA-spacer species during crRNA loading and/or ssRNA targeting. To test this, the efficiency of trans-ssRNA cleavage directed by a CRISPR array, using either wildtype LbuCas13a or a pre-crRNA processing-inactive mutant, was compared.

Figure 46A:
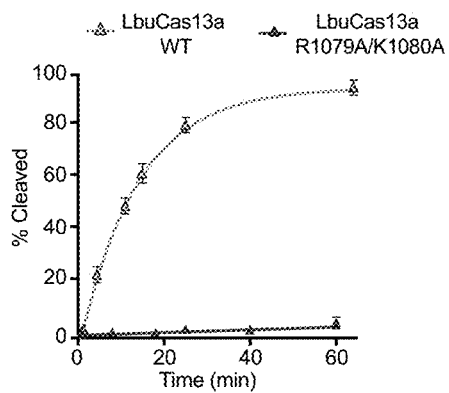
FIG. 46A-46D depict crRNA array processing by wild-type (WT) LbuCas13a and LbuCas13a R1079A/K1080A double mutant.
Figure 46B:
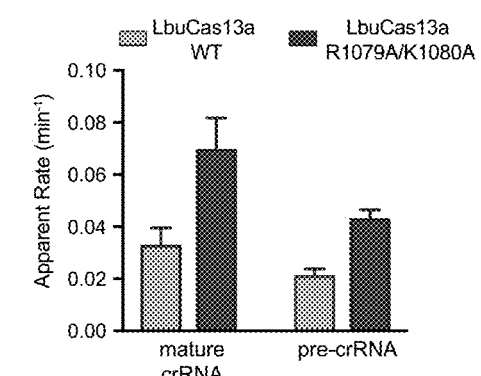
Figure 46C:
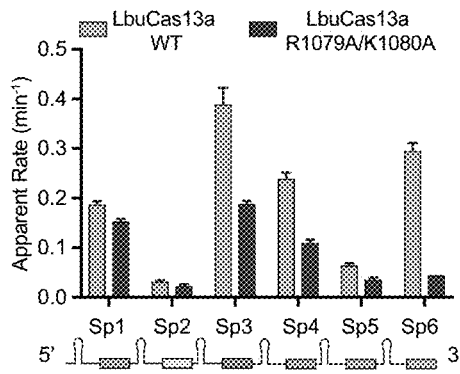
Figure 46D:
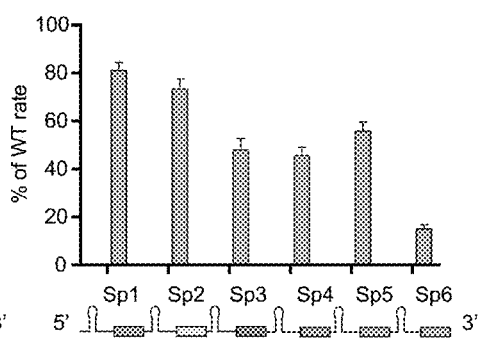
Figure 55A:
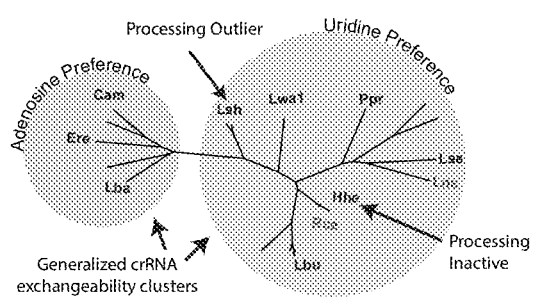
FIG. 55A-55B presents a model for Type VI-A CRISPR system function.
Figure 55B:
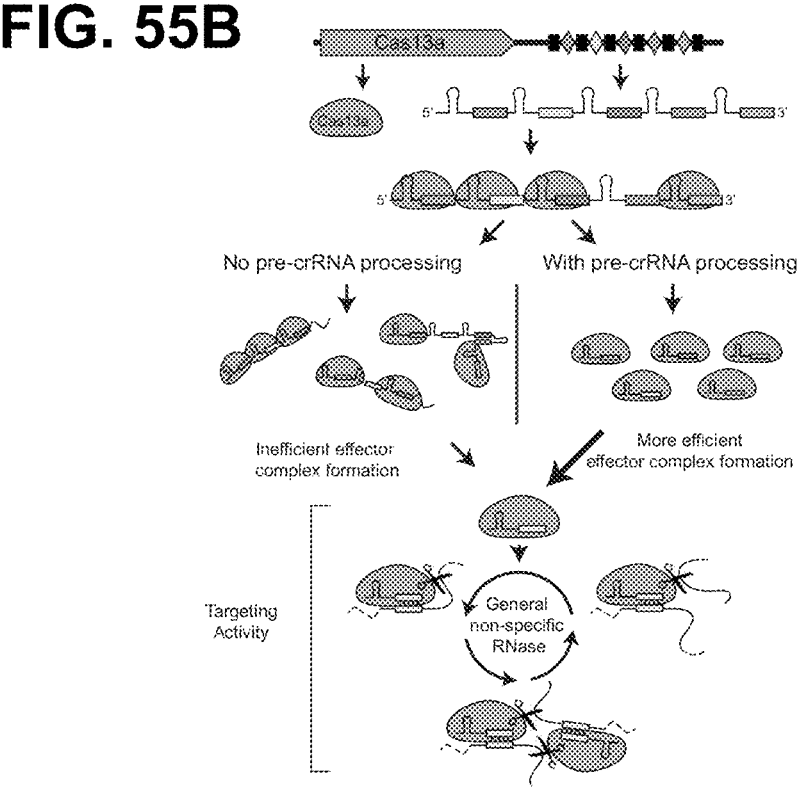

Since all processing-defective single point mutants of LbuCas13a (FIG. 40) retained low levels of pre-crRNA processing activity, a double mutant (R1079A/K1080A) was created that possessed no detectable processing activity, yet retained trans-ssRNA cleavage efficiencies similar to or greater than wildtype LbuCas13a (FIGS. 46A and 46B). This double mutant, and the wildtype LbuCas13a enzyme, were tested for ssRNA cleavage in the presence of a target RNA and a small CRISPR array transcript consisting of six distinct repeat-spacer units (FIGS. 46C and 46D). The rate of trans-ssRNA cleavage by the crRNA-processing inactive mutant was significantly reduced for all spacer sequences within the array (one-sided t-test: $p<0.001$ for all pairs). The reduced activity compared to wildtype LbuCas13a is more pronounced with each successive spacer within the array, with the last spacer directing cleavage with a rate that is only 15% of that catalyzed by the wildtype enzyme. This finding suggests that while pre-crRNA processing is not necessary for targeting, it enhances activity by liberating crRNAs from the CRISPR array, leading to a revised model for Type VI CRISPR systems (FIG. 55).

FIG. 38A-38C. Pre-crRNA processing is broadly conserved within the Cas13a protein family. (A) Schematic of crRNA biogenesis pathway catalyzed by Cas13a. pre-crRNA transcripts are cleaved by Cas13a to generate mature crRNAs. Below, a schematic of a pre-crRNA highlighting important functional features. (B) Alignment of the 5' portion of CRISPR repeat sequences from the studied type VI CRISPR systems highlighting the pre-crRNA cleavage site. Mapped cut cleavage sites are shown as red bars. Deviations from the Lbu crRNA-repeat sequence are noted in black text. Lowercase g's were required for transcription purposes and are not part of the native crRNA repeat sequences. Full CRISPR repeat sequence is diagrammed in FIG. 39B. (C) Representative gel of Cas13a-mediated pre-crRNA cleavage by 9 Cas13a homologs after 60 min incubation with 5'-radiolabelled pre-crRNA substrates.

FIG. 39A-39C. CRISPR loci and crRNA repeat architecture for Cas13a homologs used in this study (A) Maximum-likelihood phylogenetic tree of Cas13a proteins with diagrams of TypeVI-A loci adapted from (Shmakov et al., Mol Cell. 2015 Nov. 5; 60(3):385-97). Cas13a ORFs shown in teal. CRISPR arrays depicted as black boxes (repeats), yellow diamonds (spacers), and spacer array size for larger arrays noted above. ORFs of interest surrounding the loci are noted with the following abbreviations: T—Toxin, AT—antitoxin and TP—transposase. (B) Manual alignment of CRISPR repeat sequences from homologs used. pre-crRNA processing cleavage sites noted by red lines. Deviations from the Lbu crRNA-repeat sequence are noted in black text. Lowercase g's were required for transcription purposes and are not part of the native crRNA repeat sequences. Two separate Hhe crRNA sequences were tested, the first containing the native sequence and a second with four nucleotide extension to extend the atypically short native repeat. Neither crRNA repeat was cleaved by HheCas13a under any of the studied conditions. (C)pre-crRNA processing assay with HheCas13a on native crRNA repeat sequence across variable salt and pH conditions. No cleavage products were observed.

FIG. 40A-40F. Identification of residues important for pre-crRNA cleavage by LbuCas13a (A) LbuCas13a domain organization schematic with domains annotated based off a LshCas13a crystal structure (Liu et al., Cell 2017 Jan. 12;168(1-2):121-134.e12). Multiple-sequence amino acid alignment of (B) the local region in Cas13a's helical 1 domain implicated in pre-crRNA processing by studies on LshCas13a, and (C) the region within in Cas13a's HEPN2 domain implicated in pre-crRNA processing by studies on LbuCas13a. See FIG. 41 for full family tree alignment of these regions and FIG. 57 for a complete protein alignment.

Residues whose mutation severely affects pre-crRNA processing are marked by yellow diamonds, and residues whose mutation minimally affect pre-crRNA processing marked with teal diamonds. Symbols above the LbuCas13a sequences correspond to mutations made to LbuCas13a, and symbols below the LshCas13a sequence correspond to mutations made to LshCas13a by Liu et al., Cell 2017 Jan. 12;168(1-2):121-134.e12. Coloration of the matrix alignment denotes residue conservation using the ClustalX scheme, with darker hues indicating the strength of the conservation. pre-crRNA processing under single turnover conditions measured for mutants in (D) the helical 1 domain, and (E) the HEPN2 domain. Quantified data were fitted with single-exponential decays with calculated pseudo-first-order rates constants (kobs) (mean±s.d., n=3) as follows: Lbu WT 0.074±0.003 min-1, E299A 0.071±0.005 min-1, K310A 0.071±0.003 min-1, R311A 0.054±0.007 min-1, N314A 0.029±0.008 min-1, R1079A 0.009±0.007 min-1, D1078A 0.023±0.002 min-1, K1080A 0.016±0.004 min-1, and K1087A 0.076±0.007 min-1, while R1072A and K1082A could not be fitted. (F) Representative gel of pre-crRNA processing of LshCas13a, LwaCas13a, and LbuCas13a pre-crRNAs by LbuCas13a, LshCas13a and LwaCas13a proteins using standard conditions.

Hydrolysis ladder in rightmost lane allows for relative size comparisons, although subtle sequences differences across the three pre-crRNAs will alter the migration of these small fragments.

FIG. 41A-41B. Full Alignments of Helical 1 and HEPN Domains (A-B) Multiple sequence alignment of 19 Cas13a family members across (A) the helical 1 domain and (B) the HEPN2 domain. GI accession numbers are listed before each species name. Coordinates based on LbuCas13a sequence listed above the alignment and LshCas13a sequence coordinates are listed below. Mutations tested in this study are noted above the alignment by yellow and teal diamonds corresponding to alanine substitutions that negatively impacted the pre-crRNA processing reaction or those with minimal effects on pre-crRNA processing, respectively. Mutations tested by (Liu et al., Cell 2017 Jan. 12;168(1-2): 121-134.e12) are depicted below the LshCas13a sequence. Conservations scores were calculated by Jalview using the AMAS method.

FIG. 42A-42D. Members of the Cas13a protein family cleave ssRNA with a range of efficiencies (A) Schematic of ssRNA-targeting by Cas13a. For simplicity, trans-ssRNA cleavage was the focus of study. (B) Representative gel of Cas13a mediated trans-ssRNA cleavage by all ten homologs after 60 min incubation. Cas13a:crRNA complexes were formed as described in the methods using mature crRNA products with a final RNP complex concentration of 50 nM. <1 nM radiolabeled trans-ssRNA target was added to initiate reaction in the presence and absence of 50 nM unlabeled, crRNA-complementary ssRNA activator. Weak trans-ssRNA cleavage activity was observed by LshCas13a with product bands noted by double arrows to the right. (C) Heat map reporting Cas13a-catalyzed trans-ssRNA cleavage percentages for each 5-mer homopolymer ssRNA substrate, for six different Cas13a. Assay conditions were identical to part (B), except LbuCas13a and LwaCas13a which were incubated for 5 min instead of 60 min. (n=3, values with associated errors presented in FIG. 51 (Table 6). (D) Apparent cleavage rates of a fluorescent ssRNA reporter by five homologs across a range of ssRNA activator concentrations. Cas13a:crRNA complexes were pre-incubated at a 2:1 ratio respectively with a final active complex concentration of 50 nM. Complementary ssRNA activator and fluorescent ssRNA cleavage reporter were added to initiate reactions. Normalized reporter signal curves timecourses were fitted with single-exponential decays and the apparent rates are plotted (n=3). Some conditions plateaued before first measured time-point therefore their rates are minimally assumed to be 0.5 min-1 and are labeled with a * in the chart.

FIG. 43A-43D. trans-ssRNA cleavage by Cas13a homologs (A) Time course analysis trans-ssRNA cleavage by ten different Cas13a homlogs in the presence and absence of ssRNA activator. Time points were taken at 1, 10 and 60 min. ssRNA-activator specific cleavage products are noted for LbuCas13a, LwaCas13a, LbaCas13a, EreCas13a, HheCas13a, PprCas13a, CamCas13a, and LshCas13a. Dotted line denotes boundary between separate PAGE gels. (B) Mapped trans-ssRNA cleavage sites across multiple cleavage reactions for four Cas13a homologs. Different cleavage patterns are noted by red arrows. It appears LbaCas13a and EreCas13a may have a adenosine preference, while LwaCas13a appears to be more promiscuous with respect to nucleotide preference. (C-D) Representative trans-ssRNA cleavage gels of homopolymer ssRNA substrates by five Cas13a homologs.

FIG. 44A-44F. crRNA exchangeability within the Cas13a family (A) Maximum-likelihood phylogenetic tree of Cas13a proteins. Homologs used in this study are bolded and clades are highlighted. Bootstrapped values are located in FIG. 39. (B) Symmetrical similarity score matrix for CRISPR repeats from homologs used in this study. Rows and columns are ordered by CRISPR repeat clustering. (C) Asymmetrical similarity score matrix for CRISPR repeats from homologs used in this study. The same pairwise scores are presented here as in (B), except the rows are reordered to correspond to the Cas13a phylogenetic tree. (D-F) Functional activity matrix for (D) pre-crRNA processing by non-cognate proteins, (E) trans-ssRNA cleavage directed by pre-crRNAs, and (F) trans-ssRNA cleavage directed by mature crRNAs. Processing assays were performed using standard conditions and 60 min reaction endpoints were analyzed. trans-ssRNA cleavage assays were performed using the fluorescent ssRNA reporter assay with fitted initial rates. ssRNA activator concentrations were as follows: LbuCas13a:100 pM, LwaCas13a:100 pM, PprCas13a:100 nM, LbaCas13a:10 nM, and HheCas13a:100 nM. Initial rates were fit across three replicates to account for differences in fluorescence plateau values and normalized to each Cas13a:crRNA cognate pair. See FIGS. 52, 53, and 54 (Tables 7, 8, and 9, respectively) for numerical values and associated errors (n=3).

FIG. 45A-45C. Functional validation of orthogonal Cas13a subfamilies for RNA detection (A) Schematic of the RNA detection assay modified to use fluorescent homopolymer ssRNA reporter substrates to assay trans-ssRNA cleavage activation by either LbuCas13a or LbaCas13a. (B) Timecourse of raw fluorescence measurements generated by homopolymer reporters incubated with either LbuCas13a: Lbu-crRNA: 10 pM ssRNA activator or LbaCas13a: LbacrRNA: 1 nM ssRNA activator (mean±s.d., n=3). (C) Raw fluorescence measurements generated by the fluorescent homopolymer ssRNA reporters across a panel of crRNA, ssRNA activator, and Cas13a protein combinations (mean±s.d., n=3).

FIG. 46A-46D. Deciphering the role of crRNA array processing for LbuCas13a (A) Quantified timecourse data of pre-crRNA processing assays for R1079A/K1080A mutant compared to wildtype LbuCas13a. Quantified data was fitted to single-exponential decays and pseudo-first-order rate constant (kobs) (mean±s.d., n=3) for LbuCas13a WT of 0.074±0.003 min-1, while the R1079A/K1080A mutant could not be fit with sufficient confidence to yield a rate constant. (B) Apparent rate of fluorescent reporter by LbuCas13a wildtype and R1079A/K1080A processing inactive mutant as directed by pre-crRNA and mature crRNAs. Cas13a:RNA complexes were pre-incubated for 60 min at a 1:1 ratio, and then 10 pM of activator and 150 nM reporter were added to initiate reaction. (mean±s.d., n=3) (C) Apparent rates of fluorescent ssRNA reporter cleavage by 300 nM wildtype LbuCas13a or R1079A/K1080A pre-crRNA processing inactive mutant as directed by 50 nM of a CRISPR array containing six crRNA repeat-spacers. Each bar group represents the addition of 100 pM of a distinct ssRNA activator sequence complementary to schematized positions within the CRISPR array indicated below each bar group. Each rate is fitted from data from three biological replicates and the standard deviation of the rate is depicted. Mutant protein rate is statistically different from the wildtype LbuCas13a for all spacer positions (one-sided t-test: $p<0.001$). (D) Data from (C) depicted as a percentage of wildtype LbuCAs13a activity demonstrating the positional effect of the decreased trans-ssRNA targeting efficiencies by the pre-crRNA processing inactive mutant.

Figure 47A:
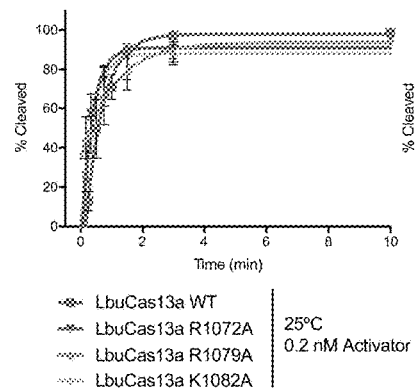
FIG. 47A-47C depict trans-cleavage by LbuCas13a point mutants in regions implicated in pre-crRNA processing.
Figure 47B:
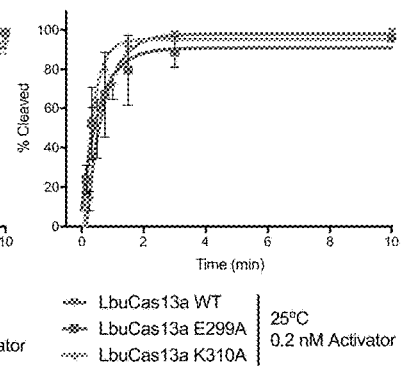
Figure 47C:
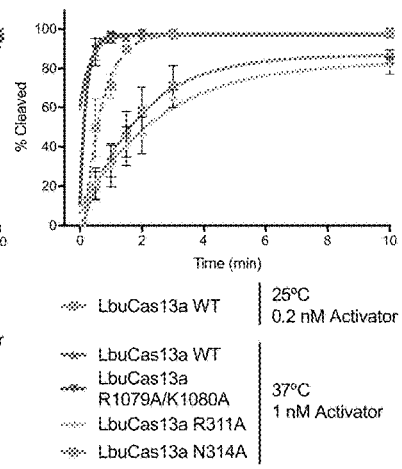

FIG. 47A-47C. trans-cleavage by LbuCas13a point mutants in regions implicated in pre-crRNA processing. (A-C) trans-ssRNA cleavage by various pre-crRNA processing 'implicated' point mutants of LbuCas13a. Cleavage reactions were performed with 50 nM Cas13a:crRNA at either 25° C. or 37° C. with 0.2 nM or 1 nM ssRNA activator as noted. Lower temperature and activator concentrations were used to slow down reaction kinetics for more accurate measurements. Fitted curves are single-exponential decays with calculated pseudo-first-order rates constants (mean±s.d., n=3) as follows: 25° C. conditions: Lbu WT 1.76±0.24 min-1, K299A 1.72±0.65 min-1, K310A 3.19±0.27 min-1, R1072A 2.95±0.53 min-1, R1079A 0.93±0.28 min-1, and K1082A 2.64±0.63 min-1 and 37° C. conditions: R311A 0.39±0.09 min-1, and N314A 0.54±0.11 min-1, while the wildtype and processing inactive mutant (R1079A/K1080A) plateaued too quickly for an accurate rate measurement: WT 2.95±1.97 min-1, and R1079A/K1080A 4.86±4.99 min-1.

Figure 48A:
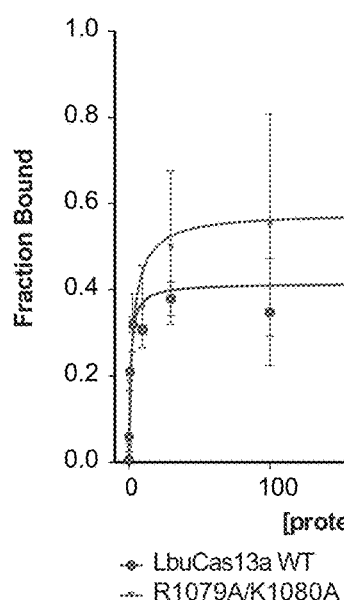
Figure 48B:
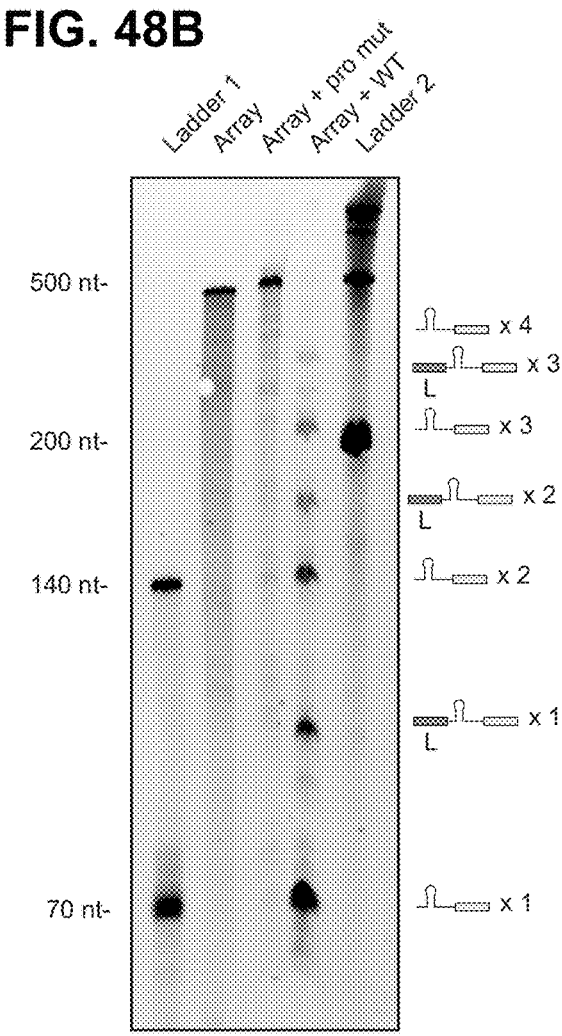

FIG. 48A-48B. crRNA processing inactive mutant R1079A/K1080A retains similar crRNA binding affinity and does not process a pre-cRNA array (A) Filter binding assays were conducted as described in the methods to determine the binding affinity of mature crRNA to LbuCas13a WT and LbuCas13a R1079A/K1080A. The quantified data were fit to standard binding isotherms. Measured dissociation constants from three independent experiments (mean±sd) were 1.21±0.57 nM (LbuCas13a WT), and 3.11±0.89 nM (LbuCas13a R1079A/K1080A). (B) pre-cRNA processing assay using a six-mer CRISPR array as the substrate with LbuCas13a and LbuCas13a R1079A/K1080A mutant along with various size markers. Product identities are depicted to the right of the gel. Due to an additional leader region that was occasionally not processed, additional sized products occasionally occurred as noted.

FIG. 49 (Table 4). CRISPR repeat consensus sequences: For homologs with multiple CRISPR loci within 10 kb of the Cas13a containing operon (RcaCas13a, LbaCas13a and EreCas13a), or long arrays with repeat variations (PprCas13a), multiple crRNA repeat sequences are listed with mutations highlighted in red text. For PprCas13a, the first crRNA repeat at the leader side of the array was chosen for this study. For RcaCas13a, LbaCas13a and EreCas13a, the crRNA repeat sequences analyzed for two factors to chose a representative crRNA for this study (1): the length of the array, and (2) capacity to direct trans-ssRNA cleavage by the cognate Cas13a protein. Sequences used in the main text are noted in the last column.

FIG. 50 (Table 5). *Oligo ID—an index number to maintain consistency for RNA substrates used in this study. **Source abbreviations: SS—single-stranded DNA oligonucleotide template was used for in-vitro transcription, HH PCR—in-vitro transcription template is a PCR product of overlapping oligonucleotides including a Hammerhead ribozyme template sequence, IDT—synthesized by IDT, PCR—in-vitro transcription template amplified from plasmid.

FIG. 51 presents Table 6. FIG. 52 presents Table 7. FIG. 53 presents Table 8. FIG. 54 presents Table 9.

FIG. 55. A revised model for Type VI-A CRISPR system function (A) Graphical summary of key findings in this study. Homologs used in this study are indicated with abbreviations in bold, with trans-ssRNA cleavage inactive homologs depicted in grey. Colored circles highlight the two orthogonal Cas13a enzyme groups, as defined by their generalized crRNA exchangeability and trans-ssRNA cleavage substrate nucleotide preference. (B) Schematic depicting a revised model for Type VI-A CRISPR system function.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An in vitro acellular method for detecting one or more target RNAs, comprising one or more target sequences, in one or more lysed cell samples, the method comprising:
   a) contacting the one or more lysed cell samples with (i), (ii), and (iii) to generate an in vitro acellular reaction:
      i) a Cas13a polypeptide;
      ii) at least one guide polynucleotide comprising a guide sequence capable of binding the one or more target sequences, and designed to form a complex with the Cas13a polypeptide; and
      iii) a labeled detector RNA comprising a non-target sequence, wherein the labeled detector RNA produces a different detectable signal when the labeled detector RNA is cleaved compared to when the labeled detector RNA is uncleaved; and
      wherein the one or more samples comprise more than 5 RNAs that differ from one another in nucleotide sequence, and
      wherein the complex comprising the Cas13a polypeptide exhibits collateral RNase activity and trans cleaves the non-target sequence of the labeled detector RNA in the presence of the one or more target RNAs; and
   b) detecting whether the one or more target RNAs was present in the one or more lysed cell samples by measuring the different detectable signal from cleavage of the non-target sequence of the labeled detector RNA in the in vitro acellular reaction.

2. The method of claim 1, wherein the labeled detector RNA comprises a quencher/fluorophore pair.

3. The method of claim 1, wherein a sample of the one or more samples is a biological sample.

4. The method of claim 1, wherein a target RNA of the one or more target RNAs is from a virus.

5. The method of claim 4, wherein the virus is a Hepatitis virus, Hepatitis A virus, Hepatitis B virus, or Hepatitis C virus.

6. The method of claim 4, wherein the virus is a Herpes virus, Herpes simplex virus 1, or a Herpes simplex virus 2.

7. The method of claim 4, wherein the virus is human papillomavirus.

8. The method of claim 4, wherein the virus is human immunodeficiency virus.

9. The method of claim 4, wherein the virus is Zika virus.

10. The method of claim 4, wherein the virus is an influenza virus.

11. The method of claim 4, wherein the virus is rabies virus, cytomegalovirus, human serum parvo-like virus, respiratory syncytial virus, varicella-zoster virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, Sendai virus, feline leukemia virus, reovirus, polio virus, simian virus 40, mouse mammary tumor virus, dengue virus, rubella virus, west Nile virus, or yellow fever virus.

12. The method of claim 1, wherein a target RNA of the one or more target RNAs is present in a sample of the one or more samples at from 1 copy per 10 non-target nucleic acids to 1 copy per $10^7$ non-target nucleic acids.

13. The method of claim 1, wherein a target RNA of the one or more target RNAs is present in a sample of the one or more samples at a concentration of from about 500 fM to about 1 nM.

14. The method of claim 1, wherein the labeled detector RNA comprises a fluorescence-emitting dye pair.

15. The method of claim 1, wherein the labeled detector RNA comprises a Förster resonance energy transfer (FRET) pair.

16. The method of claim 1, wherein detecting a signal comprises one or more of: gold nanoparticle-based detection, fluorescence polarization, colloid phase transition/dispersion, electrochemical detection, fluorescent signal detection, and semiconductor-based sensing.

17. The method of claim 1, wherein detecting a signal comprises a color detection method.

18. The method of claim 17, wherein the color detection method comprises a visual-based or sensor-based detection of the presence, absence, or ratio change of a color.

19. The method of claim 1, wherein detecting occurs within 60 minutes of said contacting.

20. The method according to claim 1, wherein said labeled detector RNA has a length of from 2 to 100 ribonucleotides.

21. The method according to claim 1, wherein said labeled detector RNA produces a greater amount of detectable signal when said labeled detector RNA is cleaved compared to when said labeled detector RNA is uncleaved.

22. The method according to claim 1, wherein said labeled detector RNA produces a lesser amount of detectable signal when said labeled detector RNA is cleaved compared to when said labeled detector RNA is uncleaved.

23. The method according to claim 1, wherein said labeled detector RNA comprises two moieties that when separated by cleavage of the labeled detector RNA produce a greater amount of the detectable signal than when said moieties are not separated by cleavage of the labeled detector RNA.

24. The method according to claim 1, wherein said labeled detector RNA comprises two moieties that when separated by cleavage of the labeled detector RNA produce a different detectable signal than when said moieties are not separated by cleavage of the labeled detector RNA.

25. The method according to claim 1, wherein the measuring does not comprise running a labeled detector RNA on a gel.

26. The method according to claim 1, wherein the measuring comprises measuring the amount of detectable signal from the labeled detector RNA in the in vitro acellular reaction; and wherein the measuring is not dependent on comparing the size of the cleaved labeled detector molecule to the size of the uncleaved labeled detector molecule.

* * * * *

SEQUENCE LISTING

<160> NUMBER OF SEQ ID NOS: 26

<210> SEQ ID NO 1
<211> LENGTH: 1120
<212> TYPE: PRT
<213> ORGANISM: Listeria seeligeri

<400> SEQUENCE: 1

Met Trp Ile Ser Ile Lys Thr Leu Ile His His Leu Gly Val Leu Phe
1               5                   10                  15

Phe Cys Asp Tyr Met Tyr Asn Arg Arg Glu Lys Lys Ile Ile Glu Val
            20                  25                  30

-continued

Lys Thr Met Arg Ile Thr Lys Val Glu Val Asp Arg Lys Lys Val Leu
           35                  40                  45

Ile Ser Arg Asp Lys Asn Gly Gly Lys Leu Val Tyr Glu Asn Glu Met
    50                  55                  60

Gln Asp Asn Thr Glu Gln Ile Met His His Lys Lys Ser Ser Phe Tyr
65                  70                  75                  80

Lys Ser Val Val Asn Lys Thr Ile Cys Arg Pro Glu Gln Lys Gln Met
               85                  90                  95

Lys Lys Leu Val His Gly Leu Leu Gln Glu Asn Ser Gln Glu Lys Ile
                100                 105                 110

Lys Val Ser Asp Val Thr Lys Leu Asn Ile Ser Asn Phe Leu Asn His
            115                 120                 125

Arg Phe Lys Lys Ser Leu Tyr Tyr Phe Pro Glu Asn Ser Pro Asp Lys
    130                 135                 140

Ser Glu Glu Tyr Arg Ile Glu Ile Asn Leu Ser Gln Leu Leu Glu Asp
145                 150                 155                 160

Ser Leu Lys Lys Gln Gln Gly Thr Phe Ile Cys Trp Glu Ser Phe Ser
                165                 170                 175

Lys Asp Met Glu Leu Tyr Ile Asn Trp Ala Glu Asn Tyr Ile Ser Ser
            180                 185                 190

Lys Thr Lys Leu Ile Lys Lys Ser Ile Arg Asn Asn Arg Ile Gln Ser
        195                 200                 205

Thr Glu Ser Arg Ser Gly Gln Leu Met Asp Arg Tyr Met Lys Asp Ile
    210                 215                 220

Leu Asn Lys Asn Lys Pro Phe Asp Ile Gln Ser Val Ser Glu Lys Tyr
225                 230                 235                 240

Gln Leu Glu Lys Leu Thr Ser Ala Leu Lys Ala Thr Phe Lys Glu Ala
                245                 250                 255

Lys Lys Asn Asp Lys Glu Ile Asn Tyr Lys Leu Lys Ser Thr Leu Gln
            260                 265                 270

Asn His Glu Arg Gln Ile Ile Glu Glu Leu Lys Glu Asn Ser Glu Leu
        275                 280                 285

Asn Gln Phe Asn Ile Glu Ile Arg Lys His Leu Glu Thr Tyr Phe Pro
    290                 295                 300

Ile Lys Lys Thr Asn Arg Lys Val Gly Asp Ile Arg Asn Leu Glu Ile
305                 310                 315                 320

Gly Glu Ile Gln Lys Ile Val Asn His Arg Leu Lys Asn Lys Ile Val
                325                 330                 335

Gln Arg Ile Leu Gln Glu Gly Lys Leu Ala Ser Tyr Glu Ile Glu Ser
            340                 345                 350

Thr Val Asn Ser Asn Ser Leu Gln Lys Ile Lys Ile Glu Glu Ala Phe
        355                 360                 365

Ala Leu Lys Phe Ile Asn Ala Cys Leu Phe Ala Ser Asn Asn Leu Arg
    370                 375                 380

Asn Met Val Tyr Pro Val Cys Lys Lys Asp Ile Leu Met Ile Gly Glu
385                 390                 395                 400

Phe Lys Asn Ser Phe Lys Glu Ile Lys His Lys Lys Phe Ile Arg Gln
                405                 410                 415

Trp Ser Gln Phe Phe Ser Gln Glu Ile Thr Val Asp Asp Ile Glu Leu
            420                 425                 430

Ala Ser Trp Gly Leu Arg Gly Ala Ile Ala Pro Ile Arg Asn Glu Ile
    435                 440                 445

```
Ile His Leu Lys Lys His Ser Trp Lys Lys Phe Phe Asn Asn Pro Thr
    450                 455                 460

Phe Lys Val Lys Lys Ser Lys Ile Ile Asn Gly Lys Thr Lys Asp Val
465                 470                 475                 480

Thr Ser Glu Phe Leu Tyr Lys Glu Thr Leu Phe Lys Asp Tyr Phe Tyr
                485                 490                 495

Ser Glu Leu Asp Ser Val Pro Glu Leu Ile Ile Asn Lys Met Glu Ser
            500                 505                 510

Ser Lys Ile Leu Asp Tyr Tyr Ser Asp Gln Leu Asn Gln Val Phe
        515                 520                 525

Thr Ile Pro Asn Phe Glu Leu Ser Leu Leu Thr Ser Ala Val Pro Phe
530                 535                 540

Ala Pro Ser Phe Lys Arg Val Tyr Leu Lys Gly Phe Asp Tyr Gln Asn
545                 550                 555                 560

Gln Asp Glu Ala Gln Pro Asp Tyr Asn Leu Lys Leu Asn Ile Tyr Asn
                565                 570                 575

Glu Lys Ala Phe Asn Ser Glu Ala Phe Gln Ala Gln Tyr Ser Leu Phe
            580                 585                 590

Lys Met Val Tyr Tyr Gln Val Phe Leu Pro Gln Phe Thr Thr Asn Asn
        595                 600                 605

Asp Leu Phe Lys Ser Ser Val Asp Phe Ile Leu Thr Leu Asn Lys Glu
    610                 615                 620

Arg Lys Gly Tyr Ala Lys Ala Phe Gln Asp Ile Arg Lys Met Asn Lys
625                 630                 635                 640

Asp Glu Lys Pro Ser Glu Tyr Met Ser Tyr Ile Gln Ser Gln Leu Met
                645                 650                 655

Leu Tyr Gln Lys Lys Gln Glu Glu Lys Glu Lys Ile Asn His Phe Glu
            660                 665                 670

Lys Phe Ile Asn Gln Val Phe Ile Lys Gly Phe Asn Ser Phe Ile Glu
        675                 680                 685

Lys Asn Arg Leu Thr Tyr Ile Cys His Pro Thr Lys Asn Thr Val Pro
    690                 695                 700

Glu Asn Asp Asn Ile Glu Ile Pro Phe His Thr Asp Met Asp Asp Ser
705                 710                 715                 720

Asn Ile Ala Phe Trp Leu Met Cys Lys Leu Leu Asp Ala Lys Gln Leu
                725                 730                 735

Ser Glu Leu Arg Asn Glu Met Ile Lys Phe Ser Cys Ser Leu Gln Ser
            740                 745                 750

Thr Glu Glu Ile Ser Thr Phe Thr Lys Ala Arg Glu Val Ile Gly Leu
        755                 760                 765

Ala Leu Leu Asn Gly Glu Lys Gly Cys Asn Asp Trp Lys Glu Leu Phe
    770                 775                 780

Asp Asp Lys Glu Ala Trp Lys Lys Asn Met Ser Leu Tyr Val Ser Glu
785                 790                 795                 800

Glu Leu Leu Gln Ser Leu Pro Tyr Thr Gln Glu Asp Gly Gln Thr Pro
                805                 810                 815

Val Ile Asn Arg Ser Ile Asp Leu Val Lys Lys Tyr Gly Thr Glu Thr
            820                 825                 830

Ile Leu Glu Lys Leu Phe Ser Ser Asp Asp Tyr Lys Val Ser Ala
        835                 840                 845

Lys Asp Ile Ala Lys Leu His Glu Tyr Asp Val Thr Glu Lys Ile Ala
    850                 855                 860

Gln Gln Glu Ser Leu His Lys Gln Trp Ile Glu Lys Pro Gly Leu Ala
```

```
                865                 870                 875                 880

Arg Asp Ser Ala Trp Thr Lys Lys Tyr Gln Asn Val Ile Asn Asp Ile
                        885                 890                 895

Ser Asn Tyr Gln Trp Ala Lys Thr Lys Val Glu Leu Thr Gln Val Arg
                        900                 905                 910

His Leu His Gln Leu Thr Ile Asp Leu Leu Ser Arg Leu Ala Gly Tyr
                        915                 920                 925

Met Ser Ile Ala Asp Arg Asp Phe Gln Phe Ser Ser Asn Tyr Ile Leu
                        930                 935                 940

Glu Arg Glu Asn Ser Glu Tyr Arg Val Thr Ser Trp Ile Leu Leu Ser
        945                 950                 955                 960

Glu Asn Lys Asn Lys Asn Lys Tyr Asn Asp Tyr Glu Leu Tyr Asn Leu
                        965                 970                 975

Lys Asn Ala Ser Ile Lys Val Ser Lys Asn Asp Pro Gln Leu Lys
                        980                 985                 990

Val Asp Leu Lys Gln Leu Arg Leu  Thr Leu Glu Tyr Leu  Glu Leu Phe
                        995                1000                1005

Asp Asn  Arg Leu Lys Glu Lys  Arg Asn Asn Ile Ser   His Phe Asn
                1010                 1015                1020

Tyr Leu  Asn Gly Gln Leu Gly  Asn Ser Ile Leu Glu   Leu Phe Asp
                1025                 1030                1035

Asp Ala  Arg Asp Val Leu Ser  Tyr Asp Arg Lys Leu   Lys Asn Ala
                1040                 1045                1050

Val Ser  Lys Ser Leu Lys Glu  Ile Leu Ser Ser His   Gly Met Glu
                1055                 1060                1065

Val Thr  Phe Lys Pro Leu Tyr  Gln Thr Asn His His   Leu Lys Ile
                1070                 1075                1080

Asp Lys  Leu Gln Pro Lys Lys  Ile His His Leu Gly   Glu Lys Ser
                1085                 1090                1095

Thr Val  Ser Ser Asn Gln Val  Ser Asn Glu Tyr Cys   Gln Leu Val
                1100                 1105                1110

Arg Thr  Leu Leu Thr Met Lys
                1115                 1120

<210> SEQ ID NO 2
<211> LENGTH: 1159
<212> TYPE: PRT
<213> ORGANISM: Leptotrichia buccalis

<400> SEQUENCE: 2

Met Lys Val Thr Lys Val Gly Gly Ile Ser His Lys Lys Tyr Thr Ser
1               5                   10                  15

Glu Gly Arg Leu Val Lys Ser Glu Ser Glu Glu Asn Arg Thr Asp Glu
                20                  25                  30

Arg Leu Ser Ala Leu Leu Asn Met Arg Leu Asp Met Tyr Ile Lys Asn
            35                  40                  45

Pro Ser Ser Thr Glu Thr Lys Glu Asn Gln Lys Arg Ile Gly Lys Leu
        50                  55                  60

Lys Lys Phe Phe Ser Asn Lys Met Val Tyr Leu Lys Asp Asn Thr Leu
65                  70                  75                  80

Ser Leu Lys Asn Gly Lys Lys Glu Asn Ile Asp Arg Glu Tyr Ser Glu
                85                  90                  95

Thr Asp Ile Leu Glu Ser Asp Val Arg Asp Lys Lys Asn Phe Ala Val
                100                 105                 110
```

-continued

```
Leu Lys Lys Ile Tyr Leu Asn Glu Asn Val Asn Ser Glu Leu Glu
        115                 120                 125

Val Phe Arg Asn Asp Ile Lys Lys Leu Asn Lys Ile Asn Ser Leu
        130                 135                 140

Lys Tyr Ser Phe Glu Lys Asn Lys Ala Asn Tyr Gln Lys Ile Asn Glu
145                 150                 155                 160

Asn Asn Ile Glu Lys Val Glu Gly Lys Ser Lys Arg Asn Ile Ile Tyr
                165                 170                 175

Asp Tyr Tyr Arg Glu Ser Ala Lys Arg Asp Ala Tyr Val Ser Asn Val
            180                 185                 190

Lys Glu Ala Phe Asp Lys Leu Tyr Lys Glu Glu Asp Ile Ala Lys Leu
        195                 200                 205

Val Leu Glu Ile Glu Asn Leu Thr Lys Leu Glu Lys Tyr Lys Ile Arg
210                 215                 220

Glu Phe Tyr His Glu Ile Ile Gly Arg Lys Asn Asp Lys Glu Asn Phe
225                 230                 235                 240

Ala Lys Ile Ile Tyr Glu Glu Ile Gln Asn Val Asn Asn Met Lys Glu
                245                 250                 255

Leu Ile Glu Lys Val Pro Asp Met Ser Glu Leu Lys Lys Ser Gln Val
            260                 265                 270

Phe Tyr Lys Tyr Tyr Leu Asp Lys Glu Glu Leu Asn Asp Lys Asn Ile
        275                 280                 285

Lys Tyr Ala Phe Cys His Phe Val Glu Ile Glu Met Ser Gln Leu Leu
        290                 295                 300

Lys Asn Tyr Val Tyr Lys Arg Leu Ser Asn Ile Ser Asn Asp Lys Ile
305                 310                 315                 320

Lys Arg Ile Phe Glu Tyr Gln Asn Leu Lys Lys Leu Ile Glu Asn Lys
                325                 330                 335

Leu Leu Asn Lys Leu Asp Thr Tyr Val Arg Asn Cys Gly Lys Tyr Asn
            340                 345                 350

Tyr Tyr Leu Gln Asp Gly Glu Ile Ala Thr Ser Asp Phe Ile Ala Arg
        355                 360                 365

Asn Arg Gln Asn Glu Ala Phe Leu Arg Asn Ile Ile Gly Val Ser Ser
        370                 375                 380

Val Ala Tyr Phe Ser Leu Arg Asn Ile Leu Glu Thr Glu Asn Glu Asn
385                 390                 395                 400

Asp Ile Thr Gly Arg Met Arg Gly Lys Thr Val Lys Asn Asn Lys Gly
                405                 410                 415

Glu Glu Lys Tyr Val Ser Gly Glu Val Asp Lys Ile Tyr Asn Glu Asn
            420                 425                 430

Lys Lys Asn Glu Val Lys Glu Asn Leu Lys Met Phe Tyr Ser Tyr Asp
        435                 440                 445

Phe Asn Met Asp Asn Lys Asn Glu Ile Glu Asp Phe Phe Ala Asn Ile
        450                 455                 460

Asp Glu Ala Ile Ser Ser Ile Arg His Gly Ile Val His Phe Asn Leu
465                 470                 475                 480

Glu Leu Glu Gly Lys Asp Ile Phe Ala Phe Lys Asn Ile Ala Pro Ser
                485                 490                 495

Glu Ile Ser Lys Lys Met Phe Gln Asn Glu Ile Asn Glu Lys Lys Leu
            500                 505                 510

Lys Leu Lys Ile Phe Arg Gln Leu Asn Ser Ala Asn Val Phe Arg Tyr
        515                 520                 525

Leu Glu Lys Tyr Lys Ile Leu Asn Tyr Leu Lys Arg Thr Arg Phe Glu
```

-continued

```
                530             535             540
    Phe Val Asn Lys Asn Ile Pro Phe Val Pro Ser Phe Thr Lys Leu Tyr
    545                 550                 555                 560

Ser Arg Ile Asp Asp Leu Lys Asn Ser Leu Gly Ile Tyr Trp Lys Thr
                        565                 570                 575

Pro Lys Thr Asn Asp Asp Asn Lys Thr Lys Glu Ile Ile Asp Ala Gln
                    580                 585                 590

Ile Tyr Leu Leu Lys Asn Ile Tyr Tyr Gly Glu Phe Leu Asn Tyr Phe
                595                 600                 605

Met Ser Asn Asn Gly Asn Phe Phe Glu Ile Ser Lys Glu Ile Ile Glu
            610                 615                 620

Leu Asn Lys Asn Asp Lys Arg Asn Leu Lys Thr Gly Phe Tyr Lys Leu
    625                 630                 635                 640

Gln Lys Phe Glu Asp Ile Gln Glu Lys Ile Pro Lys Glu Tyr Leu Ala
                        645                 650                 655

Asn Ile Gln Ser Leu Tyr Met Ile Asn Ala Gly Asn Gln Asp Glu Glu
                    660                 665                 670

Glu Lys Asp Thr Tyr Ile Asp Phe Ile Gln Lys Ile Phe Leu Lys Gly
                675                 680                 685

Phe Met Thr Tyr Leu Ala Asn Asn Gly Arg Leu Ser Leu Ile Tyr Ile
            690                 695                 700

Gly Ser Asp Glu Glu Thr Asn Thr Ser Leu Ala Glu Lys Lys Gln Glu
    705                 710                 715                 720

Phe Asp Lys Phe Leu Lys Lys Tyr Gln Asn Asn Asn Ile Lys Ile
                        725                 730                 735

Pro Tyr Glu Ile Asn Glu Phe Leu Arg Glu Ile Lys Leu Gly Asn Ile
                    740                 745                 750

Leu Lys Tyr Thr Glu Arg Leu Asn Met Phe Tyr Leu Ile Leu Lys Leu
                755                 760                 765

Leu Asn His Lys Glu Leu Thr Asn Leu Lys Gly Ser Leu Glu Lys Tyr
            770                 775                 780

Gln Ser Ala Asn Lys Glu Glu Ala Phe Ser Asp Gln Leu Glu Leu Ile
    785                 790                 795                 800

Asn Leu Leu Asn Leu Asp Asn Asn Arg Val Thr Glu Asp Phe Glu Leu
                        805                 810                 815

Glu Ala Asp Glu Ile Gly Lys Phe Leu Asp Phe Asn Gly Asn Lys Val
                    820                 825                 830

Lys Asp Asn Lys Glu Leu Lys Lys Phe Asp Thr Asn Lys Ile Tyr Phe
                835                 840                 845

Asp Gly Glu Asn Ile Ile Lys His Arg Ala Phe Tyr Asn Ile Lys Lys
            850                 855                 860

Tyr Gly Met Leu Asn Leu Leu Glu Lys Ile Ala Asp Lys Ala Gly Tyr
    865                 870                 875                 880

Lys Ile Ser Ile Glu Glu Leu Lys Lys Tyr Ser Asn Lys Lys Asn Glu
                        885                 890                 895

Ile Glu Lys Asn His Lys Met Gln Glu Asn Leu His Arg Lys Tyr Ala
                    900                 905                 910

Arg Pro Arg Lys Asp Glu Lys Phe Thr Asp Glu Asp Tyr Glu Ser Tyr
                915                 920                 925

Lys Gln Ala Ile Glu Asn Ile Glu Glu Tyr Thr His Leu Lys Asn Lys
            930                 935                 940

Val Glu Phe Asn Glu Leu Asn Leu Leu Gln Gly Leu Leu Leu Arg Ile
    945                 950                 955                 960
```

```
Leu His Arg Leu Val Gly Tyr Thr Ser Ile Trp Glu Arg Asp Leu Arg
                965                 970                 975

Phe Arg Leu Lys Gly Glu Phe Pro Glu Asn Gln Tyr Ile Glu Ile
            980                 985                 990

Phe Asn Phe Glu Asn Lys Lys Asn  Val Lys Tyr Lys Gly  Gly Gln Ile
            995                 1000                1005

Val Glu  Lys Tyr Ile Lys Phe  Tyr Lys Glu Leu His  Gln Asn Asp
    1010                1015                1020

Glu Val  Lys Ile Asn Lys Tyr  Ser Ser Ala Asn Ile  Lys Val Leu
    1025                1030                1035

Lys Gln  Glu Lys Lys Asp Leu  Tyr Ile Arg Asn Tyr  Ile Ala His
    1040                1045                1050

Phe Asn  Tyr Ile Pro His Ala  Glu Ile Ser Leu Leu  Glu Val Leu
    1055                1060                1065

Glu Asn  Leu Arg Lys Leu Leu  Ser Tyr Asp Arg Lys  Leu Lys Asn
    1070                1075                1080

Ala Val  Met Lys Ser Val Val  Asp Ile Leu Lys Glu  Tyr Gly Phe
    1085                1090                1095

Val Ala  Thr Phe Lys Ile Gly  Ala Asp Lys Lys Ile  Gly Ile Gln
    1100                1105                1110

Thr Leu  Glu Ser Glu Lys Ile  Val His Leu Lys Asn  Leu Lys Lys
    1115                1120                1125

Lys Lys  Leu Met Thr Asp Arg  Asn Ser Glu Glu Leu  Cys Lys Leu
    1130                1135                1140

Val Lys  Ile Met Phe Glu Tyr  Lys Met Glu Glu Lys  Lys Ser Glu
    1145                1150                1155

Asn

<210> SEQ ID NO 3
<211> LENGTH: 1389
<212> TYPE: PRT
<213> ORGANISM: Leptotrichia shahii

<400> SEQUENCE: 3

Met Gly Asn Leu Phe Gly His Lys Arg Trp Tyr Glu Val Arg Asp Lys
1               5                   10                  15

Lys Asp Phe Lys Ile Lys Arg Lys Val Lys Val Lys Arg Asn Tyr Asp
            20                  25                  30

Gly Asn Lys Tyr Ile Leu Asn Ile Asn Glu Asn Asn Asn Lys Glu Lys
        35                  40                  45

Ile Asp Asn Asn Lys Phe Ile Arg Lys Tyr Ile Asn Tyr Lys Lys Asn
    50                  55                  60

Asp Asn Ile Leu Lys Glu Phe Thr Arg Lys Phe His Ala Gly Asn Ile
65                  70                  75                  80

Leu Phe Lys Leu Lys Gly Lys Glu Gly Ile Ile Arg Ile Glu Asn Asn
                85                  90                  95

Asp Asp Phe Leu Glu Thr Glu Glu Val Val Leu Tyr Ile Glu Ala Tyr
            100                 105                 110

Gly Lys Ser Glu Lys Leu Lys Ala Leu Gly Ile Thr Lys Lys Lys Ile
        115                 120                 125

Ile Asp Glu Ala Ile Arg Gln Gly Ile Thr Lys Asp Asp Lys Lys Ile
    130                 135                 140

Glu Ile Lys Arg Gln Glu Asn Glu Glu Glu Ile Glu Ile Asp Ile Arg
145                 150                 155                 160
```

```
Asp Glu Tyr Thr Asn Lys Thr Leu Asn Asp Cys Ser Ile Ile Leu Arg
                165                 170                 175

Ile Ile Glu Asn Asp Glu Leu Glu Thr Lys Lys Ser Ile Tyr Glu Ile
            180                 185                 190

Phe Lys Asn Ile Asn Met Ser Leu Tyr Lys Ile Glu Lys Ile Ile
        195                 200                 205

Glu Asn Glu Thr Glu Lys Val Phe Glu Asn Arg Tyr Tyr Glu Glu His
    210                 215                 220

Leu Arg Glu Lys Leu Leu Lys Asp Asp Lys Ile Asp Val Ile Leu Thr
225                 230                 235                 240

Asn Phe Met Glu Ile Arg Glu Lys Ile Lys Ser Asn Leu Glu Ile Leu
                245                 250                 255

Gly Phe Val Lys Phe Tyr Leu Asn Val Gly Gly Asp Lys Lys Lys Ser
                260                 265                 270

Lys Asn Lys Lys Met Leu Val Glu Lys Ile Leu Asn Ile Asn Val Asp
            275                 280                 285

Leu Thr Val Glu Asp Ile Ala Asp Phe Val Ile Lys Glu Leu Glu Phe
    290                 295                 300

Trp Asn Ile Thr Lys Arg Ile Glu Lys Val Lys Lys Val Asn Asn Glu
305                 310                 315                 320

Phe Leu Glu Lys Arg Arg Asn Arg Thr Tyr Ile Lys Ser Tyr Val Leu
                325                 330                 335

Leu Asp Lys His Glu Lys Phe Lys Ile Glu Arg Glu Asn Lys Lys Asp
                340                 345                 350

Lys Ile Val Lys Phe Phe Val Glu Asn Ile Lys Asn Asn Ser Ile Lys
            355                 360                 365

Glu Lys Ile Glu Lys Ile Leu Ala Glu Phe Lys Ile Asp Glu Leu Ile
    370                 375                 380

Lys Lys Leu Glu Lys Glu Leu Lys Lys Gly Asn Cys Asp Thr Glu Ile
385                 390                 395                 400

Phe Gly Ile Phe Lys Lys His Tyr Lys Val Asn Phe Asp Ser Lys Lys
                405                 410                 415

Phe Ser Lys Lys Ser Asp Glu Glu Lys Glu Leu Tyr Lys Ile Ile Tyr
                420                 425                 430

Arg Tyr Leu Lys Gly Arg Ile Glu Lys Ile Leu Val Asn Glu Gln Lys
                435                 440                 445

Val Arg Leu Lys Lys Met Glu Lys Ile Glu Ile Glu Lys Ile Leu Asn
450                 455                 460

Glu Ser Ile Leu Ser Glu Lys Ile Leu Lys Arg Val Lys Gln Tyr Thr
465                 470                 475                 480

Leu Glu His Ile Met Tyr Leu Gly Lys Leu Arg His Asn Asp Ile Asp
                485                 490                 495

Met Thr Thr Val Asn Thr Asp Asp Phe Ser Arg Leu His Ala Lys Glu
            500                 505                 510

Glu Leu Asp Leu Glu Leu Ile Thr Phe Phe Ala Ser Thr Asn Met Glu
            515                 520                 525

Leu Asn Lys Ile Phe Ser Arg Glu Asn Ile Asn Asn Asp Glu Asn Ile
530                 535                 540

Asp Phe Phe Gly Gly Asp Arg Glu Lys Asn Tyr Val Leu Asp Lys Lys
545                 550                 555                 560

Ile Leu Asn Ser Lys Ile Lys Ile Ile Arg Asp Leu Asp Phe Ile Asp
                565                 570                 575
```

-continued

Asn Lys Asn Asn Ile Thr Asn Asn Phe Ile Arg Lys Phe Thr Lys Ile
            580                 585                 590

Gly Thr Asn Glu Arg Asn Arg Ile Leu His Ala Ile Ser Lys Glu Arg
        595                 600                 605

Asp Leu Gln Gly Thr Gln Asp Tyr Asn Lys Val Ile Asn Ile Ile
    610                 615                 620

Gln Asn Leu Lys Ile Ser Asp Glu Val Ser Lys Ala Leu Asn Leu
625                 630                 635                 640

Asp Val Val Phe Lys Asp Lys Asn Ile Ile Thr Lys Ile Asn Asp
                645                 650                 655

Ile Lys Ile Ser Glu Glu Asn Asn Asp Ile Lys Tyr Leu Pro Ser
            660                 665                 670

Phe Ser Lys Val Leu Pro Glu Ile Leu Asn Leu Tyr Arg Asn Asn Pro
        675                 680                 685

Lys Asn Glu Pro Phe Asp Thr Ile Glu Thr Glu Lys Ile Val Leu Asn
        690                 695                 700

Ala Leu Ile Tyr Val Asn Lys Glu Leu Tyr Lys Lys Leu Ile Leu Glu
705                 710                 715                 720

Asp Asp Leu Glu Glu Asn Glu Ser Lys Asn Ile Phe Leu Gln Glu Leu
                725                 730                 735

Lys Lys Thr Leu Gly Asn Ile Asp Glu Ile Asp Glu Asn Ile Ile Glu
            740                 745                 750

Asn Tyr Tyr Lys Asn Ala Gln Ile Ser Ala Ser Lys Gly Asn Asn Lys
            755                 760                 765

Ala Ile Lys Lys Tyr Gln Lys Lys Val Ile Glu Cys Tyr Ile Gly Tyr
        770                 775                 780

Leu Arg Lys Asn Tyr Glu Glu Leu Phe Asp Phe Ser Asp Phe Lys Met
785                 790                 795                 800

Asn Ile Gln Glu Ile Lys Lys Gln Ile Lys Asp Ile Asn Asp Asn Lys
                805                 810                 815

Thr Tyr Glu Arg Ile Thr Val Lys Thr Ser Asp Lys Thr Ile Val Ile
            820                 825                 830

Asn Asp Asp Phe Glu Tyr Ile Ile Ser Ile Phe Ala Leu Leu Asn Ser
        835                 840                 845

Asn Ala Val Ile Asn Lys Ile Arg Asn Arg Phe Phe Ala Thr Ser Val
850                 855                 860

Trp Leu Asn Thr Ser Glu Tyr Gln Asn Ile Ile Asp Ile Leu Asp Glu
865                 870                 875                 880

Ile Met Gln Leu Asn Thr Leu Arg Asn Glu Cys Ile Thr Glu Asn Trp
                885                 890                 895

Asn Leu Asn Leu Glu Glu Phe Ile Gln Lys Met Lys Glu Ile Glu Lys
            900                 905                 910

Asp Phe Asp Asp Phe Lys Ile Gln Thr Lys Lys Glu Ile Phe Asn Asn
        915                 920                 925

Tyr Tyr Glu Asp Ile Lys Asn Asn Ile Leu Thr Glu Phe Lys Asp Asp
    930                 935                 940

Ile Asn Gly Cys Asp Val Leu Glu Lys Lys Leu Glu Lys Ile Val Ile
945                 950                 955                 960

Phe Asp Asp Glu Thr Lys Phe Glu Ile Asp Lys Lys Ser Asn Ile Leu
                965                 970                 975

Gln Asp Glu Gln Arg Lys Leu Ser Asn Ile Asn Lys Lys Asp Leu Lys
            980                 985                 990

Lys Lys Val Asp Gln Tyr Ile Lys  Asp Lys Asp Gln Glu  Ile Lys Ser

-continued

```
            995                 1000                1005
Lys Ile Leu Cys Arg Ile Ile Phe Asn Ser Asp Phe Leu Lys Lys
            1010                1015                1020

Tyr Lys Lys Glu Ile Asp Asn Leu Ile Glu Asp Met Glu Ser Glu
            1025                1030                1035

Asn Glu Asn Lys Phe Gln Glu Ile Tyr Tyr Pro Lys Glu Arg Lys
            1040                1045                1050

Asn Glu Leu Tyr Ile Tyr Lys Lys Asn Leu Phe Leu Asn Ile Gly
            1055                1060                1065

Asn Pro Asn Phe Asp Lys Ile Tyr Gly Leu Ile Ser Asn Asp Ile
            1070                1075                1080

Lys Met Ala Asp Ala Lys Phe Leu Phe Asn Ile Asp Gly Lys Asn
            1085                1090                1095

Ile Arg Lys Asn Lys Ile Ser Glu Ile Asp Ala Ile Leu Lys Asn
            1100                1105                1110

Leu Asn Asp Lys Leu Asn Gly Tyr Ser Lys Glu Tyr Lys Glu Lys
            1115                1120                1125

Tyr Ile Lys Lys Leu Lys Glu Asn Asp Asp Phe Phe Ala Lys Asn
            1130                1135                1140

Ile Gln Asn Lys Asn Tyr Lys Ser Phe Glu Lys Asp Tyr Asn Arg
            1145                1150                1155

Val Ser Glu Tyr Lys Lys Ile Arg Asp Leu Val Glu Phe Asn Tyr
            1160                1165                1170

Leu Asn Lys Ile Glu Ser Tyr Leu Ile Asp Ile Asn Trp Lys Leu
            1175                1180                1185

Ala Ile Gln Met Ala Arg Phe Glu Arg Asp Met His Tyr Ile Val
            1190                1195                1200

Asn Gly Leu Arg Glu Leu Gly Ile Ile Lys Leu Ser Gly Tyr Asn
            1205                1210                1215

Thr Gly Ile Ser Arg Ala Tyr Pro Lys Arg Asn Gly Ser Asp Gly
            1220                1225                1230

Phe Tyr Thr Thr Thr Ala Tyr Tyr Lys Phe Phe Asp Glu Glu Ser
            1235                1240                1245

Tyr Lys Lys Phe Glu Lys Ile Cys Tyr Gly Phe Gly Ile Asp Leu
            1250                1255                1260

Ser Glu Asn Ser Glu Ile Asn Lys Pro Glu Asn Glu Ser Ile Arg
            1265                1270                1275

Asn Tyr Ile Ser His Phe Tyr Ile Val Arg Asn Pro Phe Ala Asp
            1280                1285                1290

Tyr Ser Ile Ala Glu Gln Ile Asp Arg Val Ser Asn Leu Leu Ser
            1295                1300                1305

Tyr Ser Thr Arg Tyr Asn Asn Ser Thr Tyr Ala Ser Val Phe Glu
            1310                1315                1320

Val Phe Lys Lys Asp Val Asn Leu Asp Tyr Asp Glu Leu Lys Lys
            1325                1330                1335

Lys Phe Lys Leu Ile Gly Asn Asn Asp Ile Leu Glu Arg Leu Met
            1340                1345                1350

Lys Pro Lys Lys Val Ser Val Leu Glu Leu Glu Ser Tyr Asn Ser
            1355                1360                1365

Asp Tyr Ile Lys Asn Leu Ile Glu Leu Leu Thr Lys Ile Glu
            1370                1375                1380

Asn Thr Asn Asp Thr Leu
            1385
```

```
<210> SEQ ID NO 4
<211> LENGTH: 1285
<212> TYPE: PRT
<213> ORGANISM: Rhodobacter capsulatus R121

<400> SEQUENCE: 4
```

| | | | | | | | | | | | | | | |
|---|---|---|---|---|---|---|---|---|---|---|---|---|---|---|
| Met | Gln | Ile | Gly | Lys | Val | Gln | Gly | Arg | Thr | Ile | Ser | Glu | Phe | Gly | Asp |
| 1 | | | | 5 | | | | | 10 | | | | | 15 | |

Pro Ala Gly Gly Leu Lys Arg Lys Ile Ser Thr Asp Gly Lys Asn Arg
            20                  25                  30

Lys Glu Leu Pro Ala His Leu Ser Ser Asp Pro Lys Ala Leu Ile Gly
        35                  40                  45

Gln Trp Ile Ser Gly Ile Asp Lys Ile Tyr Arg Lys Pro Asp Ser Arg
    50                  55                  60

Lys Ser Asp Gly Lys Ala Ile His Ser Pro Thr Pro Ser Lys Met Gln
65                  70                  75                  80

Phe Asp Ala Arg Asp Asp Leu Gly Glu Ala Phe Trp Lys Leu Val Ser
                85                  90                  95

Glu Ala Gly Leu Ala Gln Asp Ser Asp Tyr Asp Gln Phe Lys Arg Arg
            100                 105                 110

Leu His Pro Tyr Gly Asp Lys Phe Gln Pro Ala Asp Ser Gly Ala Lys
        115                 120                 125

Leu Lys Phe Glu Ala Asp Pro Pro Glu Pro Gln Ala Phe His Gly Arg
    130                 135                 140

Trp Tyr Gly Ala Met Ser Lys Arg Gly Asn Asp Ala Lys Glu Leu Ala
145                 150                 155                 160

Ala Ala Leu Tyr Glu His Leu His Val Asp Glu Lys Arg Ile Asp Gly
                165                 170                 175

Gln Pro Lys Arg Asn Pro Lys Thr Asp Lys Phe Ala Pro Gly Leu Val
            180                 185                 190

Val Ala Arg Ala Leu Gly Ile Glu Ser Ser Val Leu Pro Arg Gly Met
        195                 200                 205

Ala Arg Leu Ala Arg Asn Trp Gly Glu Glu Ile Gln Thr Tyr Phe
    210                 215                 220

Val Val Asp Val Ala Ala Ser Val Lys Glu Val Ala Lys Ala Val
225                 230                 235                 240

Ser Ala Ala Gln Ala Phe Asp Pro Pro Arg Gln Val Ser Gly Arg Ser
                245                 250                 255

Leu Ser Pro Lys Val Gly Phe Ala Leu Ala Glu His Leu Glu Arg Val
            260                 265                 270

Thr Gly Ser Lys Arg Cys Ser Phe Asp Pro Ala Ala Gly Pro Ser Val
        275                 280                 285

Leu Ala Leu His Asp Glu Val Lys Lys Thr Tyr Lys Arg Leu Cys Ala
    290                 295                 300

Arg Gly Lys Asn Ala Ala Arg Ala Phe Pro Ala Asp Lys Thr Glu Leu
305                 310                 315                 320

Leu Ala Leu Met Arg His Thr His Glu Asn Arg Val Arg Asn Gln Met
                325                 330                 335

Val Arg Met Gly Arg Val Ser Glu Tyr Arg Gly Gln Gln Ala Gly Asp
            340                 345                 350

Leu Ala Gln Ser His Tyr Trp Thr Ser Ala Gly Gln Thr Glu Ile Lys
        355                 360                 365

Glu Ser Glu Ile Phe Val Arg Leu Trp Val Gly Ala Phe Ala Leu Ala

-continued

```
              370                 375                 380
Gly Arg Ser Met Lys Ala Trp Ile Asp Pro Met Gly Lys Ile Val Asn
385                 390                 395                 400

Thr Glu Lys Asn Asp Arg Asp Leu Thr Ala Ala Val Asn Ile Arg Gln
                405                 410                 415

Val Ile Ser Asn Lys Glu Met Val Ala Glu Ala Met Ala Arg Arg Gly
                420                 425                 430

Ile Tyr Phe Gly Glu Thr Pro Glu Leu Asp Arg Leu Gly Ala Glu Gly
            435                 440                 445

Asn Glu Gly Phe Val Phe Ala Leu Leu Arg Tyr Leu Arg Gly Cys Arg
        450                 455                 460

Asn Gln Thr Phe His Leu Gly Ala Arg Ala Gly Phe Leu Lys Glu Ile
465                 470                 475                 480

Arg Lys Glu Leu Glu Lys Thr Arg Trp Gly Lys Ala Lys Glu Ala Glu
                485                 490                 495

His Val Val Leu Thr Asp Lys Thr Val Ala Ala Ile Arg Ala Ile Ile
            500                 505                 510

Asp Asn Asp Ala Lys Ala Leu Gly Ala Arg Leu Leu Ala Asp Leu Ser
        515                 520                 525

Gly Ala Phe Val Ala His Tyr Ala Ser Lys Glu His Phe Ser Thr Leu
    530                 535                 540

Tyr Ser Glu Ile Val Lys Ala Val Lys Asp Ala Pro Glu Val Ser Ser
545                 550                 555                 560

Gly Leu Pro Arg Leu Lys Leu Leu Lys Arg Ala Asp Gly Val Arg
                565                 570                 575

Gly Tyr Val His Gly Leu Arg Asp Thr Arg Lys His Ala Phe Ala Thr
            580                 585                 590

Lys Leu Pro Pro Pro Ala Pro Arg Glu Leu Asp Asp Pro Ala Thr
        595                 600                 605

Lys Ala Arg Tyr Ile Ala Leu Leu Arg Leu Tyr Asp Gly Pro Phe Arg
    610                 615                 620

Ala Tyr Ala Ser Gly Ile Thr Gly Thr Ala Leu Ala Gly Pro Ala Ala
625                 630                 635                 640

Arg Ala Lys Glu Ala Ala Thr Ala Leu Ala Gln Ser Val Asn Val Thr
                645                 650                 655

Lys Ala Tyr Ser Asp Val Met Glu Gly Arg Ser Ser Arg Leu Arg Pro
            660                 665                 670

Pro Asn Asp Gly Glu Thr Leu Arg Glu Tyr Leu Ser Ala Leu Thr Gly
        675                 680                 685

Glu Thr Ala Thr Glu Phe Arg Val Gln Ile Gly Tyr Glu Ser Asp Ser
    690                 695                 700

Glu Asn Ala Arg Lys Ala Glu Phe Ile Glu Asn Tyr Arg Arg Asp
705                 710                 715                 720

Met Leu Ala Phe Met Phe Glu Asp Tyr Ile Arg Ala Lys Gly Phe Asp
                725                 730                 735

Trp Ile Leu Lys Ile Glu Pro Gly Ala Thr Ala Met Thr Arg Ala Pro
            740                 745                 750

Val Leu Pro Glu Pro Ile Asp Thr Arg Gly Gln Tyr Glu His Trp Gln
        755                 760                 765

Ala Ala Leu Tyr Leu Val Met His Phe Val Pro Ala Ser Asp Val Ser
    770                 775                 780

Asn Leu Leu His Gln Leu Arg Lys Trp Glu Ala Leu Gln Gly Lys Tyr
785                 790                 795                 800
```

-continued

Glu Leu Val Gln Asp Gly Asp Ala Thr Asp Gln Ala Asp Ala Arg Arg
            805                 810                 815

Glu Ala Leu Asp Leu Val Lys Arg Phe Arg Asp Val Leu Val Leu Phe
            820                 825                 830

Leu Lys Thr Gly Glu Ala Arg Phe Glu Gly Arg Ala Ala Pro Phe Asp
            835                 840                 845

Leu Lys Pro Phe Arg Ala Leu Phe Ala Asn Pro Ala Thr Phe Asp Arg
            850                 855                 860

Leu Phe Met Ala Thr Pro Thr Thr Ala Arg Pro Ala Glu Asp Asp Pro
865                 870                 875                 880

Glu Gly Asp Gly Ala Ser Glu Pro Glu Leu Arg Val Ala Arg Thr Leu
            885                 890                 895

Arg Gly Leu Arg Gln Ile Ala Arg Tyr Asn His Met Ala Val Leu Ser
            900                 905                 910

Asp Leu Phe Ala Lys His Lys Val Arg Asp Glu Glu Val Ala Arg Leu
            915                 920                 925

Ala Glu Ile Glu Asp Glu Thr Gln Glu Lys Ser Gln Ile Val Ala Ala
            930                 935                 940

Gln Glu Leu Arg Thr Asp Leu His Asp Lys Val Met Lys Cys His Pro
945                 950                 955                 960

Lys Thr Ile Ser Pro Glu Glu Arg Gln Ser Tyr Ala Ala Ala Ile Lys
            965                 970                 975

Thr Ile Glu Glu His Arg Phe Leu Val Gly Arg Val Tyr Leu Gly Asp
            980                 985                 990

His Leu Arg Leu His Arg Leu Met Met Asp Val Ile Gly Arg Leu Ile
            995                 1000                1005

Asp Tyr Ala Gly Ala Tyr Glu Arg Asp Thr Gly Thr Phe Leu Ile
            1010                1015                1020

Asn Ala Ser Lys Gln Leu Gly Ala Gly Ala Asp Trp Ala Val Thr
            1025                1030                1035

Ile Ala Gly Ala Ala Asn Thr Asp Ala Arg Thr Gln Thr Arg Lys
            1040                1045                1050

Asp Leu Ala His Phe Asn Val Leu Asp Arg Ala Asp Gly Thr Pro
            1055                1060                1065

Asp Leu Thr Ala Leu Val Asn Arg Ala Arg Glu Met Met Ala Tyr
            1070                1075                1080

Asp Arg Lys Arg Lys Asn Ala Val Pro Arg Ser Ile Leu Asp Met
            1085                1090                1095

Leu Ala Arg Leu Gly Leu Thr Leu Lys Trp Gln Met Lys Asp His
            1100                1105                1110

Leu Leu Gln Asp Ala Thr Ile Thr Gln Ala Ala Ile Lys His Leu
            1115                1120                1125

Asp Lys Val Arg Leu Thr Val Gly Gly Pro Ala Ala Val Thr Glu
            1130                1135                1140

Ala Arg Phe Ser Gln Asp Tyr Leu Gln Met Val Ala Ala Val Phe
            1145                1150                1155

Asn Gly Ser Val Gln Asn Pro Lys Pro Arg Arg Arg Asp Asp Gly
            1160                1165                1170

Asp Ala Trp His Lys Pro Pro Lys Pro Ala Thr Ala Gln Ser Gln
            1175                1180                1185

Pro Asp Gln Lys Pro Pro Asn Lys Ala Pro Ser Ala Gly Ser Arg
            1190                1195                1200

Leu Pro Pro Pro Gln Val Gly Glu Val Tyr Glu Gly Val Val Val
1205 1210 1215

Lys Val Ile Asp Thr Gly Ser Leu Gly Phe Leu Ala Val Glu Gly
1220 1225 1230

Val Ala Gly Asn Ile Gly Leu His Ile Ser Arg Leu Arg Arg Ile
1235 1240 1245

Arg Glu Asp Ala Ile Ile Val Gly Arg Arg Tyr Arg Phe Arg Val
1250 1255 1260

Glu Ile Tyr Val Pro Pro Lys Ser Asn Thr Ser Lys Leu Asn Ala
1265 1270 1275

Ala Asp Leu Val Arg Ile Asp
1280 1285

<210> SEQ ID NO 5
<211> LENGTH: 1175
<212> TYPE: PRT
<213> ORGANISM: Carnobacterium gallinarum

<400> SEQUENCE: 5

Met Arg Ile Thr Lys Val Lys Ile Lys Leu Asp Asn Lys Leu Tyr Gln
1 5 10 15

Val Thr Met Gln Lys Glu Glu Lys Tyr Gly Thr Leu Lys Leu Asn Glu
20 25 30

Glu Ser Arg Lys Ser Thr Ala Glu Ile Leu Arg Leu Lys Lys Ala Ser
35 40 45

Phe Asn Lys Ser Phe His Ser Lys Thr Ile Asn Ser Gln Lys Glu Asn
50 55 60

Lys Asn Ala Thr Ile Lys Lys Asn Gly Asp Tyr Ile Ser Gln Ile Phe
65 70 75 80

Glu Lys Leu Val Gly Val Asp Thr Asn Lys Asn Ile Arg Lys Pro Lys
85 90 95

Met Ser Leu Thr Asp Leu Lys Asp Leu Pro Lys Lys Asp Leu Ala Leu
100 105 110

Phe Ile Lys Arg Lys Phe Lys Asn Asp Asp Ile Val Glu Ile Lys Asn
115 120 125

Leu Asp Leu Ile Ser Leu Phe Tyr Asn Ala Leu Gln Lys Val Pro Gly
130 135 140

Glu His Phe Thr Asp Glu Ser Trp Ala Asp Phe Cys Gln Glu Met Met
145 150 155 160

Pro Tyr Arg Glu Tyr Lys Asn Lys Phe Ile Glu Arg Lys Ile Ile Leu
165 170 175

Leu Ala Asn Ser Ile Glu Gln Asn Lys Gly Phe Ser Ile Asn Pro Glu
180 185 190

Thr Phe Ser Lys Arg Lys Arg Val Leu His Gln Trp Ala Ile Glu Val
195 200 205

Gln Glu Arg Gly Asp Phe Ser Ile Leu Asp Glu Lys Leu Ser Lys Leu
210 215 220

Ala Glu Ile Tyr Asn Phe Lys Lys Met Cys Lys Arg Val Gln Asp Glu
225 230 235 240

Leu Asn Asp Leu Glu Lys Ser Met Lys Lys Gly Lys Asn Pro Glu Lys
245 250 255

Glu Lys Glu Ala Tyr Lys Lys Gln Lys Asn Phe Lys Ile Lys Thr Ile
260 265 270

Trp Lys Asp Tyr Pro Tyr Lys Thr His Ile Gly Leu Ile Glu Lys Ile
275 280 285

```
Lys Glu Asn Glu Glu Leu Asn Gln Phe Asn Ile Glu Ile Gly Lys Tyr
            290                 295                 300

Phe Glu His Tyr Phe Pro Ile Lys Lys Glu Arg Cys Thr Glu Asp Glu
305                 310                 315                 320

Pro Tyr Tyr Leu Asn Ser Glu Thr Ile Ala Thr Thr Val Asn Tyr Gln
                325                 330                 335

Leu Lys Asn Ala Leu Ile Ser Tyr Leu Met Gln Ile Gly Lys Tyr Lys
            340                 345                 350

Gln Phe Gly Leu Glu Asn Gln Val Leu Asp Ser Lys Lys Leu Gln Glu
                355                 360                 365

Ile Gly Ile Tyr Glu Gly Phe Gln Thr Lys Phe Met Asp Ala Cys Val
            370                 375                 380

Phe Ala Thr Ser Ser Leu Lys Asn Ile Ile Glu Pro Met Arg Ser Gly
385                 390                 395                 400

Asp Ile Leu Gly Lys Arg Glu Phe Lys Glu Ala Ile Ala Thr Ser Ser
                405                 410                 415

Phe Val Asn Tyr His His Phe Phe Pro Tyr Phe Pro Phe Glu Leu Lys
            420                 425                 430

Gly Met Lys Asp Arg Glu Ser Glu Leu Ile Pro Phe Gly Glu Gln Thr
            435                 440                 445

Glu Ala Lys Gln Met Gln Asn Ile Trp Ala Leu Arg Gly Ser Val Gln
450                 455                 460

Gln Ile Arg Asn Glu Ile Phe His Ser Phe Asp Lys Asn Gln Lys Phe
465                 470                 475                 480

Asn Leu Pro Gln Leu Asp Lys Ser Asn Phe Glu Phe Asp Ala Ser Glu
                485                 490                 495

Asn Ser Thr Gly Lys Ser Gln Ser Tyr Ile Glu Thr Asp Tyr Lys Phe
                500                 505                 510

Leu Phe Glu Ala Glu Lys Asn Gln Leu Glu Gln Phe Phe Ile Glu Arg
            515                 520                 525

Ile Lys Ser Ser Gly Ala Leu Glu Tyr Tyr Pro Leu Lys Ser Leu Glu
            530                 535                 540

Lys Leu Phe Ala Lys Lys Glu Met Lys Phe Ser Leu Gly Ser Gln Val
545                 550                 555                 560

Val Ala Phe Ala Pro Ser Tyr Lys Lys Leu Val Lys Lys Gly His Ser
                565                 570                 575

Tyr Gln Thr Ala Thr Glu Gly Thr Ala Asn Tyr Leu Gly Leu Ser Tyr
                580                 585                 590

Tyr Asn Arg Tyr Glu Leu Lys Glu Glu Ser Phe Gln Ala Gln Tyr Tyr
            595                 600                 605

Leu Leu Lys Leu Ile Tyr Gln Tyr Val Phe Leu Pro Asn Phe Ser Gln
            610                 615                 620

Gly Asn Ser Pro Ala Phe Arg Glu Thr Val Lys Ala Ile Leu Arg Ile
625                 630                 635                 640

Asn Lys Asp Glu Ala Arg Lys Lys Met Lys Asn Lys Lys Phe Leu
                645                 650                 655

Arg Lys Tyr Ala Phe Glu Gln Val Arg Glu Met Glu Phe Lys Glu Thr
                660                 665                 670

Pro Asp Gln Tyr Met Ser Tyr Leu Gln Ser Glu Met Arg Glu Glu Lys
            675                 680                 685

Val Arg Lys Ala Glu Lys Asn Asp Lys Gly Phe Glu Lys Asn Ile Thr
            690                 695                 700
```

```
Met Asn Phe Glu Lys Leu Leu Met Gln Ile Phe Val Lys Gly Phe Asp
705                 710                 715                 720

Val Phe Leu Thr Thr Phe Ala Gly Lys Glu Leu Leu Leu Ser Ser Glu
            725                 730                 735

Glu Lys Val Ile Lys Glu Thr Glu Ile Ser Leu Ser Lys Lys Ile Asn
        740                 745                 750

Glu Arg Glu Lys Thr Leu Lys Ala Ser Ile Gln Val Glu His Gln Leu
    755                 760                 765

Val Ala Thr Asn Ser Ala Ile Ser Tyr Trp Leu Phe Cys Lys Leu Leu
770                 775                 780

Asp Ser Arg His Leu Asn Glu Leu Arg Asn Glu Met Ile Lys Phe Lys
785                 790                 795                 800

Gln Ser Arg Ile Lys Phe Asn His Thr Gln His Ala Glu Leu Ile Gln
            805                 810                 815

Asn Leu Leu Pro Ile Val Glu Leu Thr Ile Leu Ser Asn Asp Tyr Asp
        820                 825                 830

Glu Lys Asn Asp Ser Gln Asn Val Asp Val Ser Ala Tyr Phe Glu Asp
    835                 840                 845

Lys Ser Leu Tyr Glu Thr Ala Pro Tyr Val Gln Thr Asp Asp Arg Thr
850                 855                 860

Arg Val Ser Phe Arg Pro Ile Leu Lys Leu Glu Lys Tyr His Thr Lys
865                 870                 875                 880

Ser Leu Ile Glu Ala Leu Leu Lys Asp Asn Pro Gln Phe Arg Val Ala
            885                 890                 895

Ala Thr Asp Ile Gln Glu Trp Met His Lys Arg Glu Glu Ile Gly Glu
        900                 905                 910

Leu Val Glu Lys Arg Lys Asn Leu His Thr Glu Trp Ala Glu Gly Gln
    915                 920                 925

Gln Thr Leu Gly Ala Glu Lys Arg Glu Glu Tyr Arg Asp Tyr Cys Lys
930                 935                 940

Lys Ile Asp Arg Phe Asn Trp Lys Ala Asn Lys Val Thr Leu Thr Tyr
945                 950                 955                 960

Leu Ser Gln Leu His Tyr Leu Ile Thr Asp Leu Leu Gly Arg Met Val
            965                 970                 975

Gly Phe Ser Ala Leu Phe Glu Arg Asp Leu Val Tyr Phe Ser Arg Ser
        980                 985                 990

Phe Ser Glu Leu Gly Gly Glu Thr Tyr His Ile Ser Asp Tyr Lys Asn
    995                 1000                1005

Leu Ser Gly Val Leu Arg Leu Asn Ala Glu Val Lys Pro Ile Lys
    1010                1015                1020

Ile Lys Asn Ile Lys Val Ile Asp Asn Glu Glu Asn Pro Tyr Lys
    1025                1030                1035

Gly Asn Glu Pro Glu Val Lys Pro Phe Leu Asp Arg Leu His Ala
    1040                1045                1050

Tyr Leu Glu Asn Val Ile Gly Ile Lys Ala Val His Gly Lys Ile
    1055                1060                1065

Arg Asn Gln Thr Ala His Leu Ser Val Leu Gln Leu Glu Leu Ser
    1070                1075                1080

Met Ile Glu Ser Met Asn Asn Leu Arg Asp Leu Met Ala Tyr Asp
    1085                1090                1095

Arg Lys Leu Lys Asn Ala Val Thr Lys Ser Met Ile Lys Ile Leu
    1100                1105                1110

Asp Lys His Gly Met Ile Leu Lys Leu Lys Ile Asp Glu Asn His
```

```
                    1115                1120                1125

Lys Asn  Phe Glu Ile Glu  Ser Leu Ile Pro  Lys Glu  Ile Ile His
    1130                 1135             1140

Leu Lys  Asp Lys Ala Ile  Lys Thr Asn Gln  Val Ser  Glu Glu Tyr
    1145                 1150             1155

Cys Gln  Leu Val Leu Ala  Leu Leu Thr Thr  Asn Pro  Gly Asn Gln
    1160                 1165             1170

Leu Asn
    1175

<210> SEQ ID NO 6
<211> LENGTH: 1285
<212> TYPE: PRT
<213> ORGANISM: Herbinix hemicellulosilytica

<400> SEQUENCE: 6

Met Lys Leu Thr Arg Arg Arg Ile Ser Gly Asn Ser Val Asp Gln Lys
1               5                   10                  15

Ile Thr Ala Ala Phe Tyr Arg Asp Met Ser Gln Gly Leu Leu Tyr Tyr
            20                  25                  30

Asp Ser Glu Asp Asn Asp Cys Thr Asp Lys Val Ile Glu Ser Met Asp
        35                  40                  45

Phe Glu Arg Ser Trp Arg Gly Arg Ile Leu Lys Asn Gly Glu Asp Asp
    50                  55                  60

Lys Asn Pro Phe Tyr Met Phe Val Lys Gly Leu Val Gly Ser Asn Asp
65                  70                  75                  80

Lys Ile Val Cys Glu Pro Ile Asp Val Asp Ser Asp Pro Asp Asn Leu
                85                  90                  95

Asp Ile Leu Ile Asn Lys Asn Leu Thr Gly Phe Gly Arg Asn Leu Lys
            100                 105                 110

Ala Pro Asp Ser Asn Asp Thr Leu Glu Asn Leu Ile Arg Lys Ile Gln
        115                 120                 125

Ala Gly Ile Pro Glu Glu Glu Val Leu Pro Glu Leu Lys Lys Ile Lys
    130                 135                 140

Glu Met Ile Gln Lys Asp Ile Val Asn Arg Lys Glu Gln Leu Leu Lys
145                 150                 155                 160

Ser Ile Lys Asn Asn Arg Ile Pro Phe Ser Leu Glu Gly Ser Lys Leu
                165                 170                 175

Val Pro Ser Thr Lys Lys Met Lys Trp Leu Phe Lys Leu Ile Asp Val
            180                 185                 190

Pro Asn Lys Thr Phe Asn Glu Lys Met Leu Glu Lys Tyr Trp Glu Ile
        195                 200                 205

Tyr Asp Tyr Asp Lys Leu Lys Ala Asn Ile Thr Asn Arg Leu Asp Lys
    210                 215                 220

Thr Asp Lys Lys Ala Arg Ser Ile Ser Arg Ala Val Ser Glu Glu Leu
225                 230                 235                 240

Arg Glu Tyr His Lys Asn Leu Arg Thr Asn Tyr Asn Arg Phe Val Ser
                245                 250                 255

Gly Asp Arg Pro Ala Ala Gly Leu Asp Asn Gly Gly Ser Ala Lys Tyr
            260                 265                 270

Asn Pro Asp Lys Glu Glu Phe Leu Leu Phe Leu Lys Glu Val Glu Gln
        275                 280                 285

Tyr Phe Lys Lys Tyr Phe Pro Val Lys Ser Lys His Ser Asn Lys Ser
    290                 295                 300
```

```
Lys Asp Lys Ser Leu Val Asp Lys Tyr Lys Asn Tyr Cys Ser Tyr Lys
305                 310                 315                 320

Val Val Lys Lys Glu Val Asn Arg Ser Ile Ile Asn Gln Leu Val Ala
                325                 330                 335

Gly Leu Ile Gln Gln Gly Lys Leu Leu Tyr Tyr Phe Tyr Tyr Asn Asp
            340                 345                 350

Thr Trp Gln Glu Asp Phe Leu Asn Ser Tyr Gly Leu Ser Tyr Ile Gln
        355                 360                 365

Val Glu Glu Ala Phe Lys Lys Ser Val Met Thr Ser Leu Ser Trp Gly
    370                 375                 380

Ile Asn Arg Leu Thr Ser Phe Phe Ile Asp Asp Ser Asn Thr Val Lys
385                 390                 395                 400

Phe Asp Asp Ile Thr Thr Lys Lys Ala Lys Glu Ala Ile Glu Ser Asn
                405                 410                 415

Tyr Phe Asn Lys Leu Arg Thr Cys Ser Arg Met Gln Asp His Phe Lys
            420                 425                 430

Glu Lys Leu Ala Phe Phe Tyr Pro Val Tyr Val Lys Lys Lys Asp
        435                 440                 445

Arg Pro Asp Asp Asp Ile Glu Asn Leu Ile Val Leu Val Lys Asn Ala
450                 455                 460

Ile Glu Ser Val Ser Tyr Leu Arg Asn Arg Thr Phe His Phe Lys Glu
465                 470                 475                 480

Ser Ser Leu Leu Glu Leu Leu Lys Glu Leu Asp Asp Lys Asn Ser Gly
            485                 490                 495

Gln Asn Lys Ile Asp Tyr Ser Val Ala Ala Glu Phe Ile Lys Arg Asp
            500                 505                 510

Ile Glu Asn Leu Tyr Asp Val Phe Arg Glu Gln Ile Arg Ser Leu Gly
            515                 520                 525

Ile Ala Glu Tyr Tyr Lys Ala Asp Met Ile Ser Asp Cys Phe Lys Thr
530                 535                 540

Cys Gly Leu Glu Phe Ala Leu Tyr Ser Pro Lys Asn Ser Leu Met Pro
545                 550                 555                 560

Ala Phe Lys Asn Val Tyr Lys Arg Gly Ala Asn Leu Asn Lys Ala Tyr
                565                 570                 575

Ile Arg Asp Lys Gly Pro Lys Glu Thr Gly Asp Gln Gly Gln Asn Ser
            580                 585                 590

Tyr Lys Ala Leu Glu Glu Tyr Arg Glu Leu Thr Trp Tyr Ile Glu Val
        595                 600                 605

Lys Asn Asn Asp Gln Ser Tyr Asn Ala Tyr Lys Asn Leu Leu Gln Leu
610                 615                 620

Ile Tyr Tyr His Ala Phe Leu Pro Glu Val Arg Glu Asn Glu Ala Leu
625                 630                 635                 640

Ile Thr Asp Phe Ile Asn Arg Thr Lys Glu Trp Asn Arg Lys Glu Thr
                645                 650                 655

Glu Glu Arg Leu Asn Thr Lys Asn Asn Lys Lys His Lys Asn Phe Asp
            660                 665                 670

Glu Asn Asp Asp Ile Thr Val Asn Thr Tyr Arg Tyr Glu Ser Ile Pro
            675                 680                 685

Asp Tyr Gln Gly Glu Ser Leu Asp Tyr Leu Lys Val Leu Gln Arg
        690                 695                 700

Lys Gln Met Ala Arg Ala Lys Glu Val Asn Glu Lys Glu Gly Asn
705                 710                 715                 720

Asn Asn Tyr Ile Gln Phe Ile Arg Asp Val Val Val Trp Ala Phe Gly
```

-continued

```
                725                 730                 735
Ala Tyr Leu Glu Asn Lys Leu Lys Asn Tyr Lys Asn Glu Leu Gln Pro
            740                 745                 750
Pro Leu Ser Lys Glu Asn Ile Gly Leu Asn Asp Thr Leu Lys Glu Leu
            755                 760                 765
Phe Pro Glu Glu Lys Val Lys Ser Pro Phe Asn Ile Lys Cys Arg Phe
    770                 775                 780
Ser Ile Ser Thr Phe Ile Asp Asn Lys Gly Lys Ser Thr Asp Asn Thr
785                 790                 795                 800
Ser Ala Glu Ala Val Lys Thr Asp Gly Lys Glu Asp Glu Lys Asp Lys
                805                 810                 815
Lys Asn Ile Lys Arg Lys Asp Leu Leu Cys Phe Tyr Leu Phe Leu Arg
            820                 825                 830
Leu Leu Asp Glu Asn Glu Ile Cys Lys Leu Gln His Gln Phe Ile Lys
            835                 840                 845
Tyr Arg Cys Ser Leu Lys Glu Arg Arg Phe Pro Gly Asn Arg Thr Lys
    850                 855                 860
Leu Glu Lys Glu Thr Glu Leu Leu Ala Glu Leu Glu Glu Leu Met Glu
865                 870                 875                 880
Leu Val Arg Phe Thr Met Pro Ser Ile Pro Glu Ile Ser Ala Lys Ala
                885                 890                 895
Glu Ser Gly Tyr Asp Thr Met Ile Lys Lys Tyr Phe Lys Asp Phe Ile
            900                 905                 910
Glu Lys Lys Val Phe Lys Asn Pro Lys Thr Ser Asn Leu Tyr Tyr His
            915                 920                 925
Ser Asp Ser Lys Thr Pro Val Thr Arg Lys Tyr Met Ala Leu Leu Met
930                 935                 940
Arg Ser Ala Pro Leu His Leu Tyr Lys Asp Ile Phe Lys Gly Tyr Tyr
945                 950                 955                 960
Leu Ile Thr Lys Lys Glu Cys Leu Glu Tyr Ile Lys Leu Ser Asn Ile
                965                 970                 975
Ile Lys Asp Tyr Gln Asn Ser Leu Asn Glu Leu His Glu Gln Leu Glu
            980                 985                 990
Arg Ile Lys Leu Lys Ser Glu Lys  Gln Asn Gly Lys Asp  Ser Leu Tyr
            995                 1000                1005
Leu Asp Lys Lys Asp Phe Tyr  Lys Val Lys Glu Tyr  Val Glu Asn
    1010                 1015                1020
Leu Glu  Gln Val Ala Arg Tyr  Lys His Leu Gln His  Lys Ile Asn
    1025                 1030                1035
Phe Glu  Ser Leu Tyr Arg Ile  Phe Arg Ile His Val  Asp Ile Ala
    1040                 1045                1050
Ala Arg  Met Val Gly Tyr Thr  Gln Asp Trp Glu Arg  Asp Met His
    1055                 1060                1065
Phe Leu  Phe Lys Ala Leu Val  Tyr Asn Gly Val Leu  Glu Glu Arg
    1070                 1075                1080
Arg Phe  Glu Ala Ile Phe Asn  Asn Asn Asp Asp Asn  Asn Asp Gly
    1085                 1090                1095
Arg Ile  Val Lys Lys Ile Gln  Asn Asn Leu Asn Asn  Lys Asn Arg
    1100                 1105                1110
Glu Leu  Val Ser Met Leu Cys  Trp Asn Lys Lys Leu  Asn Lys Asn
    1115                 1120                1125
Glu Phe  Gly Ala Ile Ile Trp  Lys Arg Asn Pro Ile  Ala His Leu
    1130                 1135                1140
```

```
Asn His Phe Thr Gln Thr Glu Gln Asn Ser Lys Ser Ser Leu Glu
1145                1150                1155

Ser Leu Ile Asn Ser Leu Arg Ile Leu Leu Ala Tyr Asp Arg Lys
1160                1165                1170

Arg Gln Asn Ala Val Thr Lys Thr Ile Asn Asp Leu Leu Leu Asn
1175                1180                1185

Asp Tyr His Ile Arg Ile Lys Trp Glu Gly Arg Val Asp Glu Gly
1190                1195                1200

Gln Ile Tyr Phe Asn Ile Lys Glu Lys Glu Asp Ile Glu Asn Glu
1205                1210                1215

Pro Ile Ile His Leu Lys His Leu His Lys Lys Asp Cys Tyr Ile
1220                1225                1230

Tyr Lys Asn Ser Tyr Met Phe Asp Lys Gln Lys Glu Trp Ile Cys
1235                1240                1245

Asn Gly Ile Lys Glu Glu Val Tyr Asp Lys Ser Ile Leu Lys Cys
1250                1255                1260

Ile Gly Asn Leu Phe Lys Phe Asp Tyr Glu Asp Lys Asn Lys Ser
1265                1270                1275

Ser Ala Asn Pro Lys His Thr
1280                1285

<210> SEQ ID NO 7
<211> LENGTH: 30
<212> TYPE: RNA
<213> ORGANISM: Listeria seeligeri

<400> SEQUENCE: 7
gacuaccucu auaugaaaga ggacuaaaac                                    30

<210> SEQ ID NO 8
<211> LENGTH: 29
<212> TYPE: RNA
<213> ORGANISM: Leptotrichia shahii

<400> SEQUENCE: 8
ccaccccaau aucgaagggg acuaaaaca                                     29

<210> SEQ ID NO 9
<211> LENGTH: 31
<212> TYPE: RNA
<213> ORGANISM: Leptotrichia buccalis

<400> SEQUENCE: 9
gaccacccca aaaugaagg ggacuaaaac a                                   31

<210> SEQ ID NO 10
<211> LENGTH: 50
<212> TYPE: RNA
<213> ORGANISM: Listeria seeligeri

<400> SEQUENCE: 10
gacuaccucu auaugaaaga ggacuaaaac caaacaugau cugggucauc               50

<210> SEQ ID NO 11
<211> LENGTH: 55
<212> TYPE: RNA
<213> ORGANISM: Listeria seeligeri

<400> SEQUENCE: 11
```
uaagagacua ccucuauaug aaagaggacu aaaaccaaac augaucuggg ucauc        55

<210> SEQ ID NO 12
<211> LENGTH: 49
<212> TYPE: RNA
<213> ORGANISM: Leptotrichia shahii

<400> SEQUENCE: 12
ccaccccaau aucgaagggg acuaaaacag gggcagagau gaugacccu               49

<210> SEQ ID NO 13
<211> LENGTH: 58
<212> TYPE: RNA
<213> ORGANISM: Leptotrichia shahii

<400> SEQUENCE: 13
ggauuuagac caccccaaua ucgaagggga cuaaaacagg ggcagagaug augacccu     58

<210> SEQ ID NO 14
<211> LENGTH: 51
<212> TYPE: RNA
<213> ORGANISM: Leptotrichia buccalis

<400> SEQUENCE: 14
gaccacccca aaaugaagg ggacuaaaac aggggcagag augaugaccc u             51

<210> SEQ ID NO 15
<211> LENGTH: 56
<212> TYPE: RNA
<213> ORGANISM: Leptotrichia buccalis

<400> SEQUENCE: 15
auuuagacca ccccaaaaau gaagggggacu aaaacagggg cagagaugau gacccu      56

<210> SEQ ID NO 16
<211> LENGTH: 27
<212> TYPE: RNA
<213> ORGANISM: Artificial sequence
<220> FEATURE:
<223> OTHER INFORMATION: Synthetic sequence

<400> SEQUENCE: 16
agauagccca agaaagaggg caauaac                                      27

<210> SEQ ID NO 17
<211> LENGTH: 32
<212> TYPE: RNA
<213> ORGANISM: Artificial sequence
<220> FEATURE:
<223> OTHER INFORMATION: Synthetic sequence

<400> SEQUENCE: 17
guaacaaucc ccguagacag gggaacugca ac                                32

<210> SEQ ID NO 18
<211> LENGTH: 31
<212> TYPE: RNA
<213> ORGANISM: Artificial sequence
<220> FEATURE:
<223> OTHER INFORMATION: Synthetic sequence

<400> SEQUENCE: 18
caucaccgcc aagacgacgg cggacugaac c                                 31

```
<210> SEQ ID NO 19
<211> LENGTH: 30
<212> TYPE: RNA
<213> ORGANISM: Artificial sequence
<220> FEATURE:
<223> OTHER INFORMATION: Synthetic sequence

<400> SEQUENCE: 19
aauuauccca aaauugaagg gaacuacaac                                      30

<210> SEQ ID NO 20
<211> LENGTH: 30
<212> TYPE: RNA
<213> ORGANISM: Artificial sequence
<220> FEATURE:
<223> OTHER INFORMATION: Synthetic sequence

<400> SEQUENCE: 20
gaguaccuca aaacaaaaga ggacuaaaac                                      30

<210> SEQ ID NO 21
<211> LENGTH: 32
<212> TYPE: RNA
<213> ORGANISM: Artificial sequence
<220> FEATURE:
<223> OTHER INFORMATION: Synthetic sequence

<400> SEQUENCE: 21
gaccacccca auaucgaagg ggacuaaaac uu                                   32

<210> SEQ ID NO 22
<211> LENGTH: 27
<212> TYPE: RNA
<213> ORGANISM: Artificial sequence
<220> FEATURE:
<223> OTHER INFORMATION: Synthetic sequence

<400> SEQUENCE: 22
caccccaaua ucgaagggga cuaaaac                                         27

<210> SEQ ID NO 23
<211> LENGTH: 27
<212> TYPE: RNA
<213> ORGANISM: Artificial sequence
<220> FEATURE:
<223> OTHER INFORMATION: Synthetic sequence

<400> SEQUENCE: 23
aaguagcccg auauagaggg caauaac                                         27

<210> SEQ ID NO 24
<211> LENGTH: 27
<212> TYPE: RNA
<213> ORGANISM: Artificial sequence
<220> FEATURE:
<223> OTHER INFORMATION: Synthetic sequence

<400> SEQUENCE: 24
auacagcucg auauagugag caauaag                                         27

<210> SEQ ID NO 25
<211> LENGTH: 34
<212> TYPE: RNA
<213> ORGANISM: Artificial sequence
<220> FEATURE:
<223> OTHER INFORMATION: Synthetic sequence
```

```
<400> SEQUENCE: 25
ucacaucacc gccaagacga cggcggacug aacc                              34

<210> SEQ ID NO 26
<211> LENGTH: 28
<212> TYPE: RNA
<213> ORGANISM: Artificial sequence
<220> FEATURE:
<223> OTHER INFORMATION: Synthetic sequence

<400> SEQUENCE: 26
gaacagcccg auauagaggg caauagac                                    28
```